US012760378B2

(12) United States Patent
Cady et al.

(10) Patent No.: US 12,760,378 B2
(45) Date of Patent: Oct. 13, 2026

(54) NON-REPLICATIVE TRANSDUCTION PARTICLES WITH ONE OR MORE NON-NATIVE TAIL FIBERS AND TRANSDUCTION PARTICLE-BASED REPORTER SYSTEMS

(71) Applicant: Roche Molecular Systems, Inc., Pleasanton, CA (US)

(72) Inventors: Kyle C. Cady, Santa Clara, CA (US); Colin Lam, Redwood City, CA (US); Jeffrey Alexander, Hayward, CA (US); Kristina Chu, Pleasanton, CA (US); Barbara Eckert, El Cerrito, CA (US); Dylan Goldman, San Jose, CA (US); Patrick Lin, San Jose, CA (US); Kalyani Mangipudi, Pleasanton, CA (US); Misha Mehta, Pleasanton, CA (US); Arrash Moghaddasi, Sunnyvale, CA (US); Hai Nguyen, San Jose, CA (US); Natacha Sorenson, Los Gatos, CA (US)

( * ) Notice: Subject to any disclaimer, the term of this patent is extended or adjusted under 35 U.S.C. 154(b) by 768 days.

(21) Appl. No.: 18/152,432

(22) Filed: Jan. 10, 2023

(65) Prior Publication Data

US 2023/0272491 A1 Aug. 31, 2023

Related U.S. Application Data

(62) Division of application No. 16/722,724, filed on Dec. 20, 2019, now Pat. No. 11,572,595.

(60) Provisional application No. 62/926,989, filed on Oct. 28, 2019, provisional application No. 62/787,151, filed on Dec. 31, 2018.

(51) Int. Cl.

| | |
|---|---|
| ***C12N 7/00*** | (2006.01) |
| ***C12N 1/20*** | (2006.01) |
| ***C12N 15/70*** | (2006.01) |
| ***C12N 15/74*** | (2006.01) |
| ***C12Q 1/14*** | (2006.01) |
| ***C12Q 1/18*** | (2006.01) |
| ***C12Q 1/66*** | (2006.01) |
| ***C12Q 1/689*** | (2018.01) |
| ***C12Q 1/6897*** | (2018.01) |

(52) U.S. Cl.

CPC ............ *C12Q 1/6897* (2013.01); *C12N 1/20* (2013.01); *C12N 15/70* (2013.01); *C12N 15/74* (2013.01); *C12Q 1/14* (2013.01); *C12Q 1/18* (2013.01); *C12Q 1/66* (2013.01); *C12Q 1/689* (2013.01); *C12N 2795/10043* (2013.01); *C12N 2795/10152* (2013.01); *C12N 2795/10343* (2013.01); *C12N 2795/10352* (2013.01); *C12Y 113/12007* (2013.01); *G01N 2333/31* (2013.01)

(58) Field of Classification Search

None

See application file for complete search history.

(56) References Cited

FOREIGN PATENT DOCUMENTS

WO 2017114979 A1 7/2017

*Primary Examiner* — Nianxiang Zou

(57) ABSTRACT

The present invention relates to compositions comprising and methods of producing genetically engineered bacteriophages, bacteriophage-like particles and non-replicating transduction particles (NRTPs) that contain non-native tail fibers that display altered host specificity and/or reactivity. The present invention also relates to methods of using these bacteriophages and NRTPs for the development of novel diagnostics, therapeutics and/or research reagents for bacteria-related diseases.

20 Claims, 9 Drawing Sheets

Specification includes a Sequence Listing.

B)

| | | Lysate | | | | | |
|---|---|---|---|---|---|---|---|
| | | S | S' | Smrk | V3 | Double | Triple |
| Strain | Eco202 | 1 | 0 | 0 | 1 | 1 | 1 |
| | Eco109 | 0 | 1 | 0 | 1 | 1 | 1 |
| | Eco228 | 0 | 0 | 1 | 0 | 0 | 1 |

NON-REPLICATIVE TRANSDUCTION PARTICLES WITH ONE OR MORE NON-NATIVE TAIL FIBERS AND TRANSDUCTION PARTICLE-BASED REPORTER SYSTEMS

CROSS REFERENCE TO RELATED APPLICATIONS

This application is a divisional application of U.S. patent application Ser. No. 16/722,724, filed on Dec. 20, 2019, which claims the benefit of priority to U.S. Provisional Patent Application No. 62/787,151, filed on Dec. 31, 2018, and to U.S. Provisional Patent Application No. 62/926,989 filed on Oct. 28, 2019, each of which is hereby incorporated in its entirety by reference.

BACKGROUND OF THE INVENTION

Field of the Invention

The invention relates to methods and compositions for packaging and delivery of non-replicative transduction particles derived from bacteriophages with non-native tail fibers that contain reporter molecules for detecting target organisms.

REFERENCE TO SEQUENCE LISTING

This application contains a Sequence Listing submitted as electronic ST26 XML file named "34922-US3_Sequence_Listing_14Apr23", having a size in bytes of 327 kb, and created on Apr. 14, 2023, and is incorporated by reference in its entirety.

Description of the Related Art

A transduction particle refers to a virus capable of delivering a non-viral nucleic acid into a cell. Viral-based reporter systems have been used to detect the presence of cells and rely on the lysogenic phase of the virus to allow expression of a reporter molecule from the cell. These viral-based reporter systems use replication-competent transduction particles that express reporter molecules and cause a target cell to emit a detectable signal.

However, the lytic cycle of the virus has been shown to be deleterious to viral-based reporter assays. Carrière, C. et al., *Conditionally replicating luciferase reporter phages: Improved sensitivity for rapid detection and assessment of drug susceptibility of Mycobacterium tuberculosis*. Journal of Clinical Microbiology, 1997. 35(12): p. 3232-3239. Carrière et al. developed *M. tuberculosis*/bacillus Calmette-Guérin (BCG) luciferase reporter phages that have their lytic cycles suppressed at 30° C., but active at 37° C. Using this system, Carrière et al. have demonstrated the detection of BCG using phage reporters with a suppressed lytic cycle.

There are disadvantages, however, associated with suppressing but not eliminating the replication functions of the bacteriophage in bacteriophage-based reporter assays. First, controlling replication functions of the bacteriophage imposes limiting assay conditions. For example, the lytic cycle of the reporter phage phAE40 used by Carrière et al. was repressed when the phage was used to infect cells at the non-permissive temperature of 30° C. This temperature requirement imposed limiting conditions on the reporter assay in that the optimum temperature for the target bacteria was 37° C. These limiting conditions hinder optimum assay performance.

Moreover, the replication functions of the virus are difficult to control. The replication of the virus should be suppressed during the use of the transduction particles as a reporter system. For example, the lytic activity of the reporter phage phAE40 reported by Carrière et al. was reduced but was not eliminated, resulting in a drop in luciferase signal in the assay. Carrière et al. highlighted possible causes for the resulting drop in reporter signal, such as intact phage-expressed genes and temperature limitations of the assay, all stemming from the fact that the lytic cycle of the phage reporter was not eliminated.

Reporter assays relying on the natural lysogenic cycle of phages can be expected to exhibit lytic activity sporadically. In addition, assays that rely on the lysogenic cycle of the phage can be prone to superinfection immunity from target cells already lysogenized with a similar phage, as well as naturally occurring host restriction systems that target incoming virus nucleic acid, thus limiting the host range of these reporter phages.

In other examples, transduction particle production systems are designed to package exogenous nucleic acid molecules, but the transduction particle often contains a combination of exogenous nucleic acid molecules and native progeny virus nucleic acid molecules. The native virus can exhibit lytic activity that is a hindrance to assay performance, and the lytic activity of the virus must be eliminated to purify transduction particles. However, this purification is generally not possible. In U.S. 2009/0155768 A, entitled Reporter Plasmid Packaging System for Detection of Bacteria, Scholl et al. describes the development of such a transduction particle system. The product of the system is a combination of reporter transduction particles and native bacteriophage (FIG. 8 in the reference). Although the authors indicate that the transduction particle and native bacteriophage can be separated by ultracentrifugation, this separation is only possible in a system where the transduction particle and the native virus exhibit different densities that would allow separation by ultracentrifugation. While this characteristic is exhibited by the bacteriophage T7-based packaging system described in the reference, this is not a characteristic that is generally applicable for other virus systems. It is common for viral packaging machinery to exhibit headful packaging that would result in native virus and transduction particles to exhibit indistinguishable densities that cannot be separated by ultracentrifugation. Virus packaging systems also rely on a minimum amount of packaging as a requirement for proper virus structural assembly that results in native virus and transduction particles with indistinguishable densities.

Recently, methods and systems for packaging reporter nucleic acid molecules into non-replicative transduction particles (NRTPs), also referred herein as Smarticles, have been described in U.S. Pat. No. 9,388,453 and in U.S. Patent Application Publication No. 2017/0166907 (both of which are incorporated herein by reference in their entireties) in which the production of replication-competent native progeny virus nucleic acid molecules were greatly reduced due to the disruption of the packaging initiation site in the bacteriophage genome Currently NRTPs are produced from naturally occurring lysogenic bacteriophages found in nature, e.g. φ80α bacteriophage or P1 bacteriophage. It is a time consuming process to find, characterize, and modify new bacteriophages into NRTPs that are able to transduce cells with the desired host range specificity.

Several recent studies (Ando et al., Cell Systems 2015, 1: 187-196; Yosef et al., Molecular Cell 2017, 66: 721-728) have shown that T3 and T7 bacteriophages and bacteriophage/transduction particle mixtures can be re-programmed to recognize desired hosts by swapping tail/tail fibers from T3/T7-like viral sources that would enable the phage to recognize different hosts. To this end, different tail/tail fibers were constructed on the T3/T7 chassis and tested for their ability to inject DNA into different hosts. While these experiments paved the way for producing hybrid particles with novel host ranges, these effects were shown only with phages/tail/tail fibers found in T3- and T7-like bacteriophages. Particularly, these studies do not enable a phage-genome engineering platform that is based on the chassis from other bacteriophage families, such as the Myroviridae family which, unlike the T3/T7 bacteriophages, have long and contractile tails and involve completely different tail fiber genes.

One of the most well characterized Myoviridae phage is the P1 bacteriophage that infects *Escherichia coli* (*E. coli*) and other bacteria in the Enterobacteriaceae family. Host-range specificity of P1 is controlled within the tail-fiber operon that is approximately 6 kb in length (FIG. 2) and includes an invertible C-segment region where either of two alternate 3' ends of the tail fiber gene ($s_v$ or $s_v'$) can be fused to a constant 5' end ($s_c$) located outside of the invertible region. Two alternate genes u and u' are located outside of the S gene and encode alternate forms of a chaperone protein that is involved in tail fiber assembly. Two other genes in the tail-fiber operon are the r gene, whose gene product R is believed to be involved in tail fiber assembly and the gene cin which encodes a sequence specific recombinase enzyme which can "flip" the nucleic acid between the Cin recombination sites, known as cix sites, that modifies host specificity, and are described in Guidolin et al., 1989 Gene, 76: 239-243, and in Sandmeier et al., 1992, Journal of Bacteriology, 174(12): 3936-3944, both incorporated by reference herein in their entireties.

Accordingly, there is a need in the art for a quick, reliable, and scalable method to generate new NRTPs derived from the tail fibers of many types of phages. Therefore, the present invention relates to a tail fiber replacement platform (or chassis) derived from P1 bacteriophage that can be altered in only the tail fibers in order to change or extend their host specificity, and that this platform can utilize tail fibers from many viral families. Additionally, the present invention relates to methods to improve the yield of NRTPs from an engineered production line and methods of producing multiple natural or engineered tail fibers-endowed NRTPs in a single fermentation. This approach can be used for other diverse bacteriophages to develop new NRTPs with desired inclusivity and exclusivity profiles with respect to host-range specificities.

SUMMARY OF THE INVENTION

The present invention contemplates a bacteriophage lysogen genetically disrupted to the expression of one or more factors critical to native tail fiber production (examples—genes s, u, u', r and s'). This could be accomplished through any mutagenesis approach known to one skilled in the art, or through isolation of a tail fiber deficient phage remnant from natural sources. This genetically disrupted phage lysogen that lacks the ability to express functional tail fibers of its own without complementation is referred as a chassis or a "Bald" chassis. In one embodiment, the disrupted lysogen has a mutation or a deletion in one or more of the genes selected from a gene that encodes a tail fiber structural protein responsible for binding a bacteria cell receptor, a gene that encodes a chaperone protein needed for folding of one or more regions of a tail fiber structural protein, a gene that encodes a protein required for attaching the tail fiber structural protein to a tail, or any combination of these genes In another embodiment, the disrupted lysogen contains a gene coding for a selectable marker that disrupts the expression of one or more of the genesr. In yet another embodiment, the disrupted lysogen comprises a nucleotide sequence of SEQ ID NO: 97.

One aspect of the invention relates to methods involving the expression of native, new tail fiber genes, or hybrid tail fibers in a lysogen genetically disrupted for native tail fiber expression. This could be accomplished using a packaging plasmid, secondary expression plasmid, genomic expression (phage lysogen or bacterial genome), or any other method known to one skilled in the art.

Therefore, the present invention relates to a bacteriophage tail fiber replacement platform comprising a bacteriophage lysogen from the family Myoviridae (Myoviridae lysogen) that contains a genetic disruption that prevents the expression of one or more genes that are critical for the production of tail fibers native to the Myoviridae lysogen, wherein said one or more genes are selected from a gene that encodes a tail fiber structural protein responsible for binding a bacteria cell receptor, a gene that encodes a chaperone protein needed for folding of one or more regions of a tail fiber structural protein, a gene that encodes a protein required for attaching the tail fiber structural protein to a tail, or any combination of these genes; and a complementary nucleic acid molecule comprising one or more genes selected from a gene that encodes a tail fiber structural protein responsible for binding a bacteria cell receptor, a gene that encodes a chaperone protein needed for folding of one or more regions of a tail fiber structural protein, a gene that encodes a protein required for attaching the tail fiber structural protein to a tail, or any combination of these genes wherein the complementary nucleic acid complements the genetic disruption of the Myoviridae lysogen whereby functional tail fibers are produced.

In one embodiment, the Myoviridae lysogen is derived from a genus selected from: Bcep781likevirus, Bcepmulikevirus, FelixO1likevirus, Hapunalikevirus, I3likevirus, Mulikevirus, Punalikevirus, Pbunalikevirus, PhiCD119likevirus, Phihlikevirus, Phikzlikevirus, Viunalikevirus, Eucampyvirinae, Cp220likevirus, Cp8unalikevirus, Peduovirinae, Hpunalikevirus, P2likevirus, Spounavirinae, Spounalikevirus, Twortlikevirus, Tevenvirinae, Schizot4likevirus, or T4likevirus. In one embodiment, the Myoviridae lysogen is from the Punalikevirus genus. In another embodiment, the Myoviridae lysogen is Enterobacteria bacteriophage phage P1 (P1 bacteriophage).

In one embodiment, the one or more genes or the combination of genes on the complementary nucleic acid molecule contain regions that are not derived from the one or more genes that are critical for the production of tail fibers native to the Myoviridae lysogen such that the functional tail fibers that are produced are not native tail fibers. In another embodiment, the one or more genes or the combination of genes contain regions that are not derived from P1 bacteriophage such that the functional tail fibers that are produced are not native P1 bacteriophage tail fibers.

In yet another embodiment, the genetic disruption on the Myoviridae lysogen comprises one or more mutation in any of the one or more genes. In one embodiment, the one or more mutation is in any one of the P1 bacteriophage genes s, s', u, u' and r, in any combination of genes s, s', u, u' and r, or homologs, orthologs, or analogs of genes s, s', u, u' and r.

In one embodiment, the genetic disruption on the Myoviridae lysogen comprises one or more deletion in any one of the one or more genes. In one embodiment, the one or more deletion is in any one of the P1 bacteriophage genes s, s', u, u' and r, in any combination of genes s, s', u, u' and r, or homologs, orthologs, or analogs of genes s, s', u, u' and r. In another embodiment, the genetic disruption on the Myoviridae lysogen further comprises the insertion of a gene coding for a selectable marker that disrupts the expression of any one of the P1 bacteriophage genes. In one embodiment, the Myoviridae lysogen comprises a nucleic acid sequence of SEQ ID NO: 97.

In one embodiment, the complementary nucleic acid molecule is contained in a plasmid molecule. In another embodiment, the complementary nucleic acid molecule is integrated into the Myoviridae lysogen at the site of the genetic disruption. In yet another embodiment, the complementary nucleic acid molecule is integrated into the Myoviridae lysogen at a site other than the site of the genetic disruption. In yet another embodiment, the complementary nucleic acid molecule is integrated into a genome of a host bacteria cell that contains the Myoviridae lysogen.

In one embodiment, the Myoviridae lysogen contains a further disruption in one or more packaging genes that are involved in packaging the genome of the Myoviridae lysogen. In one embodiment, one or more packaging genes that complement the disruption in the one or more packaging genes in the Myoviridae lysogen are contained a plasmid molecule that also contains the complementary nucleic acid molecule. In another embodiment, one or more packaging genes that complement the disruption in the one or more packaging genes in the Myoviridae lysogen are contained in a reporter or therapeutic expression plasmid that is different from the plasmid molecule that contains the complementary nucleic acid molecule.

The present invention also relates to a bacterial cell line comprising a P1 bacteriophage lysogen that comprises a nucleic acid sequence of SEQ ID NO: 97.

The present invention further relates to a method for producing bacteriophage particles or non-replicating transduction particles (NRTPs) with non-native tail fibers comprising, providing a bacteria cell containing the bacteriophage tail fiber replacement platform of the present invention, wherein the complementary nucleic acid molecule comprises a gene that encodes a tail fiber structural protein with one or more regions that are not derived from the one or more genes that are critical for the production of tail fibers native to the Myoviridae lysogen, and providing conditions to the bacterial cell that induces a lytic phase of the Myoviridae lysogen to produce bacteriophage particles with non-native tail fibers.

In one embodiment, the one or more regions that are not derived from the one or more genes native to the Myoviridae lysogen comprises a variable region of the tail fiber structural protein (tail fiber variable region) obtained from bacteriophages within the order Caudovirales. In one embodiment, the tail fiber variable region is obtained from bacteriophages within the family Myoviridae. In another embodiment, the tail fiber variable region is obtained from bacteriophages within a genus selected from: Bcep781likevirus. Bcepmulikevirus, FelixO1likevirus, Hapunalikevirus, I3likevirus, Mulikevirus, Punalikevirus, Pbunalikevirus, PhiCD119likevirus, Phihlikevirus, Phikzlikevirus, Viunalikevirus, Eucampyvirinae, Cp220likevirus, Cp8unalikevirus, Peduovirinae, Hpunalikevirus, P2likevirus, Spounavirinae, Spounalikevirus, Twortlikevirus, Tevenvirinae, Schizot4likevirus, or T4likevirus. In one embodiment, the genus is Punalikevirus.

In one embodiment, the complementary nucleic acid molecule further comprises a gene that encodes a chaperone protein. In one embodiment, the gene that encodes the chaperone protein is obtained from bacteriophages within the order Caudovirales. In another embodiment, the gene that encodes the chaperone protein is obtained from bacteriophages within the family Myoviridae. In yet another embodiment, the gene that encodes the chaperone protein is obtained from bacteriophages from a genus selected from: Bcep781likevirus, Bcepmulikevirus, FelixO1likevirus, Hapunalikevirus, I3likevirus, Mulikevirus, Punalikevirus, Pbunalikevirus, PhiCD119likevirus, Phihlikevirus, Phikzlikevirus, Viunalikevirus, Eucampyvirinae, Cp220likevirus, Cp8unalikevirus, Peduovirinae, Hpunalikevirus, P2likevirus, Spounavirinae, Spounalikevirus, Twortlikevirus, Tevenvirinae, Schizot4likevirus, or T4likevirus. In one embodiment, the genus is Punalikevirus.

In one embodiment, the chaperone protein is obtained from bacterial genomes encoding non-replicative virus derived structures or from nucleic acid delivery particles. In one embodiment, the gene that encodes the chaperone protein comprises an amino acid sequence selected from the group consisting of SEQ ID Nos: 67-96 and 113-117.

In one embodiment, the one or more regions that are not derived from the one or more genes native to the Myoviridae lysogen comprises a variable region of the tail fiber structural protein (tail fiber variable region) obtained from bacterial genomes encoding phage tail-like particles or structures or from nucleic acid delivery particles. In one embodiment, the gene that encodes the tail fiber structural protein comprises of an amino acid sequence selected from the group consisting of SEQ ID Nos: 35-66, and 108-112. In another embodiment, the gene that encodes the tail fiber structural protein comprises a nucleotide sequence selected from the group consisting of SEQ ID Nos: 1-34, 98, 100, 102, 104 and 106.

In another aspect, the present invention contemplates expressing chimeric tail fiber genes that generate a bacteriophage and/or a NRTP displaying a host-range specificity and/or reactivity that differs from the host-range specificity and/or reactivity of the native bacteriophage chassis. Therefore, the present invention relates to a method of generating an engineered bacteriophage or a NRTP that displays a bacteria host cell specificity that differs from the bacteria host cell specificity displayed by a native bacteriophage comprising, fusing a first nucleotide sequence from one tail fiber structural protein encoding gene with a second nucleotide sequence from a second tail fiber structural protein encoding gene from a different source to generate a chimeric tail fiber structural protein encoding gene; and expressing the chimeric tail fiber structural protein gene in a bacteria cell that contains the bacteriophage tail fiber replacement platform of the present invention; and providing conditions to the bacteria cell that induces a lytic phase of the Myoviridae lysogen to generate the engineered bacteriophage or NRTP.

In one embodiment, the first nucleotide sequence is derived from the Myoviridae lysogen that contains the genetic disruption. In another embodiment, the first nucleotide sequence comprises the $s_c$ region of tail fiber gene s from P1 bacteriophage. In yet another embodiment, the first nucleotide sequence comprises a sequence with at least 90% sequence identity with the nucleotide sequence that encodes amino acid sequence 1-250 of SEQ ID NO: 53. In yet another embodiment, the first nucleotide sequence comprises a sequence with at least 90% sequence identity with the nucleotide sequence that encodes amino acid sequence 1-500 of SEQ ID NO: 53.

In one embodiment, the first nucleotide sequences comprises the $S_c$ region derived from plasmid p15B (as described in Ikeda et al., J. Mol. Biol., 1970, 50: 457-470) or from a P1-like type 11 bacteriophage in *Klebsiella pneumoniae* (Kpn).

In another aspect, the present invention relates to a method of generating engineered bacteriophages or NRTPs having multiple types of tail fibers from a single bacteria cell line wherein at least one of the tail fiber type is a non-native tail fiber comprising, providing a bacteria cell containing the bacteriophage tail fiber replacement platform of the present invention, wherein the complementary nucleic acid molecule comprises at least two receptor binding regions from tail fiber structural protein encoding genes that are fused to one or more tail interacting regions from tail fiber structural protein encoding genes, wherein at least one of the receptor binding regions is derived from a different source than the source of one of the tail interacting region; and providing conditions to the bacterial cell that induces a lytic phase of the Myoviridae lysogen to produce bacteriophages or NRTPs having multiple types of tail fibers.

In one embodiment, the complementary nucleic acid molecule is integrated into the Myoviridae lysogen at the site of the genetic disruption. In another embodiment, the complementary nucleic acid molecule is integrated into the Myoviridae lysogen at a site other than the site of the genetic disruption. In yet another embodiment, the complementary nucleic acid molecule is integrated into the genome of the bacteria cell. In yet another embodiment, the complementary nucleic acid molecule is contained in a plasmid molecule.

In one embodiment, fusing the two or more receptor binding regions to the tail interacting region is performed by a cin recombinase and in the presence of multiple cix recombination sites. In one embodiment, fusing the two or more receptor binding regions to the tail interacting region is performed by a cin recombinase or a homolog, ortholog, or paralog of the cin recombinase and in the presence of multiple associated recombination sites. In one embodiment, the two or more distinct tail fiber structural protein encoding genes are expressed in an operon. In another embodiment, the two or more distinct tail fiber structural protein encoding genes are expressed from independent promoters. In yet another embodiment, the two or more distinct tail fiber structural protein encoding genes are expressed from independent genomic locations.

In another aspect, the present invention relates to a bacterial cell packaging system for packaging a reporter or therapeutic nucleic acid molecule into a non-replicative transduction particle (NRTP) for introduction into a cell, the packaging system comprising, a host bacteria cell; a bacteriophage lysogen that contains a genetic disruption that prevents the expression of one or more genes that are critical for the production of native tail fibers, wherein said one or more genes encode a tail fiber structural protein responsible for binding a receptor, a chaperone needed for folding of one or more regions of a tail fiber structural protein, a protein required for attaching the tail fiber structural protein to the tail structure, or any combination of these genes; and also comprising a first bacteriophage gene that contains a non-functional packaging initiation site sequence, wherein the non-functional packaging initiation site sequence prevents preferential packaging of the bacteriophage genome into the NRTP; one or more complementary nucleic acid molecules comprising one or more genes selected from genes encoding a tail fiber structural protein responsible for binding a receptor, a chaperone needed for folding of one or more regions of a tail fiber structural protein, a protein required for attaching the tail fiber structural protein to the tail structure, or any combination of these genes that complements the genetic disruption of the bacteriophage lysogen whereby functional tail fibers are produced; and a reporter or therapeutic nucleic acid molecule and a second bacteriophage gene that contains a functional packaging initiation site sequence for facilitating packaging of a replicon of the reporter nucleic acid molecule into the NRTP, wherein the functional packaging initiation site sequence on the reporter nucleic acid molecule complements the non-functional packaging initiation site sequence in the bacteriophage lysogen.

In one embodiment, the reporter gene is luxAB. In another embodiment, the reporter gene is a fluorescent reporter protein which includes but is not limited to Green Fluorescent Protein (GFP), Yellow Fluorescent Protein (YFP), Cyan Fluorescent Protein (CFP), and Red Fluorescent Protein (RFP). In one embodiment, the first bacteriophage gene and the second bacteriophage gene is a pacA terminase gene. In another embodiment, the first bacteriophage gene and the second bacteriophage gene is a terS terminase gene.

In another aspect, the present invention relates to a method of generating Myoviridae-family bacteriophages or Myoviridae-family derived NRTPs that are able to recognize and transduce bacteria cells for diagnostic or therapeutic use comprising, providing a bacteria cell containing the bacteriophage tail fiber replacement platform of the present invention, wherein the complementary nucleic acid molecule comprises tail fiber genes non-native to the Myovridae lysogen and derived partially or entirely from either Myoviridae, Siphoviridae (as represented in SEQ ID Nos: 5, 10, 32, 33), or Podoviridae tail fiber sequences; and providing conditions to the bacterial cell that induces a lytic phase of the bacteriophage lysogen to produce Myoviridae-family bacteriophages or Myoviridae-family derived NRTPs capable of recognizing and transducing bacteria previously refractory to a native Myoviridae bacteriophage or Myoviridae-family derived NRTP particles for diagnostic or therapeutic use.

BRIEF DESCRIPTION OF THE DRAWINGS

These and other features, aspects, and advantages of the present invention will become better understood with regard to the following description, and accompanying drawings, where.

DETAILED DESCRIPTION OF THE INVENTION

Definitions

Figure 1:
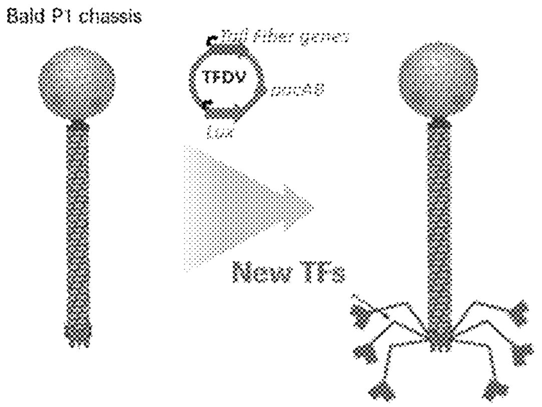
FIG. 1 is a diagram showing the tail-fiber swapping platform.

Terms used in the claims and specification are defined as set forth below unless otherwise specified.

As used herein, "reporter nucleic acid molecule" refers to a nucleotide sequence comprising a DNA or RNA molecule. The reporter nucleic acid molecule can be naturally occurring or an artificial or synthetic molecule. In some embodiments, the reporter nucleic acid molecule is exogenous to a host cell and can be introduced into a host cell as part of an exogenous nucleic acid molecule, such as a plasmid or vector. In certain embodiments, the reporter nucleic acid molecule can be complementary to a target gene in a cell. In other embodiments, the reporter nucleic acid molecule comprises a reporter gene encoding a reporter molecule (e.g., reporter enzyme, protein). In some embodiments, the reporter nucleic acid molecule is referred to as a "reporter construct" or "nucleic acid reporter construct."

As used herein, "therapeutic nucleic acid molecule" refers to a nucleotide sequence that has a therapeutic effect to treat diseases, either by sequence-specific recognition of target nucleic acid that causes the disease (e.g. antisense nucleic acids) or by encoding a gene product that possesses therapeutic activity (e.g. antimicrobial proteins). In some embodiments, the therapeutic nucleic molecule can be introduced into a host cell as part of an exogenous nucleic acid molecule, such as a plasmid. As used herein, a "therapeutic expression plasmid" refers to a plasmid that contains a therapeutic nucleic acid molecule that encodes a gene product having therapeutic activity.

A "reporter molecule" or "reporter" refers to a molecule (e.g., nucleic acid or protein) that confers onto an organism a detectable or selectable phenotype. The detectable phenotype can be colorimetric, fluorescent or luminescent, for example. Reporter molecules can be expressed from reporter genes encoding enzymes mediating luminescence reactions (luxA, luxB, luxAB, luc, ruc, nluc), genes encoding enzymes mediating colorimetric reactions (lacZ, HRP), genes encoding fluorescent proteins (GFP, eGFP, YFP, RFP, CFP, BFP, mCherry, near-infrared fluorescent proteins), nucleic acid molecules encoding affinity peptides (His-tag, 3×-FLAG), and genes encoding selectable markers (ampC, tet(M), CAT, erm). The reporter molecule can be used as a marker for successful uptake of a nucleic acid molecule or exogenous sequence (plasmid) into a cell. The reporter molecule can also be used to indicate the presence of a target gene, target nucleic acid molecule, target intracellular molecule, or a cell, as described herein. Alternatively, the reporter molecule can be a nucleic acid, such as an aptamer or ribozyme.

In some aspects of the invention, the reporter nucleic acid molecule is operatively linked to a promoter. In other aspects of the invention, the promoter can be chosen or designed to contribute to the reactivity and cross-reactivity of the reporter system based on the activity of the promoter in specific cells (e.g., specific species) and not in others. In certain aspects, the reporter nucleic acid molecule comprises an origin of replication. In other aspects, the choice of origin of replication can similarly contribute to reactivity and cross-reactivity of the reporter system, when replication of the reporter nucleic acid molecule within the target cell contributes to or is required for reporter signal production based on the activity of the origin of replication in specific cells (e.g., specific species) and not in others. In some embodiments, the reporter nucleic acid molecule forms a replicon capable of being packaged as concatameric DNA into a progeny virus during virus replication.

As used herein, a "target transcript" refers to a portion of a nucleotide sequence of a DNA sequence or an mRNA molecule that is naturally formed by a target cell including that formed during the transcription of a target gene and mRNA that is a product of RNA processing of a primary transcription product. The target transcript can also be referred to as a cellular transcript or naturally occurring transcript.

As used herein, the term "transcript" refers to a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be protein coding or non-coding. The transcript can also be transcribed from an engineered nucleic acid construct.

A transcript derived from a reporter nucleic acid molecule can be referred to as a "reporter transcript." The reporter transcript can include a reporter sequence and a cis-repressing sequence. The reporter transcript can have sequences that form regions of complementarity, such that the transcript includes two regions that form a duplex (e.g., an intermolecular duplex region). One region can be referred to as a "cis-repressing sequence" and has complementarity to a portion or all of a target transcript and/or a reporter sequence. A second region of the transcript is called a "reporter sequence" and can have complementarity to the cis-repressing sequence. Complementarity can be full complementarity or substantial complementarity. The presence and/or binding of the cis-repressing sequence with the reporter sequence can form a conformation in the reporter transcript, which can block further expression of the reporter molecule. The reporter transcript can form secondary structures, such as a hairpin structure, such that regions within the reporter transcript that are complementary to each other can hybridize to each other.

"Introducing into a cell," when referring to a nucleic acid molecule or exogenous sequence (e.g., plasmid, vector, construct), means facilitating uptake or absorption into the cell, as is understood by those skilled in the art. Absorption or uptake of nucleic acid constructs or transcripts can occur through unaided diffusive or active cellular processes, or by auxiliary agents or devices including via the use of bacteriophage, virus, and transduction particles. The meaning of this term is not limited to cells in vitro; a nucleic acid molecule may also be "introduced into a cell," wherein the cell is part of a living organism. In such instance, introduction into the cell will include the delivery to the organism. For example, for in vivo delivery, nucleic acid molecules, constructs or vectors of the invention can be injected into a tissue site or administered systemically. In vitro introduction into a cell includes methods known in the art, such as electroporation and lipofection. Further approaches are described herein or known in the art.

A "transduction particle" refers to a virus capable of delivering a non-viral nucleic acid molecule into a cell. The virus can be a bacteriophage, adenovirus, etc.

A "phage tail-like particle" or "phage tail-like structures" refers to a bacterially produced high-molecular-weight phage tail-like protein complex that resemble bacteriophage tails in form, however, do not encode or deliver replicative viral genomes and therefore are not viruses. Non-limiting examples of phage tail-like particles or structures include Type 6 Secretion Systems (T6SS) and R-type tailocins (also known as pyocins) which are found in diverse bacteria types. Further descriptions of these particles are found in Williams et al., Applied and Environmental Microbiology, 2008, 74:12, 3868-3876, and in Scholl et al., Antimicrobial Agents and Chemotherapy, 2009, 53:7, 3074-3080, both incorporated by reference herein in their entireties. While these example structures do not encode viral capsid heads, they are able to mediate binding and tail injection into target cells resulting in either killing target cells or delivering protein effectors. Phage tail-like particles or structures can harbor and utilize specificity determining elements such as tail fibers and therefore their genetic sequences can be mined to re-target cell binding specificity. One example of a pyocin-derived tail fiber is shown in the nucleotide sequence of SEQ ID NO: 11.

A "non-replicative transduction particle" or "NRTP" refers to a virus capable of delivering a non-viral nucleic acid molecule into a cell, but is incapable of packaging its own replicated viral genome into the transduction particle. The virus can be a bacteriophage, adenovirus, etc.

A "plasmid" is a small DNA molecule that is physically separate from, and can replicate independently of, chromosomal DNA within a cell. Most commonly found as small circular, double-stranded DNA molecules in bacteria, plasmids are sometimes present in archaea and eukaryotic organisms. Plasmids are considered replicons, capable of replicating autonomously within a suitable host. As used herein, the term "packaging plasmid" refers to a plasmid encoding both the elements required for being packaged into a given viral capsid (i.e. packaging genes) and an expressible reporter gene. As used herein, the term "tail fiber display vector" and abbreviated as "TFDV" refers to a plasmid encoding the elements required for being packaged into a given viral capsid, an expressible reporter gene, and a tail fiber encoded sequence that produces a binding protein able to attach to the given capsid. As used herein, the term "secondary tail fiber expression plasmid" refers to a plasmid which encodes a functional tail fiber that can be attached to a given capsid, but does not necessarily harbor a reporter molecule or packaging site/machinery.

A "vector" is a nucleic acid molecule used as a vehicle to artificially carry foreign genetic material into another cell, where it can be replicated and/or expressed.

A "virus" is a small infectious agent that replicates only inside the living cells of other organisms. Virus particles (known as virions) include two or three parts: i) the genetic material made from either DNA or RNA molecules that carry genetic information; ii) a protein coat that protects these genes; and in some cases, iii) an envelope of lipids that 9388

As used herein, the term "complement" refers to a non-disrupted sequence that is in the presence of an identical sequence that has been disrupted, or to the relationship of the non-disrupted sequence to the disrupted sequence. In one embodiment, the complement comprises a gene encoded on a polynucleotide in a cell that is functional and capable of expression, and expresses a protein with the same function as a disrupted gene on a bacteriophage prior to disruption. In some embodiments, the complement gene has greater than 80%, 85%, 90%, 91%, 92%, 93%, 94%, 95%, 96%, 97%, 98%, or 99% sequence identity to the disrupted bacteriophage gene prior to disruption, i.e., the native bacteriophage gene. In some embodiments, the complement gene is identical to the disrupted bacteriophage gene prior to disruption, i.e., the native bacteriophage gene. In some embodiments, the complement gene comprises a polynucleotide sequence that has been deleted from the bacteriophage. In some embodiments, the complement gene refers to a gene encoding packaging machinery of a bacteriophage on a plasmid, where the same gene has been disrupted in a bacteriophage. Thus, the plasmid is required to be in the presence of a bacteriophage with a mutated packaging machinery gene to provide the necessary packaging machinery necessary for packaging a polynucleotide into a transduction particle.

As used herein, the term "packaging-related enzymatic activity" refers to one or more polypeptides crucial for the interaction with a packaging initiation site sequence to package a polynucleotide into a transduction particle. In some embodiments, a pair of terminase genes is required for such an interaction, wherein each terminase encodes a packaging-related enzymatic activity. In some embodiments, the enzymatic activity is encoded by a terS and/or terL gene from a *S. aureus* bacteriophage φ11 or φ80α, a terA and terB gene from an *E. faecalis* bacteriophage φEf11, or a pacA and pacB gene of Enterobacteriaceae bacteriophage P1. In these embodiments, each of the pair of terminase genes express a packaging-related enzymatic activity, and a functional version of both are required for packaging of a polynucleotide with the packaging initiation site. In some embodiments, disruption of one of the genes of a plurality of genes associated with a packaging-related enzymatic activity eliminates the packaging-related enzymatic activity. In some embodiments, both of a pair of terminase genes are disrupted on the bacteriophage, thus disrupting the entire set of packaging-related enzymatic activity encoding genes on the bacteriophage.

The term "in situ" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention.

As used herein, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Complementary sequences are also described as binding to each other and characterized by binding affinities.

For example, a first nucleotide sequence can be described as complementary to a second nucleotide sequence when the two sequences hybridize (e.g., anneal) under stringent hybridization conditions. Hybridization conditions include temperature, ionic strength, pH, and organic solvent concentration for the annealing and/or washing steps. The term "stringent hybridization conditions" refers to conditions under which a first nucleotide sequence will hybridize preferentially to its target sequence, e.g., a second nucleotide sequence, and to a lesser extent to, or not at all to, other sequences. Stringent hybridization conditions are sequence dependent, and are different under different environmental parameters. Generally, stringent hybridization conditions are selected to be about 5° C. lower than the thermal melting point ($T_m$) for the nucleotide sequence at a defined ionic strength and pH. The $T_m$ is the temperature (under defined ionic strength and pH) at which 50% of the first nucleotide sequences hybridize to a perfectly matched target sequence. An extensive guide to the hybridization of nucleic acids is found in, e.g., Tijssen (1993) Laboratory Techniques in Biochemistry and Molecular Biology—Hybridization with Nucleic Acid Probes part I, chap. 2, "Overview of principles of hybridization and the strategy of nucleic acid probe assays," Elsevier, N.Y. ("Tijssen"). Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

This includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, provided the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between two strands of a dsRNA, or between the antisense strand of a dsRNA and a target sequence, between complementary strands of a single stranded RNA sequence or a single stranded DNA sequence, as will be understood from the context of their use.

As used herein, a "duplex structure" comprises two antiparallel and substantially complementary nucleic acid sequences. Complementary sequences in a nucleic acid construct, between two transcripts, between two regions within a transcript, or between a transcript and a target sequence can form a "duplex structure." In general, the majority of nucleotides of each strand are ribonucleotides, but as described in detail herein, each or both strands can also include at least one non-ribonucleotide, e.g., a deoxyribonucleotide and/or a modified nucleotide. The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the duplex minus any overhangs that are present in the duplex. Generally, the duplex structure is between 15 and 30 or between 25 and 30, or between 18 and 25, or between 19 and 24, or between 19 and 21, or 19, 20, or 21 base pairs in length. In one embodiment the duplex is 19 base pairs in length. In another embodiment the duplex is 21 base pairs in length. When two different siRNAs are used in combination, the duplex lengths can be identical or can differ.

As used herein, the term "region of complementarity" refers to the region on the antisense strand that is substantially complementary to a sequence, for example a target sequence, as defined herein. Where the region of complementarity is not fully complementary to the target sequence, the mismatches are most tolerated in the terminal regions and, if present, are generally in a terminal region or regions, e.g., within 6, 5, 4, 3, or 2 nucleotides of the 5' and/or 3' terminus.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term "sufficient amount" means an amount sufficient to produce a desired effect, e.g., an amount sufficient to produce a detectable signal from a cell.

The term "therapeutically effective amount" is an amount that is effective to ameliorate a symptom of a disease. A therapeutically effective amount can be a "prophylactically effective amount" as prophylaxis can be considered therapy.

It must be noted that, as used in the specification and the appended claims, the singular forms "a," "an" and "the" include plural referents unless the context clearly dictates otherwise.

Lysogenic and Lytic Cycle of Viruses

Viruses undergo lysogenic and lytic cycles in a host cell. If the lysogenic cycle is adopted, the phage chromosome can be integrated into the bacterial chromosome, or it can establish itself as a stable plasmid in the host, where it can remain dormant for long periods of time. If the lysogen is induced, the phage genome is excised from the bacterial chromosome and initiates the lytic cycle, which culminates in lysis of the cell and the release of phage particles. The lytic cycle leads to the production of new phage particles which are released by lysis of the host.

In addition, virus-based reporter assays, such as phage-based reporters, can suffer from limited reactivity (i.e., analytical inclusivity) due to limits in the phage host range caused by host-based and prophage-derived phage resistance mechanisms. These resistance mechanisms target native phage nucleic acid that can result in the degradation or otherwise inhibition of the phage DNA and functions. Such resistance mechanisms include restriction systems that cleave phage DNA and CRISPR systems that inhibit phage-derived transcripts.

Both lytic activity and phage resistance can be inhibitory to assays based on reporter phages. Lytic activity can inhibit signal by destroying or otherwise inhibiting the cell in its ability to generate a detectable signal and thus affecting limits of detection by reducing the amount of detectable signal or preventing the generation of a detectable signal. Phage resistance mechanisms can limit the host range of the phage and limit the inclusivity of the phage-based reporter, similarly affecting limits of detection by reducing the amount of detectable signal or preventing the generation of a detectable signal. Both lytic activity and phage resistance caused by the incorporation of phage DNA in a reporter phage can lead to false-negative results in assays that incorporate these phage reporters.

III. Methods for Producing Non-Replicative Transduction Particles (NRTP)

Disruption/Complementation-Based Methods for Producing Non-Replicative Transduction Particles.

Disclosed herein are non-replicative transduction particle packaging systems based on disruption of a component of the genome of a virus that is recognized by the viral packaging machinery as the element from which genomic packaging is initiated during viral production. In an embodiment, this disruption disrupts a packaging initiation site from a bacteriophage, and also disrupts a terminase function. Examples of the disrupted elements include the pac-site sequence of pac-type bacteriophages and the cos-site sequence of cos-type bacteriophages. When the packaging initiation site sequence within the phage is disrupted, the phage cannot produce functional terminases. In an example, the pac-site is encoded within a pacA gene sequence, and terminase functions require both a functional PacA and PacB. Plasmid DNA is packaged into a phage capsid by complementing said disrupted terminases and including a recognizable packaging initiation site on the plasmid DNA. The bacteriophage can be any bacteriophage, such as an Enterobacteriaceae bacteriophage P1 or φEF11, or an *S. aureus* bacteriophage φ80α or a bacteriophage φ11.

Packaging initiation sites are often found within coding regions of genes that are essential to virus production. A region of the bacteriophage genome can be disrupted by an insertion, replacement, deletion, or mutation that disrupts the packaging initiation site. Examples of disruptions that accomplish this include, but are not limited to, an allelic exchange event that replaces a sequence on the bacteriophage genome that contains the packaging initiation site sequence with another sequence such as that of an antibiotic resistance gene, or the complete deletion of the small and large terminase genes. In an example employing the terminase genes pacA and pacB, pacA can be disrupted in a manner that causes polar effects that also disrupt pacB expression and/or overall terminase function mediated by PacA and PacB. Other examples can include terminase genes can also include terS and terL genes from *S. aureus* bacteriophage φ11 or φ80α, or the terS and terL genes from *E. faecalis* bacteriophage φEf11

In one example, a cell's genome is lysogenized with a viral genome where the packaging initiation site has been disrupted. In some embodiments, the cell can be an *E. coli* cell, an *S. aureus* cell, or an *E. faecalis* cell. The cell can be Gram-negative or Gram-positive. A complementing plasmid (or reporter nucleic acid molecule) is introduced into the cell, and the plasmid DNA includes at least the gene that has been disrupted in the bacteriophage, as well as the packaging initiation site sequence, and optionally additional bacteriophage genes and a reporter gene, which can encode a detectable and/or a selectable marker. The plasmid can be constructed using methods found in U.S. Pat. No. 9,388,453, and in U.S Patent Application Publication No. 2017/0166907, hereby incorporated by reference in their entireties. One or more genes of the plasmid can be operatively linked to a promoter, such as an inducible promoter (which can be induced when packaging is initiated by inducing the bacteriophage). In some embodiments, the promoter can be a native promoter of a small terminase gene or a large terminase gene. The native promoter can be controlled by the bacteriophage, and thus effectively acts as a conditional promoter induced during packaging.

In some examples, it is preferable that the disruption/complementation is designed such that there is no homology between the mutated virus DNA and the complementing exogenous DNA. This is because lack of homology between the mutated virus DNA and the complementing exogenous DNA avoids the possibility of homologous recombination between the two DNA molecules that can result in re-introduction of a packaging sequence into the virus genome. To accomplish a lack of homology, one strategy is to delete the entire gene (or genes) that contains the packaging initiation site sequence from the virus genome and then complement this gene with an exogenous DNA molecule that preferably contains no more than exactly the DNA sequence that was deleted from virus. In this strategy, the complementing DNA molecule is designed to express the gene that was deleted from the virus. Another example of such a system is provided using the bacteriophage φ80α, a pac-type phage. The phage genome is lysogenized in a host bacterial cell, and the phage genome includes a small terminase gene where the pac-site of a pac-type prophage φ80α has been deleted. A plasmid including a complementary small terminase gene with a native pac-site is transformed into the cell. When the lytic cycle of the lysogenized prophage is induced, the bacteriophage packaging system packages plasmid DNA into progeny bacteriophage structural components, rather than packaging the native bacteriophage DNA. The packaging system thus produces non-replicative transduction particles carrying plasmid DNA.

The reporter gene encodes a detectable marker or a selectable marker. In an example, the reporter gene is selected from the group consisting of enzymes mediating luminescence reactions (luxA, luxB, luxAB, luc, ruc, nluc), enzymes mediating colorimetric reactions (lacZ, HRP), fluorescent proteins (GFP, eGFP, YFP, RFP, CFP, BFP, mCherry, near-infrared fluorescent proteins), affinity peptides (His-tag, 3×-FLAG), and selectable markers (ampC, tet(M), CAT, erm). In an embodiment, the reporter gene is luxA. In some embodiments, the resistance marker comprises an antibiotic resistance gene. In some embodiments, the resistance marker is a kanamycin resistance gene (kan). In some embodiments, the constitutive promoter comprises Pblast. In some embodiments, the bacteriophage genome disruption is accomplished by an allelic exchange event that replaces or disrupts a sequence on the bacteriophage genome that contains the packaging initiation site sequence.

In an example, a pair of terminase genes on a bacteriophage genome, e.g., pacA and pacB, terA and terB, or terS and terL, can be disrupted in a manner that causes polar effects that also disrupt expression of one of the terminase genes and/or overall terminase function mediated by the terminase genes. The disrupted bacteriophage can be complemented with a plasmid comprising terminase genes, e.g., pacA and pacB, terA and terB, or terS and terL, of the bacteriophage genome. When the mutated virus is undergoing a lytic cycle, the viral packaging proteins, produced either from the bacteriophage genome or (if disrupted) the complementing plasmid, package a replicon of the plasmid DNA into the packaging unit because it contains a packaging initiation site, and non-replicative transduction particles are produced carrying the replicated plasmid DNA.

Reporters

In some embodiments, the NRTPs and constructs of the invention comprise a reporter nucleic acid molecule including a reporter gene. The reporter gene can encode a reporter molecule, and the reporter molecule can be a detectable or selectable marker. In certain embodiments, the reporter gene encodes a reporter molecule that produces a detectable signal when expressed in a cell.

In certain embodiments, the reporter molecule can be a fluorescent reporter molecule, such as, but not limited to, a green fluorescent protein (GFP), enhanced GFP, yellow fluorescent protein (YFP), cyan fluorescent protein (CFP), blue fluorescent protein (BFP), red fluorescent protein (RFP) or mCherry, as well as near-infrared fluorescent proteins.

In other embodiments, the reporter molecule can be an enzyme mediating luminescence reactions (LuxA, LuxB, LuxAB, Luc, Ruc, nLuc, etc.). Reporter molecules can include a bacterial luciferase, a eukaryotic luciferase, an enzyme suitable for colorimetric detection (LacZ, HRP), a protein suitable for immunodetection, such as affinity peptides (His-tag, 3×-FLAG), a nucleic acid that function as an aptamer or that exhibits enzymatic activity (ribozyme), or a selectable marker, such as an antibiotic resistance gene (ampC, tet(M), CAT, erm). Other reporter molecules known in the art can be used for producing signals to detect target nucleic acids or cells.

In other aspects, the reporter molecule comprises a nucleic acid molecule. In some aspects, the reporter molecule is an aptamer with specific binding activity or that exhibits enzymatic activity (e.g., aptazyme, DNAzyme, ribozyme).

Reporters and reporter assays are described further in Section V herein.

V. NRTPs and Reporter Assays

Inducer Reporter Assay

In some embodiments, the invention comprises methods for the use of NRTPs as reporter molecules for use with endogenous or native inducers that target gene promoters within viable cells. The NRTPs of the invention can be engineered using the methods described in Section III and below in Examples 1-2.

In some embodiments, the method comprises employing a NRTP as a reporter, wherein the NRTP comprises a reporter gene that is operably linked to an inducible promoter that controls the expression of a target gene within a target cell. When the NRTP that includes the reporter gene is introduced into the target cell, expression of the reporter gene is possible via induction of the target gene promoter in the reporter nucleic acid molecule.

Transcripts

As described above, a transcript is a length of nucleotide sequence (DNA or RNA) transcribed from a DNA or RNA template sequence or gene. The transcript can be a cDNA sequence transcribed from an RNA template or an mRNA sequence transcribed from a DNA template. The transcript can be transcribed from an engineered nucleic acid construct. The transcript can have regions of complementarity within itself, such that the transcript includes two regions that can form an intra-molecular duplex. One region can be referred to as a "cis-repressing sequence" that binds to and blocks translation of a reporter sequence. A second region of the transcript is called a "reporter sequence" that encodes a reporter molecule, such as a detectable or selectable marker.

The transcripts of the invention can be a transcript sequence that can be 5, 6, 7, 8, 9, 10, 11, 12, 13, 14, 15, 16, 17, 18, 19, 20, 21, 22, 23, 24, or 25 nucleotides in length. In other embodiments, the transcript can be at least 25, 30, 40, 50, 60, 70, 80, 90, 100, 500, 1000, 1500, 2000, 3000, 4000, 5000 or more nucleotides in length. The cis-repressing sequence and the reporter sequence can be the same length or of different lengths.

In some embodiments, the cis-repressing sequence is separated from the reporter sequence by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, or more spacer nucleotides.

Vectors

In another aspect, the transcripts (including antisense and sense sequences) of the invention are expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). These sequences can be introduced as a linear construct, a circular plasmid, or a viral vector, including bacteriophage-based vectors, which can be incorporated and inherited as a transgene integrated into the host genome. The transcript can also be constructed to permit it to be inherited as an extrachromosomal plasmid (Gassmann, et al., *Proc. Natl. Acad. Sci. USA* (1995) 92:1292).

The transcript sequences can be transcribed by a promoter located on the expression plasmid. In one embodiment, the cis-repressing and reporter sequences are expressed as an inverted repeat joined by a linker polynucleotide sequence such that the transcript has a stem and loop structure.

Recombinant expression vectors can be used to express the transcripts of the invention. Recombinant expression vectors are generally DNA plasmids or viral vectors. Viral vectors expressing the transcripts can be constructed based on, but not limited to, adeno-associated virus (for a review, see Muzyczka, et al., *Curr. Topics Micro. Immunol.* (1992) 158:97-129)); adenovirus (see, for example, Berkner, et al., BioTechniques (1998) 6:616), Rosenfeld et al. (1991, Science 252:431-434), and Rosenfeld et al. (1992), Cell 68:143-155)); or alphavirus as well as others known in the art. Retroviruses have been used to introduce a variety of genes into many different cell types, including epithelial cells, in vitro and/or in vivo (see, e.g., Eglitis, et al., *Science* (1985) 230:1395-1398; Danos and Mulligan, Proc. Natl. Acad. Sci. USA (1998) 85:6460-6464; Wilson et al., 1988, Proc. Natl. Acad. Sci. USA 85:3014-3018; Armentano et al., 1990, Proc. Natl. Acad. Sci. USA 87:61416145; Huber et al., 1991, Proc. Natl. Acad. Sci. USA 88:8039-8043; Ferry et al., 1991, Proc. Natl. Acad. Sci. USA 88:8377-8381; Chowdhury et al., 1991, Science 254:1802-1805; van Beusechem. et al., 1992, Proc. Natl. Acad. Sci. USA 89:7640-19; Kay et al., 1992, Human Gene Therapy 3:641-647; Dai et al., 1992, Proc. Natl. Acad. Sci. USA 89:10892-10895; Hwu et al., 1993, J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573). Recombinant retroviral vectors capable of transducing and expressing genes inserted into the genome of a cell can be produced by transfecting the recombinant retroviral genome into suitable packaging cell lines such as PA317 and Psi-CRIP (Comette et al., 1991, Human Gene Therapy 2:5-10; Cone et al., 1984, Proc. Natl. Acad. Sci. USA 81:6349). Recombinant adenoviral vectors can be used to infect a wide variety of cells and tissues in susceptible hosts (e.g., rat, hamster, dog, and chimpanzee) (Hsu et al., 1992, J. Infectious Disease, 166:769), and also have the advantage of not requiring mitotically active cells for infection.

Any viral vector capable of accepting the coding sequences for the transcript(s) to be expressed can be used, for example, vectors derived from adenovirus (AV); adeno-associated virus (AAV); retroviruses (e.g., lentiviruses (LV), Rhabdoviruses, murine leukemia virus); herpes virus, and the like. The tropism of viral vectors can be modified by pseudotyping the vectors with envelope proteins or other surface antigens from other viruses, or by substituting different viral capsid proteins, as appropriate.

For example, lentiviral vectors featured in the invention can be pseudotyped with surface proteins from vesicular stomatitis virus (VSV), rabies, Ebola, Mokola, and the like. AAV vectors featured in the invention can be made to target different cells by engineering the vectors to express different capsid protein serotypes. Techniques for constructing AAV vectors which express different capsid protein serotypes are within the skill in the art; see, e.g., Rabinowitz J E et al. (2002), J Virol 76:791-801, the entire disclosure of which is herein incorporated by reference.

Selection of recombinant viral vectors suitable for use in the invention, methods for inserting nucleic acid sequences for expressing the transcripts into the vector, and methods of delivering the viral vector to the cells of interest are within the skill in the art. See, for example, Dornburg R (1995), Gene Therap. 2: 301-310; Eglitis M A (1988), Biotechniques 6: 608-614; Miller A D (1990), Hum Gene Therap. 1: 5-14; Anderson W F (1998), Nature 392: 25-30; and Rubinson D A et al., Nat. Genet. 33: 401-406, the entire disclosures of which are herein incorporated by reference.

Viral vectors can be derived from AV and AAV. A suitable AV vector for expressing the transcripts featured in the invention, a method for constructing the recombinant AV vector, and a method for delivering the vector into target cells, are described in Xia H et al. (2002), *Nat. Biotech.* 20: 1006-1010. Suitable AAV vectors for expressing the transcripts featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

The promoter driving transcript expression in either a DNA plasmid or viral vector featured in the invention may be a eukaryotic RNA polymerase I (e.g., ribosomal RNA promoter), RNA polymerase II (e.g., CMV early promoter or actin promoter or U1 snRNA promoter) or generally RNA polymerase III promoter (e.g., U6 snRNA or 7SK RNA promoter) or a prokaryotic promoter, for example the T7 promoter, provided the expression plasmid also encodes T7 RNA polymerase required for transcription from a T7 promoter. The promoter can also direct transgene expression to the pancreas (see, e.g., the insulin regulatory sequence for pancreas (Bucchini et al., 1986, Proc. Natl. Acad. Sci. USA 83:2511-2515)).

In addition, expression of the transcript can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals include regulation by ecdysone, by estrogen, progesterone, tetracycline, chemical inducers of dimerization, and isopropyl-beta-D-1-thiogalactopyranoside (IPTG). A person skilled in the art would be able to choose the appropriate regulatory/promoter sequence based on the intended use of the dsRNA transgene.

Generally, recombinant vectors capable of expressing transcript molecules are delivered as described below, and persist in target cells. Alternatively, viral vectors can be used that provide for transient expression of transcript molecules. Such vectors can be repeatedly administered as necessary. Once expressed, the transcript binds to target RNA and modulates its function or expression. Delivery of transcript expressing vectors can be systemic, such as by intravenous or intramuscular administration, by administration to target cells ex-planted from the patient followed by reintroduction into the patient, or by any other means that allows for introduction into a desired target cell.

Transcript expression DNA plasmids are typically transfected into target cells as a complex with cationic lipid carriers (e.g., Oligofectamine) or non-cationic lipid-based carriers (e.g., Transit-TKO™). Multiple lipid transfections for dsRNA-mediated knockdowns targeting different regions of a single PROC gene or multiple PROC genes over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

The delivery of the vector containing the recombinant DNA can by performed by abiologic or biologic systems. Including but not limited to liposomes, virus-like particles, transduction particles derived from phage or viruses, and conjugation.

Reporters for Transcript Assay

In some embodiments, the nucleic acid construct comprises a reporter sequence (e.g., a reporter gene sequence). The reporter gene encodes a reporter molecule that produces a signal when expressed in a cell. In some embodiments, the reporter molecule can be a detectable or selectable marker. In certain embodiments, the reporter molecule can be a fluorescent reporter molecule, such as a green fluorescent protein (GFP), yellow fluorescent protein (YFP), cyan fluorescent protein (CFP), blue fluorescent protein (BFP), or red fluorescent protein (RFP). In other embodiments, the reporter molecule can be a chemiluminescent protein.

Reporter molecules can be a bacterial luciferase, an eukaryotic luciferase, a fluorescent protein, an enzyme suitable for colorimetric detection, a protein suitable for immunodetection, a peptide suitable for immunodetection or a nucleic acid that function as an aptamer or that exhibits enzymatic activity.

Selectable markers can also be used as a reporter. The selectable marker can be an antibiotic resistance gene, for example.

EXAMPLES

Example 1: Disruption/Complementation-Based Methods for Producing Non-Replicative Transduction Particles with Non-Native Tail Fibers A diagram of the tail-fiber replacement platform is shown in FIG. 1. The attachment of NTRPs to their target bacteria cell is mediated by bacteriophage tail fibers. By removing the native P1 NRTP tail fiber genes, a "bald" chassis was created to test the functionality of heterologous tail fibers. New tail fibers were then expressed in the "bald" background using a Tail Fiber Display Vector (TFDV). The P1 based Smarticles genome was modified using the λ-RED Recombineering method from Murphy et al. (1998) to create a deletion in the genes encoding the S structural tail fiber protein and the U tail fiber assembly chaperone protein. This disruption created a platform to express any desired tail fibers in trans. Bacterial strains were grown on Luria-Bertani (LB) broth and LB agar with the following antibiotic concentrations Gentamicin 15 μg/mL, Cabinicillin 100 μg/mL, Spectinomycin 50 μg/mL, Zeocin 100 μg/mL and Hygromycin 150 μg/mL. New England Biolabs (NEB) cloning strain NEB5α was used to propagate and archive plasmids. Assembly of DNA for plasmids as well as linear DNA products for Recombineering were produced using NEB Gibson Assembly Master Mix. EMD Millipore KOD Xtreme Hot Start Polymerase was used for amplification of DNA in all PCR reactions.

Example 2: Construction of a "Bald" P1 Chassis

The λ-RED encoding Recombineering plasmid pKM208 was first transformed into the bacterial strain BAA-1001 (with the pacAB genes replaced with a hygromycin cassette) to facilitate the Recombineering reaction. The strain was made electrocompetent and induced with 1 mM IPTG for expression of recombination proteins. Linear DNA containing the antibiotic resistance marker spectinomycin was then transformed into the strain, this DNA contains homology to the surrounding regions of the s and u genes of P1. After recovery at 30° C., transformants were plated onto LB agar containing spectinomycin, then patched. Colony PCR for the removal of the s and u genes followed by Sanger sequencing were used to ensure the desired modification was made. During construction the u' and $s_v$' regions were left intact, but because the $s_v$' does not code for the full structural protein, the S' tail fiber cannot be produced. This bacterial lysogen represented the "Bald" P1 chassis that lacks the ability to express functional tail fibers of its own without complementation. The resulting bacterial strain containing the Bald P1 chassis was designated as SEG_170 cell line. Functional tests of the chassis consisted of packaging plasmids with and without coding sequences for the native S and U proteins. Loss of Smarticles functionality was seen from lysate derived from the packaging line with no tail fibers on the packaging plasmid. Activity was recovered from lysate derived from the packaging line with tail fibers on the packaging plasmid, achieving successful complementation in trans.

Example 3: Construction of Tail Fiber Display Vectors (TFDV)

Tail Fiber Display Vectors (TFDV) were utilized to express native and/or novel tail fibers in the bald bacteriophage P1 chassis. These display vectors utilized either Gentamicin or Zeocin resistance cassettes, pUC/RO1600 origins of replication, and tail fiber genes under the control of the pTac IPTG inducible promoter. All vectors also contained the pacAB genes/packaging site together with the P23-luxAB-TT (luciferase) cassette for transduction and light assays. Tail fiber candidates were de novo synthesized at IDT or PCR amplified from bacterial gDNA, Gibson Assembled into PCR amplified vectors, transformed into NEBa cells, patched, colony PCR verified, and sequence verified. Sequence verified plasmids were transformed into the well characterized SEG_170 bald packaging line (competent cells purchased from Lucigen). Transformants were patched onto selective media and screened in small volume lysates to determine the best Smarticles producing clones. Top clones were handed off for large volume lysate production, QC, and reactivity analysis on bacterial panels.

Example 4: Construction of Genomic Expression of Tail Fibers

Figure 2:
FIG. 2 Diagram of natural P1 tail fiber genomic region. Gene r encodes a tail fiber accessory protein putatively involved in attaching tail fibers to the tail structure. The cin gene encodes a sequence specific recombinase which flips the DNA between the Cin recombination sites (called cix sites) enabling expression of two distinct tail fibers from a single piece of DNA, sites are denoted as circles in diagram. Genes u and u' encode distinct tail fiber accessory proteins which are thought to act as chaperones to fold the binding domain of the S and S' tail fiber proteins, respectively (binding domains encoded by $s_v$ and $s_v'$ coding sequences, respectively). The conserved region of both S and S' tail fibers proteins are encoded by the $s_c$ coding sequence which is transcriptionally and translationally fused to either the $s_v$ or $s_v'$ depending on activity of the Cin recombinase.

To facilitate optimal Smarticles production with native and/or novel tail fibers, tail fiber and chaperone genes were integrated into the P1 Smarticles genome at the s and u genes native locations. This expression from the genome instead of in trans ensured the proper expression and timing with the rest of the P1 based genome, reducing the burden from in trans expression. Tail fibers were first amplified by PCR with primers containing homology to the hygromycin cassette on the C-terminal portion of the tail fiber structural gene (s gene) or tail fiber chaperone gene (u gene). PCR was also used to amplify the hygromycin cassette. These two fragments were assembled with Gibson Assembly and further amplified with primers that contain homology to the P1 genome where s was previously found and homology in the recombinase cin which lies just downstream of the native s and u genes (see FIG. 2). This Recombineering event performed the dual functions of inserting the tail fiber on the P1 genome as well as disrupting the cin recombinase responsible for switching the variable regions of the s tail fiber gene. This linear DNA product of tail fiber and hygromycin cassette was transformed into BAA-1001 containing the spectinomycin resistance cassette. Recovery at 30° C. and plating followed transformation. Cells were plated onto LB agar containing hygromycin and patched for spectinomycin sensitivity. Promising colonies were checked with colony PCR and Sanger sequencing.

Positive colonies containing the non-native tail fiber and hygromycin resistance were then transformed with a packaging plasmid. Cells were grown overnight in media containing antibiotic. Lysates were generated using a 90 minute 42° C. heat induction to inactivate the P1 master repressor and facilitate Smarticles production. Lysates were then spun down to pellet the bacterial cell debris and then filter sterilized through a 2 μm filter. Lysates were checked for proper Smarticles functionality on the new hosts similar to the process for the TFDV packaging lines described above.

Figure 6:
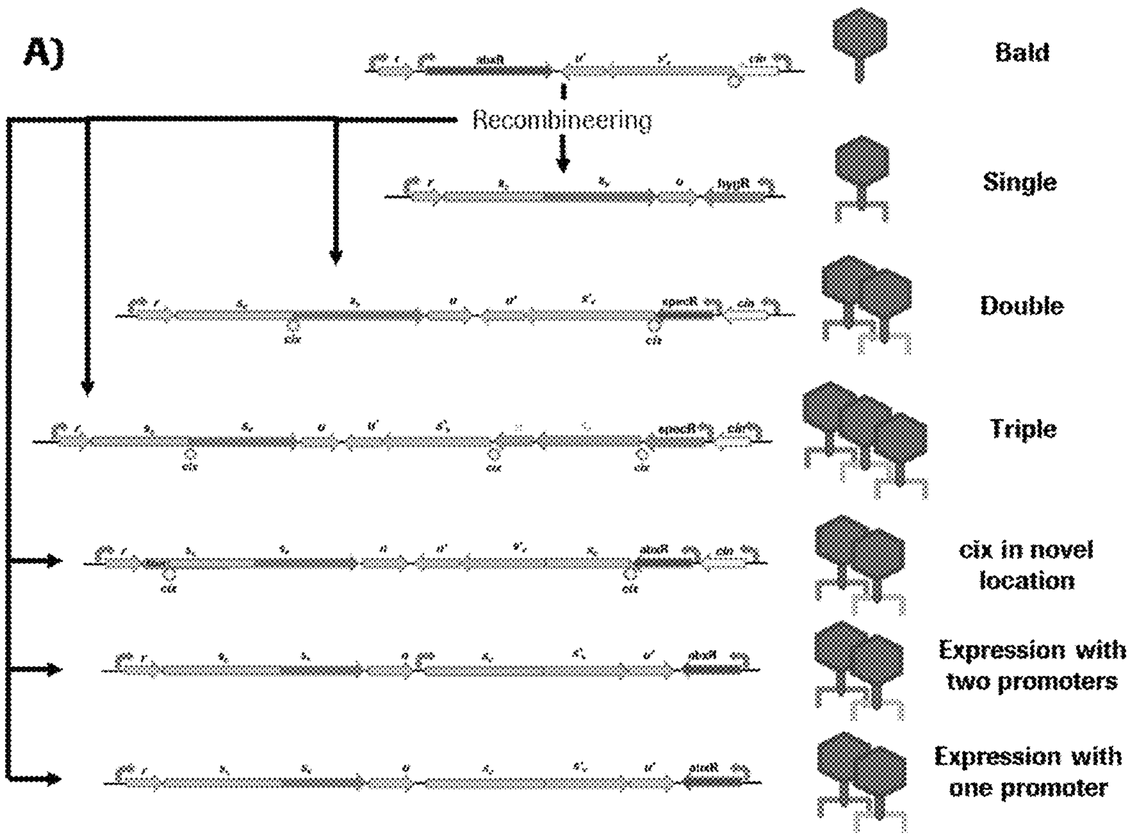
FIG. 6 Production of one, two, or more tail fibers in a single production line A) a single bacterial packaging lines that expresses one, two, three, or more functional tail fibers. S, S', and Shamrock tail fibers were added to a packaging line along with an antibiotic marker. Tail fiber genes can be arranged with cix crossover site in a novel location. Genes can also be arranged for expression not dependent on recombination in large or small operons. B) Lysates were generated from packaging lines expressing single tail fibers (indicated as S, S', Smrk) as well as engineered double and triple tail fiber strains (indicated as V3, Double, Triple). *E. coli* strains that have specific reactivity to a single tail fiber were used to demonstrate multiple functional tail fibers were expressed from a single host.

To construct a packaging line that expresses two or more tail fibers from a single Smarticles genome, a similar Recombineering approach was used as described above. The first tail fiber was similarly placed on the P1 genome, but instead of the tail fiber being linked to hygromycin resistance, it was attached to an alternative antibiotic, such as kanamycin or gentamicin. The cin recombinase was also left intact to facilitate switching of the multiple tail fibers. A second recombineering reaction was performed to place the second variable portion of the tail fiber attached to the hygromycin cassette to replacement of the kanamycin (or gentamicin) cassette already on the genome. This could be repeated to add three, four, five, etc. . . . tail fibers to the genome (see FIG. 6).

Example 5: NRTP Assay Conditions

The assay involved an initial 2.5 hour pre-treatment of bacterial cells at a concentration of 5.0E+05 CFU/mL in assay media (10 g/L Tryptone+5 g/L Yeast Extract+5% PEG8000). Following the pre-treatment step, both NRTPs and transduction salts (1M MgCl2+0.5M CaCl2) were added to the reaction and incubated for 2 hours—which allowed for transduction of the reporter molecule that contained the luciferase gene, luxAB. Light production from bacteria was measured by Relative Luminometer Units (RLU) output using a luminometer.

Example 6: Performance of NRTPs with Engineered Tail Fibers

The improved reactivity of engineered NRTPs against various species and strains can be seen on Table 1. These data clearly show 1) the diversity of tail fibers analyzed, 2) the robust alterations reactivity observed by different tail fiber protein binding domains, 3) that some tail fibers are highly specific for certain species, and 4) some tail fibers are highly reactive against many diverse species of bacteria. Both nucleotide and amino acid sequences of the tail fibers from these engineered NRTPs (e.g. "Sunset", "Indian", "Tangerine" etc.) are listed in the SEQUENCE LISTING which is submitted herewith.

TABLE 1

| | Test Panels | | | | | |
|---|---|---|---|---|---|---|
| Lysate* | Abi (n = 73) | Cfi (N = 88) | Cko (N = 88) | Eae (N = 88) | Ecl (N = 68) | Eco (N = 87) |
| 5X V3 | 45.9%*** | 56.8%* | 63.6%* | 61.4%* | 95.6%* | 88.5%* |
| S | __40.3%__** | NA | NA | NA | __67.6%__** | __71.3%__** |
| S' | __41.6%__** | NA | NA | NA | __89.7%__** | __60.9%__** |
| Sunset TFDV | __0%__** | 5.7%* | 0%* | 2.3%* | __7.4%__** | __12.6%__** |
| Indian TFDV | __1.3%__** | 10.2%* | 0%* | 4.5%* | __14.7%__** | __2.3%__** |
| Tangerine Genomic | _1.4%_*** | NA | NA | NA | _1.5%_* | _13.8%_* |
| Tangerine TFDV | NA | 3.4%* | 0%* | 0%* | NA | NA |
| Maroon TFDV | __0%__** | 0%* | 0%* | 0%* | __4.4%__** | __14.9%__** |
| Scarlett Genomic | __0%__** | 6.8%* | 6.8%* | 45.5%* | __8.8%__** | __14.9%__** |
| Bittersweet Genomic | _1.4%_*** | NA | NA | NA | _0%_* | _4.6%_* |
| Bittersweet TFDV | __2.7%__*** | 4.5%* | 0%* | 0%* | __0%__* | __3.4%__* |
| Indigo Genomic | _0%_*** | NA | NA | NA | _16.2%_* | _1.1%_* |
| 5x Indigo TFDV | 1.4%*** | NA | NA | NA | 14.7%* | 1.1%* |
| DenimTFDV | 4.1%*** | NA | NA | NA | 4.4%* | 12.6%* |
| Cobalt TFDV | 5.5%*** | NA | NA | NA | 5.9%* | 16.1%* |
| Pine TFDV | __35.1%__ | 23.9%* | 63.6%* | 47.7%* | __83.8%__ | __79.3%__** |
| Jungle TFDV | __50.6%__** | 42%* | 12.5%* | 48.9%* | __88.2%__** | __65.5%__** |
| Shamrock | __6.8%__*** | 34.1%* | 1.1%* | 1.1%* | __22.1%__* | __73.6%__* |
| Violet TFDV | __56.8%__*** | 23.9%* | 1.1%* | 35.2%* | __80.9%__* | __66.7%__* |
| Plum TFDV | __2.7%__*** | 0%* | 0%* | 0%* | __1.5%__* | __43.7%__* |
| Salmon TFDV | __40.5%__*** | 28.4%* | 76.1%* | 34.1%* | __33.8%__* | __55.2%__* |
| Jazzberry TFDV | __2.7%__*** | 1.1%* | 0%* | 0%* | __1.5%__* | __42.5%__* |
| Razzmatazz TFDV | 52.1%*** | NA | NA | NA | 85.3%* | 62.1%* |
| ShamJazz genomic | _4.1%_*** | NA | NA | NA | _14.7%_* | _72.4%_* |
| 5x Fuzzy + Chaperone TFDV | 0%*** | NA | NA | NA | 0%* | 2.3%* |
| Banana TFDV | _0%_*** | NA | NA | _1.1%_* | _82.4%_* | _0%_* |
| Mango TFDV | _13.7%_*** | NA | NA | NA | _97.1%_* | _26.4%_* |
| 10x Queen TFDV (Eco0229) | _6.8%_*** | NA | NA | NA | _25%_* | _80.5%_* |
| Tropical TFDV | _0%_*** | NA | NA | NA | _2.9%_* | _0%_* |
| Gold TFDV | _2.7%_** | _5.7%_** | NA | _37.5%_** | _22.1%_** | _32.2%_** |
| Bluetiful TFDV | _0%_** | _1.1%_** | NA | _22.7%_** | NA | _0.0%_** |
| Rio TFDV | _0%_** | _3.4%_** | NA | _3.4%_** | _92%_** | _0%_** |
| Orchid TFDV | _8.2%_** | _17.0%_** | NA | _22.7%_** | _42.6%_** | _79.3%_** |
| Limon TFDV | _1.4%_** | _56.8%_** | _34.1%_** | NA | NA | _0%_** |

| | Test Panels | | | | |
|---|---|---|---|---|---|
| Lysate* | Kox (N = 88) | Kpn (N = 89) | Pae (N = 87) | Pms (N = 88) | Sms (N = 88) |
| 5X V3 | 94.3%* | 82%* | 23%*** | 17%* | 89.8%* |
| S | NA | __75.3%__** | __10.3%__** | __20.5%__** | NA |
| S' | NA | __73.0%__** | __3.4%__** | __29.5%__** | NA |
| Sunset TFDV | 1.1%* | __1.1%__** | __0%__** | 0%* | 1.1%* |
| Indian TFDV | 40.9%* | __14.6%__** | __1.1%__** | 5.7%* | 6.8%* |
| Tangerine Genomic | NA | _0%_* | _9.2%_*** | NA | NA |
| Tangerine TFDV | 0%* | NA | NA | 0%* | 6.8%* |
| Maroon TFDV | 0%* | __0%__** | __0%__** | 0%* | 4.5%* |
| Scarlett Genomic | 47.7%* | __11.2%__** | __0%__** | 6.8%* | 11.4%* |
| Bittersweet Genomic | NA | _0%_* | _0%_*** | NA | NA |
| Bittersweet TFDV | 0%* | __0%__* | __0%__*** | 1.1%* | 0%* |

TABLE 1-continued

| | | | | | |
|---|---|---|---|---|---|
| Indigo Genomic | NA | _0%_* | _0%_*** | NA | NA |
| 5x Indigo TFDV | NA | 0%* | 0%*** | NA | NA |
| DenimTFDV | NA | 22.5%* | 0%*** | NA | NA |
| Cobalt TFDV | NA | 29.2%* | 0%*** | NA | NA |
| Pine TFDV | 78.4%* | __80.9__%** | __9.2__%** | 6.8%* | 38.6%* |
| Jungle TFDV | 90.9%* | __79.8__%** | __1.1__%** | 26.1%* | 97.7%* |
| Shamrock | 0%* | __0__%* | __8__%*** | 9.3%* | 17.1%* |
| Violet TFDV | 71.6%* | __65.2__%* | __20.7__%*** | 2.3%* | 79.6%* |
| Plum TFDV | 0%* | __0__%* | __8__%*** | 0%* | 0%* |
| Salmon TFDV | 77.3%* | __46.1__%* | __20.7__%*** | 9.1%* | 73.6%* |
| Jazzberry TFDV | 0%* | __0__%* | __8__%*** | 0%* | 0%* |
| Razzmatazz TFDV | NA | 60.7%* | 16.1%*** | NA | NA |
| ShamJazz genomic | NA | _0%_* | _0%_*** | NA | NA |
| 5x Fuzzy + Chaperone TFDV | NA | 20.2%* | 0%*** | NA | NA |
| Banana TFDV | NA | _1.1%_* | _0%_*** | NA | NA |
| Mango TFDV | NA | _47.2%_* | _2.3%_*** | NA | NA |
| 10x Queen TFDV (Eco0229) | NA | _0%_* | _0.0%_*** | NA | NA |
| Tropical TFDV | NA | _0%_* | _0%_*** | NA | NA |
| Gold TFDV | _87.5%_** | _62.9%_** | _0%_** | _22.7%_** | _68.2%_** |
| Bluetiful TFDV | _30.7%_** | NA | _0%_** | _4.5%_** | _76.1%_** |
| Rio TFDV | _84%_** | _53.9%_** | _0%_** | _86.4%_** | _80.7%_* |
| Orchid TFDV | NA | _55.1%_** | _0%_** | _5.7%_** | _63.6%_** |
| Limon TFDV | NA | NA | _0%_** | NA | NA |

| | |
|---|---|
| *A. baumannii* | Abi |
| *C. freundii* | Cfi |
| *C. koseri* | Cko |
| *E. aerogenes* | Eae |
| *E. cloacae* | Ecl |
| *E. coli* | Eco |
| *K. oxytoca* | Kox |
| *K. pneumoniae* | Kpn |
| *P. aeruginosa* | Pae |
| *P. mirabilis* | Pms |
| *S. marcescens* | Sms |

*Detection observed at 1E4 CFU/mL

**Detection observed at 5E5 CFU/mL

***Detection observed at 1E7 CFU/mL

Bold denotes lysate concentration of 1x utilized in diagnostic assay

Normal font denotes concentration of 5x utilized in diagnostic assay

Italics denote lysate concentration of 10x utilized in diagnostic assay

Figure 3:
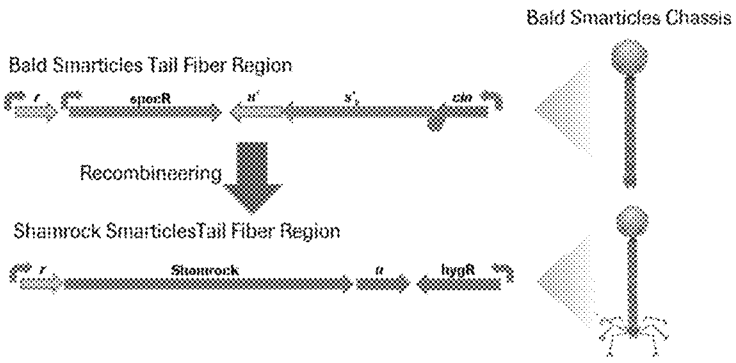
FIG. 3 Diagram of Tail Fiber Replacement Platform. A tail fiber deficient (bald) packaging line harboring a spectinomycin resistance cassette in place of the s and u genes is induced to express recombineering machinery (SEQ ID NO: 97) and comprises an operon promoter, the r gene, the spectinomycin resistance promoter, the spectinomycin resistance gene, the u' gene, the sv' coding region, the cin gene, and the cin promoter. PCR fragments harboring a new tail fiber, hygromycin resistance cassette, and flanking homology arms is then transformed into the induced strain (in this case "Shamrock" and "Shamrock" u). The recombineering machinery integrates the new tail fiber operon in place of the spectinomycin resistance cassette-u'-$s_v'$ region to generate the new chromosomal packaging line able to produce tail fiber endowed Smarticles.
Figure 4:
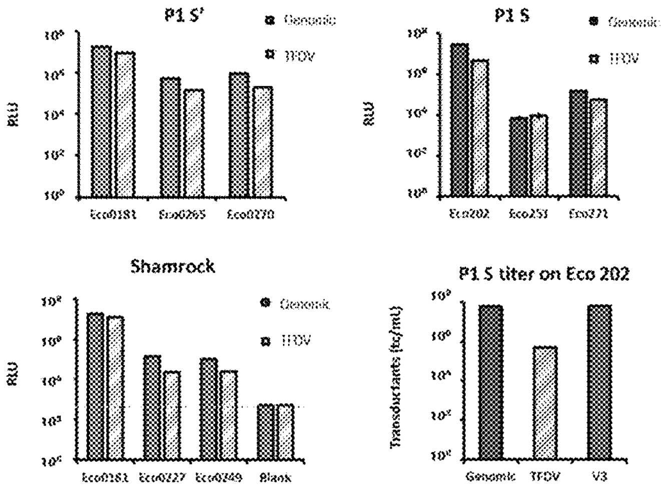
FIG. 4 Improved Smarticles performance following chromosomal integration of tail fibers. Graphs comparing performance of Smarticles endowed with tail fibers expressed from either plasmids (TFDV) or chromosomally. Reactivity of Smarticles harboring only S' (top left), S (top right), or "Shamrock" (bottom left) tail fibers on various *E. coli* strains is shown. Bottom right, improved Smarticles yield obtained from a S tail fiber packaging line genomically integrated vs. plasmid expressed. V3 Smarticles (native tail fibers region) are supplied as a positive control.

FIG. 3 graphically depicts how a bald (tail fiber deficient) P1 lysogen can be altered to express a new tail fiber from the genome. FIG. 4 depicts how genomic integration of a given tail fiber can improve performance compared to trans expression from a TFDV. Light activity is shown for 3 distinct tail fibers on 3 indicator strains for both the TFDV and genomically expressed versions. Additionally, transduction efficiency of the TFDV and genomic S tail fiber NRTPs were also compared to the WT P1 NRTP control (V3).

Figure 5:
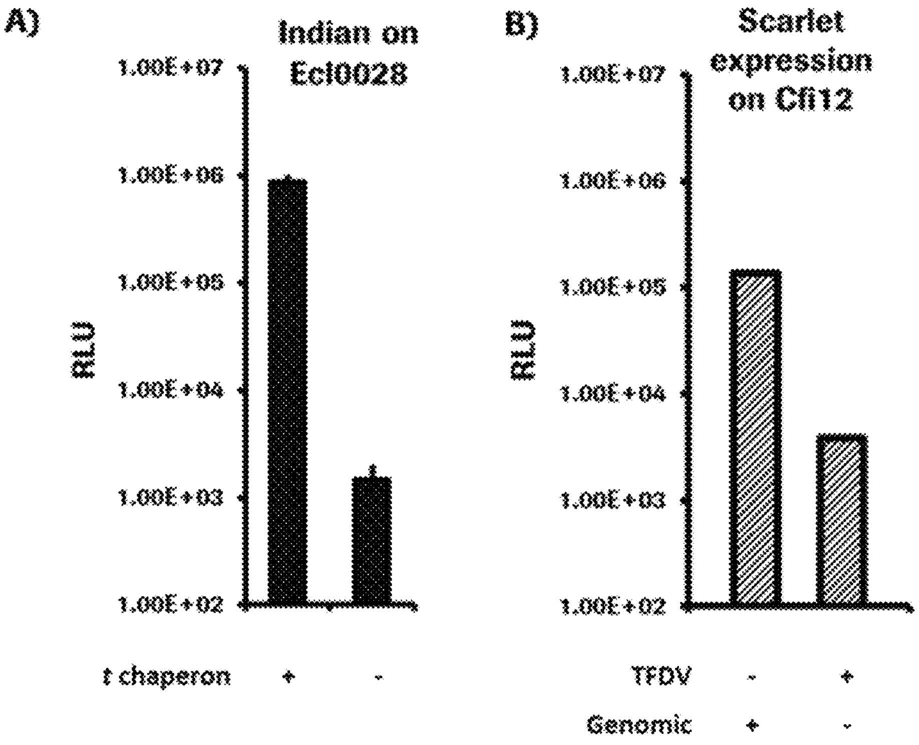
FIG. 5 Shows improved tail fiber activity with expression of native U protein homolog or from bacteriophage genome. A) Performance of "Indian" NRTP produced in packaging line expressing or not expressing plasmid p15B U protein homolog T; B) Performance of "Scarlet" NRTPs produced either from bacteriophage genome or from separate packaging plasmid.

FIG. 5A depicts a graph that show improved tail fiber activity of the engineered "Indian" NRTP as light production (RLU) comparing a packaging line that expresses the plasmid p15B U protein "t chaperon" compared to packaging line not expressing this protein. FIG. 5B depicts a graph that shows improved performance of "Scarlet" NRTPs that are produced from a bacteriophage genome compared to "Scarlet" NRTPs produced from a separate packaging plasmid (TFDV).

FIG. 6A displays the genomic arrangement of production lines harboring 0, 1, 2, or 3 distinct tail fiber genes and demonstrates how lysogens can be engineered to produce multiple NRTPs from a single fermentation. Tail fiber genes can be arranged with cix crossover site in a novel location. Genes can also be arranged for expression not dependent on recombination in large or small operons. FIG. 6B depicts indicator strains specifically detected by given NRTPs endowed individual tail fibers (left). While the right panel shows that packaging lines expressing multiple tail fibers can detect multiple indicator stains, demonstrating that multiple functional NRTPs with varying specificities can be produced at once.

Figure 7:
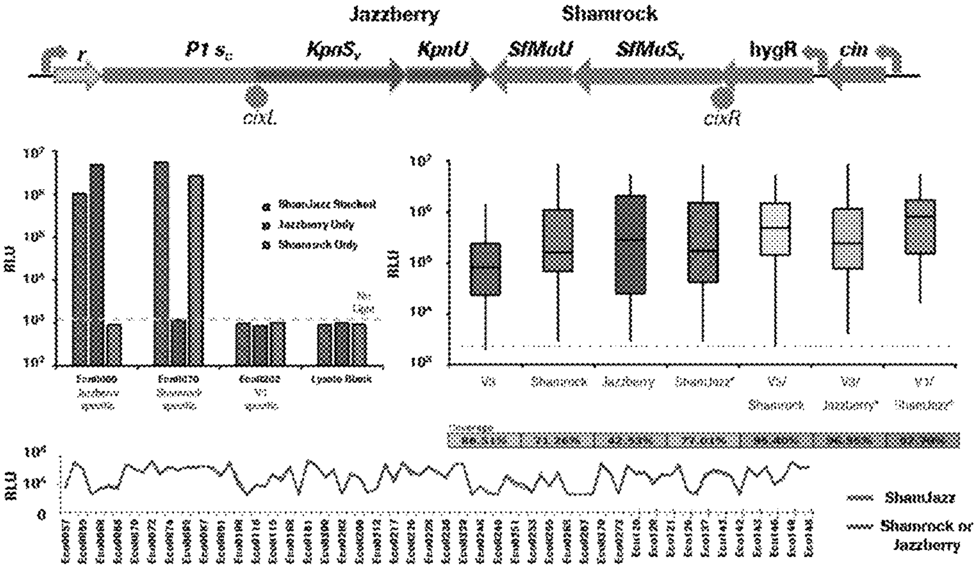
FIG. 7 Analysis of Bi-functional Smarticles packaging line. Bi-functional P1 derived Smarticles were created endowed with both "Jazzberry" and "Shamrock" tail-fibers. A) Cartoon depiction of the genetic arrangement of genome integrated "ShamJazz" dual expression system. B) Confirmation of bi-functional activity on strains that are specific for the "Jazzberry", "Shamrock", or "V3" (S and S') tail fibers. C) Predicted and/or observed activity of select individual and combined Smarticles on a collection of *E. coli* strains (EcoAD panel). Percent coverage depicted below, with stem and whisker plot depicting light distribution on the panel. D) Comparison of predicted activity of the bi-functional Smarticles and observed activity (purple) which are indistinguishable. * denotes cumulative predicted coverage vs. actual experimentally observed coverage.

FIG. 7 compares the performance of NRTPs derived from a bi-functional (two tail fiber) expression strain relative to individual NRTPs produced in separate production runs. Top image shows genomic arrangement of bi-functional tail fiber region from the Jazzberry and Shamrock tail fibers. Left middle, compares individually produced and bi-functional NRTPs on indicator strains specific for the different tail fibers. Right middle, shows how detection and light production were improved on a large panel of *E. coli* strains by making bi-functional production lines in addition to mixing into a cocktail with other NRTPs (such as the native P1 NRTP, called V3). The bottom part of FIG. 7 directly compares the performance of bi-functionally produced NRTPs to the cumulative performance of the individual tail fibers produced separately.

Figure 8:
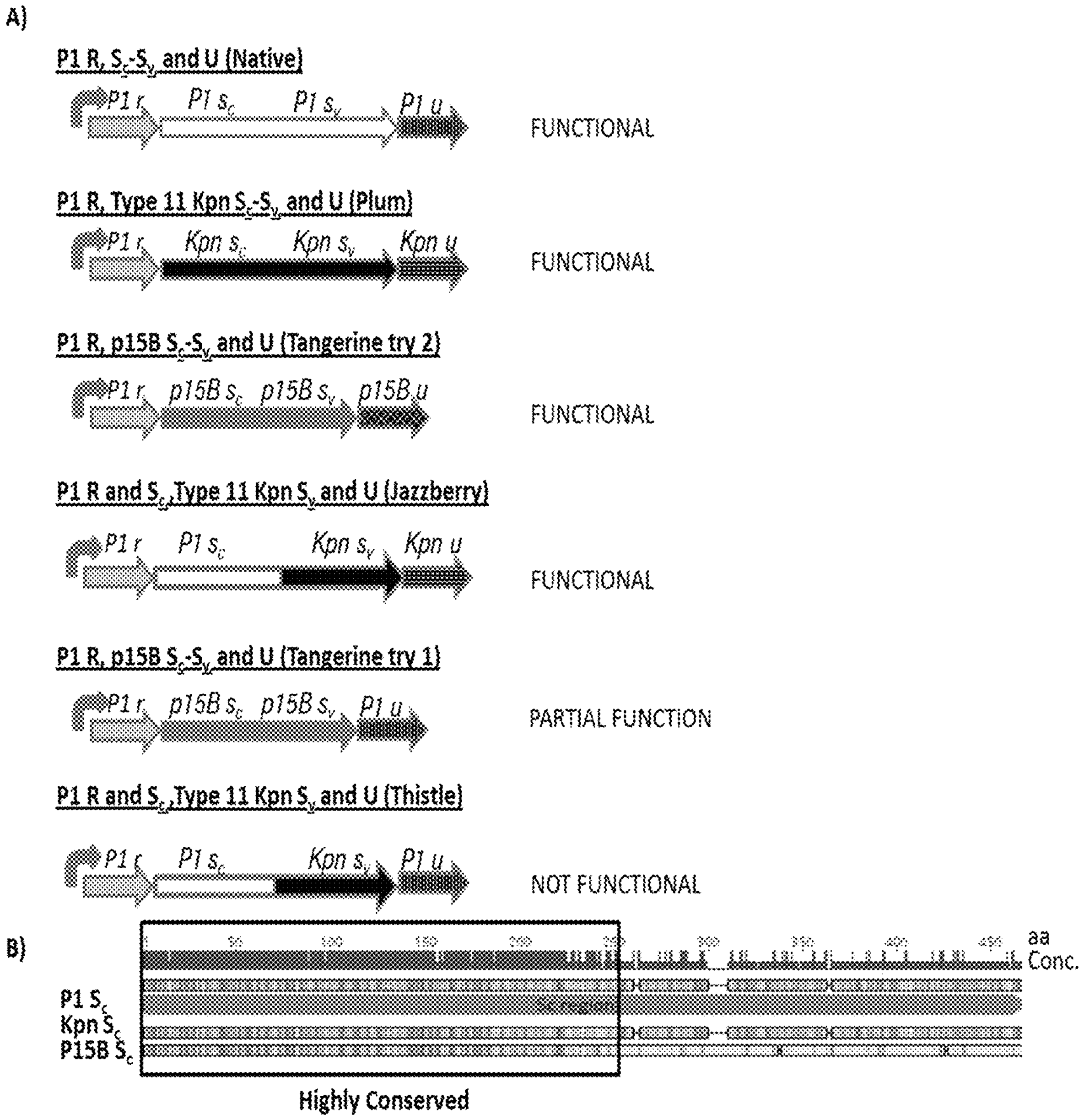
FIG. 8 Establishment of Elements Required for Functional Tail Fibers A) 3 distinct tail fiber Sc regions (see Native P1, "Plum", and "Tangerine") were functionalized on a P1 chassis, expanding the understanding of the determinants required for functional tail fibers. All constructs harbored the P1 r gene encoding the R protein. Each tail fiber variable region ($S_v$) was most functional when expressed with its cognate U accessory protein. B) Protein alignments of the 3 functional $S_c$ regions demonstrate that the N-terminal 250 amino acids are important.

FIG. 8 shows the results of experiments performed that identified the elements that are required for functionalizing new tail fibers on a viral chassis. Panel A illustrates that the P1 r gene is required and that the tail fiber variable region ($S_v$) should be pared with its cognate u homolog accessory protein for maximal activity. Additionally, panel A shows that 3 distinct tail fiber conserved regions could allow functionalization of non-native tail fibers on a new chassis. Panel B shows the alignment of the amino acid sequence of the 3 $S_c$ regions from P1 bacteriophage, type 11 Kpn bacteriophage, and p15B plasmid (related to P1), highlighting a highly conserved N-terminal 150 amino acid sequence motif.

Figure 9:
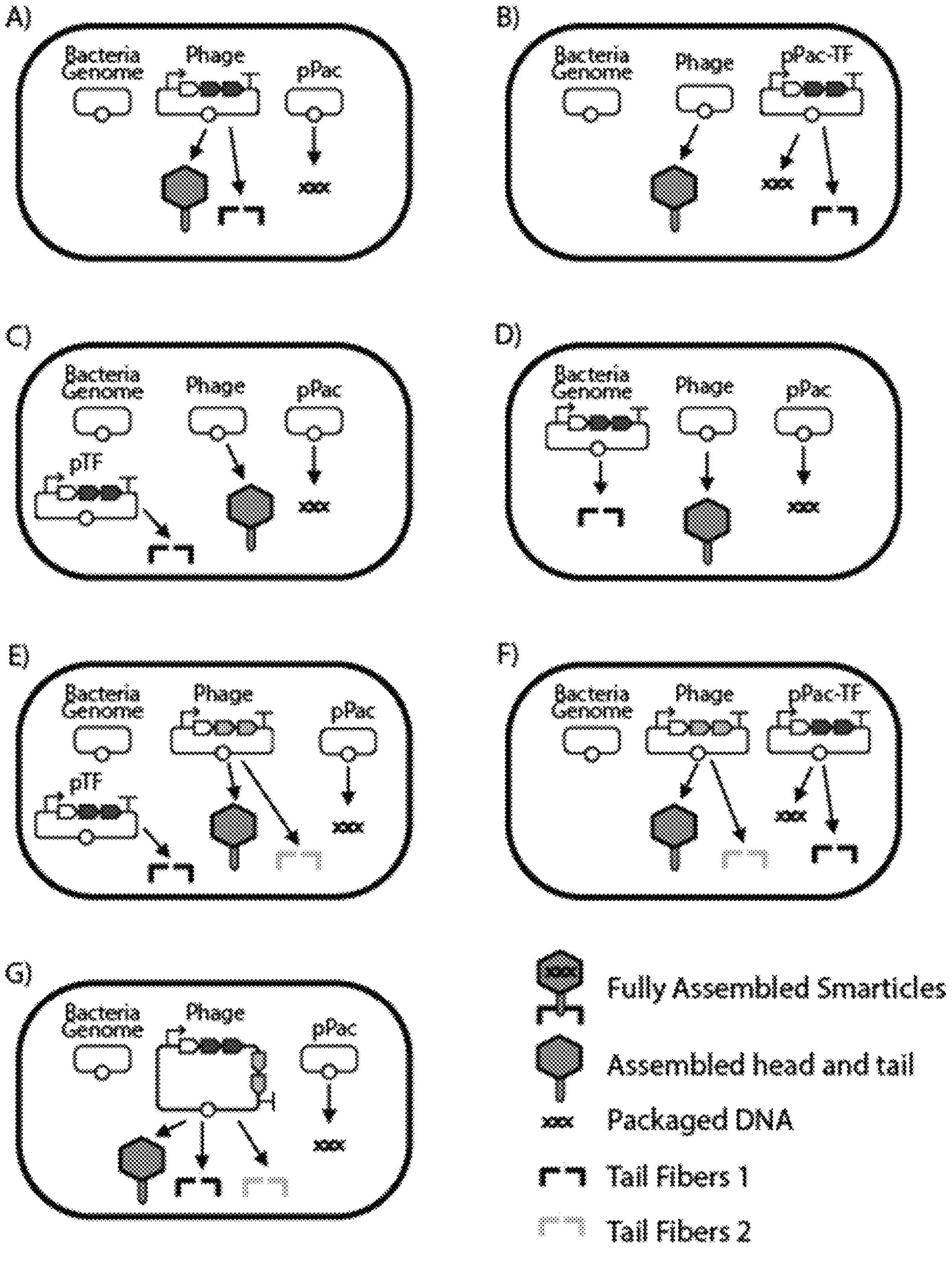
FIG. 9 Displays the various arrangements for expression of tail fiber genes from fermentation strain. A) shows expression of tail fibers and viral chassis from phage genome. B) Shows viral chassis expression from phage genome and tail fibers genes from packaging plasmid. C) Shows viral chassis from phage genome and tail fibers from independent plasmid. D) Shows viral chassis from phage genome and tail fibers from bacterial genome. E) Shows viral chassis and one set of tail fibers from phage genome. A second, unique set of tail fibers is expressed from an independent plasmid. F) Shows viral chassis and tail fibers from phage genome. A second, unique set of tail fibers is expressed from the packaging plasmid. G) Shows viral chassis and two, unique sets of tail fibers from phage genome.

FIG. 9 Displays the various arrangements for expression of tail fiber genes from fermentation strain. A) shows expression of tail fibers and viral chassis from phage genome. B) Shows viral chassis expression from phage genome and tail fibers genes from packaging plasmid. C) Shows viral chassis from phage genome and tail fibers from independent plasmid. D) Shows viral chassis from phage genome and tail fibers from bacterial genome. E) Shows viral chassis and one set of tail fibers from phage genome. A second, unique set of tail fibers is expressed from an independent plasmid. F) Shows viral chassis and tail fibers from phage genome. A second, unique set of tail fibers is expressed from the packaging plasmid. G) Shows viral chassis and two, unique sets of tail fibers from phage genome.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference, in their entirety, for all purposes.

Description of Sequences Listed in Sequence Listing:

| Nucleotide sequences of tail fibers functionally expressed on a P1 chassis. | |
|---|---|
| Asparagus Tail Fiber Nucleotide Sequence | SEQ ID NO: 1 |
| Banana Tail Fiber Nucleotide Sequence | SEQ ID NO: 2 |
| Bittersweet Tail Fiber Nucleotide Sequence | SEQ ID NO: 3 |
| Cobalt Tail Fiber Nucleotide Sequence | SEQ ID NO: 4 |
| Cornflower Tail Fiber Nucleotide Sequence | SEQ ID NO: 5 |
| Denim Tail Fiber Nucleotide Sequence | SEQ ID NO: 6 |
| Eggplant Tail Fiber Nucleotide Sequence | SEQ ID NO: 7 |
| Fern Tail Fiber Nucleotide Sequence | SEQ ID NO: 8 |
| Fuchsia Tail Fiber Nucleotide Sequence | SEQ ID NO: 9 |
| Fuzzy Tail Fiber Nucleotide Sequence | SEQ ID NO: 10 |
| Inchworm Tail Fiber Nucleotide Sequence | SEQ ID NO: 11 |
| Indian Tail Fiber Nucleotide Sequence | SEQ ID NO: 12 |
| Indigo Tail Fiber Nucleotide Sequence | SEQ ID NO: 13 |
| Jazzberry Tail Fiber Nucleotide Sequence | SEQ ID NO: 14 |
| Jazzberry-Shamrock Dual Tail Fiber Nucleotide Seq. | SEQ ID NO: 15 |
| Jungle Tail Fiber Nucleotide Sequence | SEQ ID NO: 16 |
| Mango Tail Fiber Nucleotide Sequence | SEQ ID NO: 17 |
| Maroon Tail Fiber Nucleotide Sequence | SEQ ID NO: 18 |
| Mulberry Tail Fiber Nucleotide Sequence | SEQ ID NO: 19 |
| P1_S'gene Nucleotide Sequence | SEQ ID NO: 20 |
| P1S-P1S'-Shamrock Dual Tail Fiber Nucleotide Seq. | SEQ ID NO: 21 |
| Pine Tail Fiber Nucleotide Sequence | SEQ ID NO: 22 |
| Plum Tail Fiber Nucleotide Sequence | SEQ ID NO: 23 |
| Queen Tail Fiber Nucleotide Sequence | SEQ ID NO: 24 |
| Razzmatazz Tail Fiber Nucleotide Sequence | SEQ ID NO: 25 |
| Salmon Tail Fiber Nucleotide Sequence | SEQ ID NO: 26 |
| Scarlet Tail Fiber Nucleotide Sequence | SEQ ID NO: 27 |
| Shamrock Tail Fiber Nucleotide Sequence | SEQ ID NO: 28 |
| Sunset Tail Fiber Nucleotide Sequence | SEQ ID NO: 29 |
| Tangerine Tail Fiber Nucleotide Sequence | SEQ ID NO: 30 |
| Thistle Tail Fiber Nucleotide Sequence | SEQ ID NO: 31 |

-continued

| Description of Sequences Listed in Sequence Listing: | |
|---|---|
| Tropical_pNS88 Tail Fiber Nucleotide Sequence | SEQ ID NO: 32 |
| Tropical_pNS92 Tail Fiber Nucleotide Sequence | SEQ ID NO: 33 |
| Violet Tail Fiber Nucleotide Sequence | SEQ ID NO: 34 |
| Amino Acid sequences of tail fibers functionally expressed on a P1 chassis. | |
| Asparagus_-_P1Sc-(P1Sv-MuS_hybrid)_translation | SEQ ID NO: 35 |
| Banana_-_P1Sc(aa1-114)-Ec1112(aa218-end)_translation | SEQ ID NO: 36 |
| Bittersweet_-_p15b_Sc-p15b_SvQ_translation | SEQ ID NO: 37 |
| Cobalt_-_p15bSc-Kpn_SCKP_TF4_translation | SEQ ID NO: 38 |
| Cornflower_-_P1Sc(aa1-208)-Kpn478_tail_fiber(aa131-499)_translation | SEQ ID NO: 39 |
| Denim_-_p15bSc-Kpn_SCKP_TF1_translation | SEQ ID NO: 40 |
| Eggplant_-_D6Sc-D6Sv'_translation | SEQ ID NO: 41 |
| Fern_-_P1Sc-(P1Sv-D108S_hybrid)_translation | SEQ ID NO: 42 |
| Fuchsia_-_P1Sc-D6Sv_translation | SEQ ID NO: 43 |
| Fuzzy_-_P1Sc(aa1-208)-Kpn051_TF(aa40-382)_translation | SEQ ID NO: 44 |
| Inchworm_-_P1Sc-R2_pyocin_translation | SEQ ID NO: 45 |
| Indian_-_p15bSc-p15bSvN_translation | SEQ ID NO: 46 |
| Indigo_-_p15bSc-Kpn_SCKP_TF3_translation | SEQ ID NO: 47 |
| Jazzberry_-_P1Sc-KpnSv_translation | SEQ ID NO: 48 |
| Jungle_-_P1Sc-(P1Sv'-MuS'_hybrid)_translation | SEQ ID NO: 49 |
| Mango_-_P1Sc(aa1-214)-Ec1117B(aa214-764)_translation | SEQ ID NO: 50 |
| Maroon_-_p15bSc-p15bSvP_translation | SEQ ID NO: 51 |
| Mulberry_-_D6Sc-D6Sv_translation | SEQ ID NO: 52 |
| P1_S'_-_P1Sc-P1Sv'_translation | SEQ ID NO: 53 |
| Pine_-_P1Sc(nt1-987)-P2H_translation | SEQ ID NO: 54 |
| Plum_-_KpnSc-KpnSv_translation | SEQ ID NO: 55 |
| Queen_-_S-Queen_Sv_translation | SEQ ID NO: 56 |
| Razzmatazz_-_P1Sc-P7Sv_translation | SEQ ID NO: 57 |
| Salmon_-_P1Sc-P7Sv'_translation | SEQ ID NO: 58 |
| Scarlet_-_p15bSc-p15bSvI_translation | SEQ ID NO: 59 |
| Shamrock_-_P1Sc-(P1S-SfMuS'_hybrid)_translation | SEQ ID NO: 60 |
| Sunset_-_p15bSc-p15bSvR_translation | SEQ ID NO: 61 |
| Tangerine_-_p15bSc-p15bSv0_translation | SEQ ID NO: 62 |
| Thistle_-_P1Sc-KpnSv_translation | SEQ ID NO: 63 |
| Tropical_pNS88_-_P1Sc(aa1-214)-Ec1117A(aa91-437)_translation | SEQ ID NO: 64 |
| Tropical_pNS92_-_P1Sc(aa1-214)-Ec1117A(aa96-437)_translation | SEQ ID NO: 65 |
| Violet_-_RCS47Sc-RCS47Sv_translation | SEQ ID NO: 66 |

-continued

| Description of Sequences Listed in Sequence Listing: | |
|---|---|
| **Amino Acid sequences of chaperone proteins** | |
| Asparagus_-_MuU translation | SEQ ID NO: 67 |
| Banana_-_Ec1112_U_chaperone_translation | SEQ ID NO: 68 |
| Bittersweet_-_p15b_T_translation | SEQ ID NO: 69 |
| Cobalt_-_p15b_T_translation | SEQ ID NO: 70 |
| Denim_-_p15b_T_translation | SEQ ID NO: 71 |
| Eggplant_-_P1_U_translation | SEQ ID NO: 72 |
| Fern_-_D108_U_translation | SEQ ID NO: 73 |
| Fuchsia_-_P1_U'_translation | SEQ ID NO: 74 |
| Fuzzy_-_PROKKA_00043_(Kpn478_chaperone)_translation | SEQ ID NO: 75 |
| Inchworm_-_PA0621_translation | SEQ ID NO: 76 |
| Indian_-_p15b_T_translation | SEQ ID NO: 77 |
| Indigo_-_p15b_T_translation | SEQ ID NO: 78 |
| Jazzberry_-_Kpn_U_translation | SEQ ID NO: 79 |
| Jungle_-_Mu_U'_translation | SEQ ID NO: 80 |
| Mango_-_Ec1117B_U_chaperone_translation | SEQ ID NO: 81 |
| Maroon_-_p15_T_translation | SEQ ID NO: 82 |
| Mulberry_-_P1_U'_translation | SEQ ID NO: 83 |
| P1_S'_-_P1_U'_translation | SEQ ID NO: 84 |
| Pine_-_P2_G_translation | SEQ ID NO: 85 |
| Plum_-_Kpn_U_translation | SEQ ID NO: 86 |
| Queen_-_Queen_U_chaperone_translation | SEQ ID NO: 87 |
| Razzmatazz_-_P7_Ua_translation | SEQ ID NO: 88 |
| Razzmatazz_-_P7_Ub_translation | SEQ ID NO: 89 |
| Salmon_-_P7_U_'translation | SEQ ID NO: 90 |
| Scarlet_-_p15b_T_translation | SEQ ID NO: 91 |
| Shamrock_-_SfMuU'_translation | SEQ ID NO: 92 |
| Sunset_-_p15b_T_translation | SEQ ID NO: 93 |
| Tangerine_-_p15_T_translation | SEQ ID NO: 94 |
| Thistle_-_KpnU_translation | SEQ ID NO: 95 |
| Violet_-_RCS47_U_translation | SEQ ID NO: 96 |
| **Other Sequences** | |
| Bald_Chassis_tail_fiber_region_P1_s-u::aadA | SEQ ID NO: 97 |
| Rio_Tail_Fiber_s_hybrid_nucleotide_sequence | SEQ ID NO: 98 |
| Rio_Chaperone_u_nucleotide_sequence | SEQ ID NO: 99 |
| Limon_Tail_Fiber_s_hybrid_nucleotide_sequence | SEQ ID NO: 100 |
| Limon_Chaperone_u_nucleotide_sequence | SEQ ID NO: 101 |
| Orchid_Tail_Fiber_s_hybrid_nucleotide_sequence | SEQ ID NO: 102 |

-continued

| Description of Sequences Listed in Sequence Listing: | |
|---|---|
| Orchid_Chaperone_u_nucleotide_sequence | SEQ ID NO: 103 |
| Gold_Tail_Fiber_s_hybrid_nucleotide_sequence | SEQ ID NO: 104 |
| Gold_Chaperone_u_nucleotide_sequence | SEQ ID NO: 105 |
| Bluetiful_Tail_Fiber_s_hybrid_nucleotide_sequence | SEQ ID NO: 106 |
| Bluetiful_Chaperone_u_nucleotide_sequence | SEQ ID NO: 107 |
| Rio_Tail_Fiber_S_hybrid_amino_acid_sequence | SEQ ID NO: 108 |
| Limon_Tail_Fiber_S_hybrid_amino_acid_sequence | SEQ ID NO: 109 |
| Orchid_Tail_Fiber_S_hybrid_amino_acid_sequence | SEQ ID NO: 110 |
| Gold_Tail_Fiber_S_hybrid_amino_acid_sequence | SEQ ID NO: 111 |
| Bluetiful_Tail_Fiber_S_hybrid_amino_acid_sequence | SEQ ID NO: 112 |
| Rio_Chaperone_U_amino_acid_sequence | SEQ ID NO: 113 |
| Limon_Chaperone_U_amino_acid_sequence | SEQ ID NO: 114 |
| Orchid_Chaperone_U_amino_acid_sequence | SEQ ID NO: 115 |
| Gold_Chaperone_U_amino_acid_sequence | SEQ ID NO: 116 |
| Bluetiful_Chaperone_U_amino_acid_sequence | SEQ ID NO: 117 |

The invention claimed is:

1. A method for producing bacteriophage particles or non-replicative transduction particles (NRTPs) with non-native tail fibers comprising:

a) providing a bacteria cell containing a bacteriophage tail fiber replacement platform comprising:

a bacteriophage lysogen from the family Myoviridae (Myoviridae lysogen) that contains a genetic disruption that prevents the expression of one or more genes that are critical for the production of tail fibers native to the Myoviridae lysogen, comprising the nucleic acid sequence of SEQ ID NO: 97; and a complementary nucleic acid molecule comprising one or more genes selected from a gene that encodes a tail fiber structural protein responsible for binding a bacteria cell receptor, a gene that encodes a chaperone protein needed for folding of one or more regions of a tail fiber structural protein, a gene that encodes a protein required for attaching the tail fiber structural protein to a tail, or any combination of these genes, wherein the complementary nucleic acid complements the genetic disruption of the Myoviridae lysogen whereby functional tail fibers are produced; wherein the complementary nucleic acid molecule comprises a gene that encodes a tail fiber structural protein with one or more regions that are not derived from the one or more genes that are critical for the production of tail fibers native to the Myoviridae lysogen; and b) providing conditions to the bacterial cell that induces a lytic phase of the Myoviridae lysogen to produce bacteriophage particles with non-native tail fibers.

2. The method of claim 1, wherein the one or more regions that are not derived from the one or more genes native to the Myoviridae lysogen comprises a variable region of the tail fiber structural protein (tail fiber variable region) obtained from bacteriophages within the order Caudovirales.

3. The method of claim 2, wherein the tail fiber variable region is obtained from bacteriophages within the family Myoviridae.

4. The method of claim 3, wherein the tail fiber variable region is obtained from bacteriophages within a genus selected from: Bcep781likevirus, Bcepmulikevirus, FelixO1likevirus, Hapunalikevirus, I3likevirus, Mulikevirus, Punalikevirus, Pbunalikevirus, PhiCD119likevirus, Phihlikevirus, Phikzlikevirus, Viunalikevirus, Eucampyvirinae, Cp220likevirus, Cp8unalikevirus, Peduovirinae, Hpunalikevirus, P2likevirus, Spounavirinae, Spounalikevirus, Twortlikevirus, Tevenvirinae, Schizot4likevirus, or T4likevirus.

5. The method of claim 4, wherein the genus is Punalikevirus.

6. The method of claim 1, wherein the complementary nucleic acid molecule further comprises a gene that encodes a chaperone protein.

7. The method of claim 6, wherein the gene that encodes the chaperone protein is obtained from bacteriophages within the order Caudovirales.

8. The method of claim 7, wherein the gene that encodes the chaperone protein is obtained from bacteriophages within the family Myoviridae.

9. The method of claim 8, wherein the gene that encodes the chaperone protein is obtained from bacteriophages from a genus selected from: Bcep781likevirus, Bcepmulikevirus, FelixO1likevirus, Hapunalikevirus, I3likevirus, Mulikevirus, Punalikevirus, Pbunalikevirus, PhiCD119likevirus, Phihlikevirus, Phikzlikevirus, Viunalikevirus, Eucampyvirinae, Cp220likevirus, Cp8unalikevirus, Peduovirinae, Hpunalikevirus, P2likevirus, Spounavirinae, Spounalikevirus, Twortlikevirus, Tevenvirinae, Schizot4likevirus, or T4likevirus.

10. The method of claim 9, wherein the genus is Punalikevirus.

11. The method of claim 6, wherein the chaperone protein is obtained from bacterial genomes encoding non-replicative virus derived structures or from nucleic acid delivery particles.

12. The method of claim 6, wherein the gene that encodes the chaperone protein comprises a nucleotide sequence encoding an amino acid sequence selected from the group consisting of SEQ ID Nos: 67-96 and 113-117.

13. The method of claim 1, wherein the one or more regions that are not derived from the one or more genes native to the Myoviridae lysogen comprises a variable region of the tail fiber structural protein (tail fiber variable region) obtained from bacterial genomes encoding phage tail-like particles or structures or from nucleic acid delivery particles.

14. The method of claim 1, wherein the gene that encodes the tail fiber structural protein comprises a nucleotide sequence encoding of an amino acid sequence selected from the group consisting of SEQ ID Nos: 35-66, and 108-112.

15. The method of claim 1, wherein the gene that encodes the tail fiber structural protein comprises a nucleotide sequence selected from the group consisting of SEQ ID Nos: 1-34, 98, 100, 102, 104 and 106.

16. A method of generating an engineered bacteriophage or a non-replicative transduction particle (NRTP) that displays a bacteria host cell specificity that differs from the bacteria host cell specificity displayed by a native bacteriophage comprising:

a) fusing a first nucleotide sequence from one tail fiber structural protein encoding gene with a second nucleotide sequence from a second tail fiber structural protein encoding gene from a different source to generate a chimeric tail fiber structural protein encoding gene;

b) expressing the chimeric tail fiber structural protein gene in a bacteria cell that contains a bacteriophage tail fiber replacement platform comprising:

a bacteriophage lysogen from the family Myoviridae (Myoviridae lysogen) that contains a genetic disruption that prevents the expression of one or more genes that are critical for the production of tail fibers native to the Myoviridae lysogen, comprising the nucleic acid sequence of SEQ ID NO: 97; and a complementary nucleic acid molecule comprising one or more genes selected from a gene that encodes a tail fiber structural protein responsible for binding a bacteria cell receptor, a gene that encodes a chaperone protein needed for folding of one or more regions of a tail fiber structural protein, a gene that encodes a protein required for attaching the tail fiber structural protein to a tail, or any combination of these genes, wherein the complementary nucleic acid complements the genetic disruption of the Myoviridae lysogen whereby functional tail fibers are produced; wherein the complementary nucleic acid molecule comprises a gene that encodes a tail fiber structural protein with one or more regions that are not derived from the one or more genes that are critical for the production of tail fibers native to the Myoviridae lysogen; and c) providing conditions to the bacteria cell that induces a lytic phase of the Myoviridae lysogen to generate the engineered bacteriophage or NRTP.

17. The method of claim 16 wherein the first nucleotide sequence comprises the $s_c$ region of tail fiber gene s from P1 bacteriophage.

18. The method of claim 17 wherein the first nucleotide sequence comprises a sequence with at least 90% sequence identity with the nucleotide sequence that encodes amino acid sequence 1-250 of SEQ ID NO: 53.

19. The method of claim 18 wherein the first nucleotide sequence comprises a sequence with at least 90% sequence identity with the nucleotide sequence that encodes amino acid sequence 1-500 of SEQ ID NO: 53.

20. The method of claim 16 wherein the first nucleotide sequence comprises the $s_c$ region of tail fiber gene s from plasmid p15B.

* * * * *

SEQUENCE LISTING

```
Sequence total quantity: 117
SEQ ID NO: 1            moltype = DNA  length = 3949
FEATURE                 Location/Qualifiers
misc_feature            1..3949
                        note = Asparagus Tail Fiber
source                  1..3949
                        mol_type = other DNA
                        organism = synthetic construct
SEQUENCE: 1
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cgggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
aataccttgg tttaagagaa ctcggtacca gcggtgaaaa gatccccctg ttgagcacgg  1860
ctaacacatg gagtgcacgc cagactttca acggcgggat caccggggcg ctgacaggga  1920
```

-continued

```
acgccgatac cgcaacgaaa ttgaaaacag ccagaaacat taatggcgtc aggttcgatg  1980
gttctggtga cattaatatc aatactctgg tatcgcgcgg tcgcgtaacg gccctggagg  2040
cgaatgcaca gggaacatcc gggattcagc tgtatgaggc atacaacaat ggctaccctt  2100
cccccctatgg caatgtgctt caccttaaag gtgccaccgc tgctggcgaa ggtgagttat  2160
tcattggctg gagtggcacg agcggtgccc atgcgcccgt acatatccgt tcgcggcggg  2220
atactgattc tgccaactgg tctgaatggg cgcaggtcta tacgtcaaaa gattcaattc  2280
ccggcgtcaa tgccaaaggg gatcaggata cctctggtaa tgcggctaca gcgaccaagt  2340
tgcagacagc atgtactatc aacggcgtct cgtttgacgg ttctaaaaat attgagctaa  2400
cggcggaaga tttaaatcta caggaaacgg taaacaaggc tgataacgcg gttcaaaaga  2460
caggcgatac cttgtccggt ggacttactt ttgaaaacga ctcaatcctt gcctggattc  2520
ggaatactga ctgggcgaag attggtttta aaaatgatgc cgacagcgat actgattcat  2580
acatgtggtt tgaaacaggc gacaacggca atgaatattt caaatggaga agcaaacaaa  2640
gtaccacaac aaaagacctg atgaatctta aatgggatgc tttgtctgtt cttgtcaatg  2700
ccattgtaaa tggcgaagtc atatcaaaat cagcaaacgg cctccgtatt gcttatggta  2760
attacggatt ctttattcgt aatgatggtt caaatacata cttcatgttg acaaactccg  2820
gtgacaacat ggggacttat aacggattaa ggccattatg gattaataac gctactggcg  2880
ctgtttcgat ggggcgtggt cttaatgttt caggggatac actttcagac cgttttgcta  2940
ttaacagcag taatggtatg tggattcaga tgcgcgataa caacgctatc tttgggaaaa  3000
atatagttaa cactgatagc gctcaggcgt tgcttcgcca gaatcacgcc gaccgcaaat  3060
ttatgattgg cggtctggga aataagcaat ttggcatcta catgattaat aactcaagga  3120
cagccaatgg caccgatggt caggcgtaca tggataataa cggaaactgg ttatgcggtg  3180
ctcaggtcat tccgggaaat tacgccaact ttgactcccg ctacgtgcgt gacgttcggc  3240
tgggaactca gtcactgact ggcggcttgt ctcgtgatta caaggcgcca tccggtcatg  3300
ttattacagg ttttcatacc aatggcgact gggaaatgca gggaggggat gacaaggttt  3360
atatccgtcc ggttcagaag aatatcaacg gtacctggta taatgtagcg agcgcctgat  3420
tatgatgcat ctgaaaaaca ttaagtcaga aaatccaaaa actaaagagc aatatcagct  3480
aacaaagaat tttgatgtta tctggttatg gtccgaagac gggaaaaact ggtatgaaga  3540
agtaaataac tttcaggacg acaccataaa gattgtatac gacgaaaata atattattgt  3600
tgccataacc aaagatgcct caacgcttaa tcccgaaggc tttagcgtcg ttgagattcc  3660
agatataaca gccaaccgcc gcgctgatga ttcaggaaag tggatgttta aggatggagc  3720
tgtagttaaa cggatttata cggcagacga acagcaacaa caagccgaat cacaaaaggc  3780
cgcattgctt tccgaagctg aatcagtcat ccagccgctg gaacgcgctg tcaggctgaa  3840
tatggcgacg gatgaggaac gcgcacgact ggagtcatgg gaacgctaca gtgttctggt  3900
cagccgtgtg gatacggcaa atcccgaatg gccacaaaag cctgaataa              3949
```

```
SEQ ID NO: 2            moltype = DNA  length = 3161
FEATURE                 Location/Qualifiers
misc_feature            1..3161
                        note = Banana Tail Fiber
source                  1..3161
                        mol_type = other DNA
                        organism = synthetic construct
SEQUENCE: 2
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tgcggtgggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaac cacagcaaga aaaggtatcg tccagctcag tagtgcaacc gacagtactt  1140
cggaggcgct ggcggcaacg ccgaaagccg ttaaggccgt gaatgacaac gctaacgggc  1200
gcgtaccatc agcgcgtaag gtaaacggca gggcgctggc ttcggatatc agcattacgg  1260
cgcaggatat tttcaacggg caggccgtgg caattggcaa cgccgccgac ctgaacgcct  1320
acaccacgcc gggactgtat taccagccag cgaacgcgca ggctcaaacc ggcaggaatt  1380
atccagaagc caacgccggt tcgctggaag tttataagca tgccggtatc acgcagattt  1440
accggattta taacagctcc cgctcgtaca ttcgcacgct ttacagcggg acgtggtcag  1500
cctgggttaa acagtatgat gcggccaata aaccctcccc ggctgatatt aatgccgtga  1560
ataagggcgg cgatacaatg accggggggc ttaagattcg cgctgctgat gcgttgcgca  1620
tttacgatgc ggcatacggt atgatttttc gccgttcaga aaataatttt taccttatcc  1680
cgaccgcaaa agaccagggc gaagatggcg gtataagtgg actacgcccg ctttatatcg  1740
acctcaccaa cggcagagtg acgctgggta acggagcggt tgttaacggc ggtcttgggc  1800
tgggtgtagt cagcggcctt ggggggaact ctattgccct gggggataat gacaccggct  1860
tcaaacagaa cggagatggt gtgctggatg tttatgctaa cagcaagcag gtaatgcgat  1920
tcctgaacag tggcataacg agttatatgc tcttcaacat gaatgcaggc gcatcagtaa  1980
gcagcactct cacctttaaa aacggtagcg gtatcacttc agagaaaact ggtgccaacc  2040
cccgaaacgg ccgaatttac tggggcggtg atgcgagtcg cggcaacagg atagagtttg  2100
cagatgatgc cggctggaaa gcttacattg agcgtcatcc ctcaaacggt gttcagttag  2160
```

-continued

```
tcgtaaatgg gcgaatcaat ggaagtattg tttattccag tggtgaagta ctggcaggag  2220
gagggagcgc acgctttgct gctgatggaa atatatttgg ctcaaaatgg ggcaatcaat  2280
ggcttgatgc ctatttaaaa aatacctatc agccaaaggg caattatacc ccggcaggtc  2340
aggcttatac aaaagtagag tctgacggac gttttcagcc taaagggagt tataccccccg  2400
cggggcaggc ttacacgaag gcggaaagcg atgcgcggta taacctcaaa aataccgcaa  2460
ccaaatcagc caatgccatg acgcataaag atgcttcaac aggtgttatg gaagtcgtta  2520
tgagtaatat caacgttcca aacaaaacaa atgttaacgt gacatttcct gcggcttttc  2580
caaatgcatg tgtaggggtt gtaattacat ataatggggc agggcatggg tctggcgatg  2640
attcggcaat ttatgttccg tcttattcac gtactggatg cacattatat gctcataacg  2700
ccgatggcaa atttatgcta attgctaaag gatattgaat gaggatttat tttagcccta  2760
gcgaaattgg tttttatcat gaatcagata aacaagctta tttactagcg ggtacttggc  2820
cgaatgattt acttgaaatt tcggagaagt ggttcctgta tctgttggaa ggtcaacaga  2880
aaggtaaggt aatcactgta aatgattacg atcagcctgt tcttgtagac ccgccaaccg  2940
ccactaaaga gcagctcctt gccgaggctg atgctcagaa ggaagcgctc atgaactctg  3000
ccagtgccgt aattgagcca ttgaaagatg ccgttgagtt gggtatgtca acagatgaag  3060
aggaaggttt actgttggca tggcagcaat atagggtgct gttgatgcgg gttgatacat  3120
cgcatgcacc agatatcgag tggcctgtat tgccagcatg a                        3161

SEQ ID NO: 3            moltype = DNA  length = 3308
FEATURE                 Location/Qualifiers
misc_feature            1..3308
                        note = Bittersweet Tail Fiber
source                  1..3308
                        mol_type = other DNA
                        organism = synthetic construct
SEQUENCE: 3
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgtcac cgttgttacg agtgttacct  480
acccctcgcc tgagtcatta gcgttagttg cagacgttca gtaccacgaa ccgtatcttt  540
cagcagctct taaccgtaaa ttccgcggaa ttgtcgatcc aggattttac gccgggttcc  600
tgcctaagcc tggcggcggc atgaatcttc tgattacgtc agtcgacggg gataaaactg  660
cgggagcggc atcggtagat atcggggaat tctaccaggt tacaattcaa catcgtaaag  720
acatttcgtt agcacttaac gctgggaaga aatacgccat tgtcttgaaa ggccgctatt  780
tgttaggtga agatacgtac caggtcaata cagcaagtca catccacgcc gctgaatttg  840
tcgcacgtac atataccgat tcctaccagc ttggggatgg tgagttactt gtgtgcaccg  900
tgaacattcc tgctggagtg tcaacgatca cgcaggagat gatcgatact tcagagcgta  960
ttaatcgcac gatcgggatt gatatttcag acagcgtcac ctcgactcgc tcagatgtcg  1020
cggcttcatc tcttgcagtg aaaaaggcct acgacctggc caagtcgaag tacacagctc  1080
aggacgcgag caccacccaa aagggtctgg tacagttatc atctgcgacg aattcaacat  1140
ccgaggttct tgcagcgaca cctaaagcgg taaaagccgc gtatgatctt gccaatggga  1200
aatacaccgc acaggacgcc acaactacac aaaagggtat tgtgcagttg tcgagtgaca  1260
ccaactcaac gtcggagaca ctggcggcca cgccgaaagc agtcaaagct gcatacgacc  1320
ttgcggctgg taaagcgccc tcatcccaca ctcacccctg gaatcagatt actggtgtac  1380
ccaccgcaag cttaactgca aagggtatca ctcaattgag ttccgcgacc aacagcacca  1440
gtgaagtttt agctgctacc ccaaaggcag ttaaagccgc ttacgacttg gctaatggaa  1500
aatatacagc gcaggacgcg accactgcac aaaaaggaat tgtgcaactt tcgagcgcaa  1560
cgaactccac aagtgaagtt ttggcagcta cgcctaaagc cgtcaaagcc gcgtatgatt  1620
tggcgaatgg taagtatact gcgcaagatg cgacgactac gcagaaaggt attgtccaac  1680
tgtcaagtga caccaacagc acgtcagaga ccttggctgc tacacctaaa gcagtgaaag  1740
ctgcctatga tcttgcggct gggaaagccc cgtcatcaca cacacatcca tggaaccaga  1800
ttacggtcgt acctacggcc tctttaactg cgaagggcat tacacaatta tcatccgcga  1860
ctaacagcac cagtgaggtt ttagctgcaa caccgaaagc agtgaaggca gcctacgatt  1920
tggcgaacgg taaatatacg gctcaagatg cgaccaccgc gcaaaagggc attgtgcaac  1980
tgtcgtctgc aacaaattca acgtcggaag ttctggcagc aactccaaag gcagtgaaag  2040
ccgcctatga cttagcaaac ggtaaacagg ccgcggatgc gacgttaacg gcattggcgg  2100
ctcttgcaac tgcagcggac aagttaccgt atttcacggg cgttgaccgt gctgccctga  2160
cagcgttaac ctctgttggg cgtgccattt taggcaagac ctcgattcaa tctgttttag  2220
attaccttgg tttgggggaa ggctcagcat tgcctgttgg cgtacctgtt ccgtggccct  2280
cagccactcc gccaacgggg tggctgaaat gtaacggagc agcattttct tctgaaaagt  2340
acccaaatct ggcaaaggct taccctacta ataaattgcc ggatttacgc ggtgaattta  2400
ttcgtggctg ggatgacgga cgtggtgtgg atgccgggcg acaattatta tcttcacagg  2460
gggatgcaat aagaaatatt gaggggttcg cagatggcgg gatcggcatg tcttttgatg  2520
caatcagagg ggctttttac gatgcaggaa cacgatcagc gagaatgccg aataacacaa  2580
ctactataga caaaaccgat gaccttggat tcgacgcctc tcgtgtcgtg ccaacagcta  2640
atgaaaaccg tcctcgtaat attgccttta attatatcgt aagggcggca taaattatgg  2700
ataatgcgat attaaatagc gaacttatag ccatacaggc aggaaacatt atcgtttata  2760
actatgatgg tggtaatcgg gaatatattt ctgcatcaac tgaatatctt gctgttggcg  2820
ttggtattcc ggcaaattct tgtttggatg ctccaggctc acataaagca ggttatgcga  2880
ttctccgttc agaggattta agttcatggg agtatgtgcc agatcatcgt ggcgaaactg  2940
tctatagcat tgacacaggg aatcccgaag aaatcacggt gttgggtgac tatccggaaa  3000
atacaaccac tatcgccccg ctaacaccat acgacaaatg ggatggagag aaatgggtgg  3060
ttgatactga ggctcaacat agtgcagctg tagaggcagc agaaacaaaa cgtcagtcat  3120
tgattgatac tgcgatggat tccattagtc tgattcagtt gaaattacgg gctggacgga  3180
```

```
agttgacgca ggcagaaacc acgcagctta actccgtgct agattatata gacgagctga  3240
acgcgatgga tttaaccacg gcaccagatc tcaactggcc tgaaaaacaa ctttctacag  3300
ccagttga                                                           3308

SEQ ID NO: 4           moltype = DNA  length = 3272
FEATURE                Location/Qualifiers
misc_feature           1..3272
                       note = Cobalt Tail Fiber
source                 1..3272
                       mol_type = other DNA
                       organism = synthetic construct
SEQUENCE: 4
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgtcac cgttgttacg agtgttacct  480
acccctcgcc tgagtcatta gcgttagttg cagacgttca gtaccacgaa ccgtatcttt  540
cagcagctct taaccgtaaa ttccgcggaa ttgtcgatcc aggattttac gccgggttcc  600
tgcctaagcc tggcggcggc atgaatcttc tgattacgtc agtcgacggg gataaaactg  660
cgggagcggc atcggtagat atcggggaat tctaccaggt tacaattcaa catcgtaaag  720
acatttcgtt agcacttaac gctgggaaga aatacgccat tgtcttgaaa ggccgctatt  780
tgttaggtga agatacgtac caggtcaata cagcaagtca catccacgcc gctgaatttg  840
tcgcacgtac atataccgat tcctaccagc ttggggatgg tgagttactt gtgtgcaccg  900
tgaacattcc tgctggagtg tcaacgatca cgcaggagat gatcgatact tcagagcgta  960
ttaatcgcac gatcgggatt gatatttcag acagcgtcac ctcgactcgc tcagatgtcg  1020
cggcttcatc tcttgcagtg aaaaaggcct acgacctggc caagtcgaag tacacagctc  1080
aggacgcgag caccacccaa aagggtctgg tacagttatc atctgcgacg aattcaacat  1140
ccgaggttct tgcagcgaca cctaaagcgg taaaagccgc gtatgatctt gccaatggga  1200
aatacaccgc acaggacgcc acaactacac aaaagggtat tgtgcagttg tcgagtgaca  1260
ccaactcaac gtcggagaca ctggcggcca cgccgaaagc agtcaaagct gcatacgacc  1320
ttgcggctgg taaagcgccc tcatcccaca ctcacccctg gaatcagatt actggtgtac  1380
ccaccgcaag cttaactgca aagggtatca ctcaattgag ttccgcgacc aacagcacca  1440
gtgaagtttt agctgctacc ccaaaggcag ttaaagccgc ttacgacttg gctaatggaa  1500
aatatacagc gcaggacgcg accactgcac aaaaaggaat tgtgcaactt tcgagcgcaa  1560
cgaactccac aagtgaagtt ttggcagcta cgcctaaagc cgtcaaagcc gcgtatgatt  1620
tggcgaatgg taagtatact gcgcaagatg cgacgactac gcagaaaggt attgtccaac  1680
tgtcaagtga caccaacagc acgtcagaga ccttggctgc tacacctaaa gcagtgaaag  1740
ctgcctatga tcttgcggct gggaaagccc cgtcatcaca cacacatcca tggaaccaga  1800
ttacggtcgt acctacggcc tctttaactg cgaagggcat tacacaatta tcatccgcga  1860
ctaacagcac cagtgaggtt ttagctgcaa caccgaaagc agtgaaggca gcctacgatt  1920
tggcgaacgg taaatatacg gctcaagatg cgaccaccgc gcaaaagggc attgtgcaac  1980
tgtcgtctgc aacaaattca acgtcggaag ttctggcagc aactccaaag gcagtgaaag  2040
ccgcctatga cttagcaaac ggtaaacagg ccgcggatgc gacgttaacg gcattggcgg  2100
ctcttgcaac tgcagcggac aagttaccgt atttcacggg cgttgaccgt gctgccctga  2160
cagcgttaac ctctgttggg cgtgccattt taggcaagac ctcgattcaa tctgttttag  2220
attaccttgg tttaggggaa ggctctgcac tgcctgttgg tgtgcccgtt ccgtggccct  2280
tagaaacacc accaacgggc tggctaaaat gcaatggtgc agcattttct tctgaaatgt  2340
atcccaaact ggcaaaagcc taccccacca ataaattacc ggatttacgc ggtgaattta  2400
tccgtggctg ggatgatggg cgcgggattg atgcgggacg aaccctgctt tcagggcagg  2460
atggtacaag tttttctcat tacggaggta atttcgacat tgggtctggt cattcaatca  2520
ataactatga ccaaattgtt tctaaccaac caggattttc ccgtttttca tttgcagggc  2580
cttcacgagg tgatggggtt aattatgtaa ccattcgtcc tcgtaacatt gcgtttaatt  2640
atatcgtaag ggcggcatga atggataatg cgatattaaa tagcgaactt atagccatac  2700
aggcaggaaa cattatcgtt tataactatg atggtggtaa tcgggaatat atttctgcat  2760
caactgaata tcttgctgtt ggcgttggta ttccggcaaa ttcttgtttg gatgctccag  2820
gctcacataa agcaggttat gcgattctcc gttcagagga tttaagttca tgggagtatg  2880
tgccagatca tcgtggcgaa actgtctata gcattgacac agggaatccc gaagaaatca  2940
cggtgttggg tgactatccg gaaaatacaa ccactatcgc cccgctaaca ccatacgaca  3000
aatgggatgg agagaaatgg gtggttgata ctgaggctca acatagtgca gctgtagagg  3060
cagcagaaac aaaacgtcag tcattgattg atactgcgat ggattccatt agtctgattc  3120
agttgaaatt acgggctgga cggaagttga cgcaggcaga aaccacgcag cttaactccg  3180
tgctagatta tatagacgag ctgaacgcga tggatttaac cacggcacca gatctcaact  3240
ggcctgaaaa acaactttct acagccagtt ga                                3272

SEQ ID NO: 5           moltype = DNA  length = 2183
FEATURE                Location/Qualifiers
misc_feature           1..2183
                       note = Cornflower Tail Fiber
source                 1..2183
                       mol_type = other DNA
                       organism = synthetic construct
SEQUENCE: 5
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
```

```
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag gcggcgatag  1080
ccgggatggc gaaggcatcg gatcttaacg cactggcaaa actcacagga ggaaacaaac  1140
tcgacggctc gcaggttata accagcgata atgccggttt tattctcggt aagaactcag  1200
atctggctct gctcaaaaaa caggggcaag gcgggacaat tgccgttggc tcgggaacac  1260
cgtttagggt tcagcgttca agagcgacca ctgtatcacc ggcagacacc tttgatgaca  1320
tcctcgttat tgatgccaac aaccgaacga cactacctgg cgcgctgact gccggcggcg  1380
acatcgacaa cacgacgaag gggttgctgt atacccaggc gattgagctg tcatttagca  1440
cgccatacat cgactttcat tttaactaca gcaccgacga cttcaccggg cggattatgg  1500
ccactgccgc cgatcaaatt agtgtacaag gtagtcattg gcgagttgac agggatcttc  1560
gtgttggtgg tatggcagat attgcagggt gggcgcaatg cggagtcgac ctctcggcca  1620
acaggacaga ctttggttcc cctgctattg gttcgttggt ttcaggcgga cgtattcgat  1680
ccagaatgct gggacgcggc ggtaacgttg acccctccgg ggcgtggggc ggtttctatg  1740
ttgaagagca cgtaggaacc gaacacagga ttatcatgta tatggacggc ttcgggagaa  1800
ccgacgcatg gtcattccgc gcaggtgggg taatttccac gcccaagggc gacgtcatga  1860
cgaccggttc cgacgtgcga ctgaaaactg acttcacaca agcgcctgga aacgcctcag  1920
agcgcattga acgcttaggg gtgtgtgagt accggatgaa gggggaaacg cgccggaggc  1980
gtggttttat cgctcagcag gctgaaaaag ctgatgatct gtatactttc ctcggcatcg  2040
agcaggagat tgatggcgaa aaatttaagg tgatgaatgt ggattacacg gcaatcattg  2100
ctgacctggt tacggtggcg cagggtttac tggttaaaaa tcaggaactg gaaaggcgta  2160
tatctgtact ggaggggatc tga                                          2183

SEQ ID NO: 6           moltype = DNA  length = 3272
FEATURE                Location/Qualifiers
misc_feature           1..3272
                       note = Denim Tail Fiber
source                 1..3272
                       mol_type = other DNA
                       organism = synthetic construct
SEQUENCE: 6
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgtcac cgttgttacg agtgttacct  480
acccctcgcc tgagtcatta gcgttagttg cagacgttca gtaccacgaa ccgtatcttt  540
cagcagctct taaccgtaaa ttccgcggaa ttgtcgatcc aggattttac gccgggttcc  600
tgcctaagcc tggcggcggc atgaatcttc tgattacgtc agtcgacggg gataaaactg  660
cgggagcggc atcggtagat atcggggaat tctaccaggt tacaattcaa catcgtaaag  720
acatttcgtt agcacttaac gctgggaaga aatacgccat tgtcttgaaa ggccgctatt  780
tgttaggtga agatacgtac caggtcaata cagcaagtca catccacgcc gctgaatttg  840
tcgcacgtac atataccgat tcctaccagc ttggggatgg tgagttactt gtgtgcaccg  900
tgaacattcc tgctggagtg tcaacgatca cgcaggagat gatcgatact tcagagcgta  960
ttaatcgcac gatcgggatt gatatttcag acagcgtcac ctcgactcgc tcagatgtcg  1020
cggcttcatc tcttgcagtg aaaaaggcct acgacctggc caagtcgaag tacacagctc  1080
aggacgcgag caccacccaa aagggtctgg tacagttatc atctgcgacg aattcaacat  1140
ccgaggttct tgcagcgaca cctaaagcgg taaaagccgc gtatgatctt gccaatggga  1200
aatacaccgc acaggacgcc acaactacac aaaagggtat tgtgcagttg tcgagtgaca  1260
ccaactcaac gtcggagaca ctggcggcca cgccgaaagc agtcaaagct gcatacgacc  1320
ttgcggctgg taaagcgccc tcatcccaca ctcacccctg gaatcagatt actggtgtac  1380
ccaccgcaag cttaactgca aagggtatca ctcaattgag ttccgcgacc aacagcacca  1440
gtgaagtttt agctgctacc ccaaaggcag ttaaagccgc ttacgacttg gctaatggaa  1500
aatatacagc gcaggacgcg accactgcac aaaaaggaat tgtgcaactt tcgagcgcaa  1560
cgaactccac aagtgaagtt ttggcagcta cgcctaaagc cgtcaaagcc gcgtatgatt  1620
tggcgaatgg taagtatact gcgcaagatg cgacgactac gcagaaaggt attgtccaac  1680
tgtcaagtga caccaacagc acgtcagaga ccttggctgc tacacctaaa gcagtgaaag  1740
ctgcctatga tcttgcggct gggaaagccc cgtcatcaca cacacatcca tggaaccaga  1800
ttacggtcgt acctacggcc tctttaactg cgaagggcat tacacaatta tcatccgcga  1860
ctaacagcac cagtgaggtt ttagctgcaa caccgaaagc agtgaaggca gcctacgatt  1920
tggcgaacgg taaatatacg gctcaagatg cgaccaccgc gcaaaagggc attgtgcaac  1980
tgtcgtctgc aacaaattca acgtcggaag ttctggcagc aactccaaag gcagtgaaag  2040
ccgcctatga cttagcaaac ggtaaacagg ccgcggatgc gacgttaacg gcattggcgg  2100
ctcttgcaac tgcagcggac aagttaccgt atttcacggg cgttgaccgt gctgccctga  2160
```

```
cagcgttaac ctctgttggg cgtgccattt taggcaagac ctcgattcaa tctgttttag  2220
attaccttgg tttaggggaa ggctcggcgc tgcccgttgg tgtacctgtt ccatggccct  2280
ccgccacacc accaacgggg tggctgaaat gtaacggagc agcattttct tctgaaaagt  2340
acccaaatct ggcaaaggtt taccccacta ataaattgcc ggatctacgg ggcgaattta  2400
ttcgaggttg ggatgatgga cgaggtgtgg acaatgggcg agcattatta agcagccaag  2460
aggctacaaa cttttctcag cgtgccggaa atataggcga tggtgcaggg cacgcaatta  2520
attttcatga tggcatcgtc ggaaatcagc caggattttc acgatttaat ttcaccagta  2580
actctgtagg tgatggtata aattttgttg ctgtcaggcc gcgaaatatc gcatttaatt  2640
acatcgtaag ggcggcataa atggataatg cgatattaaa tagcgaactt atagccatac  2700
aggcaggaaa cattatcgtt tataactatg atggtggtaa tcgggaatat atttctgcat  2760
caactgaata tcttgctgtt ggcgttggta ttccggcaaa ttcttgtttg gatgctccag  2820
gctcacataa agcaggttat gcgattctcc gttcagagga tttaagttca tgggagtatg  2880
tgccagatca tcgtggcgaa actgtctata gcattgacac agggaatccc gaagaaatca  2940
cggtgttggg tgactatccg gaaaatacaa ccactatcgc cccgctaaca ccatacgaca  3000
aatgggatgg agagaaatgg gtggttgata ctgaggctca acatagtgca gctgtagagg  3060
cagcagaaac aaaacgtcag tcattgattg atactgcgat ggattccatt agtctgattc  3120
agttgaaatt acgggctgga cggaagttga cgcaggcaga aaccacgcag cttaactccg  3180
tgctagatta tatagacgag ctgaacgcga tggatttaac cacggcacca gatctcaact  3240
ggcctgaaaa acaactttct acagccagtt ga                              3272
```

```
SEQ ID NO: 7           moltype = DNA  length = 3797
FEATURE                Location/Qualifiers
misc_feature           1..3797
                       note = Eggplant Tail Fiber
source                 1..3797
                       mol_type = other DNA
                       organism = synthetic construct
SEQUENCE: 7
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatgg gggctgataa aacgaacaac ataatgacac  480
tatcctctgg tgtctcacag cctttgcttg ctgatgttca atatttcgaa ctctatagta  540
gttcggctct taacagaaaa cttaaaaata ttgttttgcc tggcttttac tgtggatttg  600
aaccagttcc cggcacaggg ttgagtgttc gtataacttc tgaaaactca gaaggtaaag  660
gggctgcttc agtagatgta aataatgttc agatatccgt tcagcaaata gaagatgtga  720
ctgtctcggt aaaggctggg gctaccaaca ttattgtgct ggaagccaat tttgaacatg  780
gtgtaaaaac gacacaggta gatagcgcat cttctgtcag tgctgcaaga atttacgcgc  840
gtacggacaa tactattggg cagaatcaaa ttgaattatg tcgagttatc gtgcctaacg  900
gcgcaacggc tgtgactaaa gaaatgattg tgcttaaata ccgggttaac cgtgctgttg  960
gtgtcgaatt ctctaatgaa ataagcagta cagaagaaag aaaagcggct acacctctgg  1020
ctgtcaaaac tctccatgat ttggttgata caaaagctcc gctcgatagt ccgcatctgt  1080
caggtacgcc gacttcgccg acacctgaac ccggtacaaa caacacacag atcgcaaatg  1140
cggcctttgt ctatgctgct ataaatgcgc ttatcaatgg tgctccggga acgatggaca  1200
cgctgaaaga aatagcggct gcgatcaata acgacccgaa tttcagcaca actatcaaca  1260
atgctctggc tcttaaagct cctttagcaa gtcctgcatt aacgggaata cctactgcgc  1320
ctaccgctgc acagggtacg aataacacgc agattgctac gaccgcttat gtaagagctg  1380
ccatatccgc attggttggt tcatcaccag aagctcttga taccctgaat gagcttgccg  1440
cagcacttgg taatgacccg aactttgcga caacaatgac aaatgcgctg gcaggcaaac  1500
agcctctgga tgcaacttta accgcgctcg ctggccttgc gactggtgca aacaaactgc  1560
cttatttcac cggtaaggat acggtagcgc agactgattt aacgtcagtc ggtcgcgata  1620
ttctggctaa aacaagcaca ctggccgtta tccaatacct tggtttaaga gaactcggta  1680
ccagcggtga aaagatcccc ctgttgagca cggctaacac gtggagtgca cgccagactt  1740
tcaacggcgg gatcaccggg gcgctgacag ggaacgccga taccgcgacg aaattaaaaa  1800
cagccataaa cattaatggc gtcaggttcg atggttctac gaacatttcg ataccaacaa  1860
ttacgtctag aggacgcgtt actgcgctta ccggtacaac gcaaggtgct gctactggat  1920
tgcagatgta tgaggcatac aacaatggct acccttcccc ctatggcaat gtgcttcacc  1980
ttaaaggtgc caccgctgct ggcgaaggtg agttattcat tggctggagt ggcacaaatg  2040
gcgctcatgc acctgctttc attcgatcca aaagagatag cactgctgcg gcatggtccg  2100
agtgggcaca gatctatacg tcaaaagatt cagttcccgg cgtcaatgcc aaagggaatc  2160
aggacacctc tggtaatgcg gctacagcga ccaaattgca gatagcatgt actatcaacg  2220
gcgtctcgtt tgacggttct aaaaatattg agctaacggc ggaagattta aatctacagg  2280
aaacggtaaa caaggctgat aacgcggttc aaaagacagg cgataccttg tccggtggac  2340
ttacttttga aaacgactca atccttgcct ggattcggaa tactgactgg gcgaagattg  2400
gttttaaaaa tgatgccgac agcgatactg attcatacat gtggtttgag acaggcgaca  2460
acggcaatga atatttcaaa tggagaagca aacaaagtac cacaacaaaa gacctgatga  2520
atcttaaatg ggatgctttg tatgttcttg tcaatgccat tgtaaatggc gaagtcatat  2580
caaaatcagc aaacggccta cgtattgctt atggtaatta cggattcttt attcgtaatg  2640
atggttcaaa tacatacttc atgttgacaa actccggtga caacatgggg acttataacg  2700
gattaaggcc attatggatt aataacgcta ctggcgctgt ttcgatggga cgtggtctta  2760
atgtttcagg ggagacactt tcagaccgtt ttgctattaa cagcagtaat ggtatgtgga  2820
ttcagatgcg cgataacaac gctatctttg ggaaaaatat agttaacact gatagcgctc  2880
aggcgttact tcgccagaat cacgccgacc gaaagttcat gataggtgga ctggggaaca  2940
agcaatttgg catctacatg attaataact caaggacagc caatggcacc gatggtcagg  3000
cgtacatgga taataacggt aactggcttt gtggtgcgca agttattccc ggcaattatg  3060
```

```
gcaattttga ctcacgctat gtgagagatg tccgacttgg cacacgtgtt gttcaattga  3120
tggcgcgtgg tggtcgttat gaaaaagccg gacacgcaat taccggatta agaatcattg  3180
gtgaagtaga tggcgatgat gaagccatct tcaggccaat acaaaaaatac atcaatggca  3240
catggtataa cgtcgcacag gtgtaaatta tgcagcactt aaaaaatatc aggtcaggaa  3300
acccaaagac aaaagagcaa taccaattaa caaagaattt tgacgtaatc tggttgtggt  3360
ctgaagacgg aaaaaactgg tatgaggaag tgaaaaactt tcaaccagac accataaaga  3420
ttgtttacga tgaaaataat attattgtcg ccatcaccaa agatgcctcc acgcttaacc  3480
ctgaaggttt tagcgtcgtt gaggttcccg acataacagc caaccgccgc gctgatgatt  3540
caggaaagtg gatgtttaag gatggagctg tagttaaacg gatttatacg gcagacgaac  3600
agcaacaaca agccgaatca caaaaggccg cattgctttc cgaagctgaa tcagtcatcc  3660
agccgctgga acgcgctgtc aggctgaata tggcaacaga cgaggaacgc acacgactgg  3720
aagcatggga acgctacagt gttctggtca gccgtgtgga tacggcaaat cctgaatggc  3780
cacaaaagcc tgaataa                                                 3797

SEQ ID NO: 8            moltype = DNA  length = 3938
FEATURE                 Location/Qualifiers
misc_feature            1..3938
                        note = Fern Tail Fiber
source                  1..3938
                        mol_type = other DNA
                        organism = synthetic construct
SEQUENCE: 8
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cgggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
aataccttgg tttaagagaa ctcggtacca gcggtgaaaa gatccccctg ttgagcacgg  1860
ctaacacatg gagtgcacgc cagactttca acggcgggat caccggggcg ctgacaggga  1920
acgccgatac cgcaacgaaa ttgaaaacag ccagaaacat taatggcgtc aggttcgatg  1980
gttctggtga cattaatatc aatactctgg tatcgcgcgg tcgcgtaacg gccctggagg  2040
cgaatgcaca gggaacatcc gggattcagc tgtatgaggc atacaacaat ggctaccctt  2100
ccccctatgg caatgtgctt caccttaaag gtgccaccgc tgctggcgaa ggtgagttat  2160
tcattggctg gagtggcacg agcggtgccc atgcgcccgt acatatccgt tcgcggcggg  2220
atactgattc tgccaactgg tctgaatggg cgcaggtcta tacgtcaaaa gattcaattc  2280
ccggcgtcaa tgccaaaggg gatcaggata cctctggtaa tgcggctaca gcgaccaagt  2340
tgcagacagc atgtactatc aacggcgtct cgtttgacgg ttctaaaaat attgagctaa  2400
cggcggaaga tttaaatcta caggaaacgg taaacaaggc tggtaacgct gttcaaaaga  2460
caggcgatac cttgtccggt gggcttactt ttgaaaatga ctcaatcctt gcctggattc  2520
gaaatactga ctgggcgaag attggattta aaaatgatgc cgatggtgac actgattcat  2580
acatgtggtt tgaaacaggc gacaacggca atgaatattt caaatggaga agcaaacgag  2640
gcaccacaac aaaagacctg atgaatctta aatgggatgc tttgtatgtt cttgtcaatg  2700
ccattgtaaa cggcgaagtc atatcaaaat cagcaaacgg cctacgtatt gcttatggta  2760
attacggatt ctttattcgt aatgatggtt caaatacata cttcatgttg acaaactccg  2820
gtgacaacat ggggacttat aacggattaa ggccattatg gattaataac gctactggcg  2880
ctgtttcgat ggggcgtggc cttaatgttt caggggagac gcttcagacc gtttgctata  2940
acagcagtaa tggtatgtgg attcagatgc gcgataacaa cgctatcttt gggaaaaata  3000
tagttaacac tgatagcgct caggcgttgc ttcgccagaa tcacgctgac cgcaagttca  3060
tgataggtgg actggggaac aagcaatttg gcatctacat gattaataac tcaaggacag  3120
ccaatggcac cgatggtcag gcgtacatgg acaataacgg taactggctt tgcggtgcgc  3180
aaattattcc cggaaattat ggcaattttg actcacgcta tgtgagcgat gtccgacttg  3240
gcacacgtgt tgttcagact atgcaaaaag gcgtgatgta tgagaaatca ggtcatgcaa  3300
ttacggggct tggcattgtc ggtgaagttg atggcgatga tccggcagta ttcagaccaa  3360
tacaaaaata catcaatggc acatggtata acgtcgcaca ggtgtaattt atgcagcatt  3420
```

```
taaaaaatat taagtctgga aatccaaaaa caaaagaaca atatcagcta acaaagaatt  3480
ttgatgttat ctggttatgg tccgaagacg gaaaaaactg gtatgaggaa gtgaaaaact  3540
ttcagccaga cacaataaag attgtttacg atgcaaataa tattattgtc gccatcacca  3600
aagatgcctc cacgcttaac cctgaaggtt atagcgtcgt tgaggttcct gatattacag  3660
ctaatcgtcg tgctgatgat tccggtaagt ggatgtttaa ggacggagct gtggttaaac  3720
ggatttatac ggcagacgag caacaacaac aggccgaatc acaaaaggcc gcgttacttt  3780
ccgaagcaga aaacgttatt cagccactgg aacgcgctgt caggctgaat atggcgacgg  3840
atgaggaacg cgcacgactg gagtcatggg aacgctatag tgttctggtc agccgtgtgg  3900
atacggcaaa tcctgaatgg ccacaaaagc ctgaataa                        3938

SEQ ID NO: 9            moltype = DNA  length = 3901
FEATURE                 Location/Qualifiers
misc_feature            1..3901
                        note = Fuchsia Tail Fiber
source                  1..3901
                        mol_type = other DNA
                        organism = synthetic construct
SEQUENCE: 9
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cgggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
atggtttaag agaactcggt accagtggtg aaaagatccc cctgttgagt acggctaaca  1860
catggagtgc gcgccagact ttcaatggcg ggatcaccgg ggcgctgata gggaacgccg  1920
acaccgcgac gaaattgaaa acagccataa acattaatgg cgtcaggttc gatggttcgg  1980
ctgacattaa tatcaatact ctggtatcgc gtggtcgcgt aacggctctg gggcgaatg   2040
cacaggggac atccgggatt cagctgtatg aggcatacaa caatggctat ccttccccct  2100
atggcaatgt gcttcacctt aaaggtgcca ccgctgctgg cgaaggtgaa ttattcattg  2160
gctggagtgt ctcgagcggt gaccatgcgc ccgtacatat ccgttcgcgg cgtgatattg  2220
attctgccaa ctggtctgaa tggcacaggg tctatacgtc aaaagattca gttcccggcg  2280
ttaatgccaa agggaatcag gatacctctg gtaatgcggc tacagcgacc aaattgcaga  2340
cggcgtgtac tatcaacggt gtctcgtttg atggttctaa aaacattgag ctaacggcgg  2400
aagatttaaa tcttgagcaa accgtagaat tagccgcagg agcattgcag aaaaaccaga  2460
acggtgcaga tattccgaat aaagataaat tcatacaaaa cacaggggcc tgtcgtgcat  2520
ttagcggtca gactgatatc gatggttcac aaggtgaatg gtcgacagtt gcatttatct  2580
cgtggctgga gaataacgga gctttccgac atccatactg gatgtgtaaa gggtcatggt  2640
cctatgccag aaacagggtt attacggata ccggttgtgg aaatatctgc cttgccggag  2700
ccgtgattga ggttatggga acccgcggcg caatgaccat acgcgttacc acgccgagca  2760
cgtccagcgg tggcggaatc actaacgctc aattcactta tattaatcat ggtgatgctt  2820
acgctcctgg ctggcgacga gactacaaca cgaaaaacca gcagcctgca tttgctttag  2880
ggcaaacagg acgcagggtc gcaaatgata aagctgttgg ctggaactgg aatagcggcg  2940
tttatgatgc agatatcagt ggcgcatcga cattaatcct ccactttaat atgaatgcgg  3000
ggagttgccc tgctgtacag ttccgcgtga attacagaaa tggcggtatc ttttatcgtt  3060
cagcgcgtga tggttatggc tttgaagcta actggtcaga gttttacacc acaacacgca  3120
aaccctctgc gggagatgtt ggtgcatata cgcaggcaga atgtaactca aggtttatta  3180
caggtattcg ccttggcggt ctgtcatctg ttcagacatg gaatggtcct ggctggtctg  3240
acaggtcagg ttatgtcgtt actggttcag ttaacggaaa ccgtgatgaa ttaattgata  3300
caactcaggc aaggccaatt cagtattgca ttaatggaac gtggtataac gcggggagta  3360
tttaattatg atgcacttaa gaaatattac agctggcaac cctaaaacaa aagagcaata  3420
ccagctaacg aaacaattta acatcaaatg gctttataca gaggatggaa aaaactggta  3480
tgaggaacaa aagaatttcc agtatgatac gttgaaaatg gcctatgacc acaacggcgt  3540
tattatttgt attgaaaagg atgtttcagc aattaatcca gaaggcgcaa gcgtcgttga  3600
attacctgat attacagcaa atcgccgggc tgatatttct ggtaaatgga tgttcaaaga  3660
```

```
tggcgtagtg gtaaagcgaa cttataccga ggaagagcag aggcaacaag cggaaaatga  3720
aaagcaaagt ctgctacagc tcgtcaggga taaaacccag ctatgggact cacagctacg  3780
gctgggtatc atttccgccg agaataagca gaaattaacc gagtggatgc tctttgcgca  3840
gaaagtcgaa tccacagaca cctccagcct accagtaaca tttcccgaac aacctgaatg  3900
a                                                                  3901

SEQ ID NO: 10          moltype = DNA  length = 2713
FEATURE                Location/Qualifiers
misc_feature           1..2713
                       note = Fuzzy Tail Fiber
source                 1..2713
                       mol_type = other DNA
                       organism = synthetic construct
SEQUENCE: 10
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag aaaccggacg  1080
gaacaacggg gacggtaaaa tcgtgggcgc agttcctcag cgaatacagt tcccgccaga  1140
ctgctatcga tggcgcgatc acagcagcag ggaagaacgt tgccagaacg tcatcaacca  1200
acacgttcac gcagcctcag acattcagca atggcgtcac attcagcgcc acaataaccg  1260
ctgctgggca aatactccgg aataacagcg gcacacaatt tacggcgatt gatgccggaa  1320
gtctggaaat cagcagcgat accacgccct atattgattt tcatcataaa ggtagcgtag  1380
cggattatac gcacaggatt atcacggaag acggtgcgct ggccgtctac cctggccttc  1440
gtgttcgcgg tggttttggt ctttatggcg tggggacggt ttacggtgat gcttattcgc  1500
agggatttat tgcgcgtctt aataatgatc caaacgcatc tattggagac attcttgctt  1560
ctccgcgttt cacggttcgg tttaactcac gaggcagtga cagtaacgta gacggcgggc  1620
agggggcaat gtggtttgaa gagcaggtgg gcaccaacca tcgccttgta ttaatggccg  1680
gcgggtttag tgccaacgtt cagtactggc aatttctggc agacggcagg atttatagta  1740
gccagaacgg aaacgttcaa tggcaaggaa catccgatgc acgcctgaag cacgatattg  1800
aaccaacaga tggccagttg tctgtcgaac gtatccgcaa gctggagttg gtcacgttcg  1860
tctataacga tgacgagcag aacaggacac ggcgggggat tatcgctcag caggcacaga  1920
aagtggaccc gcagtacgtt aagcaggtga acacgtcata catgaggaac ggtgagcagg  1980
taaacgacga tcgcctgcaa ttggataata acgtgatcat gatggacaca ctggcggcgg  2040
taaaagtact gcttgagcga gtagacgaac tagaggagcg attatcggca catggataaa  2100
agaaggagat ataccatgga tgcaagaaac catgacgaga atagaactgt ctggagtcct  2160
gggtaaaacc tttgggaagg ttcattatcg tttaataaag aacatcaatg aagccggaga  2220
ggcattatct gcgacgatcc ctggatttga aaggttcatg atatccagtg aggagcgtgg  2280
attgacctat gcagtattta aagggaataa gaatatcggg catgatgatt taggattccc  2340
tgtaagtggc gaaattatcc gcatagtccc tgttatcatt ggcagtaaga aggcaggaat  2400
tctccaaaca atccttggtg cagttattgt tgcggcaagt gttgcctatg gttttttcac  2460
agaggattgg gctaatgccg cgtatggtat tcaagctggc ggcgccatga tgctcggcgg  2520
cgtcgttcag atgctctccc cacagccagc tggcctggca cgaaaagaat ccgctgacaa  2580
taaagcgtcc tacgcctttg gggcgtgac gaacactgcc tctcagggat acccggtccc  2640
tttgctttat ggcaaacggc gaattggcgg cgccattata tctgccggta tttacgtaga  2700
agaccagcaa taa                                                     2713

SEQ ID NO: 11          moltype = DNA  length = 3112
FEATURE                Location/Qualifiers
misc_feature           1..3112
                       note = Inchworm Tail Fiber
source                 1..3112
                       mol_type = other DNA
                       organism = synthetic construct
SEQUENCE: 11
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
```

```
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaaagcaag gtcgctgccg  1080
atttcaaggg ccgcaagatc ctggctggca atggcctgct cggtgggggc gatctttctg  1140
ccgaccgcag cattggcctg gcgccttccg gcgtgacggc gggcagctat cgttcggtca  1200
cggtgaacgc caacggggtg gtcacccagg gcagcaatcc gaccaccctg gccggctatg  1260
cgatcggaga tgcctatacc aaggccgata ccgacggaaa actggcgcag aaagcgaaca  1320
aggccaccac cctggccggc tatggcatca ccgatgcgct gcgagtcgat ggcaacgccg  1380
tgtcatccag caggctggcc gcaccgcgca gcctggcagc cagtggcgat gcctcctggt  1440
cggtgacctt cgacggcagt gccaatgttt ctgcgccgct gagtctttcc gctaccggtg  1500
tggcggcggg cagctatccg aaggtgaccg tggatacgaa gggaagggtg actgctggaa  1560
tggcgctggc ggcgacggac attcccgggc tggatgcgtc gaagctggtc agcggggtgc  1620
tggccgagca gcgtttgccg gtattcgcgc gcgggttggc tactgctgtc tcgaacagta  1680
gcgatccgaa caccgcgacc gtgccgttga tgctgaccaa tcatgcgaac ggacctgttg  1740
ccggacgata cttctacatc cagtcgatgt tctatccgga tcagaacggc aatgcttcgc  1800
agattgcaac gagctacaac gctacatccg agatgtatgt acgggtgtcc tacgcggcca  1860
accctagcat ccgggagtgg ttgccctggc agcgctgcga cattggaggt tccttcacca  1920
aagaggccga tggtgaactg cctggaggcg tcaacctgga ttcgatggtg acctcagggt  1980
ggtggagcca gagttttact gcccaagctg ccagtggagc caactaccct atagttcggg  2040
ccggcctgct tcatgtgtac gccgcgagta gcaatttcat ctatcagacg tatcaagcct  2100
acgatggtga gagtttctat ttccggtgcc ggcattcaaa tacctggttt ccctggcgtc  2160
gcatgtggca tggcggagac ttcaacccca gtgactatct gttgaagtcg gggttctatt  2220
ggaatgcgtt accgggaaaa cctgccactt ttccaccatc cgcacataac catgacgtcg  2280
gacagcttac ttcgggcatt ctccccctgg cacgtggcgg cgtcggttcg aatacggcag  2340
cgggagcacg tagcactatc ggagcagggg ttcctgcgac tgcttccctt ggggcgagcg  2400
gatggtggcg ggacaatgac actggcctca ttaggcaatg gggcaggtc acttgccccg  2460
ccgatgccga tgcttcgatt acgttcccga ttcctttccc tacgctatgc ctcggcggat  2520
atgcgaatca gacgagtgct ttccatccgg gaacggatgc cagtacaggt ttccgtggag  2580
cgactaccac taccgcggtg attcgcaatg gctactttgc tcaggcggtt ctttcatggg  2640
aggcatttgg acgatgaagg gcgaatatta tttctctcca agccaggtgg cattctatcc  2700
ggcctccttg cgagaggttt atgaatacgc aggctgctgg ccagtcgatg gcgagtgggt  2760
cagcgcagag ctacatgaac aactgatgaa cgaacaggcg gcaggccgag caatcagttc  2820
cgacgtgaat gggaacccag tagcgatcga gcgccctccg ctttcccgtc agcaacgtag  2880
cacccatgag cggagatggc gggatagtca gctgttggcg accgacggcc tagttgttcg  2940
ccatcgagat caattggaaa ccggaaagga aacgacctta ctccctgtcc aataccatga  3000
actcatgtcg tacagagcca gcttacggga ttggccggaa gagcctttat ttcccgacag  3060
tggcggacgc ccgtccgtac cagattggct cagacgttat gtcacccccct ga          3112
```

```
SEQ ID NO: 12          moltype = DNA  length = 3350
FEATURE                Location/Qualifiers
misc_feature           1..3350
                       note = Indian Tail Fiber
source                 1..3350
                       mol_type = other DNA
                       organism = synthetic construct
SEQUENCE: 12
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgtcac cgttgttacg agtgttacct  480
acccctcgcc tgagtcatta gcgttagttg cagacgttca gtaccacgaa ccgtatcttt  540
cagcagctct taaccgtaaa ttccgcggaa ttgtcgatcc aggattttac gccgggttcc  600
tgcctaagcc tggcggcggc atgaatcttc tgattacgtc agtcgacggg gataaaactg  660
cgggagcggc atcggtagat atcggggaat tctaccaggt tacaattcaa catcgtaaag  720
acatttcgtt agcacttaac gctgggaaga aatacgccat tgtcttgaaa ggccgctatt  780
tgttaggtga agatacgtac caggtcaata cagcaagtca catccacgcc gctgaatttg  840
tcgcacgtac atataccgat tcctaccagc ttggggatgg tgagttactt gtgtgcaccg  900
tgaacattcc tgctggagtg tcaacgatca cgcaggagat gatcgatact tcagagcgta  960
ttaatcgcac gatcgggatt gatatttcag acagcgtcac ctcgactcgc tcagatgtcg  1020
cggcttcatc tcttgcagtg aaaaaggcct acgacctggc caagtcgaag tacacagctc  1080
aggacgcgag caccacccaa aagggtctgg tacagttatc atctgcgacg aattcaacat  1140
ccgaggttct tgcagcgaca cctaaagcgg taaaagccgc gtatgatctt gccaatggga  1200
aatacaccgc acaggacgcc acaactacac aaaagggtat tgtgcagttg tcgagtgaca  1260
ccaactcaac gtcggagaca ctggcggcca cgccgaaagc agtcaaagct gcatacgacc  1320
ttgcggctgg taaagcgccc tcatcccaca ctcacccctg gaatcagatt actggtgtac  1380
ccaccgcaag cttaactgca aagggtatca ctcaattgag ttccgcgacc aacagcacca  1440
gtgaagtttt agctgctacc ccaaaggcag ttaaagccgc ttacgacttg gctaatggaa  1500
aatatacagc gcaggacgcg accactgcac aaaaaggaat tgtgcaactt tcgagcgcaa  1560
cgaactccac aagtgaagtt ttggcagcta cgcctaaagc cgtcaaagcc gcgtatgatt  1620
tggcgaatgg taagtatact gcgcaagatg cgacgactac gcagaaaggt attgtccaac  1680
```

```
tgtcaagtga caccaacagc acgtcagaga ccttggctgc tacacctaaa gcagtgaaag  1740
ctgcctatga tcttgcggct gggaaagccc cgtcatcaca cacacatcca tggaaccaga  1800
ttacggtcgt acctacggcc tctttaactg cgaagggcat tacacaatta tcatccgcga  1860
ctaacagcac cagtgaggtt ttagctgcaa caccgaaagc agtgaaggca gcctacgatt  1920
tggcgaacgg taaatatacg gctcaagatg cgaccaccgc gcaaaagggc attgtgcaac  1980
tgtcgtctgc aacaaattca acgtcggaag ttctggcagc aactccaaag gcagtgaaag  2040
ccgcctatga cttagcaaac ggtaaacagg ccgcggatgc gacgttaacg gcattggcgg  2100
ctcttgcaac tgcagcggac aagttaccgt atttcacggg cgttgaccgt gctgccctga  2160
cagcgttaac ctctgttggg cgtgccattt taggcaagac ctcgattcaa tctgttttag  2220
attaccttgg tttgggggaa ggctctgcac tgcctgttgg tgtgcccgtt ccgtggccct  2280
tagaaacacc accaacgggc tggctaaaat gcaatggtgc agcattttct tctgaaatgt  2340
atcccaaact ggcaaaagcc taccccacca ataaattacc ggatttacgc ggtgaattta  2400
tccgtggctg ggatgatggg cgcggggtgg atgctggccg cgctttgctt aattggcagc  2460
cacacacaat tttggaccat gcacactata tggaattatg gacaggggac ggactcgccg  2520
caggaagtgc acgggaaggc gtaaatccag gaatactagc tacatacggt gacgggggaa  2580
tagttaaaac ggacgaaccc ggtcataagg tgccttcctc actacgagct attagctctc  2640
gtagtgttaa acgttatggt gaaattagtg gaaatgtagg tacagaaact cgccctcgca  2700
acgttgcatt taattacatc gtaagggcgg cataaattat ggataatgcg atattaaata  2760
gcgaacttat agccatacag gcaggaaaca ttatcgttta taactatgat ggtggtaatc  2820
gggaatatat ttctgcatca actgaatatc ttgctgttgg cgttggtatt ccggcaaatt  2880
cttgtttgga tgctccaggc tcacataaag caggttatgc gattctccgt tcagaggatt  2940
taagttcatg ggagtatgtg ccagatcatc gtggcgaaac tgtctatagc attgacacag  3000
ggaatcccga agaaatcacg gtgttgggtg actatccgga aaatacaacc actatcgccc  3060
cgctaacacc atacgacaaa tgggatggag agaaatgggt ggttgatact gaggctcaac  3120
atagtgcagc tgtagaggca gcagaaacaa aacgtcagtc attgattgat actgcgatgg  3180
attccattag tctgattcag ttgaaattac gggctggacg gaagttgacg caggcagaaa  3240
ccacgcagct taactccgtg ctagattata tagacgagct gaacgcgatg gatttaacca  3300
cggcaccaga tctcaactgg cctgaaaaac aactttctac agccagttga             3350
```

```
SEQ ID NO: 13          moltype = DNA  length = 3311
FEATURE                Location/Qualifiers
misc_feature           1..3311
                       note = Indigo Tail Fiber
source                 1..3311
                       mol_type = other DNA
                       organism = synthetic construct
SEQUENCE: 13
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgtcac cgttgttacg agtgttacct  480
acccctcgcc tgagtcatta gcgttagttg cagacgttca gtaccacgaa ccgtatcttt  540
cagcagctct taaccgtaaa ttccgcggaa ttgtcgatcc aggattttac gccgggttcc  600
tgcctaagcc tggcggcggc atgaatcttc tgattacgtc agtcgacggg gataaaactg  660
cgggagcggc atcggtagat atcggggaat tctaccaggt tacaattcaa catcgtaaag  720
acatttcgtt agcacttaac gctgggaaga aatacgccat tgtcttgaaa ggccgctatt  780
tgttaggtga agatacgtac caggtcaata cagcaagtca catccacgcc gctgaatttg  840
tcgcacgtac atataccgat tcctaccagc ttggggatgg tgagttactt gtgtgcaccg  900
tgaacattcc tgctggagtg tcaacgatca cgcaggagat gatcgatact tcagagcgta  960
ttaatcgcac gatcgggatt gatatttcag acagcgtcac ctcgactcgc tcagatgtcg  1020
cggcttcatc tcttgcagtg aaaaaggcct acgacctggc caagtcgaag tacacagctc  1080
aggacgcgag caccacccaa aagggtctgg tacagttatc atctgcgacg aattcaacat  1140
ccgaggttct tgcagcgaca cctaaagcgg taaaagccgc gtatgatctt gccaatggga  1200
aatacaccgc acaggacgcc acaactacac aaaagggtat tgtgcagttg tcgagtgaca  1260
ccaactcaac gtcggagaca ctggcggcca cgccgaaagc agtcaaagct gcatacgacc  1320
ttgcggctgg taaagcgccc tcatcccaca ctcacccctg gaatcagatt actggtgtac  1380
ccaccgcaag cttaactgca aagggtatca ctcaattgag ttccgcgacc aacagcacca  1440
gtgaagtttt agctgctacc ccaaaggcag ttaaagccgc ttacgacttg gctaatggaa  1500
aatatacagc gcaggacgcg accactgcac aaaaaggaat tgtgcaactt tcgagcgcaa  1560
cgaactccac aagtgaagtt ttggcagcta cgcctaaagc cgtcaaagcc gcgtatgatt  1620
tggcgaatgg taagtatact gcgcaagatg cgacgactac gcagaaaggt attgtccaac  1680
tgtcaagtga caccaacagc acgtcagaga ccttggctgc tacacctaaa gcagtgaaag  1740
ctgcctatga tcttgcggct gggaaagccc cgtcatcaca cacacatcca tggaaccaga  1800
ttacggtcgt acctacggcc tctttaactg cgaagggcat tacacaatta tcatccgcga  1860
ctaacagcac cagtgaggtt ttagctgcaa caccgaaagc agtgaaggca gcctacgatt  1920
tggcgaacgg taaatatacg gctcaagatg cgaccaccgc gcaaaagggc attgtgcaac  1980
tgtcgtctgc aacaaattca acgtcggaag ttctggcagc aactccaaag gcagtgaaag  2040
ccgcctatga cttagcaaac ggtaaacagg ccgcggatgc gacgttaacg gcattggcgg  2100
ctcttgcaac tgcagcggac aagttaccgt atttcacggg cgttgaccgt gctgccctga  2160
cagcgttaac ctctgttggg cgtgccattt taggcaagac ctcgattcaa tctgttttag  2220
attaccttgg tttaggggaa ggctcggcgc tgcccgttgg tgtgcccgtt ccgtggccct  2280
tagaaacacc accaacgggc tggctaaaat gcaatggtgc agcattttct tctgaaaagt  2340
acccaaatct ggcaaaggct taccctacta ataaattgcc ggatttacgc ggtgaattta  2400
ttcgtggctg ggatgacggg cgggggattg actctggccg taatttatta tctgcacaga  2460
atgatgcaat tcagaatatt gttggttctt tcgggcgtac tcagcttttt agagatgtac  2520
```

```
ttagttcagg gccatttagt caacatggcc aagtattatc tacaggccta aaggaaacgg  2580
aaattattga gggttatggc tcttataact ggacattcga cgcctctcgc tcagttcgta  2640
cagcatctga aacccgcccc cgtaatattg catttaatta catcgtaagg gcggcataaa  2700
tggataatgc gatattaaat agcgaactta tagccataca ggcaggaaac attatcgttt  2760
ataactatga tggtggtaat cgggaatata tttctgcatc aactgaatat cttgctgttg  2820
gcgttggtat tccggcaaat tcttgtttgg atgctccagg ctcacataaa gcaggttatg  2880
cgattctccg ttcagaggat ttaagttcat gggagtatgt gccagatcat cgtggcgaaa  2940
ctgtctatag cattgacaca gggaatcccg aagaaatcac ggtgttgggt gactatccgg  3000
aaaatacaac cactatcgcc ccgctaacac catacgacaa atgggatgga gagaaatggg  3060
tggttgatac tgaggctcaa catagtgcag ctgtagaggc agcagaaaca aaacgtcagt  3120
cattgattga tactgcgatg gattccatta gtctgattca gttgaaatta cgggctggac  3180
ggaagttgac gcaggcagaa accacgcagc ttaactccgt gctagattat atagacgagc  3240
tgaacgcgat ggatttaacc acggcaccag atctcaactg gcctgaaaaa caactttcta  3300
cagccagttg a                                                       3311

SEQ ID NO: 14          moltype = DNA  length = 4610
FEATURE                Location/Qualifiers
misc_feature           1..4610
                       note = Jazzberry Tail Fiber
source                 1..4610
                       mol_type = other DNA
                       organism = synthetic construct
SEQUENCE: 14
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cgggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
aataccttgg tttaagagaa ctcggcacaa gcggtgaaaa gatccccctg ttgagcacgg  1860
ctaacacatg gagtgcacgc cagactttta acggcgggat caccggggcg ctgacaggga  1920
acgccgatac cgcgacgaag ttgaaaacag cacggaagat taacaacgtt tcatttgatg  1980
gttcggcaga cataacgctg acacctgaga accttggcgt caccagtctg acgtttgaga  2040
aaaacaacgg tgaaatgcct attgatgctg acctaaatac tttcggtccc gttgaggctt  2100
atcttggtgt ctggtccaaa gcaacatcca ccaacgcaac actggagaaa aatttcccgg  2160
aagataatgc tgtcggtgtg cttgaggtat ttgctgccgg aaattttgca ggtacgcaac  2220
gctttaccac gagagacggc aatgtataca tacgcagact cgccaataag tggaatggct  2280
ctgatggtcc gtggggcata tggcgtcaca ctcaatcagc tacccgccct ttgagtacga  2340
ctatagacct gaatacgctt ggagccgccg aacatcttgg tttatggcgt aacagtagct  2400
cggctatagc ttcatatgaa cgcaattatc cagaggaagg cggctttgct caggggggtgc  2460
ttgagatcct cgaaggcggg aattatggaa gaacgcaacg ttataccact cgccgcggaa  2520
atatgtatgt ccgctgcctt gcggcaagct gggatgcatc aaatccgcag tgggaaccgt  2580
ggttaaaagt cggtcatcag tcagagagtc gttattacga aggtgattta aatgttctaa  2640
ccgaccccgg tatttacagt gttacaggaa aggcaacaaa cggtccgatg ctggacaccg  2700
ttggcgcgac actacttggg atactggaag taatcagacg ttttgatggt gtgtctgtct  2760
ggcagcgtta cacaaccaca gggaaatcag aaaccacaca gggacgcact tttgagcgcg  2820
tctacgccgg gagcaaatgg accgaatggc gagaagtata taactccttt tcgttgcctc  2880
tgaatctggg catcggtggc gcagtggcaa aactatccag tctggactgg cagacctacg  2940
attttgtgcc gggcagtctg ataaccgtgc ggcttgataa catgaccaac attcccgacg  3000
gtatggactg gggcgtcatt gatggcaacc tgataaacat cgcagttggt ccgagtgatg  3060
attccggtac ggggcgctca atgcatgtat ggcgcagcac tgtaagtaaa gcgaactacc  3120
gctttttttat ggtgcgtatt tcaggaaatc cgggaagccg cacgatcaca gcaagacgag  3180
taccaatcat tgacgaagcc cagacatggg gcgcgaaaca gacattcagt gctggccttt  3240
ctggtgaact gtccggcaat gcggcgacag caacaaagct gaaaacagcc cgtaaaatta  3300
ataacgtttc gtttgatggt tccggggata ttgaggtcct tcctgttggt gttccgctgc  3360
```

```
cgtggccatc agatactgtg ccgtctggtt acgccctgat gcagggacag acttttgaca  3420
aatctgcata cccgaaactt gcagccgctt atccgtcagg cgtgatcccg gatatgcgtg  3480
gctggacaat caagggcaaa cccgccagtg gtcgggacgt attgtctctg gaacaggatg  3540
gcattaaatc gcacacccac agcgccagcg catccaatac ggatttgggt acgaaaacca  3600
catcttcgtt tgattacggt actaaatcaa cgaataacac aggtgcacat acccacaatg  3660
tatctggtac tgcaaatagt gctggcgcac atactcatac cgtgccatta aggagaccaa  3720
acagtggcgg tatgaatttc gactggctgg atggtgcatc aagtggcacg gtggtgggga  3780
atggaactgt gccttcttct ggcgcacata cccactcagt atcaggcacc gctacaagtg  3840
ctggggcaca tgcacacact gttggtattg gcgctcatac gcactctgtt gcgattggtt  3900
cacatggaca taccatcacc gttaacgctg ctggcaacgc ggaaaacacc gttaaaaaca  3960
tcgcatttaa ttatattgtg aggcttgcat aaatggcatt cagaatgagt gaacaatcac  4020
gtactgtaaa aatttataac ctgctggccg gaactaatga gtttattggt gaaggtgacg  4080
catatattcc acctcataca gggctgccag ctaattctac agatatcgcc ccaccggaaa  4140
ttcctgctgg ctttgtggca gtttttaaca gtgaaaatga atcgtggaat attgttgaag  4200
accatcgtgg taaaacggtc tatgacgtgg catcggggga cgcgttgttt atttctgaac  4260
ccggaccgct accagagaat gtcacctggt tgtcgccagc aggggaatat cagaagtggg  4320
acggcgtatc ctgggtgaag gatgaggaag cagaaaaact gtttcggata cgggaagcgg  4380
aagagaaaaa ggcaaggttg atccaggagg caacagataa catcgcaatt ctgcaggatg  4440
cagttaatct tgaaatagca acaaacgagg aaaattcaca actggattcc tggagaaaat  4500
acagagtatt agtgagtaga attgacacca gtacagctcc ggatatcgta tggccagagc  4560
tgatgaatca gggttatgtg cgggaggacg agcagataac ttcagactga             4610
```

```
SEQ ID NO: 15          moltype = DNA  length = 6917
FEATURE                Location/Qualifiers
misc_feature           1..6917
                       note = Jazzberry-Shamrock Tail Fiber
source                 1..6917
                       mol_type = other DNA
                       organism = synthetic construct
SEQUENCE: 15
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
aataccttgg tttaagagaa ctcggcacaa gcggtgaaaa gatccccctg ttgagcacgg  1860
ctaacacatg gagtgcacgc cagactttta acggcgggat caccggggcg ctgacaggga  1920
acgccgatac cgcgacgaag ttgaaaacag cacggaagat taacaacgtt tcatttgatg  1980
gttcggcaga cataacgctg acacctgaga accttggcgt caccagtctg acgtttgaga  2040
aaaacaacgg tgaaatgcct attgatgctg acctaaatac tttcggtccc gttgaggctt  2100
atcttggtgt ctggtccaaa gcaacatcca ccaacgcaac actggagaaa aatttcccgg  2160
aagataatgc tgtcggtgtg cttgaggtat ttgctgccgg aaattttgca ggtacgcaac  2220
gctttaccac gagagacggc aatgtataca tacgcagact cgccaataag tggaatggct  2280
ctgatggtcc gtggggcata tggcgtcaca ctcaatcagc tacccgccct ttgagtacga  2340
ctatagacct gaatacgctt ggagccgccg aacatcttgg tttatggcgt aacagtagct  2400
cggctatagc ttcatatgaa cgcaattatc cagaggaagg cggctttgct cagggggtgc  2460
ttgagatcct cgaaggcggg aattatggaa gaacgcaacg ttataccact cgccgcggaa  2520
atatgtatgt ccgctgcctt gcggcaagct gggatgcatc aaatccgcag tgggaaccgt  2580
ggttaaaagt cggtcatcag tcagagagtc gttattacga aggtgattta aatgttctaa  2640
ccgaccccgg tatttacagt gttacaggaa aggcaacaaa cggtccgatg ctggacaccg  2700
ttggcgcgac actacttggg atactggaag taatcagacg ttttgatggt gtgtctgtct  2760
ggcagcgtta cacaaccaca gggaaatcag aaaccacaca gggacgcact tttgagcgcg  2820
tctacgccgg gagcaaatgg accgaatggc gagaagtata taactccttt tcgttgcctc  2880
tgaatctggg catcggtggc gcagtggcaa aactatccag tctggactgg cagacctacg  2940
```

```
attttgtgcc gggcagtctg ataaccgtgc ggcttgataa catgaccaac attcccgacg  3000
gtatggactg gggcgtcatt gatggcaacc tgataaacat cgcagttggt ccgagtgatg  3060
attccggtac ggggcgctca atgcatgtat ggcgcagcac tgtaagtaaa gcgaactacc  3120
gctttttttat ggtgcgtatt tcaggaaatc cgggaagccg cacgatcaca gcaagacgag  3180
taccaatcat tgacgaagcc cagacatggg gcgcgaaaca gacattcagt gctggccttt  3240
ctggtgaact gtccggcaat gcggcgacag caacaaagct gaaaacagcc cgtaaaatta  3300
ataacgtttc gtttgatggt tccggggata ttgaggtcct tcctgttggt gttccgctgc  3360
cgtggccatc agatactgtg ccgtctggtt acgccctgat gcagggacag acttttgaca  3420
aatctgcata cccgaaactt gcagccgctt atccgtcagg cgtgatcccg gatatgcgtg  3480
gctggacaat caagggcaaa cccgccagtg gtcgggacgt attgtctctg gaacaggatg  3540
gcattaaatc gcacacccac agcgccagcg catccaatac ggatttgggt acgaaaacca  3600
catcttcgtt tgattacggt actaaatcaa cgaataacac aggtgcacat acccacaatg  3660
tatctggtac tgcaaatagt gctggcgcac atactcatac cgtgccatta aggagaccaa  3720
acagtggcgg tatgaatttc gactggctgg atggtgcatc aagtggcacg gtggtgggga  3780
atggaactgt gccttcttct ggcgcacata cccactcagt atcaggcacc gctacaagtg  3840
ctggggcaca tgcacacact gttggtattg gcgctcatac gcactctgtt gcgattggtt  3900
cacatggaca taccatcacc gttaacgctg ctggcaacgc ggaaaacacc gttaaaaaca  3960
tcgcatttaa ttatattgtg aggcttgcat aaatggcatt cagaatgagt gaacaatcac  4020
gtactgtaaa aatttataac ctgctggccg gaactaatga gtttattggt gaaggtgacg  4080
catatattcc acctcataca gggctgccag ctaattctac agatatcgcc ccaccggaaa  4140
ttcctgctgg ctttgtggca gtttttaaca gtgaaaatga atcgtggaat attgttgaag  4200
accatcgtgg taaaacggtc tatgacgtgg catcggggga cgcgttgttt atttctgaac  4260
ccggaccgct accagagaat gtcacctggt tgtcgccagc aggggaatat cagaagtggg  4320
acggcgtatc ctgggtgaag gatgaggaag cagaaaaact gtttcggata cgggaagcgg  4380
aagagaaaaa ggcaaggttg atccaggagg caacagataa catcgcaatt ctgcaggatg  4440
cagttaatct tgaaatagca acaaacgagg aaaattcaca actggattcc tggagaaaat  4500
acagagtatt agtgagtaga attgacacca gtacagctcc ggatatcgta tggccagagc  4560
tgatgaatca gggttatgtg cgggaggacg agcagataac ttcagactga gacaaggccc  4620
gatagcgggc cttaatttcg cgttggccga ttcattaatg cagctgcaaa aaacccctca  4680
agacccgttt agaggcccca aggggttatg ctagttattg ctcagcggtg gcagcagctt  4740
attcaggctt ttgtggccat tcaggatttg ccgtatccac acggctgacc agaacactgt  4800
agcgttccca tgactccagt cgtgcgtgtt cctcatccgt cgccatattc agcctgacag  4860
cgcgttccag cggctggatg actgattcag cttcggaaag taacgcggcc ttttgtgatt  4920
cggcctgttg ctgctgttcg tctgctgtat aagtcctcct gaccaccgct ccgtccttaa  4980
acatccactt ccctgaatca tcggcacgac ggttagctgt tatatcgggg atttcaacga  5040
cgctaaaacc ttcaggatta agcgtggagg catctttagt gacggcgaca ataatattat  5100
tttcgtcgta aacaatcttt attgtatccg gctgaaagtt cttcacttcc tcataccagt  5160
ttttcccgtc ttcagcgtaa agccagatga ctccgtgctt ctttgttaac tcatactgct  5220
ccagtgtttt agcattaccc gcttttatgt tctttaagtg catcatatta aacgctcgct  5280
acattatacc atgtgccatt tatatacttt tgaacgggtc tgtaataaac gccagctata  5340
ttatcggcag agtttttgcc tgtatcctga acattaatac cagacaatac atgacctgaa  5400
gggcactgga aattccatgt ttgccagtta ttcacaccat aatattgctg tgagccaagc  5460
cggacatctt tcacatatct ggagtcaaaa ttgccataat tgccgggaat aacttgcgca  5520
ccacaaagcc agttaccgtt attatccatg tacgcctgac catcggtgcc attggctgtc  5580
cttgagttat taatcatgta gatgccaaat tgcttatttc ccagaccgcc aatcataaat  5640
ttgcggtcgg catggtcctg acggagcaaa gcctgagcac catcagtgga taccgcatta  5700
cgtcccaaaa taacattctg gtcacgcata tgaatccaca tgccggtact actgttaatt  5760
gcaaaacggt ttgcaaatat atcccctgta acatcaagac catgccccat gcttatccgg  5820
ccagttctga gattaagcgt aaaggggcgt agtggccccta tattaccatt ttcccccttca  5880
ttctctcgtg tagggatgat atgcaggcat tcttcagaac gacgaaaaat ggcaccaaaa  5940
gatgaattaa atatcctcag tgcattgact gtcgatattt tcacttcact gctgaaaagg  6000
gcttcaacaa gaacagacaa agcattccat ttaagattca tcaggtcttt aggccgggtg  6060
ccaatgatgc ggtgtctcca tttgaaatat tcattgccgt tgttgcctgt ttcaaaccac  6120
atgtaggaat cggtgtctgc atccgaatta tttttaaaac caatcttcgc ccagtcagta  6180
ttccgaatcc aggcaaggat tgagtcgttt tcaaaagtaa gtccaccgga caaggtatcg  6240
cctgtctttt gaaccgcgtt atcagccttg tttaccgttt cctgtagatt taaatcttcc  6300
gccgttagct caatattttt agaaccgtca aacgagacgc cgttgatagt acatgctgtc  6360
tgcaacttgg tcgctgtagc cgcattacca gaggtatcct gatccccttt ggcattgacg  6420
ccgggaattg aatcttttga cgtatagacc tgcgcccatt cagaccagtt ggcagaatca  6480
gtatcccgcc gcgaacggat atgtacgggc gcatgggcac cgctcgtgcc actccagcca  6540
atgaataact caccttcgcc agcagcggtg gcacctttaa ggtgaagcac attgccatag  6600
ggggaagggt agccattgtt gtatgcctca tacagctgaa tcccggatgt tccctgtgca  6660
ttcgcctcca gggccgttac gcgaccgcgc gataccagag tattgatatt aatgtcacca  6720
gaaccatcga acctgacgcc attaatgttt ctggctgttt tcaatttcgt tgcggtatcg  6780
gcgttccctg tcagcgcccc ggtgatcccg ccgttgaaag tctggcgtgc actccatgtg  6840
ttagccgtgc tcaacagggg gatcttttca ccgctggtac cgagttctct taaaccaagg  6900
tattggataa cagcaag                                                 6917
```

```
SEQ ID NO: 16          moltype = DNA  length = 3907
FEATURE                Location/Qualifiers
misc_feature           1..3907
                       note = Jungle Tail Fiber
source                 1..3907
                       mol_type = other DNA
                       organism = synthetic construct
SEQUENCE: 16
atgtctgacg tctcaacaaa cctctataag agtcagttgt tggactatta ctatcagcgg  60
cgcgctgaat cgtccattaa caaaggctct cgatttttaa tcagcaaggc cgtttcggt  120
accagttcgc tggttactaa gaaaggagat ggcacttatg agattggaga actgccaaag  180
```

```
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
aataccttgg tttaagagaa ctcggtacca gcggtgaaaa gatccccctg ttgagcacgg  1860
ctaacacatg gagtgcacgc cagactttca acggcgggat caccggggcg ctgacaggga  1920
acgccgatac cgcaacgaaa ttgaaaacag ccagaaacat taatggcgtc aggttcgatg  1980
gttctggtga cattaatatc aatactctgg tatcgcgcgg tcgcgtaacg gccctggagg  2040
cgaatgcaca gggaacatcc gggattcagc tgtatgaggc atacaacaat ggctaccctt  2100
ccccctatgg caatgtgctt caccttaaag gtgccaccgc tgctggcgaa ggtgagttat  2160
tcattggctg gagtggcacg agcggtgccc atgcgcccgt acatatccgt tcgcggcggg  2220
atactgattc tgccaactgg tctgaatggg cgcaggtcta tacgtcaaaa gattcaattc  2280
ccggcgtcaa tgccaaaggg gatcaggata cctctggtaa tgcggctaca gcgaccaagt  2340
tgcagacagc atgtactatc aacggtgtct cgtttgatgg ttctaaaaat attgagctaa  2400
cggctgaaaa tttaaatctt gagcgaacag tagaattagc cgctgggtca ttgcagaaaa  2460
atcagaacgg cgcggatatt cctggaaaag ataccttcac aaaaaatatt ggtgcatgtc  2520
gcgcttatag cgcatggctg aatattggtg gcgatagtca ggtctggaca accgcacaat  2580
ttatttcgtg gctggagagt cagggggcat ttaaccatcc ttactggatg tgcaaaggct  2640
catgggctta tgcaaacaat aaggtcatta cagatacagg ttgcggaaat atttgtcttg  2700
caggtgctgt ggtggaagtt attggcactc gcggcgcaat gaccatacgc gttactacgc  2760
cgagtacgtc cagcggcggc ggaatcacta acgctcaatt cacttatatt aatcatggtg  2820
atgcttatgc tcctggctgg cgacgagact acaacacgaa aaaccagcag cctgcatttg  2880
ctttaggaca aacaggaagc actgtcggaa atgataaagc tgttggctgg aactggaata  2940
gcggggtcta taacgcaaat attggtggcg catcgacatt aatcctccac ttcaatatga  3000
atacggggag ttgccctgcc gtacagttcc gtgtgaatta caggaacggc ggtatttttt  3060
atcgttcagc gcgtgatggt tacggattcg aagctgactg gtcagaaatt tacaccacaa  3120
cacgtaagcc atcagcggga gatgttggtg catatacgca ggcagaatgt aactcaaggt  3180
ttattacagg tattcgtctt ggcggtctgt catctgttca gacatggaat ggtcccggct  3240
ggtctgacag gtcaggttat gtcgttacgg gttcagttaa cggaaaccgt gatgaattaa  3300
ttgatacaac tcaggcaagg ccaattcagt attgcattaa tggaacgtgg tataacgcgg  3360
ggagtattta attatgatgc acttaaaaaa tattactgct ggcaacccta aaacaaaaga  3420
gcaataccag ctaacgaaac aatttaacat caaatggctt tatacagagg atgggaaaaa  3480
ctggtatgag gaacaaaaga actttcagcc tgatacgttg aaaatggtct atgaccacaa  3540
cggcgttatt atttgtattg aaaaggatgt ttcagcaatt aatccagaag gcgcaaacgt  3600
cgttgaggtt cctgatatta cagcaaatcg ccgggctgat atttcgggta aatggatgtt  3660
caaagatggt gtagtgataa agcgaactta taccgaggaa gagcagaggc aacaagcgga  3720
aaatgaaaag caaagcctgc tacagctcgt cagggataaa acacagctat gggactcaca  3780
gctacggctg ggcatcattt ccgacgagaa taaacaaaaa ttaacagagt ggatgctcta  3840
cgcgcagaag gtcgaatcca cagacacctc cagcctgcca gtaacgtttc cagaacaacc  3900
agaatga                                                            3907
```

```
SEQ ID NO: 17          moltype = DNA  length = 3167
FEATURE                Location/Qualifiers
misc_feature           1..3167
                       note = Mango Tail Fiber
source                 1..3167
                       mol_type = other DNA
                       organism = synthetic construct
SEQUENCE: 17
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
```

```
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaac cacggcgcgt aaggggatcg ttcagctgag tagcgccact gacagcgtgt  1140
ctgaggtgct ggcggcaacg ccgaaggcgg tgaagactgc gtatgatctg gcgaacgcca  1200
agtacactgc ggtggatgcc actacggcgc gtaaggggct tgtccagctc agcagtgcga  1260
ttgacagtgt gtcggagatg ctggcagcga cgccgaaggc ggttaaatcc gcaaacgaca  1320
acgctactgc agccaatata aatgccagtg agcgagttag taaagccggt gacagtatga  1380
ccggaacatt aaatcaggac gctgtagcac aggccaccta caacttaacg gcactttcca  1440
acgccacgac aggcaataaa aattatcttc gtaaaatgcg cggcggagcg acggacacta  1500
tctggcatga aaccgttcag gggggcgaat accgtctggc gacaggcagt accgattcgc  1560
aggaggagct ggcgattagc actaataccg gcctgagagt gagaggtaat ttaacctcac  1620
aacttggcgg attttattca gggaatacga aaaaattctc tttttattca tcaaataacct  1680
ctgacaagaa tgcagctctg cgcctctggg gaaatgtaga ccgcccatct gtagtcgaac  1740
tgggggatga caccggctac cattttttact ctcagcgaaa taaagatggc tcgctattgc  1800
ttcaggcaaa cggcgccgga caatttagcg gttatttacg ttcaaacgga gaagtacaat  1860
ccatttccgc aaatagttat cggattgcat atggaaacta cgggtgtttc tggcgcaacg  1920
acggtaataa tctttatctg atgctgacga ataagggcga tgcttacgga aactacaatt  1980
cattgcgtcc attacgggtt agcctggaaa ccggggcatt acaatctgag acaccattta  2040
ctgtaggcaa caccattttc gctacgaagg aaattacagc gggttatgcc ggtgcacttg  2100
catgggcaga acagtacaaa acaaaagcag cttttttttaa ctcatattcg acaaccggtg  2160
cgagtgaata ccatccagct ttaaaacaac aggcaagcat tgccggtgtc aattcatggg  2220
ctttttcaat ggggtctctt gtcgctgata ccgctctttc atggcatttg cacatgaaag  2280
gcagtggcgg tcaggatgtc aattataaat gggataccag tggtaatttt agcgcgccag  2340
gccagctcat tcccggaagt tttgctaatt tcgactcccg ttattatacc aaagggcaaa  2400
gcgatgcggg ttatatggca aaaaccggag catacacaaa agccgaaagc gatgctcgtt  2460
ataatctgaa aaacacggcc agtagggctg caagcggttg ggagaaagac aacactacag  2520
gaattatgaa gcagtggggg attgcaacac gtacagcgga ctctacacgg ataaccttcc  2580
caactgcgtt tccaactact tgcgtcagcg tgcagctaac actgctttat accaatgggt  2640
tccatgatca gaatatttat gttcaaaatc ctgatgcttc aggttttacc tacattgctg  2700
gtagtggtga agtcaaagtg tatttcgaag cgagaggtta ttaaatggga tatgtttatt  2760
gtcacgctac gggcgctttt tataatgatg ctctggtggc agactaccgt tccgccggtt  2820
cgtggccgga taattatgta actgtgctgg atgacgatta tgaatcattg atggcagggc  2880
aggctgttgg gaaaatgatt gtttctgata ataatggtta tcctgttctg acggaaccac  2940
cggaaccgac acacgaagaa caagtaaatc aggcatcgtc acaaaaaatta tttttgatga  3000
aaacggcgaa tgaaattatt actccgctcg aggatgcagt cgagctcgga attgccaccg  3060
atgaagaagc ggccacgctg ctactctgga agcgttaccg cgtattgtta aacagactgg  3120
atctcagcaa agccccagat attcaatggc cagaacgccc ggcctga                3167
```

```
SEQ ID NO: 18           moltype = DNA  length = 3323
FEATURE                 Location/Qualifiers
misc_feature            1..3323
                        note = Maroon Tail Fiber
source                  1..3323
                        mol_type = other DNA
                        organism = synthetic construct
SEQUENCE: 18
atgtctgacg tctcaacaaa cctctataag agtcagttgt tggactatta ctatcagcgg  60
cgcgctgaat cgtccattaa caaaggctct cgattttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgtcac cgttgttacg agtgttacct  480
acccctcgcc tgagtcatta gcgttagttg cagacgttca gtaccacgaa ccgtatcttt  540
cagcagctct taaccgtaaa ttccgcggaa ttgtcgatcc aggattttac gccgggttcc  600
tgcctaagcc tggcggcggc atgaatcttc tgattacgtc agtcgacggg gataaaactg  660
cgggagcggc atcggtagat atcggggaat tctaccaggt tacaattcaa catcgtaaag  720
acatttcgtt agcacttaac gctgggaaga aatacgccat tgtcttgaaa ggccgctatt  780
tgttaggtga agatacgtac caggtcaata cagcaagtca catccacgcc gctgaatttg  840
tcgcacgtac atataccgat tcctaccagc ttggggatgg tgagttactt gtgtgcaccg  900
tgaacattcc tgctggagtg tcaacgatca cgcaggagat gatcgatact tcagagcgta  960
ttaatcgcac gatcgggatt gatatttcag acagcgtcac ctcgactcgc tcagatgtcg  1020
cggcttcatc tcttgcagtg aaaaaggcct acgacctggc caagtcgaag tacacagctc  1080
aggacgcgag caccacccaa aagggtctgg tacagttatc atctgcgacg aattcaacat  1140
ccgaggttct tgcagcgaca cctaaagcgg taaaagccgc gtatgatctt gccaatggga  1200
aatacaccgc acaggacgcc acaactacac aaaagggtat tgtgcagttg tcgagtgaca  1260
ccaactcaac gtcggagaca ctggcggcca cgccgaaagc agtcaaagct gcatacgacc  1320
ttgcggctgg taaagcgccc tcatcccaca ctcacccctg gaatcagatt actggtgtac  1380
ccaccgcaag cttaactgca aagggtatca ctcaattgag ttccgcgacc aacagcacca  1440
```

```
gtgaagtttt agctgctacc ccaaaggcag ttaaagccgc ttacgacttg gctaatggaa  1500
aatatacagc gcaggacgcg accactgcac aaaaaggaat tgtgcaactt tcgagcgcaa  1560
cgaactccac aagtgaagtt ttggcagcta cgcctaaagc cgtcaaagcc gcgtatgatt  1620
tggcgaatgg taagtatact gcgcaagatg cgacgactac gcagaaaggt attgtccaac  1680
tgtcaagtga caccaacagc acgtcagaga ccttggctgc tacacctaaa gcagtgaaag  1740
ctgcctatga tcttgcggct gggaaagccc cgtcatcaca cacacatcca tggaaccaga  1800
ttacggtcgt acctacggcc tctttaactg cgaagggcat tacacaatta tcatccgcga  1860
ctaacagcac cagtgaggtt ttagctgcaa caccgaaagc agtgaaggca gcctacgatt  1920
tggcgaacgg taaatatacg gctcaagatg cgaccaccgc gcaaaagggc attgtgcaac  1980
tgtcgtctgc aacaaattca acgtcggaag ttctggcagc aactccaaag gcagtgaaag  2040
ccgcctatga cttagcaaac ggtaaacagg ccgcggatgc gacgttaacg gcattggcgg  2100
ctcttgcaac tgcagcggac aagttaccgt atttcacggg cgttgaccgt gctgccctga  2160
cagcgttaac ctctgttggg cgtgccattt taggcaagac ctcgattcaa tctgttttag  2220
attaccttgg tttaggggaa ggctcggcgc tgcccgttgg tgtacctgtt ccatggccct  2280
ccgccacacc accaacgggg tggctgaaat gtaacggagc agcattttct tctgaaatgt  2340
atcccaaact ggcaaaggcc taccccacca ataaattacc ggatttacgg ggagaattta  2400
ttcgcggctg ggatgatggg cgcggggtgg atgcgggacg tgctttattg agcattcaga  2460
caggaatgct ggaaaagcac cgacatattg ttgtagccaa tgatggttac gacacaaaag  2520
atgaatggga gctggcgaca attttcaaaa aaacatacac acaaggacgg gggcttgatg  2580
cctcaaatac aggagggaat ttgattccat caccgacact tcattctcga gggagtattg  2640
gtaatactgg cgggagtgaa acccgtccac gaaatatcgc atttaattac atcgtaaggg  2700
cggcataaat tatggataat gcgatattaa atagcgaact tatagccata caggcaggaa  2760
acattatcgt ttataactat gatggtggta atcgggaata tatttctgca tcaactgaat  2820
atcttgctgt tggcgttggt attccggcaa attcttgttt ggatgctcca ggctcacata  2880
aagcaggtta tgcgattctc cgttcagagg atttaagttc atgggagtat gtgccagatc  2940
atcgtggcga aactgtctat agcattgaca cagggaatcc cgaagaaatc acggtgttgg  3000
gtgactatcc ggaaaataca accactatcg ccccgctaac accatacgac aaatgggatg  3060
gagagaaatg ggtggttgat actgaggctc aacatagtgc agctgtagag gcagcagaaa  3120
caaaacgtca gtcattgatt gatactgcga tggattccat tagtctgatt cagttgaaat  3180
tacgggctgg acggaagttg acgcaggcag aaaccacgca gcttaactcc gtgctagatt  3240
atatagacga gctgaacgcg atggatttaa ccacggcacc agatctcaac tggcctgaaa  3300
aacaactttc tacagccagt tga                                         3323
```

```
SEQ ID NO: 19          moltype = DNA  length = 3760
FEATURE                Location/Qualifiers
misc_feature           1..3760
                       note = Mulberry Tail Fiber
source                 1..3760
                       mol_type = other DNA
                       organism = synthetic construct
SEQUENCE: 19
atgtctgacg tctcaacaaa cctctataag agtcagttgt tggactatta ctatcagcgg  60
cgcgctgaat cgtccattaa caaaggctct cgatttttaa tcagcaaggc cgtttttcggt 120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatgg gggctgataa aacgaacaac ataatgacac  480
tatcctctgg tgtctcacag cctttgcttg ctgatgttca atatttcgaa ctctatagta  540
gttcggctct taacagaaaa cttaaaaata ttgttttgcc tggcttttac tgtggatttg  600
aaccagttcc cggcacaggg ttgagtgttc gtataacttc tgaaaactca gaaggtaaag  660
gggctgcttc agtagatgta aataatgttc agatatccgt tcagcaaata gaagatgtga  720
ctgtctcggt aaaggctggg gctaccaaca ttattgtgct ggaagccaat tttgaacatg  780
gtgtaaaaac gacacaggta gatagcgcat cttctgtcag tgctgcaaga atttacgcgc  840
gtacggacaa tactattggg cagaatcaaa ttgaattatg tcgagttatc gtgcctaacg  900
gcgcaacggc tgtgactaaa gaaatgattg tgcttaaata ccgggttaac cgtgctgttg  960
gtgtcgaatt ctctaatgaa ataagcagta cagaagaaag aaaagcggct acacctctgg  1020
ctgtcaaaac tctccatgat ttggttgata caaaagctcc gctcgatagt ccgcatctgt  1080
caggtacgcc gacttcgccg acacctgaac ccggtacaaa caacacacag atcgcaaatg  1140
cggcctttgt ctatgctgct ataaatgcgc ttatcaatgg tgctccggga acgatggaca  1200
cgctgaaaga aatagcggct gcgatcaata acgacccgaa tttcagcaca actatcaaca  1260
atgctctggc tcttaaagct cctttagcaa gtcctgcatt aacgggaata cctactgcgc  1320
ctaccgctgc acagggtacg aataacacgc agattgctac gaccgcttat gtaagagctg  1380
ccatatccgc attggttggt tcatcaccag aagctcttga taccctgaat gagcttgccg  1440
cagcacttgg taatgacccg aactttgcga caacaatgac aaatgcgctg gcaggcaaac  1500
agcctctgga tgcaacttta accgcgctcg ctggccttgc gactggtgca aacaaactgc  1560
cttatttcac cggtaaggat acggtagcgc agactgattt aacgtcagtc ggtcgcgata  1620
ttctggctaa aacaagcaca ctggccgtta tccaatacct tggtttaaga gaactcggta  1680
ccagtggtga aaagatcccc ctgttgagta cggctaacac atggagtgcg cgccagactt  1740
tcaatggcgg gatcaccggg gcgctgatag ggaacgccga caccgcgacg aaattgaaaa  1800
cagccataaa cattaatggc gtcaggttcg atggttcggc tgacattaat atcaatactc  1860
tggtatcgcg tggtcgcgta acggctctgg gggcgaatgc acaggggaca tccgggattc  1920
agctgtatga ggcatacaac aatggctatc cttcccccta tggcaatgtg cttcacctta  1980
aaggtgccac cgctgctggc gaaggtgaat tattcattgg ctggagtgtc tcgagcggtg  2040
accatgcgcc cgtacatatc cgttcgcggc gtgatattga ttctgccaac tggtctgaat  2100
gggcacaggt ctatacgtca aaagattcag ttcccggcgt taatgccaaa gggaatcagg  2160
atacctctgg taatgcggct acagcgacca aattgcagac ggcgtgtact atcaacggtg  2220
tctcgtttga tggttctaaa aacattgagc taacggcgga agatttaaat cttgagcaaa  2280
```

ccgtagaatt agccgcagga gcattgcaga aaaaccagaa cggtgcagat attccgaata 2340
aagataaatt catacaaaac acaggggcct gtcgtgcatt tagcggtcag actgatatcg 2400
atggttcaca aggtgaatgg tcgacagttg catttatctc gtggctggag aataacggag 2460
ctttccgaca tccatactgg atgtgtaaag ggtcatggtc ctatgccaga aacagggtta 2520
ttacggatac cggttgtgga aatatctgcc ttgccggagc cgtgattgag gttatgggaa 2580
cccgcggcgc aatgaccata cgcgttacca cgccgagcac gtccagcggt ggcggaatca 2640
ctaacgctca attcacttat attaatcatg gtgatgctta cgctcctggc tggcgacgag 2700
actacaacac gaaaaaccag cagcctgcat ttgctttagg gcaaacagga cgcagggtcg 2760
caaatgataa agctgttggc tggaactgga atagcggcgt ttatgatgca gatatcagtg 2820
gcgcatcgac attaatcctc cactttaata tgaatgcggg gagttgccct gctgtacagt 2880
tccgcgtgaa ttacagaaat ggcggtatct tttatcgttc agcgcgtgat ggttatggct 2940
ttgaagctaa ctggtcagag ttttacacca caacacgcaa accctctgcg ggagatgttg 3000
gtgcatatac gcaggcagaa tgtaactcaa ggtttattac aggtattcgc cttggcggtc 3060
tgtcatctgt tcagacatgg aatggtcctg gctggtctga caggtcaggt tatgtcgtta 3120
ctggttcagt taacggaaac cgtgatgaat taattgatac aactcaggca aggccaattc 3180
agtattgcat taatggaacg tggtataacg cggggagtat ttaattatga tgcacttaag 3240
aaatattaca gctggcaacc ctaaaacaaa agagcaatac cagctaacga aacaatttaa 3300
catcaaatgg ctttatacag aggatggaaa aaactggtat gaggaacaaa agaatttcca 3360
gtatgatacg ttgaaaatgg cctatgacca caacggcgtt attatttgta ttgaaaagga 3420
tgtttcagca attaatccag aaggcgcaag cgtcgttgaa ttacctgata ttacagcaaa 3480
tcgccgggct gatatttctg gtaaatggat gttcaaagat ggcgtagtgg taaagcgaac 3540
ttataccgag gaagagcaga ggcaacaagc ggaaaatgaa aagcaaagtc tgctacagct 3600
cgtcagggat aaaacccagc tatgggactc acagctacgg ctgggtatca tttccgccga 3660
gaataagcag aaattaaccg agtggatgct ctttgcgcag aaagtcgaat ccacagacac 3720
ctccagccta ccagtaacat ttcccgaaca acctgaatga 3760

SEQ ID NO: 20 moltype = DNA length = 3951
FEATURE Location/Qualifiers
misc_feature 1..3951
note = P1 S' tail fiber gene
source 1..3951
mol_type = genomic DNA
organism = Bacteriophage P1
SEQUENCE: 20
atgtctgacg tctcaacaaa cctctataag agtcagttgt tggactatta ctatcagcgg 60
cgcgctgaat cgtccattaa caaaggctct cgatttttaa tcagcaaggc cgttttcggt 120
accagttcgc tggttactaa gaaaggagat ggcacttatg agattggaga actgccaaag 180
gctttcgaac tggcagaact gaccagtcaa ttttgcacca tcaacctcgt cccaacctac 240
tcaggcggga taattactgt ccgaatggac cttgatcaaa gccagttgca ggaagggaaa 300
aactacccat tcaacactct ggttgttctg gataacgaga acaagccaat cgccattatt 360
tgtgtccagg aagactcgct gtatgtgggc aaaacatata ccgcagttat ggccataaac 420
acgactacag cataaggata tgcttgatga atgacgttac agttgttaca tcggttactt 480
acccatcatc cgagtcgttg gctctggtgg ccgatgtgca ataccacgaa ccatatctgt 540
cagccgcgct aaaccgaaaa ttcaggggga ttgttgaccc gggattttat gccggtttct 600
tacctaagcc tggcggtggg atgaacctgt taattacctc agtggatggt gataaaaccg 660
caggcgcggc gtcggtggat attggtgaat tttaccaggt aactattcag caacgtaagg 720
atatttctct tgcacttagt gcaggcaaga aatatgcaat tgtgctgaag ggaagatacc 780
tccttggaga agatacctac caggtgaata ccgcgtcaca tattcatgcg gctgaatttg 840
ttgccagaac ctataccgat tcatatcagt taggagatgg ggagctgctt gtttgtacgg 900
tgaatatccc tgctagtgta tctgccatta cccaggagat gattgataca tccgagcgta 960
tcaaccgctc gatcggcatt gatatttcag actctgtaac cagtaccaga agtgatgttg 1020
ctgcaagttc gctggcagtt aaaaaagcct acgatctggc gaaaagcaag tatacggcac 1080
aggatgcaag cacaacgcaa aagggattag ttcagctcag tagcgcaact aacagcgaca 1140
gcgaaacaat ggcggctacc cctaaagctg ttaagtctat aaaagatctg gctgatacca 1200
aagcgccaat agaaagcccg agtctgacag gaacgccaac cgcgccgacg gcagcgcaag 1260
gtacaaacag cacgcagatc gcaaatacag cctttgttaa ggcagctata actgcactta 1320
tcaacggtgc gcctggcaca ctggatacgc tgaaagaaat agcggctgcg atcaataacg 1380
acccgaatta cagcacaact atcaacaatg ccttggctct caaagcgcct ttggcaagcc 1440
ctgcattaac gggtgtccct actgcgccta cggctgcaca gggcacaaac aatacgcaga 1500
tcgctacgac tgcttacgta cgggctgcta tctctgcatt ggtcggctca tcacctgaag 1560
ctcttgatac cctgtatgag cttgcagcag cactgggcaa tgacccgaac tttgcgacaa 1620
caatgacaaa tgcgctggca gggaaacagc cacttgatgc aactttaacc gcgcttgctg 1680
gtcttgcgac aggcgcaaat aaattgccgt actttaccgg tacagacact gtttctcaga 1740
ctgacttaac gtcagttggt cgcgatattc tggccaaaac aagcattctt gctgttatcc 1800
aataccttgg tttaagagaa ctcggtacca gcggtgaaaa gatccccctg ttgagcacgg 1860
ctaacacatg gagtgcacgc cagactttca acggcgggat caccggggcg ctgacaggga 1920
acgccgatac cgcaacgaaa ttgaaaacag ccagaaacat taatggcgtc aggttcgatg 1980
gttctggtga cattaatatc aatactctgg tatcgcgcgg tcgcgtaacg gccctggagg 2040
cgaatgcaca gggaacatcc gggattcagc tgtatgaggc atacaacaat ggctaccctt 2100
ccccctatgg caatgtgctt caccttaaag gtgccaccgc tgctggcgaa ggtgagttat 2160
tcattggctg gagtggcacg agcggtgccc atgcgcccgt acatatccgt tcgcggcggg 2220
atactgattc tgccaactgg tctgaatggg cgcaggtcta tacgtcaaaa gattcaattc 2280
ccggcgtcaa tgccaaaggg gatcaggata cctctggtaa tgcggctaca gcgaccaagt 2340
tgcagacagc atgtactatc aacggtgtct cgtttgatgg ttctaaaaat attgagctaa 2400
cggctgaaaa tttaaatctt gagcgaacag tagaattagc cgctgggtca ttgcagaaaa 2460
atcagaacgg cgcggatatt cctggaaaag ataccttcac aaaaaatatt ggtgcatgtc 2520
gcgcttttca cagttctatt agtacaggtg cagggaactg gacaacggca caattgattg 2580
aatggctgga ttctcaaggg gcattcaatc acccatactg gatgtgcaaa tgttcatggt 2640
cgtacggcaa taataaaatt ataaccgata ctggctgtgg aactattcat cttgcaggtt 2700

```
gcgttattga ggttatgggt aataaaggtg ccatgaccat ccgtgtaaca acaccaagca  2760
cttccagcgg tggcggaatc actaacgctc aattcactta tattaatcat ggtgatgctt  2820
acgctcctgg ctggcgacga gactacaaca cgaaaaacct gcaacctgca tttgctttag  2880
ggcagacagg aaacagggtt gcaaatgata aagctgttgg ctggaactgg aatagcggtg  2940
tttatgatgc agacctaaaa ggcgcatcaa cattaattct tcatttcaat atgaacgcgg  3000
gtagctgccc ggctgtacaa ttacgcgtga attataagaa cggcggtatt tattatcgtt  3060
cagcgcgtga tggttatgga tttgaggctg actggtcaga gttttacacc acaacccgca  3120
aaccctctgc gggggatgtt ggtgcatata cgcaggcaga atgtaactca aggtttatta  3180
caggtattcg cctgggcggt ctgtcatctg tccagacatg gaatggcccc ggctggtctg  3240
acaggtcagg ttatgtcgtt acgggttcag ttaacgggaa ccgtgatgaa ttaattgata  3300
caacacaggc aaggccaatt cagtattgca ttaatgggac gtggtataac gcggggagta  3360
tttaattatg atgcacttaa gaaatattac agctggcaac cctaaaacaa aagagcaata  3420
ccagctaacg aaacaattta acatcaaatg gctttataca gaggatggaa aaaactggta  3480
tgaggaacaa aagaatttcc agtatgatac gttgaaaatg gcctatgacc acaacggcgt  3540
tattatttgt attgaaaagg atgtttcagc aattaatcca gaaggcgcaa gcgtcgttga  3600
attacctgat attacagcaa atcgccgggc tgatatttct ggtaaatgga tgttcaaaga  3660
tggcgtagtg gtaaagcgaa cttataccga ggaagagcag aggcaacaag cggaaaatga  3720
aaagcaaagt ctgctacagc tcgtcaggga taaaacccag ctatgggact cacagctacg  3780
gctgggtatc atttccgccg agaataagca gaaattaacc gagtggatgc tctttgcgca  3840
gaaagtcgaa tccacagaca cctccagcct accagtaaca tttcccgaac aacctgaatg  3900
agacaaggcc cgatagcggg ccttaatttt ctctcggctt gaacgaattg t           3951

SEQ ID NO: 21          moltype = DNA  length = 8085
FEATURE                Location/Qualifiers
misc_feature           1..8085
                       note = P1S-P1S'-Shamrock Tail Fiber
source                 1..8085
                       mol_type = other DNA
                       organism = synthetic construct
SEQUENCE: 21
cgaatggacc ttgatcaaag ccagttgcag gaagggaaaa actacccatt caacactctg  60
gttgttctgg ataacgagaa caagccaatc gccattattt gtgtccagga agactcgctg  120
tatgtgggca aaacatatac cgcagttatg gccataaaca cgactacagc ataaggatat  180
gcttgatgaa tgacgttaca gttgttacat cggttactta cccatcatcc gagtcgttgg  240
ctctggtggc cgatgtgcaa taccacgaac catatctgtc agccgcgcta aaccgaaaat  300
tcagggggat tgttgacccg ggattttatg ccggtttctt acctaagcct ggcggtggga  360
tgaacctgtt aattacctca gtggatggtg ataaaaccgc aggcgcggcg tcggtggata  420
ttggtgaatt ttaccaggta actattcagc aacgtaagga tatttctctt gcacttagtg  480
caggcaagaa atatgcaatt gtgctgaagg gaagatacct ccttggagaa gatacctacc  540
aggtgaatac cgcgtcacat attcatgcgg ctgaatttgt tgccagaacc tataccgatt  600
catatcagtt aggagatggg gagctgcttg tttgtacggt gaatatccct gctagtgtat  660
ctgccattac ccaggagatg attgatacat ccgagcgtat caaccgctcg atcggcattg  720
atatttcaga ctctgtaacc agtaccagaa gtgatgttgc tgcaagttcg ctggcagtta  780
aaaaagccta cgatctggcg aaaagcaagt atacggcaca ggatgcaagc acaacgcaaa  840
agggattagt tcagctcagt agcgcaacta acagcgacag cgaaacaatg gcggctaccc  900
ctaaagctgt taagtctata aaagatctgg ctgataccaa agcgccaata gaaagcccga  960
gtctgacagg aacgccaacc gcgccgacgg cagcgcaagg tacaaacagc acgcagatcg  1020
caaatacagc ctttgttaag gcagctataa ctgcacttat caacggtgcg cctggcacac  1080
tggatacgct gaaagaaata gcggctgcga tcaataacga cccgaattac agcacaacta  1140
tcaacaatgc cttggctctc aaagcgcctt tggcaagccc tgcattaacg ggtgtcccta  1200
ctgcgcctac ggctgcacag ggcacaaaca atacgcagat cgctacgact gcttacgtac  1260
gggctgctat ctctgcattg gtcggctcat cacctgaagc tcttgatacc ctgtatgagc  1320
ttgcagcagc actgggcaat gacccgaact ttgcgacaac aatgacaaat gcgctggcag  1380
ggaaacagcc acttgatgca actttaaccg cgcttgctgg tcttgcgaca ggcgcaaata  1440
aattgccgta ctttaccggt acagacactg tttctcagac tgacttaacg tcagttggtc  1500
gcgatattct ggccaaaaca agcattcttg ctgttatcca ataccttggt ttaagagaac  1560
tcggtaccag cggtgaaaag atccccctgt tgagcacggc taacacatgg agtgcacgcc  1620
agactttcaa cggcgggatc accggggcgc tgacagggaa cgccgatacc gcaacgaaat  1680
tgaaaacagc cagaaacatt aatggcgtca ggttcgatgg ttctggtgac attaatatca  1740
atactctggt atcgcgcggt cgcgtaacgg ccctggaggc gaatgcacag ggaacatccg  1800
ggattcagct gtatgaggca tacaacaatg gctacccttc cccctatggc aatgtgcttc  1860
accttaaagg tgccaccgct gctggcgaag gtgagttatt cattggctgg agtggcacga  1920
gcggtgccca tgcgcccgta catatccgtt cgcggcggga tactgattct gccaactggt  1980
ctgaatgggc gcaggtctat acgtcaaaag attcaattcc cggcgtcaat gccaaagggg  2040
atcaggatac ctctggtaat gcggctacag cgaccaagtt gcagacagca tgtactatca  2100
acggcgtctc gtttgacggt tctaaaaata ttgagctaac ggcggaagat ttaaatctac  2160
aggaaacggt aaacaaggct gataacgcgg ttcaaaagac aggcgatacc ttgtccggtg  2220
gacttacttt tgaaaacgac tcaatccttg cctggattcg gaatactgac tgggcgaaga  2280
ttggttttaa aaatgatgcc gacagcgata ctgattcata catgtggttt gaaacaggcg  2340
acaacggcaa tgaatatttc aaatggagaa gcaaacaaag taccacaaca aaagacctga  2400
tgaatcttaa atgggatgct ttgtatgttc ttgtcaatgc cattgtaaat ggcgaagtca  2460
tatcaaaatc agcaaacggc ctacgtattg cttatggtaa ttacggattc tttattcgta  2520
atgatggttc aaatacatac ttcatgttga caaactccgg tgacaacatg ggacttata   2580
acggattaag gccattatgg attaataacg ctactggcgc tgtttcgatg gggcgtggcc  2640
ttaatgtttc aggggagaca ctttcagacc gttttgctat taacagcagt aatggtatgt  2700
ggattcagat gcgcgataac aacgctatct ttgggaaaaa tatagttaac actgatagca  2760
ctcaggcgtt acttcgccag aatcacgccg accgaaagtt catgataggt ggactgggga  2820
acaagcaatt tggcatctac atgattaata actcaaggac agccaatggc accgatggtc  2880
aggcgtacat ggacaataac ggtaactggc tttgcggtgc gcaaattatt cccggaaatt  2940
```

-continued

```
atggcaattt tgactcacgc tatgtgagag atgtccgact tggcacacgt gttgttcaat  3000
tgatggcgcg tggagggcgt tatgaaagag ccggacacgc acttaccgga ttaaggatta  3060
ttggtgaagt tgatggcgat gatgacgcta tcttcaggcc gatacaaaaa tacatcaatg  3120
gcatatggta taacgtcgca caggtgtaaa ttatgcagca cttaaaaaat atcaggtcag  3180
gaaacccaaa gacaaaagag caataccaat taacaaagaa ttttgacgta atctggttgt  3240
ggtctgaaga cggaaaaaac tggtatgagg aagtgaaaaa ctttcaacca gacaccataa  3300
agattgttta cgatgaaaat aatattattg tcgccatcac caaagatgcc tccacgctta  3360
accctgaagg ttttagcgtc gttgaggttc ccgacataac agccaaccgc cgcgctgatg  3420
attcaggaaa gtggatgttt aaggatggag ctgtagttaa acggatttat acggcagacg  3480
aacagcaaca acaagccgaa tcacaaaagg ccgcattgct ttccgaagct gaatcagtca  3540
tccagccgct ggaacgcgct gtcaggctga atatggcaac agacgaggaa cgcacacgac  3600
tggaagcatg ggaacgctac agtgttctgg tcagccgtgt ggatacggca aatcctgaat  3660
ggccacaaaa gcctgaataa aaattaaggc ccgctatcgg gccttgtctc attcaggttg  3720
ttcgggaaat gttactggta ggctggaggt gtctgtggat tcgactttct gcgcaaagag  3780
catccactcg gttaatttct gcttattctc ggcggaaatg atacccagcc gtagctgtga  3840
gtcccatagc tgggttttat ccctgacgag ctgtagcaga ctttgctttt cattttccgc  3900
ttgttgcctc tgctcttcct cggtataagt tcgctttacc actacgccat ctttgaacat  3960
ccatttacca gaaatatcag cccggcgatt tgctgtaata tcaggtaatt caacgacgct  4020
tgcgccttct ggattaattg ctgaaacatc cttttcaata caaataataa cgccgttgtg  4080
gtcataggcc attttcaacg tatcatactg gaaattcttt tgttcctcat accagttttt  4140
tccatcctct gtataaagcc atttgatgtt aaattgtttc gttagctggt attgctcttt  4200
tgttttaggg ttgccagctg taatatttct taagtgcatc ataattaaat actccccgcg  4260
ttataccacg tcccattaat gcaatactga attggccttg cctgtgttgt atcaattaat  4320
tcatcacggt tcccgttaac tgaacccgta acgacataac ctgacctgtc agaccagccg  4380
gggccattcc atgtctggac agatgacaga ccgcccaggc gaatacctgt aataaacctt  4440
gagttacatt ctgcctgcgt atatgcacca acatcccccg cagagggttt gcgggttgtg  4500
gtgtaaaact ctgaccagtc agcctcaaat ccataaccat cacgcgctga acgataataa  4560
ataccgccgt tcttataatt cacgcgtaat tgtacagccg ggcagctacc cgcgttcata  4620
ttgaaatgaa gaattaatgt tgatgcgcct tttaggtctg catcataaac accgctattc  4680
cagttccagc caacagcttt atcatttgca accctgtttc ctgtctgccc taaagcaaat  4740
gcaggttgca ggttttcgt gttgtagtct cgtcgccagc caggagcgta agcatcacca  4800
tgattaatat aagtgaattg agcgttagtg attccgccac cgctggaagt gcttggtgtt  4860
gttacacgga tggtcatggc acctttatta cccataacct caataacgca acctgcaaga  4920
tgaatagttc cacagccagt atcggttata attttattat tgccgtacga ccatgaacat  4980
ttgcacatcc agtatgggtg attgaatgcc ccttgagaat ccagccattc aatcaattgt  5040
gccgttgtcc agttccctgc acctgtacta atagaactgt gaaaagcgcg acatgcacca  5100
atatttttg tgaaggtatc ttttccagga atatccgcgc cgttctgatt tttctgcaat  5160
gacccagcgg ctaattctac tgttcgctca agatttaaat tttcagccgt tagctcaata  5220
tttttagaac catcaaacga gacaccgttg atagtacatg ctgtctgcaa cttggtcgct  5280
gtagccgcat taccagaggt atcctgatcc cctttggcat tgacgccggg aattgaatct  5340
tttgacgtat agacctgcgc ccattcagac cagttggcag aatcagtatc ccgccgcgaa  5400
cggatatgta cgggcgcatg ggcaccgctc gtgccactcc agccaatgaa taactcacct  5460
tcgccagcag cggtggcacc tttaaggtga agcacattgc catagggga agggtagcca  5520
ttgttgtatg cctcatacag ctgaatcccg gatgttccct gtgcattcgc ctccagggcc  5580
gttacgcgac cgcgcgatac cagagtattg atattaatgt caccagaacc atcgaacctg  5640
acgccattaa tgtttctggc tgttttcaat ttcgttgcgg tatcggcgtt ccctgtcagc  5700
gccccggtga tcccgccgtt gaaagtctgg cgtgcactcc atgtgttagc cgtgctcaac  5760
aggggatct tttcaccgct ggtaccgagt tctcttaaac caaggtttag gattgacgcg  5820
ttggccgatt cattaatgca gctgcaaaaa acccctcaag acccgtttag aggccccaag  5880
gggttatgct agttattgct cagcggtggc agcagcttat tcaggctttt gtggccattc  5940
aggatttgcc gtatccacac ggctgaccag aacactgtag cgttcccatg actccagtcg  6000
tgcgtgttcc tcatccgtcg ccatattcag cctgacagcg cgttccagcg gctggatgac  6060
tgattcagct tcggaaagta acgcggcctt ttgtgattcg gcctgttgct gctgttcgtc  6120
tgctgtataa gtcctcctga ccaccgctcc gtccttaaac atccacttcc ctgaatcatc  6180
ggcacgacgg ttagctgtta tatcggggat ttcaacgacg ctaaaacctt caggattaag  6240
cgtggaggca tctttagtga cggcgacaat aatattattt tcgtcgtaaa caatctttat  6300
tgtatccggc tgaaagttct tcacttcctc ataccagttt ttcccgtctt cagcgtaaag  6360
ccagatgact ccgtgcttct ttgttaactc atactgctcc agtgttttag cattacccgc  6420
ttttatgttc tttaagtgca tcatattaaa cgctcgctac attataccat gtgccattta  6480
tatactttg aacgggtctg taataaacgc cagctatatt atcggcagag tttttgcctg  6540
tatcctgaac attaatacca gacaatacat gacctgaagg gcactggaaa ttccatgttt  6600
gccagttatt cacaccataa tattgctgtg agccaagccg gacatctttc acatatctgg  6660
agtcaaaatt gccataattg ccgggaataa cttgcgcacc acaaagccag ttaccgttat  6720
tatccatgta cgcctgacca tcggtgccat tggctgtcct tgagttatta atcatgtaga  6780
tgccaaattg cttatttccc agaccgccaa tcataaattt gcggtcggca tggtcctgac  6840
ggagcaaagc ctgagcacca tcagtggata ccgcattacg tcccaaaata acattctggt  6900
cacgcatatg aatccacatg ccggtactac tgttaattgc aaaacggttt gcaaatatat  6960
cccctgtaac atcaagacca tgccccatgc ttatccggcc agttctgaga ttaagcgtaa  7020
aggggcgtag tggccctata ttaccatttt cccctcatt ctctcgtgta gggatgatat  7080
gcaggcattc ttcagaacga cgaaaaatgg caccaaaaga tgaattaaat atcctcagtg  7140
cattgactgt cgatattttc acttcactgc tgaaaagggc ttcaacaaga acagacaaag  7200
cattccattt aagattcatc aggtctttag gccgggtgcc aatgatgcgg tgtctccatt  7260
tgaaatattc attgccgttg ttgcctgttt caaaccacat gtaggaatcg gtgtctgcat  7320
ccgaattatt tttaaaacca atcttcgccc agtcagtatt ccgaatccag gcaaggattg  7380
agtcgttttc aaaagtaagt ccaccggaca aggtatcgcc tgtcttttga accgcgttat  7440
cagccttgtt taccgtttcc tgtagattta aatcttccgc cgttagctca atattttag  7500
aaccgtcaaa cgagacgccg ttgatagtac atgctgtctg caacttggtc gctgtagccg  7560
cattaccaga ggtatcctga tcccctttgg cattgacgcc gggaattgaa tcttttgacg  7620
tatagacctg cgcccattca gaccagttgg cagaatcagt atcccgccgc gaacggatat  7680
```

```
gtacgggcgc atgggcaccg ctcgtgccac tccagccaat gaataactca ccttcgccag  7740
cagcggtggc acctttaagg tgaagcacat tgccataggg ggaagggtag ccattgttgt  7800
atgcctcata cagctgaatc ccggatgttc cctgtgcatt cgcctccagg gccgttacgc  7860
gaccgcgcga taccagagta ttgatattaa tgtcaccaga accatcgaac ctgacgccat  7920
taatgtttct ggctgttttc aatttcgttg cggtatcggc gttccctgtc agcgccccgg  7980
tgatcccgcc gttgaaagtc tggcgtgcac tccatgtgtt agccgtgctc aacaggggga  8040
tcttttcacc gctggtaccg agttctctta aaccaaggta ttgga                  8085

SEQ ID NO: 22          moltype = DNA  length = 3212
FEATURE                Location/Qualifiers
misc_feature           1..3212
                       note = Pine Tail Fiber
source                 1..3212
                       mol_type = other DNA
                       organism = synthetic construct
SEQUENCE: 22
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcagggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttgaacagcc  1440
ctgcactgac cggaacgcca acgacgccaa ctgcgcgaca gggaacgaat aatactcaga  1500
tcgcaaacac ggctttcgtt atggccgcga ttgccgccct tgtagactcg tcgcctgacg  1560
cactgaatac gctgaacgag ctggcggcgg cgctgggcaa tgacccgaat tttgctacca  1620
ccatgactaa tgcgcttgcg ggtaagcaac cgaaagatgc taccctgacg gcgctggcgg  1680
ggcttgctac tgcggcagac aggtttccgt attttacggg gaatgatgtt gccagcctgg  1740
cgaccctgac aaaagtcggg cgggatattc tggctaaatc gaccgttgcc gccgttatcg  1800
aatatctcgg tttacaggaa acggtaaacc gagccgggaa cgccgtgcaa aaaaatggcg  1860
ataccttgtc cggtggactt acttttgaaa acgactcaat ccttgcctgg attcgaaata  1920
ctgactgggc gaagattgga tttaaaaatg atgccgatgg tgacactgat tcatacatgt  1980
ggtttgaaac gggggataac ggcaatgaat atttcaaatg gagaagccgc cagagtacca  2040
caacaaaaga cctgatgacg ttgaaatggg atgcactaaa tattcttgtt aatgccgtca  2100
ttaatggctg ttttggagtt ggtacgacga atgcactagg tggtagctct attgttcttg  2160
gtgataatga taccggattt aaacagaatg gagacggtat tcttgatgtt tatgctaaca  2220
gtcagcgtgt attccgtttt cagaatggag tggctattgc ttttaaaaat attcaggcag  2280
gtgatagtaa aaagttctcg ctatccagct ctaatacatc cacgaagaat attaccttta  2340
atttatgggg tgcttccacc cgtccagtgg ttgcagagtt aggcgatgag gccggatggc  2400
atttctatag ccagcgaaat acagataact cggtaatatt tgctgttaac ggtcagatgc  2460
aacccagcaa ctggggaaat tttgattccc gctatgtgaa agatgttcgc ctgggtacgc  2520
gagttgttca attgatggcg cgaggtggtc gttatgaaaa agccggacac acgattaccg  2580
gattaagaat cattggtgaa gtagatggcg atgatgaagc catcttcagg ccgatacaaa  2640
aatacatcaa tggcacatgg tataacgttg cgcaggtgta agttatgcag catttaaaga  2700
acattaagtc aggtaatcca aaaacaaaag agcaatatca gctaacaaag aattttgatg  2760
ttatctggtt atggtccgaa gacggaaaaa actggtatga ggaagtgaag aactttcagc  2820
cagacacaat aaagattgtt tacgatgaaa ataatattat tgtcgctatc accagagatg  2880
cttcaacgct taatcctgaa ggttttagcg ttgttgaggt tcctgatatt acctccaacc  2940
gacgtgctga cgactcaggt aaatggatgt ttaaggatgg tgctgtggtt aaacggattt  3000
atacggcaga tgaacagcaa caacaggcag aatcacaaaa ggccgcgtta ctttccgaag  3060
cggaaaacgt tattcagcca ctggaacgcg ctgtcaggct gaatatggcg acggatgagg  3120
aacgtgcacg actggagtca tgggaacgtt acagcgttct ggtcagccgt gtggatcctg  3180
caaatcctga atggccggaa atgccgcaat aa                                3212

SEQ ID NO: 23          moltype = DNA  length = 4609
FEATURE                Location/Qualifiers
misc_feature           1..4609
                       note = Plum Tail Fiber
source                 1..4609
                       mol_type = other DNA
                       organism = synthetic construct
SEQUENCE: 23
```

```
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcagttactt  480
acccatcgcc tgagtcactg gctctggtgg ctgatgtgca ataccacgaa ccatatctgt  540
cagccgcgct aaaccgaaaa ttcaggggaa ttgttgaccc tggattttat gcaggtttcc  600
tgccgaagcc tggtggtggg atgaacctgt taatcacctc agtggatggt gataaaactg  660
ctggcgctgc gtcagtggat attggtgaat tctaccaggt aactattcag caccgtaagg  720
atatttctct tgcacttagt gcaggcaaga aatatgcaat tgtgctgaag ggaagatacc  780
tccttggaga ggatacctat caggttaata ccgcgtcaca tattcatgcg gctgaatttg  840
ttgccagaac ctataccgat tcatatcagt taggagatgg ggagctgctt gtttgtacgg  900
tgaatatccc tgctggcgta tcagccatta cccaggagat gattgataca tccgagcgta  960
ttaaccgcac gatcggcatt gatatttcag actctgtaac cagtagcaga agtgatgttg  1020
ctgcaagttc gctggcagtt aaaaaagcct acgatctggc gaaaagcaag tatacggcgc  1080
aggatgcaag cacaacgcaa aagggattag ttcagctcag tagcgaaact aacagcgaca  1140
gcgaaacaat ggcggctacc cctaaagcca ttaagtctgt aaaagatctt gctgatacca  1200
aagcgccaat agaaagcccg agtctgacag gaacgccaac cgcgccgacg gcagcgcaag  1260
gtacaaatag cacgcagatc gcaaatacag cctttgttaa ggcagctata acggcactta  1320
tcaacggtgc acctggcaca ctggatacgc ttaaagaaat agctgctgcg atcaataacg  1380
acccgaattt cagcacaact atcaacaatg ctctggctct taaagctcct ttagcaagtc  1440
ctgcattaac gggaatacct actgcgccaa ccgctgcaca gggtacgaat aacacgcaga  1500
ttgctacgac cgcttatgta agagctgcca tatccgcatt ggttggttca tcaccagaag  1560
ctcttgatac cctgaatgag cttgccgcag cacttggtaa tgacccgaac tttgcgacaa  1620
caatgacaaa tgcgctggca ggcaaacagc ctctggatgc aactttaacc gcgcttgcgg  1680
gtcttgctac aggcgcaaat aaattgccgt actttaccgg tacagacact gtttctcaga  1740
ctgacttaac gtcagtcggt cgcgatattc tggccaaaac aagcgtcctt gctgttatcc  1800
aataccttgg tttaagagaa ctcggcacaa gcggtgaaaa gatccccctg ttgagcacgg  1860
ctaacacatg gagtgcacgc cagactttta acggcgggat caccggggcg ctgacaggga  1920
acgccgatac cgcgacgaag ttgaaaacag cacggaagat taacaacgtt tcatttgatg  1980
gttcggcaga cataacgctg acacctgaga accttggcgt caccagtctg acgtttgaga  2040
aaaacaacgg tgaaatgcct attgatgctg acctaaatac tttcggtccc gttgaggctt  2100
atcttggtgt ctggtccaaa gcaacatcca ccaacgcaac actggagaaa aatttcccgg  2160
aagataatgc tgtcggtgtg cttgaggtat ttgctgccgg aaattttgca ggtacgcaac  2220
gctttaccac gagagacggc aatgtataca tacgcagact cgccaataag tggaatggct  2280
ctgatggtcc gtggggcata tggcgtcaca ctcaatcagc tacccgccct ttgagtacga  2340
ctatagacct gaatacgctt ggagccgccg aacatcttgg tttatggcgt aacagtagct  2400
cggctatagc ttcatatgaa cgcaattatc cagaggaagg cggctttgct caggggggtgc  2460
ttgagatcct cgaaggcggg aattatggaa gaacgcaacg ttataccact cgccgcggaa  2520
atatgtatgt ccgctgcctt gcggcaagct gggatgcatc aaatccgcag tgggaaccgt  2580
ggttaaaagt cggtcatcag tcagagagtc gttattacga aggtgattta aatgttctaa  2640
ccgaccccgg tatttacagt gttacaggaa aggcaacaaa cggtccgatg ctggacaccg  2700
ttggcgcgac actacttggg atactggaag taatcagacg ttttgatggt gtgtctgtct  2760
ggcagcgtta cacaaccaca gggaaatcag aaaccacaca gggacgcact tttgagcgcg  2820
tctacgccgg gagcaaatgg accgaatggc gagaagtata taactccttt tcgttgcctc  2880
tgaatctggg catcggtggc gcagtggcaa aactatccag tctggactgg cagacctacg  2940
attttgtgcc gggcagtctg ataaccgtgc ggcttgataa catgaccaac attcccgacg  3000
gtatggactg gggcgtcatt gatggcaacc tgataaacat cgcagttggt ccgagtgatg  3060
attccggtac ggggcgctca atgcatgtat ggcgcagcac tgtaagtaaa gcgaactacc  3120
gctttttat ggtgcgtatt tcaggaaatc cgggaagccg cacgatcaca gcaagacgag  3180
taccaatcat tgacgaagcc cagacatggg gcgcgaaaca gacattcagt gctggccttt  3240
ctggtgaact gtccggcaat gcggcgacag caacaaagct gaaaacagcc cgtaaaatta  3300
ataacgtttc gtttgatggt tccggggata ttgaggtcct tcctgttggt gttccgctgc  3360
cgtggccatc agatactgtg ccgtctggtt acgccctgat gcagggacag actttgaca  3420
aatctgcata cccgaaactt gcagccgctt atccgtcagg cgtgatcccg gatatgcgtg  3480
gctggacaat caagggcaaa cccgccagtg gtcgggacgt attgtctctg gaacaggatg  3540
gcattaaatc gcacacccac agcgccagcg catccaatac ggatttgggt acgaaaacca  3600
catcttcgtt tgattacggt actaaatcaa cgaataacac aggtgcacat acccacaatg  3660
tatctggtac tgcaaatagt gctggcgcac atactcatac cgtgccatta aggagaccaa  3720
acagtggcgg tatgaatttc gactggctgg atggtgcatc aagtggcacg gtggtgggga  3780
atggaactgt gccttcttct ggcgcacata cccactcagt atcaggcacc gctacaagtg  3840
ctggggcaca tgcacacact gttggtattg gcgctcatac gcactctgtt gcgattggtt  3900
cacatggaca taccatcacc gttaacgctg ctggcaacgc ggaaaacacc gttaaaaaca  3960
tcgcatttaa ttatattgtg aggcttgcat aatggcattc agaatgagtg aacaatcacg  4020
tactgtaaaa atttataacc tgctggccgg aactaatgag tttattggtg aaggtgacgc  4080
atatattcca cctcatacag ggctgccagc taattctaca gatatcgccc caccggaaat  4140
tcctgctggc tttgtggcag tttttaacag tgaaaatgaa tcgtggaata ttgttgaaga  4200
ccatcgtggt aaaacggtct atgacgtggc atcgggggac gcgttgttta tttctgaacc  4260
cggaccgcta ccagagaatg tcacctggtt gtcgccagca ggggaatatc agaagtggga  4320
cggcgtatcc tgggtgaagg atgaggaagc agaaaaactg tttcggatac gggaagcgga  4380
agagaaaaag gcaaggttga tccaggaggc aacagataac atcgcaattc tgcaggatgc  4440
agttaatctt gaaatagcaa caaacgagga aaattcacaa ctggattcct ggagaaaata  4500
cagagtatta gtgagtagaa ttgacaccag tacagctccg gatatcgtat ggccagagct  4560
gatgaatcag ggttatgtgc gggaggacga gcagataact tcagactga  4609
```

SEQ ID NO: 24 moltype = DNA length = 4723

```
FEATURE                 Location/Qualifiers
misc_feature            1..4723
                        note = Queen Tail Fiber
variation               2370
                        note = n is a, c, g, or t
variation               2385
                        note = n is a, c, g, or t
variation               2431
                        note = n is a, c, g, or t
source                  1..4723
                        mol_type = other DNA
                        organism = synthetic construct
SEQUENCE: 24
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cgggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
aataccttgg tttaagagaa ctcggtacca gcggtgaaaa gatccccctg ttgagcacgg  1860
ctaacacatg gagtgcacgc cagactttca acggcgggat caccgggggcg ctgacaggga  1920
acgccgatac cgcaacgaaa ttgaaaacaa aaaggtcgct tcaagttgac ctccaaagtg  1980
ataacgccat cgactttgat ggttcatcaa atgctcttct gggcataaaa ggtattttac  2040
caattactca tgggggatta ggtgcatcca gcgtctctgg agggcgtact aatcttggat  2100
taggtgttgc ggacatcccc caatttaagg gtatcaatct tgttaactca acagactctg  2160
atttagcggc gtcagggatt gtaagtggtt atctgaataa ttcagctggg gtacagagga  2220
gtcgtttcag aatttattca gagataagga gtgacaaccg ctcatggctg acgttacatc  2280
tacaatctga taccaacacc aataaatatg ccggattaga cattgacggt aattttctga  2340
ttaccggtga tagcaaatgc cgagcattan aaccaactga tgtancgtta acaagaaaaa  2400
atattgatgt ttacagcaaa gccgaagtag nccttaaaaa agggatgaaa ttcaccagag  2460
tcaatgctcc ttctggagct gaagagggta aattctatcc tgtagtcatc aagagatctg  2520
caacgagcaa tggtgaactt gcttctcggg ttattatttc cactgcgccg cgccaagctg  2580
cacatcgcat gaacaactgc gaattcaatg gttttgtgat gcctgctggt tggagtgaca  2640
gagggcggta cgcatacggg atgttctggc aatatcagga tgcagaacgg gcgattcatt  2700
ctattgcgat gagcaataaa gacgatgaag ttagctcagt tttttatatt gaaggcggag  2760
catttccagt atgcgttctt gtggaggagg ggctttctgt tgttgtccct acaacggatt  2820
atrttgttgg acaaaccaca tacaaatggg gggcaaccaa ccctaaagct gaatgtatag  2880
ctgccgacat aattattgat tttagcaatg gtcgtggttt ctatagctct ggaaacctca  2940
atggtaatgc tgcaacagca actaaattac agaccgccag aacaatcaac ggagtaacct  3000
tcgatggcac tactgatatt tcgttgacac cagagaacat tggcgcgctg tcactatccg  3060
gaggcacatt attaggaggt ctgacagctc ctttacttac cactaaaagc gatcttattt  3120
ttagtagcca tacaagccgt catatccgct ttacatatac gaaaaatgac ggcacaacac  3180
taactgatgg gtacatattt aaagatggtg tcgataaccc taacagacga ccaggtatcc  3240
ggataaattg tgctgcgccg aatgamgtgc tcrcgtcagt tgttgacgat gcaaaaatgt  3300
atctgcgacg tttccgctcc agcacaggtg caagcatatg gcatgaaaca atagagaata  3360
acgtttatcg cttatgcaca ggaacaactg acgctcagga agagttagtc ttgaggactg  3420
gttcctatgc gaaattcgct ggcgagatta tttccaaatc ggcgaatggt cttcgtattg  3480
cctatggcaa ctatggattc tttatccgaa acgatggttc aagcacatac ttcatgttga  3540
ccgcctcggg tgacaatctt ggaacatgga atagtttaag accgcttacc attaacaacg  3600
ctaacggggc tgtttcaatc ggtaatggac tcaatgtaac tggcgatata agaaccaatg  3660
catgggtata tgcaaacaga ttttctgtta atagcagctc aggttcttgg attagtatgc  3720
gagatcaaaa tgttattttt ggtcttaata aggtatcaac cagttccgcc caggcattat  3780
taagacaaga ccatgctgac agaaagttct ttattggtgg tcttggtaat agtcaattcg  3840
gcttttacat gattaacaac tcaagaacat caaatggtac agatggccag gcatttcttg  3900
atagcagtgg taacttccag tgcggcgggc aaatacttcc aactaactat agtaattttg  3960
```

```
actcgcgcta cacattaaaa acggcttgtg tgacaagcgt aagaatggga tctgctgcca  4020
gttataaacc atcaagcaat ggtgtttcct ggactcagaa tctaggaagc ggactggtta  4080
tgacaggtat tattgttcaa gaaacaggag gtaattcagc cgacaatatc ggcgggattt  4140
attatcgacc ggttcagtat tgtatcaacg gtacatggta cacagcagca tcagtataat  4200
gagagagcat atgaataact ttaaaaattt cgcaccatat acgcctggtg aagataaaag  4260
agagcttgtt gatgcaggag ttttattcct gttggatgaa aatggtaacg actggtatga  4320
atgtcaaaag ttattttcgg aatgtacaaa ggtaattgcg tatgatagca acaatatcgt  4380
tgtcagcatt acagatgacg cctcaaccct ttggcccata ggattatctg tagcagaagt  4440
ggatagttta cctgaagatg tagatatcaa cggtggttgg gtgtttagag acaactctgt  4500
tgttaaacgc atatattctg atacggagtt acaacagcaa gctgaatcaa aaaaggctgc  4560
cttactttca catgccgaat cagttattgt aactcttgag cgggcggtta aattgaatat  4620
ggcaacagat gaggaacgag ctaaactgga agcatgggag cgttatagcg tgttggttta  4680
tcgcgtagat acagctaaac cagaatggcc agaagaaccg tag                    4723

SEQ ID NO: 25          moltype = DNA  length = 3908
FEATURE                Location/Qualifiers
misc_feature           1..3908
                       note = Razzmatazz Tail Fiber
source                 1..3908
                       mol_type = other DNA
                       organism = synthetic construct
SEQUENCE: 25
atgtctgacg tctcaacaaa cctctataag agtcagttgt tggactatta ctatcagcgg  60
cgcgctgaat cgtccattaa caaaggctct cgattttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgtcaca tcggttactt  480
acccatcacc cgagtcgttg gctctggtgg ctgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taatcacctc agtggatggt gataaaaccg  660
caggcgcggc gtcggtggat attggtgaat tctaccaggt aactattcag caacgtaagg  720
atatttctct tgcacttagt gcaggcaaga aatatgcaat tgtgctgaag ggaagatacc  780
tccttggaga agatacctat caggtgaata ccgcgtcaca tattcatgcg gctgaatttg  840
ttgccagaac ctataccgat tcatatcagt taggagatgg ggagctgctt gtttgtacgg  900
tgaatatccc tgctggtgta tctgccatta cccaggagat gattgataca tccgagcgta  960
tcaaccgcac gatcggcatt gatatttcag actctgtaac cagtaccaga agtgatgttg  1020
ctgcaagttc gctggcagtt aaaaaagcct acgatctggc gaaaagcaag tatacggcgc  1080
aggatgcaag cataacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaag cgcgccgacg gcagcgcaag  1260
gtacaaacag cacgcagata gcaaatacag cctttgttaa ggcagctata actgcactta  1320
tcaacggtgc acctggcaca ctggatacac ttaaagaaat agctgctgcg atcaataacg  1380
acccgaattt cagcacaact gtcaacaatg ctctggccct taaagcgcct ttagcaagtc  1440
ctgcattaac gggaatacct actgcgccta ccgctgcaca gggtacgaat aacacgcaga  1500
ttgctacgac cgcttatgta agagctgcca tatccgcact ggtcggctca tcacctgaag  1560
ctcttgatac cctgaatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac agacgcaaat aaattgccgt actttaccgg tacagacact gtttctcaga  1740
ctgacttaac gtcagtcggt cgcgatattc tggccaaaac aagcgttctt gctgttatcc  1800
aataccttgg tttaagagaa ctcggtacca gtggtgaaaa gatccccctg ttgagcacgg  1860
ctaacacatg gagtgcacgc cagactttta acggcgggat caccggggcg ctgacaggga  1920
acgccgacac cgcgacgaaa ttaaaaacag ccataaacat taatggcgtc agattcgatg  1980
gttctacgaa catttcgata ccaacaatta cgtctagagg acgcgttact gcgcttaccg  2040
gtacaacgca aggtgctgct actggattgc agatgtatga ggcatacaac aatggttatc  2100
cgacgactta cgggaatgta cttcacctga agggagctgc atccactggt gaaggcgagt  2160
tgctcattgg ctggagtggc acaaatggcg ctcatgcacc agctttcatt cgatccaaaa  2220
gagatagcac tgctgcggca tggtccgaat gggcacagat ctatacgtca aaagattccg  2280
ttcccggcgt taataccaaa gggaatcagg acacctctgg taatgcggct acagcgacca  2340
aattgcagac ggcgtgtact atcaacggtg tctcgtttga cggttctaaa aatattgagc  2400
taacggcggc agatttaaat cttgagcaaa ctgtagaatt agccgcagga gcattacaga  2460
aaaaccagaa cggcgcagat attccgggaa aagatacctt caccaaaaat attggtgcct  2520
gccgcgcata tagcgcatgg ctgaatattg gtggcgatag tcaggtctgg acaaccgcgc  2580
aatttatttc gtggctggag agtcagggag catttaacca tccttactgg atgtgcaaag  2640
gctcatgggc ttatgcaaat aataaggtca ttacagatac aggttgcgga aatatttgtc  2700
ttgcaggtgc tgtggtggaa gttattggca ctcgcggcgc aatgaccata cgcgttacta  2760
cgccgagcac gtccagcggt ggcggaatta ctaacgctca attcacttat attaatcatg  2820
gtgatgctta tgctcctggc tggcgaagag actacaacac gaaaaaccag cagcctgcat  2880
ttgctttagg gcaaacagga agcagggttg caaatgataa agctgttggc tggaactgga  2940
atagcggcgt ttatgatgca gatatcagtg gcgcatcgac attaatcctc cacttcaata  3000
tgaatgcggg gagttgccct gctgtacagt tccgcgtgaa ttataagaac ggcggtatct  3060
tttatcgttc agcgcgtgat ggttatggct ttgaagctaa ctggtcagag ttttacacca  3120
caacccgcaa accctctgcg ggggatgttg gtgcatatac gcaggcagaa tgtaactcaa  3180
ggtttattac aggtattcgc ctaggcggtc tgtcatctgt tcagacatgg aatggtcccg  3240
gctggtctga caggtcaggt tatgtcgtta caggttcagt taacggaaac cgtgatgaat  3300
taattgatac aactcaggca aggccaattc agtattgcat taatgggacg tggtataacg  3360
cggggagtat ttaaatgatg cacttaaaaa acattactgc tggcaaccct aaaacaaaag  3420
```

```
agcaatacca gctaacgaaa caatttaaca tcaaatggct ttatacagag gatgggaaaa  3480
actggtatga ggaacaaaag aactttcagc ctgatacgtt gaaaatggtc tatgaccaca  3540
acgacgttat tatttgtatt gaaaaggatg tttcagcaat taatccagaa ggcgcaagcg  3600
tcgttgaggt tcctgatatt acagcaaatc gccgggctga tatttcgggt aaatagatgt  3660
tcaaagatgg cgtagtgata aagcgaactt ataccgagga ggaacaaagg cagcaggcag  3720
agaatgaaaa acaaagcctg ttgcaacttg tcagggataa aacccagcta tgggactcac  3780
agctacggct gggcatcatt tccgacgaga ataaacaaaa attaactgag tggatgctct  3840
atgcgcagaa agtcgaatct acagacacct ccagcctgcc agtaacattt cccgaacaac  3900
ctgaatga                                                           3908

SEQ ID NO: 26          moltype = DNA  length = 3683
FEATURE                Location/Qualifiers
misc_feature           1..3683
                       note = Salmon Tail Fiber
source                 1..3683
                       mol_type = other DNA
                       organism = synthetic construct
SEQUENCE: 26
atgtctgacg tctcaacaaa cctctataag agtcagttgt tggactatta ctatcagcgg  60
cgcgctgaat cgtccattaa caaaggctct cgattttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agataccctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cgggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
aataccttgg tttaagagaa ctcggtacca gcggtgaaaa gatccccctg ttgagcacgg  1860
ctaacacatg gagtgcgcgc cagactttca acggagggat caccggggca ctgacaggga  1920
acgccgacac cgcgacgaaa ttgaaaacag cacgcactat tggcggtgtg gcatttgatg  1980
gtactgcgaa tattaattta cctggtgtta acgttgcggg taatcagaat acatccggta  2040
acgcggctac agcgaccaag ttgcagacag catgtactat caacggcgtc tcgtttgatg  2100
gttctaaaaa tattgagcta acggcggaag atttaaatct acaggaattt attaataaag  2160
caaataatgc cgttcagcgt tcaggcgata tcttgtccgg cggacttact tttgaaaacg  2220
actcaatcct tgcctggatt cgaaatactg actgggcaaa gattggattt aaaaatgatg  2280
ccgacagcga cacagattca tacatgtggt ttgaaacagg cgacaacggc aatgaatatt  2340
tcaaatggag aagcaaacaa agcaccacaa caaaagacct gatgaatctt aaatgggatg  2400
ctttgtctgt tcttgttaaa gccctttcca gcagtgaagt aaaaatatcg acagtcaatg  2460
cactgaggat atttaattca tcttttggtg ccatttttcg ccgttctgaa gaatgcctgc  2520
atatcatccc tacacgagag aatgaggggg aaaatggtga tatagggcca ctacgtccct  2580
ttacgcttaa tctcagaact ggccgcataa ctatggggca tggtctggat gttacaggag  2640
atataacaac taacgcctgg gtgtatgcaa acaggtttgc tattaatagt ggctcaacct  2700
catggattga tatgcgaaac cagaatgtca ttttggtag aaacgcagta tcaacaagtt  2760
ctgcgcaggc tttgttaaga caagaccatg cagaacgcaa attttttgtc ggtggacttg  2820
gtaactacca gtttggtttt tacatgatta ataactcaag gacagccaat ggcaccgatg  2880
gtcaggcgta catggataat aacggtaact ggctttgtgg ctcgcaagtt attcctggca  2940
actatggcaa ttttgattcc agatatgtga gagatgttcg cctgggtacg cgagttgttc  3000
aattgatggc gcgtggtggt cgttatgaaa aagccggaca cgcaattacc ggattaagaa  3060
tcattggtga agtagatggc gatgatgaag ccatcttcag gccaatacaa aaatacatca  3120
atggcacatg gtataacgtc gcacaggtgt aaatgatgca gcatttaaaa aatattaagt  3180
ctggaaatcc taaaacgaaa gaacaatatc agctaacaaa gaattttgat gttatctggt  3240
tatggtccga agacgataaa aactggtatg aggaagtgaa aaactttcag ccagacacaa  3300
taaagattgt ttacgatgca aataatatta ttgtcgccat cactaaagat gcctccacgc  3360
ttaaccctga aggttttagc gtcgttgagg ttcctgatat tacagccaac cgccgcgctg  3420
atgattcagg aaagtggatg tttaaggatg gagctgtagt taaacggatt tatacggcag  3480
acgaacagca acaacaggcc gaatcacaaa aggccgcatt gctttccgaa gctgaatcag  3540
tcatccagcc gctggaacgc gctgtcaggc tgaatatggc aacagacgag gaacgcacac  3600
gactggaagc atgggaacgc tacagtgttc tggtcagccg tgtggatacg gcaaatcctg  3660
```

```
aatggccaca aaagcctgaa taa                                          3683

SEQ ID NO: 27          moltype = DNA  length = 3301
FEATURE                Location/Qualifiers
misc_feature           1..3301
                       note = Scarlet Tail Fiber
source                 1..3301
                       mol_type = other DNA
                       organism = synthetic construct
SEQUENCE: 27
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgtcac cgttgttacg agtgttacct  480
acccctcgcc tgagtcatta gcgttagttg cagacgttca gtaccacgaa ccgtatcttt  540
cagcagctct taaccgtaaa ttccgcggaa ttgtcgatcc aggattttac gccgggttcc  600
tgcctaagcc tggcggcggc atgaatcttc tgattacgtc agtcgacggg gataaaactg  660
cgggagcggc atcggtagat atcggggaat tctaccaggt tacaattcaa catcgtaaag  720
acatttcgtt agcacttaac gctgggaaga aatacgccat tgtcttgaaa ggccgctatt  780
tgttaggtga agatacgtac caggtcaata cagcaagtca catccacgcc gctgaatttg  840
tcgcacgtac atataccgat tcctaccagc ttggggatgg tgagttactt gtgtgcaccg  900
tgaacattcc tgctggagtg tcaacgatca cgcaggagat gatcgatact tcagagcgta  960
ttaatcgcac gatcgggatt gatatttcag acagcgtcac ctcgactcgc tcagatgtcg  1020
cggcttcatc tcttgcagtg aaaaaggcct acgacctggc caagtcgaag tacacagctc  1080
aggacgcgag caccacccaa aagggtctgg tacagttatc atctgcgacg aattcaacat  1140
ccgaggttct tgcagcgaca cctaaagcgg taaaagccgc gtatgatctt gccaatggga  1200
aatacaccgc acaggacgcc acaactacac aaaagggtat tgtgcagttg tcgagtgaca  1260
ccaactcaac gtcggagaca ctggcggcca cgccgaaagc agtcaaagct gcatacgacc  1320
ttgcggctgg taaagcgccc tcatcccaca ctcacccctg gaatcagatt actggtgtac  1380
ccaccgcaag cttaactgca aagggtatca ctcaattgag ttccgcgacc aacagcacca  1440
gtgaagtttt agctgctacc ccaaaggcag ttaaagccgc ttacgacttg gctaatggaa  1500
aatatacagc gcaggacgcg accactgcac aaaaaggaat tgtgcaactt tcgagcgcaa  1560
cgaactccac aagtgaagtt ttggcagcta cgcctaaagc cgtcaaagcc gcgtatgatt  1620
tggcgaatgg taagtatact gcgcaagatg cgacgactac gcagaaaggt attgtccaac  1680
tgtcaagtga caccaacagc acgtcagaga ccttggctgc tacacctaaa gcagtgaaag  1740
ctgcctatga tcttgcggct gggaaagccc cgtcatcaca cacacatcca tggaaccaga  1800
ttacggtcgt acctacggcc tctttaactg cgaagggcat tacacaatta tcatccgcga  1860
ctaacagcac cagtgaggtt ttagctgcaa caccgaaagc agtgaaggca gcctacgatt  1920
tggcgaacgg taaatatacg gctcaagatg cgaccaccgc gcaaaagggc attgtgcaac  1980
tgtcgtctgc aacaaattca acgtcggaag ttctggcagc aactccaaag gcagtgaaag  2040
ccgcctatga cttagcaaac ggtaaacagg ccgcggatgc gacgttaacg gcattggcgg  2100
ctcttgcaac tgcagcggac aagttaccgt atttcacggg cgttgaccgt gctgccctga  2160
cagcgttaac ctctgttggg cgtgccattt taggcaagac ctcgattcaa tctgttttag  2220
attaccttgg tttgggggaa ggctctgcac tgcctgttgg tgtgcccgtt ccgtggccct  2280
tagaaacacc accaacgggc tggctaaaat gcaatggtgc agcattttct tctgaaatgt  2340
atcccaaact ggcaaaggcc taccccacca ataaattacc ggatttacgc ggtgagttta  2400
tccgtggttg ggatgatggg cgaggtgtgg atgcgggaag ggtcatctta agcatacagg  2460
ggtggttaac aggaagtcat tatcataata ttcggtcatg ggacgcgtgg gataacacgg  2520
tattggtgcc aaatgacaga ggggggggata gtctgttgtc gacagataac gccgtccggc  2580
aaggagcgat taatggtaaa tttaccagtc aatacagaac ggagttatct gggggggaatg  2640
aaacccgccc acgtaacatt gccttcaatt atattgtgag agcagcataa tggataatgc  2700
gatattaaat agcgaactta tagccataca ggcaggaaac attatcgttt ataactatga  2760
tggtggtaat cgggaatata tttctgcatc aactgaatat cttgctgttg gcgttggtat  2820
tccggcaaat tcttgtttgg atgctccagg ctcacataaa gcaggttatg cgattctccg  2880
ttcagaggat ttaagttcat gggagtatgt gccagatcat cgtggcgaaa ctgtctatag  2940
cattgacaca gggaatcccg aagaaatcac ggtgttgggt gactatccgg aaaatacaac  3000
cactatcgcc ccgctaacac catacgacaa atggatggga gagaaatggg tggttgatac  3060
tgaggctcaa catagtgcag ctgtagaggc agcagaaaca aaacgtcagt cattgattga  3120
tactgcgatg gattccatta gtctgattca gttgaaatta cgggctggac ggaagttgac  3180
gcaggcagaa accacgcagc ttaactccgt gctagattat atagacgagc tgaacgcgat  3240
ggatttaacc acggcaccag atctcaactg gcctgaaaaa caactttcta cagccagttg  3300
a                                                                  3301

SEQ ID NO: 28          moltype = DNA  length = 3965
FEATURE                Location/Qualifiers
misc_feature           1..3965
                       note = Shamrock Tail Fiber
source                 1..3965
                       mol_type = other DNA
                       organism = synthetic construct
SEQUENCE: 28
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
```

```
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cgggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
aataccttgg tttaagagaa ctcggtacca gcggtgaaaa gatccccctg ttgagcacgg  1860
ctaacacatg gagtgcacgc cagactttca acggcgggat caccggggcg ctgacaggga  1920
acgccgatac cgcaacgaaa ttgaaaacag ccagaaacat taatggcgtc aggttcgatg  1980
gttctggtga cattaatatc aatactctgg tatcgcgcgg tcgcgtaacg gccctggagg  2040
cgaatgcaca gggaacatcc gggattcagc tgtatgaggc atacaacaat ggctaccctt  2100
cccccctatgg caatgtgctt caccttaaag gtgccaccgc tgctggcgaa ggtgagttat  2160
tcattggctg gagtggcacg agcggtgccc atgcgcccgt acatatccgt tcgcggcggg  2220
atactgattc tgccaactgg tctgaatggg cgcaggtcta tacgtcaaaa gattcaattc  2280
ccggcgtcaa tgccaaaggg gatcaggata cctctggtaa tgcggctaca gcgaccaagt  2340
tgcagacagc atgtactatc aacggcgtct cgtttgacgg ttctaaaaat attgagctaa  2400
cggcggaaga tttaaatcta caggaaacgg taaacaaggc tgataacgcg gttcaaaaga  2460
caggcgatac cttgtccggt ggacttactt ttgaaaacga ctcaatcctt gcctggattc  2520
ggaatactga ctgggcgaag attggtttta aaaataattc ggatgcagac accgattcct  2580
acatgtggtt tgaaacaggc aacaacggca atgaatattt caaatggaga caccgcatca  2640
ttggcacccg gcctaaagac ctgatgaatc ttaaatggaa tgctttgtct gttcttgttg  2700
aagccctttt cagcagtgaa gtgaaaatat cgacagtcaa tgcactgagg atatttaatt  2760
catcttttgg tgccattttt cgtcgttctg aagaatgcct gcatatcatc cctacacgag  2820
agaatgaagg ggaaaatggt aatatagggc cactacgccc ctttacgctt aatctcagaa  2880
ctggccggat aagcatgggg catggtcttg atgttacaggg ggatatattt gcaaaccgtt  2940
ttgcaattaa cagtagtacc ggcatgtgga ttcatatgcg tgaccagaat gttattttgg  3000
gacgtaatgc ggtatccact gatggtgctc aggctttgct ccgtcaggac catgccgacc  3060
gcaaatttat gattggcggt ctgggaaata agcaatttgg catctacatg attaataact  3120
caaggacagc caatggcacc gatggtcagg cgtacatgga taataacggt aactggcttt  3180
gtggtgcgca agttattccc ggcaattatg gcaattttga ctccagatat gtgaaagatg  3240
tccggcttgg ctcacagcaa tattatggtg tgaataactg gcaaacatgg aatttccagt  3300
gcccttcagg tcatgtattg tctggtatta atgttcagga tacaggcaaa aactctgccg  3360
ataatatagc tggcgtttat tacagacccg ttcaaaagta tataaatggc acatggtata  3420
atgtagcgag cgtttaaatg atgcacttaa agaacataaa agcgggtaat gctaaaacac  3480
tggagcagta tgagttaaca aagaagcacg gagtcatctg gctttacgct gaagacggga  3540
aaaactggta tgaggaagtg aagaactttc agccggatac aataaagatt gtttacgacg  3600
aaaataatat tattgtcgcc gtcactaaag atgcctccac gcttaatcct gaaggtttta  3660
gcgtcgttga aatccccgat ataacagcta accgtcgtgc cgatgattca gggaagtgga  3720
tgtttaagga cggagcggtg gtcaggagga cttatacagc agacgaacag cagcaacagg  3780
ccgaatcaca aaaggccgcg ttactttccg aagctgaatc agtcatccag ccgctggaac  3840
gcgctgtcag gctgaatatg gcgacggatg aggaacacgc acgactggag tcatgggaac  3900
gctacagtgt tctggtcagc cgtgtggata cggcaaatcc tgaatggcca caaaagcctg  3960
aataa                                                              3965
```

```
SEQ ID NO: 29          moltype = DNA  length = 3344
FEATURE                Location/Qualifiers
misc_feature           1..3344
                       note = Sunset Tail Fiber
source                 1..3344
                       mol_type = other DNA
                       organism = synthetic construct
SEQUENCE: 29
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
```

```
acgactacag cataaggata tgcttgatga atgacgtcac cgttgttacg agtgttacct  480
acccctcgcc tgagtcatta gcgttagttg cagacgttca gtaccacgaa ccgtatcttt  540
cagcagctct taaccgtaaa ttccgcggaa ttgtcgatcc aggattttac gccgggttcc  600
tgcctaagcc tggcggcggc atgaatcttc tgattacgtc agtcgacggg gataaaactg  660
cgggagcggc atcggtagat atcggggaat tctaccaggt tacaattcaa catcgtaaag  720
acatttcgtt agcacttaac gctgggaaga aatacgccat tgtcttgaaa ggccgctatt  780
tgttaggtga agatacgtac caggtcaata cagcaagtca catccacgcc gctgaatttg  840
tcgcacgtac atataccgat tcctaccagc ttggggatgg tgagttactt gtgtgcaccg  900
tgaacattcc tgctggagtg tcaacgatca cgcaggagat gatcgatact tcagagcgta  960
ttaatcgcac gatcgggatt gatatttcag acagcgtcac ctcgactcgc tcagatgtcg  1020
cggcttcatc tcttgcagtg aaaaaggcct acgacctggc caagtcgaag tacacagctc  1080
aggacgcgag caccacccaa aagggtctgg tacagttatc atctgcgacg aattcaacat  1140
ccgaggttct tgcagcgaca cctaaagcgg taaaagccgc gtatgatctt gccaatggga  1200
aatacaccgc acaggacgcc acaactacac aaaagggtat tgtgcagttg tcgagtgaca  1260
ccaactcaac gtcggagaca ctggcggcca cgccgaaagc agtcaaagct gcatacgacc  1320
ttgcggctgg taaagcgccc tcatcccaca ctcacccctg gaatcagatt actggtgtac  1380
ccaccgcaag cttaactgca aagggtatca ctcaattgag ttccgcgacc aacagcacca  1440
gtgaagtttt agctgctacc ccaaaggcag ttaaagccgc ttacgacttg gctaatggaa  1500
aatatacagc gcaggacgcg accactgcac aaaaaggaat tgtgcaactt tcgagcgcaa  1560
cgaactccac aagtgaagtt ttggcagcta cgcctaaagc cgtcaaagcc gcgtatgatt  1620
tggcgaatgg taagtatact gcgcaagatg cgacgactac gcagaaaggt attgtccaac  1680
tgtcaagtga caccaacagc acgtcagaga ccttggctgc tacacctaaa gcagtgaaag  1740
ctgcctatga tcttgcggct gggaaagccc cgtcatcaca cacacatcca tggaaccaga  1800
ttacggtcgt acctacggcc tctttaactg cgaagggcat tacacaatta tcatccgcga  1860
ctaacagcac cagtgaggtt ttagctgcaa caccgaaagc agtgaaggca gcctacgatt  1920
tggcgaacgg taaatatacg gctcaagatg cgaccaccgc gcaaaagggc attgtgcaac  1980
tgtcgtctgc aacaaattca acgtcggaag ttctggcagc aactccaaag gcagtgaaag  2040
ccgcctatga cttagcaaac ggtaaacagg ccgcggatgc gacgttaacg gcattggcgg  2100
ctcttgcaac tgcagcggac aagttaccgt atttcacggg cgttgaccgt gctgccctga  2160
cagcgttaac ctctgttggg cgtgccattt taggcaagac ctcgattcaa tctgttttag  2220
attaccttgg tttaggggaa ggctcggcgc tgcccgttgg tgtgcctgtt ccgtggccct  2280
cagccacacc gccaacgggg tggctgaaat gcaatggtgc agcattttct tctgaaaagt  2340
acccaaatct ggcaaaggtt tacccaacgt taaaattacc tgatttacgc ggtgagttta  2400
tccgtggctg ggatgatggg cgagggattg actctggtcg ctctatttta agcgagcaag  2460
gatatgcaac ggaggatcat gctcacggat taccgtcaaa atcaaccgta gcaactgacc  2520
gctcaattaa tttctacttt gacgaggcat gggctactag tggtaatacg ggagttatca  2580
gatgggggaa cacaagcgat gcaggattgc cagcccctaa ttatggaact tttaaaacat  2640
ataaacagtc cgtagctaat ttaggtactg ctggcttaga aacccgccct cgtaatattg  2700
catttaatta tattgtgagg gcggattaaa ttatggataa tgcgatatta aatagcgaac  2760
ttatagccat acaggcagga aacattatcg tttataacta tgatggtggt aatcgggaat  2820
atatttctgc atcaactgaa tatcttgctg ttggcgttgg tattccggca aattcttgtt  2880
tggatgctcc aggctcacat aaagcaggtt atgcgattct ccgttcagag gatttaagtt  2940
catgggagta tgtgccagat catcgtggcg aaactgtcta tagcattgac acagggaatc  3000
ccgaagaaat cacggtgttg ggtgactatc cggaaaatac aaccactatc gccccgctaa  3060
caccatacga caaatgggat ggagagaaat gggtggttga tactgaggct caacatagtg  3120
cagctgtaga ggcagcagaa acaaaacgtc agtcattgat tgatactgcg atggattcca  3180
ttagtctgat tcagttgaaa ttacgggctg gacggaagtt gacgcaggca gaaaccacgc  3240
agcttaactc cgtgctagat tatatagacg agctgaacgc gatggattta accacggcac  3300
cagatctcaa ctggcctgaa aaacaacttt ctacagccag ttga                   3344
```

```
SEQ ID NO: 30           moltype = DNA  length = 3350
FEATURE                 Location/Qualifiers
misc_feature            1..3350
                        note = Tangerine Tail Fiber
source                  1..3350
                        mol_type = other DNA
                        organism = synthetic construct
SEQUENCE: 30
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgtcac cgttgttacg agtgttacct  480
acccctcgcc tgagtcatta gcgttagttg cagacgttca gtaccacgaa ccgtatcttt  540
cagcagctct taaccgtaaa ttccgcggaa ttgtcgatcc aggattttac gccgggttcc  600
tgcctaagcc tggcggcggc atgaatcttc tgattacgtc agtcgacggg gataaaactg  660
cgggagcggc atcggtagat atcggggaat tctaccaggt tacaattcaa catcgtaaag  720
acatttcgtt agcacttaac gctgggaaga aatacgccat tgtcttgaaa ggccgctatt  780
tgttaggtga agatacgtac caggtcaata cagcaagtca catccacgcc gctgaatttg  840
tcgcacgtac atataccgat tcctaccagc ttggggatgg tgagttactt gtgtgcaccg  900
tgaacattcc tgctggagtg tcaacgatca cgcaggagat gatcgatact tcagagcgta  960
ttaatcgcac gatcgggatt gatatttcag acagcgtcac ctcgactcgc tcagatgtcg  1020
cggcttcatc tcttgcagtg aaaaaggcct acgacctggc caagtcgaag tacacagctc  1080
aggacgcgag caccacccaa aagggtctgg tacagttatc atctgcgacg aattcaacat  1140
ccgaggttct tgcagcgaca cctaaagcgg taaaagccgc gtatgatctt gccaatggga  1200
aatacaccgc acaggacgcc acaactacac aaaagggtat tgtgcagttg tcgagtgaca  1260
```

```
ccaactcaac gtcggagaca ctggcggcca cgccgaaagc agtcaaagct gcatacgacc  1320
ttgcggctgg taaagcgccc tcatcccaca ctcacccctg gaatcagatt actggtgtac  1380
ccaccgcaag cttaactgca aagggtatca ctcaattgag ttccgcgacc aacagcacca  1440
gtgaagtttt agctgctacc ccaaaggcag ttaaagccgc ttacgacttg gctaatggaa  1500
aatatacagc gcaggacgcg accactgcac aaaaaggaat tgtgcaactt tcgagcgcaa  1560
cgaactccac aagtgaagtt ttggcagcta cgcctaaagc cgtcaaagcc gcgtatgatt  1620
tggcgaatgg taagtatact gcgcaagatg cgacgactac gcagaaaggt attgtccaac  1680
tgtcaagtga caccaacagc acgtcagaga ccttggctgc tacacctaaa gcagtgaaag  1740
ctgcctatga tcttgcggct gggaaagccc cgtcatcaca cacacatcca tggaaccaga  1800
ttacggtcgt acctacggcc tctttaactg cgaagggcat tacacaatta tcatccgcga  1860
ctaacagcac cagtgaggtt ttagctgcaa caccgaaagc agtgaaggca gcctacgatt  1920
tggcgaacgg taaatatacg gctcaagatg cgaccaccgc gcaaaagggc attgtgcaac  1980
tgtcgtctgc aacaaattca acgtcggaag ttctggcagc aactccaaag gcagtgaaag  2040
ccgcctatga cttagcaaac ggtaaacagg ccgcggatgc gacgttaacg gcattggcgg  2100
ctcttgcaac tgcagcggac aagttaccgt atttcacggg cgttgaccgt gctgccctga  2160
cagcgttaac ctctgttggg cgtgccattt taggcaagac ctcgattcaa tctgttttag  2220
attaccttgg tttaggggaa ggctcggcgc tgcccgttgg tgtgcctgtt ccgtggccct  2280
ccgccacacc accaacgggg tggctgaaat gtaacggagc agcattttct tctgaaaagt  2340
acccaaatct ggcaaaggtt tacccaacgt taaaattacc tgatttacgc ggtgagttta  2400
tccgtggttg ggatgattcg agagggattg atacagggcg ttcattgcta agtggtcaga  2460
ctgcaacatt tattcgtaca gctttgcagg attattacgg tgtcgatctg actactaatg  2520
tcaaagtagg tatcgcttat gctactgctg attctgttat aactgttgga aaccctgcta  2580
atcctaaagc aggagataat agcgattatg ttccagcatc atcagataac tccataacag  2640
gcactcaaag gacggcagag gataatttta ccggggcatg gatatcaatg cgcccccgca  2700
acgttgcttt taattacatt gtaagggcca cataaattat ggataatgcg atattaaata  2760
gcgaacttat agccatacag gcaggaaaca ttatcgttta taactatgat ggtggtaatc  2820
gggaatatat ttctgcatca actgaatatc ttgctgttgg cgttggtatt ccggcaaatt  2880
cttgtttgga tgctccaggc tcacataaag caggttatgc gattctccgt tcagaggatt  2940
taagttcatg ggagtatgtg ccagatcatc gtggcgaaac tgtctatagc attgacacag  3000
ggaatcccga agaaatcacg gtgttgggtg actatccgga aaatacaacc actatcgccc  3060
cgctaacacc atacgacaaa tgggatggag agaaatgggt ggttgatact gaggctcaac  3120
atagtgcagc tgtagaggca gcagaaacaa aacgtcagtc attgattgat actgcgatgg  3180
attccattag tctgattcag ttgaaattac gggctggacg gaagttgacg caggcagaaa  3240
ccacgcagct taactccgtg ctagattata tagacgagct gaacgcgatg gatttaacca  3300
cggcaccaga tctcaactgg cctgaaaaac aactttctac agccagttga             3350
```

```
SEQ ID NO: 31          moltype = DNA  length = 4520
FEATURE                Location/Qualifiers
misc_feature           1..4520
                       note = Thistle Tail Fiber
source                 1..4520
                       mol_type = other DNA
                       organism = synthetic construct
SEQUENCE: 31
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaag cacaacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaac cgcgccgacg gcagcgcaag  1260
gtacaaacag cacgcagatc gcaaatacag cctttgttaa ggcagctata actgcactta  1320
tcaacggtgc gcctggcaca ctggatacgc tgaaagaaat agcggctgcg atcaataacg  1380
acccgaatta cagcacaact atcaacaatg ccttggctct caaagcgcct ttggcaagcc  1440
ctgcattaac gggtgtccct actgcgccta cggctgcaca gggcacaaac aatacgcaga  1500
tcgctacgac tgcttacgta cgggctgcta tctctgcatt ggtcggctca tcacctgaag  1560
ctcttgatac cctgtatgag cttgcagcag cactgggcaa tgacccgaac tttgcgacaa  1620
caatgacaaa tgcgctggca gggaaacagc cacttgatgc aactttaacc gcgcttgctg  1680
gtcttgcgac aggcgcaaat aaattgccgt actttaccgg tacagacact gtttctcaga  1740
ctgacttaac gtcagttggt cgcgatattc tggccaaaac aagcattctt gctgttatcc  1800
aataccttgg tttaagagaa ctcggcacaa gcggtgaaaa gatccccctg ttgagcacgg  1860
ctaacacatg gagtgcacgc cagactttta acggcgggat caccggggcg ctgacaggga  1920
acgccgatac cgcgacgaag ttgaaaacag cacggaagat taacaacgtt tcatttgatg  1980
gttcggcaga cataacgctg acacctgaga accttggcgt caccagtctg acgtttgaga  2040
aaaacaacgg tgaaatgcct attgatgctg acctaaatac tttcggtccc gttgaggctt  2100
```

```
atcttggtgt ctggtccaaa gcaacatcca ccaacgcaac actggagaaa aatttcccgg  2160
aagataatgc tgtcggtgtg cttgaggtat ttgctgccgg aaattttgca ggtacgcaac  2220
gctttaccac gagagacggc aatgtataca tacgcagact cgccaataag tggaatggct  2280
ctgatggtcc gtggggcata tggcgtcaca ctcaatcagc tacccgccct ttgagtacga  2340
ctatagacct gaatacgctt ggagccgccg aacatcttgg tttatggcgt aacagtagct  2400
cggctatagc ttcatatgaa cgcaattatc cagaggaagg cggctttgct cagggggtgc  2460
ttgagatcct cgaaggcggg aattatggaa gaacgcaacg ttataccact cgccgcggaa  2520
atatgtatgt ccgctgcctt gcggcaagct gggatgcatc aaatccgcag tgggaaccgt  2580
ggttaaaagt cggtcatcag tcagagagtc gttattacga aggtgattta aatgttctaa  2640
ccgaccccgg tatttacagt gttacaggaa aggcaacaaa cggtccgatg ctggacaccg  2700
ttggcgcgac actacttggg atactggaag taatcagacg ttttgatggt gtgtctgtct  2760
ggcagcgtta cacaaccaca gggaaatcag aaaccacaca gggacgcact tttgagcgcg  2820
tctacgccgg gagcaaatgg accgaatggc gagaagtata taactccttt tcgttgcctc  2880
tgaatctggg catcggtggc gcagtggcaa aactatccag tctggactgg cagacctacg  2940
attttgtgcc gggcagtctg ataaccgtgc ggcttgataa catgaccaac attcccgacg  3000
gtatggactg gggcgtcatt gatggcaacc tgataaacat cgcagttggt ccgagtgatg  3060
attccggtac ggggcgctca atgcatgtat ggcgcagcac tgtaagtaaa gcgaactacc  3120
gctttttat ggtgcgtatt tcaggaaatc cgggaagccg cacgatcaca gcaagacgag  3180
taccaatcat tgacgaagcc cagacatggg gcgcgaaaca gacattcagt gctggccttt  3240
ctggtgaact gtccggcaat gcggcgacag caacaaagct gaaaacagcc cgtaaaatta  3300
ataacgtttc gtttgatggt tccggggata ttgaggtcct tcctgttggt gttccgctgc  3360
cgtggccatc agatactgtg ccgtctggtt acgccctgat gcagggacag acttttgaca  3420
aatctgcata cccgaaactt gcagccgctt atccgtcagg cgtgatcccg gatatgcgtg  3480
gctggacaat caagggcaaa cccgccagtg gtcgggacgt attgtctctg gaacaggatg  3540
gcattaaatc gcacacccac agcgccagcg catccaatac ggatttgggt acgaaaacca  3600
catcttcgtt tgattacggt actaaatcaa cgaataacac aggtgcacat acccacaatg  3660
tatctggtac tgcaaatagt gctggcgcac atactcatac cgtgccatta aggagaccaa  3720
acagtggcgg tatgaatttc gactggctgg atggtgcatc aagtggcacg gtggtgggga  3780
atggaactgt gccttcttct ggcgcacata cccactcagt atcaggcacc gctacaagtg  3840
ctggggcaca tgcacacact gttggtattg gcgctcatac gcactctgtt gcgattggtt  3900
cacatggaca taccatcacc gttaacgctg ctggcaacgc ggaaaacacc gttaaaaaca  3960
tcgcatttaa ttatattgtg aggcttgcat aaatgcagca cttaaaaaat atcaggtcag  4020
gaaacccaaa gacaaaagag caataccaat taacaaagaa ttttgacgta atctggttgt  4080
ggtctgaaga cggaaaaaac tggtatgagg aagtgaaaaa ctttcaacca gacaccataa  4140
agattgttta cgatgaaaat aatattattg tcgccatcac caaagatgcc tccacgctta  4200
accctgaagg ttttagcgtc gttgaggttc ccgacataac agccaaccgc cgcgctgatg  4260
attcaggaaa gtggatgttt aaggatggag ctgtagttaa acggatttat acggcagacg  4320
aacagcaaca acaagccgaa tcacaaaagg ccgcattgct ttccgaagct gaatcagtca  4380
tccagccgct ggaacgcgct gtcaggctga atatggcaac agacgaggaa cgcacacgac  4440
tggaagcatg ggaacgctac agtgttctgg tcagccgtgt ggatacggca aatcctgaat  4500
ggccacaaaa gcctgaataa                                             4520

SEQ ID NO: 32          moltype = DNA  length = 2132
FEATURE                Location/Qualifiers
misc_feature           1..2132
                       note = Tropical_pNS88 Tail Fiber
source                 1..2132
                       mol_type = other DNA
                       organism = synthetic construct
SEQUENCE: 32
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcact catcaaagag tacgacgaga acattggcgc gtgggagacg ttcgccacca  1140
cctcagcaaa ccagagcatc acagttacca tcaatggcac ccccgtgact atccccggca  1200
tcggtaagct ggcacagaaa gggaccaacg gtgctctccc gattgaccag ggcgggactg  1260
gtgcaacgaa cgctgcagat gttcgcacaa acctcggttt aggagacagc gtcacagcca  1320
acttcggaag cctcgaaatt ggagcgaaaa atgcctcttc tgcaagcttc gttgatttcc  1380
attttcttgg cactaatgac tatgacgcgc gcatcctgtg tggtggtaat tcgaatggag  1440
ggatggggaa aggtgatttc actttctatg ctggaaaata cacttttatc ggtgacagtt  1500
ttgagtttcg aaatcctatc acctgccaga acagcataac tgcttcaggg agcattagcg  1560
caggcggctc actaagagcc gtaacgtcat caaacgtatg ggcctccagc gatacacaga  1620
acgctcacgt gtggttttac ggtgcgggag gtattgaatc acgaggggta atctatgcgc  1680
ccagggaagg taccatccgg ctcaggcctg ataataatga taatggtgga gcaaatggct  1740
```

```
atagcttctc tttcggagct gatggcaggt ttacctgtat ttctgtgaac cagacttcgg  1800
atgagcgagt gaagttcgac aaagagcccg tcagtaacgc tctggagaag atttgttccc  1860
tgacgggtta tacattcggc atccaactga ctgaatcgga atcggtgcac agcgcaggca  1920
tcatagctca ggatttggaa aaagtgttgc ccgttgctgt aagttctggc gggaccggca  1980
ctacaccgac cggagaagag attaacgatc taaaaaccgt ggactacagt gcgatgagcg  2040
ccttgtatgt tgaggccatg aaggagctgg ccaaccgggt aaaaagtata gagagtgagt  2100
ttgccgaact caaagcccga tccgcgatat ag                                2132

SEQ ID NO: 33           moltype = DNA  length = 2117
FEATURE                 Location/Qualifiers
misc_feature            1..2117
                        note = Tropical_pNS92 Tail Fiber
source                  1..2117
                        mol_type = other DNA
                        organism = synthetic construct
SEQUENCE: 33
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgttaca tcggttactt  480
acccatcatc cgagtcgttg gctctggtgg ccgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taattacctc agtggatggt gataaaaccg  660
caggcgcggc gtcggtggat attggtgaat tttaccaggt aactattcag caacgtaagg  720
atatttctct tgcacttagt gcaggcaaga aatatgcaat tgtgctgaag ggaagatacc  780
tccttggaga agatacctac caggtgaata ccgcgtcaca tattcatgcg gctgaatttg  840
ttgccagaac ctataccgat tcatatcagt taggagatgg ggagctgctt gtttgtacgg  900
tgaatatccc tgctagtgta tctgccatta cccaggagat gattgataca tccgagcgta  960
tcaaccgctc gatcggcatt gatatttcag actctgtaac cagtaccaga agtgatgttg  1020
ctgcaagttc gctggcagtt aaaaaagcct acgatctggc gaaaagcaag tatacggcac  1080
aggatgcaga cgagaacatt ggcgcgtggg agacgttcgc caccacctca gcaaaccaga  1140
gcatcacagt taccatcaat ggcacccccg tgactatccc cggcatcggt aagctggcac  1200
agaaagggac caacggtgct ctcccgattg accagggcgg gactggtgca acgaacgctg  1260
cagatgttcg cacaaacctc ggtttaggag acagcgtcac agccaacttc ggaagcctcg  1320
aaattggagc gaaaaatgcc tcttctgcaa gcttcgttga tttccatttt cttggcacta  1380
atgactatga cgcgcgcatc ctgtgtggtg gtaattcgaa tggagggatg gggaaaggtg  1440
atttcacttt ctatgctgga aaatacactt ttatcggtga cagttttgag tttcgaaatc  1500
ctatcacctg ccagaacagc ataactgctt cagggagcat tagcgcaggc ggctcactaa  1560
gagccgtaac gtcatcaaac gtatgggcct ccagcgatac acagaacgct cacgtgtggt  1620
tttacggtgc gggaggtatt gaatcacgag ggtaatcta tgcgcccagg gaaggtacca  1680
tccggctcag gcctgataat aatgataatg gtggagcaaa tggctatagc ttctctttcg  1740
gagctgatgg caggtttacc tgtatttctg tgaaccagac ttcggatgag cgagtgaagt  1800
tcgacaaaga gcccgtcagt aacgctctgg agaagatttg ttccctgacg ggttatacat  1860
tcggcatcca actgactgaa tcggaatcgg tgcacagcgc aggcatcata gctcaggatt  1920
tggaaaaagt gttgcccgtt gctgtaagtt ctggcgggac cggcactaca ccgaccggag  1980
aagagattaa cgatctaaaa accgtggact acagtgcgat gagcgccttg tatgttgagg  2040
ccatgaagga gctggccaac cgggtaaaaa gtatagagag tgagtttgcc gaactcaaag  2100
cccgatccgc gatatag                                                 2117

SEQ ID NO: 34           moltype = DNA  length = 3908
FEATURE                 Location/Qualifiers
misc_feature            1..3908
                        note = Violet Tail Fiber
source                  1..3908
                        mol_type = other DNA
                        organism = synthetic construct
SEQUENCE: 34
atgtctgacg tctcaacaaa cctctataag agtcagttgt tggactatta ctatcagcgg  60
cgcgctgaat cgtccattaa caaaggctct cgatttttaa tcagcaaggc cgttttcggt  120
accagttcgc tggttactaa gaaaggagat ggcacttatg agattggaga actgccaaag  180
gctttcgaac tggcagaact gaccagtcaa ttttgcacca tcaacctcgt cccaacctac  240
tcaggcggga taattactgt ccgaatggac cttgatcaaa gccagttgca ggaagggaaa  300
aactacccat tcaacactct ggttgttctg gataacgaga acaagccaat cgccattatt  360
tgtgtccagg aagactcgct gtatgtgggc aaaacatata ccgcagttat ggccataaac  420
acgactacag cataaggata tgcttgatga atgacgttac agttgtcaca tcggttactt  480
acccatcacc cgagtcgttg gctctggtgg ctgatgtgca ataccacgaa ccatatctgt  540
cagccgcgct aaaccgaaaa ttcaggggga ttgttgaccc gggattttat gccggtttct  600
tacctaagcc tggcggtggg atgaacctgt taatcacctc agtggatggt gataaaaccg  660
caggcgcggc gtcggtggat attggtgaat tctaccaggt aactattcag caacgtaagg  720
atatttctct tgcacttagt gcaggcaaga aatatgcaat tgtgctgaag ggaagatacc  780
tccttggaga agatacctat caggtgaata ccgcgtcaca tattcatgcg gctgaatttg  840
ttgccagaac ctataccgat tcatatcagt taggagatgg ggagctgctt gtttgtacgg  900
tgaatatccc tgctggtgta tctgccatta cccaggagat gattgataca tccgagcgta  960
tcaaccgcac gatcggcatt gatatttcag actctgtaac cagtaccaga agtgatgttg  1020
ctgcaagttc gctggcagtt aaaaaagcct acgatctggc gaaaagcaag tatacggcgc  1080
```

```
aggatgcaag cataacgcaa aagggattag ttcagctcag tagcgcaact aacagcgaca  1140
gcgaaacaat ggcggctacc cctaaagctg ttaagtctat aaaagatctg gctgatacca  1200
aagcgccaat agaaagcccg agtctgacag gaacgccaag cgcgccgacg gcagcgcaag  1260
gtacaaacag cacgcagata gcaaatacag cctttgttaa ggcagctata actgcactta  1320
tcaacggtgc acctggcaca ctggatacac ttaaagaaat agctgctgcg atcaataacg  1380
acccgaattt cagcacaact gtcaacaatg ctctggccct taaagcgcct ttagcaagtc  1440
ctgcattaac gggaatacct actgcgccta ccgctgcaca gggtacgaat aacacgcaga  1500
ttgctacgac cgcttatgta agagctgcca tatccgcatt ggttggttca tcaccagaag  1560
ctcttgatac cctgaatgag cttgccgcag cacttggtaa tgacccgaac tttgcgacaa  1620
caatgacaaa tgcgctggca ggcaaacagc ctctggatgc aactttaacc gcgctcgctg  1680
gccttgcgac tggtgcaaac aaactgcctt atttcaccgg taaggatacg gtagcgcaga  1740
ctgatttaac gtcagtcggt cgcgatattc tggccaaaac aagcgttctt gctgttatcc  1800
aataccttgg tttaagagaa ctcggtacca gtggtgaaaa gatccccctg ttgagcacgg  1860
ctaacacatg gagtgcacgc cagactttta acggcgggat caccggggcg ctgacaggga  1920
acgccgacac cgcgacgaaa ttaaaaacag ccataaacat taatggcgtc agattcgatg  1980
gttctacgaa catttcgata ccaacaatta cgtctagagg acgcgttact gcgcttaccg  2040
gtacaacgca aggtgctgct actggattgc agatgtatga ggcatacaac aatggttatc  2100
cgacgactta cgggaatgta cttcacctga agggagctgc atccactggt gaaggcgagt  2160
tgctcattgg ctggagtggc acaaatggcg ctcatgcacc agctttcatt cgatccaaaa  2220
gagatatcac tgctgcggca tggtccgaat gggcacagat ctatacgtca aaagattccg  2280
ttcccggcgt taataccaaa gggaatcagg acacctctgg taatgcggct acagcgacca  2340
aattgcagac ggcgtgtact atcaacggtg tctcgtttga cggttctaaa aatattgagc  2400
taacggcggc agatttaaat cttgagcaaa ctgtagaatt agccgcagga gcattacaga  2460
aaaaccagaa cggcgcagat attccgggaa aagatacctt taccaaaaat attggtgcct  2520
gccgcgcata tagcgcatgg ctgaatattg gtggcgatag tcaggtctgg acaaccgcgc  2580
aatttatttc gtggctggag agtcagggag catttaacca tccttactgg atgtgcaaag  2640
gctcatgggc ttatgcaaat aataaggtca ttacagatac aggttgcgga aatatttgtc  2700
ttgcaggtgc tgtggtggaa gttattggca ctcgcggcgc aatgaccata cgcgttacta  2760
cgccgagcac gtccagcggt ggcggaatta ctaacgctca attcacttat attaatcatg  2820
gtgatgctta tgctcctggc tggcgaagag actacaacac gaaaaaccag cagcctgcat  2880
ttgctttagg gcaaacagga agcagggttg caaatgataa agctgttggc tggaactgga  2940
atagcggcgt ttatgatgca gatatcagtg gcgcatcgac attaatcctc cacttcaata  3000
tgaatgcggg gagttgccct gctgtacagt tccgcgtgaa ttataagaac ggcggtatct  3060
tttatcgttc agcgcgtgat ggttatggct ttgaagctaa ctggtcagag ttttacacca  3120
caacccgcaa accctctgcg gggatgttg gtgcatatac gcaggcagaa tgtaactcaa  3180
ggtttattac aggtattcgc ctgggcggtc tgtcatctgt tcagacatgg aatggtcccg  3240
gctggtctga caggtcaggt tatgtcgtta caggttcagt taacggaaac cgtgatgaat  3300
taattgatac aactcaggca aggccaattc agtattgcat taatgggacg tggtataacg  3360
cggggagtat ttaaatgatg cacttaaaaa acattactgc tggcaaccct aaaacaaaag  3420
agcaatacca gctaacgaaa caatttaaca tcaaatggct ttatacagag gatgggaaaa  3480
actggtatga ggaacaaaag aactttcagc ctgatacgtt gaaaatggtc tatgaccaca  3540
acgacgttat tatttgtatt gaaaaggatg tttcagcaat taatccagaa ggcgcaagcg  3600
tcgttgaggt tcctgatatt acagcaaatc gccgggctga tatttcgggt aaatggatgt  3660
tcaaagatgg cgtagtgata aagcgaactt ataccgagga ggaacaaagg cagcaggcag  3720
agaatgaaaa acaaagcctg ttgcaacttg tcagggataa aacccagcta tgggactcac  3780
agctacggct gggcatcatt tccgacgaga ataaacaaaa attaactgag tggatgctct  3840
atgcgcagaa agtcgaatct acagacacct ccagcctgcc agtaacattt cccgaacaac  3900
ctgaatga                                                           3908
```

```
SEQ ID NO: 35          moltype = AA  length = 990
FEATURE                Location/Qualifiers
REGION                 1..990
                       note = Asparagus Tail Fiber
source                 1..990
                       mol_type = protein
                       organism = synthetic construct
SEQUENCE: 35
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TARNINGVRF DGSGDININT LVSRGRVTAL EANAQGTSGI  540
QLYEAYNNGY PSPYGNVLHL KGATAAGEGE LFIGWSGTSG AHAPVHIRSR RDTDSANWSE  600
WAQVYTSKDS IPGVNAKGDQ DTSGNAATAT KLQTACTING VSFDGSKNIE LTAEDLNLQE  660
TVNKADNAVQ KTGDTLSGGL TFENDSILAW IRNTDWAKIG FKNDADSDTD SYMWFETGDN  720
GNEYFKWRSK QSTTTKDLMN LKWDALSVLV NAIVNGEVIS KSANGLRIAY GNYGFFIRND  780
GSNTYFMLTN SGDNMGTYNG LRPLWINNAT GAVSMGRGLN VSGDTLSDRF AINSSNGMWI  840
QMRDNNAIFG KNIVNTDSAQ ALLRQNHADR KFMIGGLGNK QFGIYMINNS RTANGTDGQA  900
YMDNNGNWLC GAQVIPGNYA NFDSRYVRDV RLGTQSLTGG LSRDYKAPSG HVITGFHTNG  960
DWEMQGGDDK VYIRPVQKNI NGTWYNVASA                                   990

SEQ ID NO: 36          moltype = AA  length = 763
FEATURE                Location/Qualifiers
REGION                 1..763
                       note = Banana Tail Fiber
```

```
source                  1..763
                        mol_type = protein
                        organism = synthetic construct
SEQUENCE: 36
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDATTARKG IVQLSSATDS TSEALAATPK  240
AVKAVNDNAN GRVPSARKVN GRALASDISI TAQDIFNGQA VAIGNAADLN AYTTPGLYYQ  300
PANAQAQTGR NYPEANAGSL EVYKHAGITQ IYRIYNSSRS YIRTLYSGTW SAWVKQYDAA  360
NKPSPADINA VNKGGDTMTG GLKIRAADAL RIYDAAYGMI FRRSENNFYL IPTAKDQGED  420
GGISGLRPLY IDLTNGRVTL GNGAVVNGGL GLGVVSGLGG NSIALGDNDT GFKQNGDGVL  480
DVYANSKQVM RFLNSGITSY MLFNMNAGAS VSSTLTFKNG SGITSEKTGA NPRNGRIYWG  540
GDASRGNRIE FADDAGWKAY IERHPSNGVQ LVVNGRINGS IVYSSGEVLA GGGSARFAAD  600
GNIFGSKWGN QWLDAYLKNT YQPKGNYTPA GQAYTKVESD GRFQPKGSYT PAGQAYTKAE  660
SDARYNLKNT ATKSANAMTH KDASTGVMEV VMSNINVPNK TNVNVTFPAA FPNACVGVVI  720
TYNGAGHGSG DDSAIYVPSY SRTGCTLYAH NADGKFMLIA KGY                  763

SEQ ID NO: 37           moltype = AA  length = 748
FEATURE                 Location/Qualifiers
REGION                  1..748
                        note = Bittersweet Tail Fiber
source                  1..748
                        mol_type = protein
                        organism = synthetic construct
SEQUENCE: 37
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALNAG KKYAIVLKGR YLLGEDTYQV  120
NTASHIHAAE FVARTYTDSY QLGDGELLVC TVNIPAGVST ITQEMIDTSE RINRTIGIDI  180
SDSVTSTRSD VAASSLAVKK AYDLAKSKYT AQDASTTQKG LVQLSSATNS TSEVLAATPK  240
AVKAAYDLAN GKYTAQDATT TQKGIVQLSS DTNSTSETLA ATPKAVKAAY DLAAGKAPSS  300
HTHPWNQITG VPTASLTAKG ITQLSSATNS TSEVLAATPK AVKAAYDLAN GKYTAQDATT  360
AQKGIVQLSS ATNSTSEVLA ATPKAVKAAY DLANGKYTAQ DATTTQKGIV QLSSDTNSTS  420
ETLAATPKAV KAAYDLAAGK APSSHTHPWN QITVVPTASL TAKGITQLSS ATNSTSEVLA  480
ATPKAVKAAY DLANGKYTAQ DATTAQKGIV QLSSATNSTS EVLAATPKAV KAAYDLANGK  540
QAADATLTAL AALATAADKL PYFTGVDRAA LTALTSVGRA ILGKTSIQSV LDYLGLGEGS  600
ALPVGVPVPW PSATPPTGWL KCNGAAFSSE KYPNLAKAYP TNKLPDLRGE FIRGWDDGRG  660
VDAGRQLLSS QGDAIRNIEG FADGGIGMSF DAIRGAFYDA GTRSARMPNN TTTIDKTDDL  720
GFDASRVVPT ANENRPRNIA FNYIVRAA                                   748

SEQ ID NO: 38           moltype = AA  length = 737
FEATURE                 Location/Qualifiers
REGION                  1..737
                        note = Cobalt Tail Fiber
source                  1..737
                        mol_type = protein
                        organism = synthetic construct
SEQUENCE: 38
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALNAG KKYAIVLKGR YLLGEDTYQV  120
NTASHIHAAE FVARTYTDSY QLGDGELLVC TVNIPAGVST ITQEMIDTSE RINRTIGIDI  180
SDSVTSTRSD VAASSLAVKK AYDLAKSKYT AQDASTTQKG LVQLSSATNS TSEVLAATPK  240
AVKAAYDLAN GKYTAQDATT TQKGIVQLSS DTNSTSETLA ATPKAVKAAY DLAAGKAPSS  300
HTHPWNQITG VPTASLTAKG ITQLSSATNS TSEVLAATPK AVKAAYDLAN GKYTAQDATT  360
AQKGIVQLSS ATNSTSEVLA ATPKAVKAAY DLANGKYTAQ DATTTQKGIV QLSSDTNSTS  420
ETLAATPKAV KAAYDLAAGK APSSHTHPWN QITVVPTASL TAKGITQLSS ATNSTSEVLA  480
ATPKAVKAAY DLANGKYTAQ DATTAQKGIV QLSSATNSTS EVLAATPKAV KAAYDLANGK  540
QAADATLTAL AALATAADKL PYFTGVDRAA LTALTSVGRA ILGKTSIQSV LDYLGLGEGS  600
ALPVGVPVPW PLETPPTGWL KCNGAAFSSE MYPKLAKAYP TNKLPDLRGE FIRGWDDGRG  660
IDAGRTLLSG QDGTSFSHYG GNFDIGSGHS INNYDQIVSN QPGFSRFSFA GPSRGDGVNY  720
VTIRPRNIAF NYIVRAA                                               737

SEQ ID NO: 39           moltype = AA  length = 578
FEATURE                 Location/Qualifiers
REGION                  1..578
                        note = Cornflower Tail Fiber
source                  1..578
                        mol_type = protein
                        organism = synthetic construct
SEQUENCE: 39
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKAA IAGMAKASDL NALAKLTGGN KLDGSQVITS  240
DNAGFILGKN SDLALLKKQG QGGTIAVGSG TPFRVQRSRA TTVSPADTFD DILVIDANNR  300
TTLPGALTAG GDIDNTTKGL LYTQAIELSF STPYIDFHFN YSTDDFTGRI MATAADQISV  360
QGSHWRVDRD LRVGGMADIA GWAQCGVDLS ANRTDFGSPA IGSLVSGGRI RSRMLGRGGN  420
VDPSGAWGGF YVEEHVGTEH RIIMYMDGFG RTDAWSFRAG GVISTPKGDV MTTGSDVRLK  480
TDFTQAPGNA SERIERLGVC EYRMKGETRR RRGFIAQQAE KADDLYTFLG IEQEIDGEKF  540
```

```
KVMNVDYTAI IADLVTVAQG LLVKNQELER RISVLEGI                       578

SEQ ID NO: 40          moltype = AA  length = 737
FEATURE                Location/Qualifiers
REGION                 1..737
                       note = Denim Tail Fiber
source                 1..737
                       mol_type = protein
                       organism = synthetic construct
SEQUENCE: 40
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALNAG KKYAIVLKGR YLLGEDTYQV  120
NTASHIHAAE FVARTYTDSY QLGDGELLVC TVNIPAGVST ITQEMIDTSE RINRTIGIDI  180
SDSVTSTRSD VAASSLAVKK AYDLAKSKYT AQDASTTQKG LVQLSSATNS TSEVLAATPK  240
AVKKAAYDLAN GKYTAQDATT TQKGIVQLSS DTNSTSETLA ATPKAVKAAY DLAAGKAPSS  300
HTHPWNQITG VPTASLTAKG ITQLSSATNS TSEVLAATPK AVKKAAYDLAN GKYTAQDATT  360
AQKGIVQLSS ATNSTSEVLA ATPKAVKAAY DLANGKYTAQ DATTTQKGIV QLSSDTNSTS  420
ETLAATPKAV KAAYDLAAGK APSSHTHPWN QITVVPTASL TAKGITQLSS ATNSTSEVLA  480
ATPKAVKAAY DLANGKYTAQ DATTAQKGIV QLSSATNSTS EVLAATPKAV KAAYDLANGK  540
QAADATLTAL AALATAADKL PYFTGVDRAA LTALTSVGRA ILGKTSIQSV LDYLGLGEGS  600
ALPVGVPVPW PSATPPTGWL KCNGAAFSSE KYPNLAKVYP TNKLPDLRGE FIRGWDDGRG  660
VDNGRALLSS QEATNFSQRA GNIGDGAGHA INFHDGIVGN QPGFSRFNFT SNSVGDGINF  720
VAVRPRNIAF NYIVRAA                                              737

SEQ ID NO: 41          moltype = AA  length = 939
FEATURE                Location/Qualifiers
REGION                 1..939
                       note = Eggplant Tail Fiber
source                 1..939
                       mol_type = protein
                       organism = synthetic construct
SEQUENCE: 41
MGADKTNNIM TLSSGVSQPL LADVQYFELY SSSALNRKLK NIVLPGFYCG FEPVPGTGLS  60
VRITSENSEG KGAASVDVNN VQISVQQIED VTVSVKAGAT NIIVLEANFE HGVKTTQVDS  120
ASSVSAARIY ARTDNTIGQN QIELCRVIVP NGATAVTKEM IVLKYRVNRA VGVEFSNEIS  180
STEERKAATP LAVKTLHDLV DTKAPLDSPH LSGTPTSPTP EPGTNNTQIA NAAFVYAAIN  240
ALINGAPGTM DTLKEIAAAI NNDPNFSTTI NNALALKAPL ASPALTGIPT APTAAQGTNN  300
TQIATTAYVR AAISALVGSS PEALDTLNEL AAALGNDPNF ATTMTNALAG KQPLDATLTA  360
LAGLATGANK LPYFTGKDTV AQTDLTSVGR DILAKTSTLA VIQYLGLREL GTSGEKIPLL  420
STANTWSARQ TFNGGITGAL TGNADTATKL KTAININGVR FDGSTNISIP TITSRGRVTA  480
LTGTTQGAAT GLQMYEAYNN GYPSPYGNVL HLKGATAAGE GELFIGWSGT NGAHAPAFIR  540
SKRDSTAAAW SEWAQIYTSK DSVPGVNAKG NQDTSGNAAT ATKLQIACTI NGVSFDGSKN  600
IELTAEDLNL QETVNKADNA VQKTGDTLSG GLTFENDSIL AWIRNTDWAK IGFKNDADSD  660
TDSYMWFETG DNGNEYFKWR SKQSTTTKDL MNLKWDALYV LVNAIVNGEV ISKSANGLRI  720
AYGNYGFFIR NDGSNTYFML TNSGDNMGTY NGLRPLWINN ATGAVSMGRG LNVSGETLSD  780
RFAINSSNGM WIQMRDNNAI FGKNIVNTDS AQALLRQNHA DRKFMIGGLG NKQFGIYMIN  840
NSRTANGTDG QAYMDNNGNW LCGAQVIPGN YGNFDSRYVR DVRLGTRVVQ LMARGGRYEK  900
AGHAITGLRI IGEVDGDDEA IFRPIQKYIN GTWYNVAQV                      939

SEQ ID NO: 42          moltype = AA  length = 986
FEATURE                Location/Qualifiers
REGION                 1..986
                       note = Fern Tail Fiber
source                 1..986
                       mol_type = protein
                       organism = synthetic construct
SEQUENCE: 42
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TARNINGVRF DGSGDININT LVSRGRVTAL EANAQGTSGI  540
QLYEAYNNGY PSPYGNVLHL KGATAAGEGE LFIGWSGTSG AHAPVHIRSR RDTDSANWSE  600
WAQVYTSKDS IPGVNAKGDQ DTSGNAATAT KLQTACTING VSFDGSKNIE LTAEDLNLQE  660
TVNKAGNAVQ KTGDTLSGGL TFENDSILAW IRNTDWAKIG FKNDADGDTD SYMWFETGDN  720
GNEYFKWRSK RGTTTKDLMN LKWDALYVLV NAIVNGEVIS KSANGLRIAY GNYGFFIRND  780
GSNTYFMLTN SGDNMGTYNG LRPLWINNAT GAVSMGRGLN VSGETLQTVC YNSSNGMWIQ  840
MRDNNAIFGK NIVNTDSAQA LLRQNHADRK FMIGGLGNKQ FGIYMINNSR TANGTDGQAY  900
MDNNGNWLCG AQIIPGNYGN FDSRYVSDVR LGTRVVQTMQ KGVMYEKSGH AITGLGIVGE  960
VDGDDPAVFR PIQKYINGTW YNVAQV                                    986

SEQ ID NO: 43          moltype = AA  length = 972
FEATURE                Location/Qualifiers
REGION                 1..972
                       note = Fuchsia Tail Fiber
```

-continued

```
source                  1..972
                        mol_type = protein
                        organism = synthetic construct
SEQUENCE: 43
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IHGLRELGTS GEKIPLLSTA NTWSARQTFN  480
GGITGALIGN ADTATKLKTA ININGVRFDG SADININTLV SRGRVTALGA NAQGTSGIQL  540
YEAYNNGYPS PYGNVLHLKG ATAAGEGELF IGWSVSSGDH APVHIRSRRD IDSANWSEWA  600
QVYTSKDSVP GVNAKGNQDT SGNAATATKL QTACTINGVS FDGSKNIELT AEDLNLEQTV  660
ELAAGALQKN QNGADIPNKD KFIQNTGACR AFSGQTDIDG SQGEWSTVAF ISWLENNGAF  720
RHPYWMCKGS WSYARNRVIT DTGCGNICLA GAVIEVMGTR GAMTIRVTTP STSSGGGITN  780
AQFTYINHGD AYAPGWRRDY NTKNQQPAFA LGQTGRRVAN DKAVGWNWNS GVYDADISGA  840
STLILHFNMN AGSCPAVQFR VNYRNGGIFY RSARDGYGFE ANWSEFYTTT RKPSAGDVGA  900
YTQAECNSRF ITGIRLGGLS SVQTWNGPGW SDRSGYVVTG SVNGNRDELI DTTQARPIQY  960
CINGTWYNAG SI                                                    972

SEQ ID NO: 44           moltype = AA  length = 550
FEATURE                 Location/Qualifiers
REGION                  1..550
                        note = Fuzzy Tail Fiber
source                  1..550
                        mol_type = protein
                        organism = synthetic construct
SEQUENCE: 44
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKKP DGTTGTVKSW AQFLSEYSSR QTAIDGAITA  240
AGKNVARTSS TNTFTQPQTF SNGVTFSATI TAAGQILRNN SGTQFTAIDA GSLEISSDTT  300
PYIDFHHKGS VADYTHRIIT EDGALAVYPG LRVRGGFGLY GVGTVYGDAY SQGFIARLNN  360
DPNASIGDIL ASPRFTVRFN SRGSDSNVDG GQGAMWFEEQ VGTNHRLVLM AGGFSANVQY  420
WQFLADGRIY SSQNGNVQWQ GTSDARLKHD IEPTDGQLSV ERIRKLELVT FVYNDDEQNR  480
TRRGIIAQQA QKVDPQYVKQ VNTSYMRNGE QVNDDRLQLD NNVIMMDTLA AVKVLLERVD  540
ELEERLSAHG                                                       550

SEQ ID NO: 45           moltype = AA  length = 736
FEATURE                 Location/Qualifiers
REGION                  1..736
                        note = Inchworm Tail Fiber
source                  1..736
                        mol_type = protein
                        organism = synthetic construct
SEQUENCE: 45
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKVA ADFKGRKILA GNGLLGGGDL SADRSIGLAP  240
SGVTAGSYRS VTVNANGVVT QGSNPTTLAG YAIGDAYTKA DTDGKLAQKA NKATTLAGYG  300
ITDALRVDGN AVSSSRLAAP RSLAASGDAS WSVTFDGSAN VSAPLSLSAT GVAAGSYPKV  360
TVDTKGRVTA GMALAATDIP GLDASKLVSG VLAEQRLPVF ARGLATAVSN SSDPNTATVP  420
LMLTNHANGP VAGRYFYIQS MFYPDQNGNA SQIATSYNAT SEMYVRVSYA ANPSIREWLP  480
WQRCDIGGSF TKEADGELPG GVNLDSMVTS GWWSQSFTAQ AASGANYPIV RAGLLHVYAA  540
SSNFIYQTYQ AYDGESFYFR CRHSNTWFPW RRMWHGGDFN PSDYLLKSGF YWNALPGKPA  600
TFPPSAHNHD VGQLTSGILP LARGGVGSNT AAGARSTIGA GVPATASLGA SGWWRDNDTG  660
LIRQWGQVTC PADADASITF PIPFPTLCLG GYANQTSAFH PGTDASTGFR GATTTTAVIR  720
NGYFAQAVLS WEAFGR                                                736

SEQ ID NO: 46           moltype = AA  length = 762
FEATURE                 Location/Qualifiers
REGION                  1..762
                        note = Indian Tail Fiber
source                  1..762
                        mol_type = protein
                        organism = synthetic construct
SEQUENCE: 46
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALNAG KKYAIVLKGR YLLGEDTYQV  120
NTASHIHAAE FVARTYTDSY QLGDGELLVC TVNIPAGVST ITQEMIDTSE RINRTIGIDI  180
SDSVTSTRSD VAASSLAVKK AYDLAKSKYT AQDASTTQKG LVQLSSATNS TSEVLAATPK  240
AVKAAYDLAN GKYTAQDATT TQKGIVQLSS DTNSTSETLA ATPKAVKAAY DLAAGKAPSS  300
HTHPWNQITG VPTASLTAKG ITQLSSATNS TSEVLAATPK AVKAAYDLAN GKYTAQDATT  360
AQKGIVQLSS ATNSTSEVLA ATPKAVKAAY DLANGKYTAQ DATTTQKGIV QLSSDTNSTS  420
ETLAATPKAV KAAYDLAAGK APSSHTHPWN QITVVPTASL TAKGITQLSS ATNSTSEVLA  480
```

```
ATPKAVKAAY DLANGKYTAQ DATTAQKGIV QLSSATNSTS EVLAATPKAV KAAYDLANGK  540
QAADATLTAL AALATAADKL PYFTGVDRAA LTALTSVGRA ILGKTSIQSV LDYLGLGEGS  600
ALPVGVPVPW PLETPPTGWL KCNGAAFSSE MYPKLAKAYP TNKLPDLRGE FIRGWDDGRG  660
VDAGRALLNW QPHTILDHAH YMELWTGDGL AAGSAREGVN PGILATYGDG GIVKTDEPGH  720
KVPSSLRAIS SRSVKRYGEI SGNVGTETRP RNVAFNYIVR AA                     762

SEQ ID NO: 47          moltype = AA  length = 750
FEATURE                Location/Qualifiers
REGION                 1..750
                       note = Indigo Tail Fiber
source                 1..750
                       mol_type = protein
                       organism = synthetic construct
SEQUENCE: 47
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALNAG KKYAIVLKGR YLLGEDTYQV  120
NTASHIHAAE FVARTYTDSY QLGDGELLVC TVNIPAGVST ITQEMIDTSE RINRTIGIDI  180
SDSVTSTRSD VAASSLAVKK AYDLAKSKYT AQDASTTQKG LVQLSSATNS TSEVLAATPK  240
AVKAAYDLAN GKYTAQDATT TQKGIVQLSS DTNSTSETLA ATPKAVKAAY DLAAGKAPSS  300
HTHPWNQITG VPTASLTAKG ITQLSSATNS TSEVLAATPK AVKAAYDLAN GKYTAQDATT  360
AQKGIVQLSS ATNSTSEVLA ATPKAVKAAY DLANGKYTAQ DATTTQKGIV QLSSDTNSTS  420
ETLAATPKAV KAAYDLAAGK APSSHTHPWN QITVVPTASL TAKGITQLSS ATNSTSEVLA  480
ATPKAVKAAY DLANGKYTAQ DATTAQKGIV QLSSATNSTS EVLAATPKAV KAAYDLANGK  540
QAADATLTAL AALATAADKL PYFTGVDRAA LTALTSVGRA ILGKTSIQSV LDYLGLGEGS  600
ALPVGVPVPW PLETPPTGWL KCNGAAFSSE KYPNLAKAYP TNKLPDLRGE FIRGWDDGRG  660
IDSGRNLLSA QNDAIQNIVG SFGRTQLFRD VLSSGPFSQH GQVLSTGLKE TEIIEGYGSY  720
NWTFDASRSV RTASETRPRN IAFNYIVRAA                                   750

SEQ ID NO: 48          moltype = AA  length = 1181
FEATURE                Location/Qualifiers
REGION                 1..1181
                       note = Jazzberry Tail Fiber
source                 1..1181
                       mol_type = protein
                       organism = synthetic construct
SEQUENCE: 48
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TARKINNVSF DGSADITLTP ENLGVTSLTF EKNNGEMPID  540
ADLNTFGPVE AYLGVWSKAT STNATLEKNF PEDNAVGVLE VFAAGNFAGT QRFTTRDGNV  600
YIRRLANKWN GSDGPWGIWR HTQSATRPLS TTIDLNTLGA AEHLGLWRNS SSAIASYERN  660
YPEEGGFAQG VLEILEGGNY GRTQRYTTRR GNMYVRCLAA SWDASNPQWE PWLKVGHQSE  720
SRYYEGDLNV LTDPGIYSVT GKATNGPMLD TVGATLLGIL EVIRRFDGVS VWQRYTTTGK  780
SETTQGRTFE RVYAGSKWTE WREVYNSFSL PLNLGIGGAV AKLSSLDWQT YDFVPGSLIT  840
VRLDNMTNIP DGMDWGVIDG NLINIAVGPS DDSGTGRSMH VWRSTVSKAN YRFFMVRISG  900
NPGSRTITAR RVPIIDEAQT WGAKQTFSAG LSGELSGNAA TATKLKTARK INNVSFDGSG  960
DIEVLPVGVP LPWPSDTVPS GYALMQGQTF DKSAYPKLAA AYPSGVIPDM RGWTIKGKPA  1020
SGRDVLSLEQ DGIKSHTHSA SASNTDLGTK TTSSFDYGTK STNNTGAHTH NVSGTANSAG  1080
AHTHTVPLRR PNSGGMNFDW LDGASSGTVV GNGTVPSSGA HTHSVSGTAT SAGAHAHTVG  1140
IGAHTHSVAI GSHGHTITVN AAGNAENTVK NIAFNYIVRL A                      1181

SEQ ID NO: 49          moltype = AA  length = 974
FEATURE                Location/Qualifiers
REGION                 1..974
                       note = Jungle Tail Fiber
source                 1..974
                       mol_type = protein
                       organism = synthetic construct
SEQUENCE: 49
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TARNINGVRF DGSGDININT LVSRGRVTAL EANAQGTSGI  540
QLYEAYNNGY PSPYGNVLHL KGATAAGEGE LFIGWSGTSG AHAPVHIRSR RDTDSANWSE  600
WAQVYTSKDS IPGVNAKGDQ DTSGNAATAT KLQTACTING VSFDGSKNIE LTAENLNLER  660
TVELAAGSLQ KNQNGADIPG KDTFTKNIGA CRAYSAWLNI GGDSQVWTTA QFISWLESQG  720
AFNHPYWMCK GSWAYANNKV ITDTGCGNIC LAGAVVEVIG TRGAMTIRVT TPSTSSGGGI  780
TNAQFTYINH GDAYAPGWRR DYNTKNQQPA FALGQTGSTV GNDKAVGWNW NSGVYNANIG  840
```

```
GASTLILHFN MNTGSCPAVQ FRVNYRNGGI FYRSARDGYG FEADWSEIYT TTRKPSAGDV  900
GAYTQAECNS RFITGIRLGG LSSVQTWNGP GWSDRSGYVV TGSVNGNRDE LIDTTQARPI  960
QYCINGTWYN AGSI                                                   974

SEQ ID NO: 50          moltype = AA  length = 765
FEATURE                Location/Qualifiers
REGION                 1..765
                       note = Mango Tail Fiber
source                 1..765
                       mol_type = protein
                       organism = synthetic construct
SEQUENCE: 50
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDATTARKG IVQLSSATDS VSEVLAATPK  240
AVKTAYDLAN AKYTAVDATT ARKGLVQLSS AIDSVSEMLA ATPKAVKSAN DNATAANINA  300
SERVSKAGDS MTGTLNQDAV AQATYNLTAL SNATTGNKNY LRKMRGGATD TIWHETVQGG  360
EYRLATGSTD SQEELAISTN TGLRVRGNLT SQLGGFYSGN TKKFSFYSSN TSDKNAALRL  420
WGNVDRPSVV ELGDDTGYHF YSQRNKDGSL LLQANGAGQF SGYLRSNGEV QSISANSYRI  480
AYGNYGCFWR NDGNNLYLML TNKGDAYGNY NSLRPLRVSL ETGALQSETP FTVGNTIFAT  540
KEITAGYAGA LAWAEQYKTK AAFFNSYSTT GASEYHPALK QQASIAGVNS WAFSMGSLVA  600
DTALSWHLHM KGSGGQDVNY KWDTSGNFSA PGQLIPGSFA NFDSRYYTKG QSDAGYMAKT  660
GAYTKAESDA RYNLKNTASR AASGWEKDNT TGIMKQWGIA TRTADSTRIT FPTAFPTTCV  720
SVQLTLLYTN GFHDQNIYVQ NPDASGFTYI AGSGEVKVYF EARGY                 765

SEQ ID NO: 51          moltype = AA  length = 753
FEATURE                Location/Qualifiers
REGION                 1..753
                       note = Maroon Tail Fiber
source                 1..753
                       mol_type = protein
                       organism = synthetic construct
SEQUENCE: 51
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALNAG KKYAIVLKGR YLLGEDTYQV  120
NTASHIHAAE FVARTYTDSY QLGDGELLVC TVNIPAGVST ITQEMIDTSE RINRTIGIDI  180
SDSVTSTRSD VAASSLAVKK AYDLAKSKYT AQDASTTQKG LVQLSSATNS TSEVLAATPK  240
AVKAAYDLAN GKYTAQDATT TQKGIVQLSS DTNSTSETLA ATPKAVKAAY DLAAGKAPSS  300
HTHPWNQITG VPTASLTAKG ITQLSSATNS TSEVLAATPK AVKAAYDLAN GKYTAQDATT  360
AQKGIVQLSS ATNSTSEVLA ATPKAVKAAY DLANGKYTAQ DATTTQKGIV QLSSDTNSTS  420
ETLAATPKAV KAAYDLAAGK APSSHTHPWN QITVVPTASL TAKGITQLSS ATNSTSEVLA  480
ATPKAVKAAY DLANGKYTAQ DATTAQKGIV QLSSATNSTS EVLAATPKAV KAAYDLANGK  540
QAADATLTAL AALATAADKL PYFTGVDRAA LTALTSVGRA ILGKTSIQSV LDYLGLGEGS  600
ALPVGVPVPW PSATPPTGWL KCNGAAFSSE MYPKLAKAYP TNKLPDLRGE FIRGWDDGRG  660
VDAGRALLSI QTGMLEKHRH IVVANDGYDT KDEWELATIF KKTYTQGRGL DASNTGGNLI  720
PSPTLHSRGS IGNTGGSETR PRNIAFNYIV RAA                              753

SEQ ID NO: 52          moltype = AA  length = 925
FEATURE                Location/Qualifiers
REGION                 1..925
                       note = Mulberry Tail Fiber
source                 1..925
                       mol_type = protein
                       organism = synthetic construct
SEQUENCE: 52
MGADKTNNIM TLSSGVSQPL LADVQYFELY SSSALNRKLK NIVLPGFYCG FEPVPGTGLS  60
VRITSENSEG KGAASVDVNN VQISVQQIED VTVSVKAGAT NIIVLEANFE HGVKTTQVDS  120
ASSVSAARIY ARTDNTIGQN QIELCRVIVP NGATAVTKEM IVLKYRVNRA VGVEFSNEIS  180
STEERKAATP LAVKTLHDLV DTKAPLDSPH LSGTPTSPTP EPGTNNTQIA NAAFVYAAIN  240
ALINGAPGTM DTLKEIAAAI NNDPNFSTTI NNALALKAPL ASPALTGIPT APTAAQGTNN  300
TQIATTAYVR AAISALVGSS PEALDTLNEL AAALGNDPNF ATTMTNALAG KQPLDATLTA  360
LAGLATGANK LPYFTGKDTV AQTDLTSVGR DILAKTSTLA VIQYLGLREL GTSGEKIPLL  420
STANTWSARQ TFNGGITGAL IGNADTATKL KTAININGVR FDGSADININ TLVSRGRVTA  480
LGANAQGTSG IQLYEAYNNG YPSPYGNVLH LKGATAAGEG ELFIGWSVSS GDHAPVHIRS  540
RRDIDSANWS EWAQVYTSKD SVPGVNAKGN QDTSGNAATA TKLQTACTIN GVSFDGSKNI  600
ELTAEDLNLE QTVELAAGAL QKNQNGADIP NKDKFIQNTG ACRAFSGQTD IDGSQGEWST  660
VAFISWLENN GAFRHPYWMC KGSWSYARNR VITDTGCGNI CLAGAVIEVM GTRGAMTIRV  720
TTPSTSSGGG ITNAQFTYIN HGDAYAPGWR RDYNTKNQQP AFALGQTGRR VANDKAVGWN  780
WNSGVYDADI SGASTLILHF NMNAGSCPAV QFRVNYRNGG IFYRSARDGY GFEANWSEFY  840
TTTRKPSAGD VGAYTQAECN SRFITGIRLG GLSSVQTWNG PGWSDRSGYV VTGSVNGNRD  900
ELIDTTQARP IQYCINGTWY NAGSI                                       925

SEQ ID NO: 53          moltype = AA  length = 972
FEATURE                Location/Qualifiers
REGION                 1..972
                       note = MISC_FEATURE - P1-S' tail fiber protein
source                 1..972
                       mol_type = protein
```

```
                         organism = Bacteriophage P1
SEQUENCE: 53
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TARNINGVRF DGSGDININT LVSRGRVTAL EANAQGTSGI  540
QLYEAYNNGY PSPYGNVLHL KGATAAGEGE LFIGWSGTSG AHAPVHIRSR RDTDSANWSE  600
WAQVYTSKDS IPGVNAKGDQ DTSGNAATAT KLQTACTING VSFDGSKNIE LTAENLNLER  660
TVELAAGSLQ KNQNGADIPG KDTFTKNIGA CRAFHSSIST GAGNWTTAQL IEWLDSQGAF  720
NHPYWMCKCS WSYGNNKIIT DTGCGTIHLA GCVIEVMGNK GAMTIRVTTP STSSGGGITN  780
AQFTYINHGD AYAPGWRRDY NTKNLQPAFA LGQTGNRVAN DKAVGWNWNS GVYDADLKGA  840
STLILHFNMN AGSCPAVQLR VNYKNGGIYY RSARDGYGFE ADWSEFYTTT RKPSAGDVGA  900
YTQAECNSRF ITGIRLGGLS SVQTWNGPGW SDRSGYVVTG SVNGNRDELI DTTQARPIQY  960
CINGTWYNAG SI                                                  972

SEQ ID NO: 54            moltype = AA  length = 744
FEATURE                  Location/Qualifiers
REGION                   1..744
                         note = Pine Tail Fiber
source                   1..744
                         mol_type = protein
                         organism = synthetic construct
SEQUENCE: 54
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLN SPALTGTPTT PTARQGTNNT QIANTAFVMA  360
AIAALVDSSP DALNTLNELA AALGNDPNFA TTMTNALAGK QPKDATLTAL AGLATAADRF  420
PYFTGNDVAS LATLTKVGRD ILAKSTVAAV IEYLGLQETV NRAGNAVQKN GDTLSGGLTF  480
ENDSILAWIR NTDWAKIGFK NDADGDTDSY MWFETGDNGN EYFKWRSRQS TTTKDLMTLK  540
WDALNILVNA VINGCFGVGT TNALGGSSIV LGDNDTGFKQ NGDGILDVYA NSQRVFRFQN  600
GVAIAFKNIQ AGDSKKFSLS SSNTSTKNIT FNLWGASTRP VVAELGDEAG WHFYSQRNTD  660
NSVIFAVNGQ MQPSNWGNFD SRYVKDVRLG TRVVQLMARG GRYEKAGHTI TGLRIIGEVD  720
GDDEAIFRPI QKYINGTWYN VAQV                                     744

SEQ ID NO: 55            moltype = AA  length = 1181
FEATURE                  Location/Qualifiers
REGION                   1..1181
                         note = Plum Tail Fiber
source                   1..1181
                         mol_type = protein
                         organism = synthetic construct
SEQUENCE: 55
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALSAG KKYAIVLKGR YLLGEDTYQV  120
NTASHIHAAE FVARTYTDSY QLGDGELLVC TVNIPAGVSA ITQEMIDTSE RINRTIGIDI  180
SDSVTSSRSD VAASSLAVKK AYDLAKSKYT AQDASTTQKG LVQLSSETNS DSETMAATPK  240
AIKSVKDLAD TKAPIESPSL TGTPTAPTAA QGTNSTQIAN TAFVKAAITA LINGAPGTLD  300
TLKEIAAAIN NDPNFSTTIN NALALKAPLA SPALTGIPTA PTAAQGTNNT QIATTAYVRA  360
AISALVGSSP EALDTLNELA AALGNDPNFA TTMTNALAGK QPLDATLTAL AGLATGANKL  420
PYFTGTDTVS QTDLTSVGRD ILAKTSVLAV IQYLGLRELG TSGEKIPLLS TANTWSARQT  480
FNGGITGALT GNADTATKLK TARKINNVSF DGSADITLTP ENLGVTSLTF EKNNGEMPID  540
ADLNTFGPVE AYLGVWSKAT STNATLEKNF PEDNAVGVLE VFAAGNFAGT QRFTTRDGNV  600
YIRRLANKWN GSDGPWGIWR HTQSATRPLS TTIDLNTLGA AEHLGLWRNS SSAIASYERN  660
YPEEGGFAQG VLEILEGGNY GRTQRYTTRR GNMYVRCLAA SWDASNPQWE PWLKVGHQSE  720
SRYYEGDLNV LTDPGIYSVT GKATNGPMLD TVGATLLGIL EVIRRFDGVS VWQRYTTTGK  780
SETTQGRTFE RVYAGSKWTE WREVYNSFSL PLNLGIGGAV AKLSSLDWQT YDFVPGSLIT  840
VRLDNMTNIP DGMDWGVIDG NLINIAVGPS DDSGTGRSMH VWRSTVSKAN YRFFMVRISG  900
NPGSRTITAR RVPIIDEAQT WGAKQTFSAG LSGELSGNAA TATKLKTARK INNVSFDGSG  960
DIEVLPVGVP LPWPSDTVPS GYALMQGQTF DKSAYPKLAA AYPSGVIPDM RGWTIKGKPA  1020
SGRDVLSLEQ DGIKSHTHSA SASNTDLGTK TTSSFDYGTK STNNTGAHTH NVSGTANSAG  1080
AHTHTVPLRR PNSGGMNFDW LDGASSGTVV GNGTVPSSGA HTHSVSGTAT SAGAHAHTVG  1140
IGAHTHSVAI GSHGHTITVN AAGNAENTVK NIAFNYIVRL A                  1181

SEQ ID NO: 56            moltype = AA  length = 1250
FEATURE                  Location/Qualifiers
REGION                   1..1250
                         note = Queen Tail Fiber
SITE                     642
                         note = misc_feature - Xaa can be any naturally occurring
                          amino acid
SITE                     647
```

```
                         note = misc_feature - Xaa can be any naturally occurring
                          amino acid
SITE                     662
                         note = misc_feature - Xaa can be any naturally occurring
                          amino acid
SITE                     793
                         note = misc_feature - Xaa can be any naturally occurring
                          amino acid
SITE                     940
                         note = misc_feature - Xaa can be any naturally occurring
                          amino acid
SITE                     943
                         note = misc_feature - Xaa can be any naturally occurring
                          amino acid
source                   1..1250
                         mol_type = protein
                         organism = synthetic construct
SEQUENCE: 56
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TKRSLQVDLQ SDNAIDFDGS SNALLGIKGI LPITHGGLGA  540
SSVSGGRTNL GLGVADIPQF KGINLVNSTD SDLAASGIVS GYLNNSAGVQ RSRFRIYSEI  600
RSDNRSWLTL HLQSDTNTNK YAGLDIDGNF LITGDSKCRA LXPTDVXLTR KNIDVYSKAE  660
VXLKKGMKFT RVNAPSGAEE GKFYPVVIKR SATSNGELAS RVIISTAPRQ AAHRMNNCEF  720
NGFVMPAGWS DRGRYAYGMF WQYQDAERAI HSIAMSNKDD EVSSVFYIEG GAFPVCVLVE  780
EGLSVVVPTT DYXVGQTTYK WGATNPKAEC IAADIIIDFS NGRGFYSSGN LNGNAATATK  840
LQTARTINGV TFDGTTDISL TPENIGALSL SGGTLLGGLT APLLTTKSDL IFSSHTSRHI  900
RFTYTKNDGT TLTDGYIFKD GVDNPNRRPG IRINCAAPNX VLXSVVDDAK MYLRRFRSST  960
GASIWHETIE NNVYRLCTGT TDAQEELVLR TGSYAKFAGE IISKSANGLR IAYGNYGFFI  1020
RNDGSSTYFM LTASGDNLGT WNSLRPLTIN NANGAVSIGN GLNVTGDIRT NAWVYANRFS  1080
VNSSSGSWIS MRDQNVIFGL NKVSTSSAQA LLRQDHADRK FFIGGLGNSQ FGFYMINNSR  1140
TSNGTDGQAF LDSSGNFQCG GQILPTNYSN FDSRYTLKTA CVTSVRMGSA ASYKPSSNGV  1200
SWTQNLGSGL VMTGIIVQET GGNSADNIGG IYYRPVQYCI NGTWYTAASV             1250

SEQ ID NO: 57            moltype = AA  length = 975
FEATURE                  Location/Qualifiers
REGION                   1..975
                         note = Razzmatazz Tail Fiber
source                   1..975
                         mol_type = protein
                         organism = synthetic construct
SEQUENCE: 57
MNDVTVVTSV TYPSPESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPAGVSA ITQEMIDTSE RINRTIGIDI  180
SDSVTSTRSD VAASSLAVKK AYDLAKSKYT AQDASITQKG LVQLSSATNS DSETMAATPK  240
AVKSIKDLAD TKAPIESPSL TGTPSAPTAA QGTNSTQIAN TAFVKAAITA LINGAPGTLD  300
TLKEIAAAIN NDPNFSTTVN NALALKAPLA SPALTGIPTA PTAAQGTNNT QIATTAYVRA  360
AISALVGSSP EALDTLNELA AALGNDPNFA TTMTNALAGK QPLDATLTAL AGLATDANKL  420
PYFTGTDTVS QTDLTSVGRD ILAKTSVLAV IQYLGLRELG TSGEKIPLLS TANTWSARQT  480
FNGGITGALT GNADTATKLK TAININGVRF DGSTNISIPT ITSRGRVTAL TGTTQGAATG  540
LQMYEAYNNG YPTTYGNVLH LKGAASTGEG ELLIGWSGTN GAHAPAFIRS KRDSTAAAWS  600
EWAQIYTSKD SVPGVNTKGN QDTSGNAATA TKLQTACTIN GVSFDGSKNI ELTAADLNLE  660
QTVELAAGAL QKNQNGADIP GKDTFTKNIG ACRAYSAWLN IGGDSQVWTT AQFISWLESQ  720
GAFNHPYWMC KGSWAYANNK VITDTGCGNI CLAGAVVEVI GTRGAMTIRV TTPSTSSGGG  780
ITNAQFTYIN HGDAYAPGWR RDYNTKNQQP AFALGQTGSR VANDKAVGWN WNSGVYDADI  840
SGASTLILHF NMNAGSCPAV QFRVNYKNGG IFYRSARDGY GFEANWSEFY TTTRKPSAGD  900
VGAYTQAECN SRFITGIRLG GLSSVQTWNG PGWSDRSGYV VTGSVNGNRD ELIDTTQARP  960
IQYCINGTWY NAGSI                                                   975

SEQ ID NO: 58            moltype = AA  length = 901
FEATURE                  Location/Qualifiers
REGION                   1..901
                         note = Salmon Tail Fiber
source                   1..901
                         mol_type = protein
                         organism = synthetic construct
SEQUENCE: 58
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
```

```
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TARTIGGVAF DGTANINLPG VNVAGNQNTS GNAATATKLQ  540
TACTINGVSF DGSKNIELTA EDLNLQEFIN KANNAVQRSG DILSGGLTFE NDSILAWIRN  600
TDWAKIGFKN DADSDTDSYM WFETGDNGNE YFKWRSKQST TTKDLMNLKW DALSVLVKAL  660
FSSEVKISTV NALRIFNSSF GAIFRRSEEC LHIIPTRENE GENGDIGPLR PFTLNLRTGR  720
ITMGHGLDVT GDITTNAWVY ANRFAINSGS TSWIDMRNQN VIFGRNAVST SSAQALLRQD  780
HAERKFFVGG LGNYQFGFYM INNSRTANGT DGQAYMDNNG NWLCGSQVIP GNYGNFDSRY  840
VRDVRLGTRV VQLMARGGRY EKAGHAITGL RIIGEVDGDD EAIFRPIQKY INGTWYNVAQ  900
V                                                                  901

SEQ ID NO: 59          moltype = AA  length = 747
FEATURE                Location/Qualifiers
REGION                 1..747
                       note = Scarlet Tail Fiber
source                 1..747
                       mol_type = protein
                       organism = synthetic construct
SEQUENCE: 59
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALNAG KKYAIVLKGR YLLGEDTYQV  120
NTASHIHAAE FVARTYTDSY QLGDGELLVC TVNIPAGVST ITQEMIDTSE RINRTIGIDI  180
SDSVTSTRSD VAASSLAVKK AYDLAKSKYT AQDASTTQKG LVQLSSATNS TSEVLAATPK  240
AVKAAYDLAN GKYTAQDATT TQKGIVQLSS DTNSTSETLA ATPKAVKAAY DLAAGKAPSS  300
HTHPWNQITG VPTASLTAKG ITQLSSATNS TSEVLAATPK AVKAAYDLAN GKYTAQDATT  360
AQKGIVQLSS ATNSTSEVLA ATPKAVKAAY DLANGKYTAQ DATTTQKGIV QLSSDTNSTS  420
ETLAATPKAV KAAYDLAAGK APSSHTHPWN QITVVPTASL TAKGITQLSS ATNSTSEVLA  480
ATPKAVKAAY DLANGKYTAQ DATTAQKGIV QLSSATNSTS EVLAATPKAV KAAYDLANGK  540
QAADATLTAL AALATAADKL PYFTGVDRAA LTALTSVGRA ILGKTSIQSV LDYLGLGEGS  600
ALPVGVPVPW PLETPPTGWL KCNGAAFSSE MYPKLAKAYP TNKLPDLRGE FIRGWDDGRG  660
VDAGRVILSI QGWLTGSHYH NIRSWDAWDN TVLVPNDRGG DSLLSTDNAV RQGAINGKFT  720
SQYRTELSGG NETRPRNIAF NYIVRAA                                      747

SEQ ID NO: 60          moltype = AA  length = 996
FEATURE                Location/Qualifiers
REGION                 1..996
                       note = Shamrock Tail Fiber
source                 1..996
                       mol_type = protein
                       organism = synthetic construct
SEQUENCE: 60
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TARNINGVRF DGSGDININT LVSRGRVTAL EANAQGTSGI  540
QLYEAYNNGY PSPYGNVLHL KGATAAGEGE LFIGWSGTSG AHAPVHIRSR RDTDSANWSE  600
WAQVYTSKDS IPGVNAKGDQ DTSGNAATAT KLQTACTING VSFDGSKNIE LTAEDLNLQE  660
TVNKADNAVQ KTGDTLSGGL TFENDSILAW IRNTDWAKIG FKNNSDADTD SYMWFETGNN  720
GNEYFKWRHR IIGTRPKDLM NLKWNALSVL VEALFSSEVK ISTVNALRIF NSSFGAIFRR  780
SEECLHIIPT RENEGENGNI GPLRPFTLNL RTGRISMGHG LDVTGDIFAN RFAINSSTGM  840
WIHMRDQNVI LGRNAVSTDG AQALLRQDHA DRKFMIGGLG NKQFGIYMIN NSRTANGTDG  900
QAYMDNNGNW LCGAQVIPGN YGNFDSRYVK DVRLGSQQYY GVNNWQTWNF QCPSGHVLSG  960
INVQDTGKNS ADNIAGVYYR PVQKYINGTW YNVASV                            996

SEQ ID NO: 61          moltype = AA  length = 760
FEATURE                Location/Qualifiers
REGION                 1..760
                       note = Sunset Tail Fiber
source                 1..760
                       mol_type = protein
                       organism = synthetic construct
SEQUENCE: 61
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALNAG KKYAIVLKGR YLLGEDTYQV  120
NTASHIHAAE FVARTYTDSY QLGDGELLVC TVNIPAGVST ITQEMIDTSE RINRTIGIDI  180
SDSVTSTRSD VAASSLAVKK AYDLAKSKYT AQDASTTQKG LVQLSSATNS TSEVLAATPK  240
AVKAAYDLAN GKYTAQDATT TQKGIVQLSS DTNSTSETLA ATPKAVKAAY DLAAGKAPSS  300
HTHPWNQITG VPTASLTAKG ITQLSSATNS TSEVLAATPK AVKAAYDLAN GKYTAQDATT  360
AQKGIVQLSS ATNSTSEVLA ATPKAVKAAY DLANGKYTAQ DATTTQKGIV QLSSDTNSTS  420
ETLAATPKAV KAAYDLAAGK APSSHTHPWN QITVVPTASL TAKGITQLSS ATNSTSEVLA  480
ATPKAVKAAY DLANGKYTAQ DATTAQKGIV QLSSATNSTS EVLAATPKAV KAAYDLANGK  540
QAADATLTAL AALATAADKL PYFTGVDRAA LTALTSVGRA ILGKTSIQSV LDYLGLGEGS  600
ALPVGVPVPW PSATPPTGWL KCNGAAFSSE KYPNLAKVYP TLKLPDLRGE FIRGWDDGRG  660
```

```
IDSGRSILSE QGYATEDHAH GLPSKSTVAT DRSINFYFDE AWATSGNTGV IRWGNTSDAG  720
LPAPNYGTFK TYKQSVANLG TAGLETRPRN IAFNYIVRAD                        760

SEQ ID NO: 62           moltype = AA  length = 762
FEATURE                 Location/Qualifiers
REGION                  1..762
                        note = Tangerine Tail Fiber
source                  1..762
                        mol_type = protein
                        organism = synthetic construct
SEQUENCE: 62
MNDVTVVTSV TYPSPESLAL VADVQYHEPY LSAALNRKFR GIVDPGFYAG FLPKPGGGMN  60
LLITSVDGDK TAGAASVDIG EFYQVTIQHR KDISLALNAG KKYAIVLKGR YLLGEDTYQV  120
NTASHIHAAE FVARTYTDSY QLGDGELLVC TVNIPAGVST ITQEMIDTSE RINRTIGIDI  180
SDSVTSTRSD VAASSLAVKK AYDLAKSKYT AQDASTTQKG LVQLSSATNS TSEVLAATPK  240
AVKKAAYDLAN GKYTAQDATT TQKGIVQLSS DTNSTSETLA ATPKAVKAAY DLAAGKAPSS  300
HTHPWNQITG VPTASLTAKG ITQLSSATNS TSEVLAATPK AVKAAYDLAN GKYTAQDATT  360
AQKGIVQLSS ATNSTSEVLA ATPKAVKAAY DLANGKYTAQ DATTTQKGIV QLSSDTNSTS  420
ETLAATPKAV KAAYDLAAGK APSSHTHPWN QITVVPTASL TAKGITQLSS ATNSTSEVLA  480
ATPKAVKAAY DLANGKYTAQ DATTAQKGIV QLSSATNSTS EVLAATPKAV KAAYDLANGK  540
QAADATLTAL AALATAADKL PYFTGVDRAA LTALTSVGRA ILGKTSIQSV LDYLGLGEGS  600
ALPVGVPVPW PSATPPTGWL KCNGAAFSSE KYPNLAKVYP TLKLPDLRGE FIRGWDDSRG  660
IDTGRSLLSG QTATFIRTAL QDYYGVDLTT NVKVGIAYAT ADSVITVGNP ANPKAGDNSD  720
YVPASSDNSI TGTQRTAEDN FTGAWISMRP RNVAFNYIVR AT                     762

SEQ ID NO: 63           moltype = AA  length = 1181
FEATURE                 Location/Qualifiers
REGION                  1..1181
                        note = Thistle Tail Fiber
source                  1..1181
                        mol_type = protein
                        organism = synthetic construct
SEQUENCE: 63
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TARKINNVSF DGSADITLTP ENLGVTSLTF EKNNGEMPID  540
ADLNTFGPVE AYLGVWSKAT STNATLEKNF PEDNAVGVLE VFAAGNFAGT QRFTTRDGNV  600
YIRRLANKWN GSDGPWGIWR HTQSATRPLS TTIDLNTLGA AEHLGLWRNS SSAIASYERN  660
YPEEGGFAQG VLEILEGGNY GRTQRYTTRR GNMYVRCLAA SWDASNPQWE PWLKVGHQSE  720
SRYYEGDLNV LTDPGIYSVT GKATNGPMLD TVGATLLGIL EVIRRFDGVS VWQRYTTTGK  780
SETTQGRTFE RVYAGSKWTE WREVYNSFSL PLNLGIGGAV AKLSSLDWQT YDFVPGSLIT  840
VRLDNMTNIP DGMDWGVIDG NLINIAVGPS DDSGTGRSMH VWRSTVSKAN YRFFMVRISG  900
NPGSRTITAR RVPIIDEAQT WGAKQTFSAG LSGELSGNAA TATKLKTARK INNVSFDGSG  960
DIEVLPVGVP LPWPSDTVPS GYALMQGQTF DKSAYPKLAA AYPSGVIPDM RGWTIKGKPA  1020
SGRDVLSLEQ DGIKSHTHSA SASNTDLGTK TTSSFDYGTK STNNTGAHTH NVSGTANSAG  1080
AHTHTVPLRR PNSGGMNFDW LDGASSGTVV GNGTVPSSGA HTHSVSGTAT SAGAHAHTVG  1140
IGAHTHSVAI GSHGHTITVN AAGNAENTVK NIAFNYIVRL A                      1181

SEQ ID NO: 64           moltype = AA  length = 561
FEATURE                 Location/Qualifiers
REGION                  1..561
                        note = Tropical_pNS88 Tail Fiber
source                  1..561
                        mol_type = protein
                        organism = synthetic construct
SEQUENCE: 64
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDALIKEYD ENIGAWETFA TTSANQSITV  240
TINGTPVTIP GIGKLAQKGT NGALPIDQGG TGATNAADVR TNLGLGDSVT ANFGSLEIGA  300
KNASSASFVD FHFLGTNDYD ARILCGGNSN GGMGKGDFTF YAGKYTFIGD SFEFRNPITC  360
QNSITASGSI SAGGSLRAVT SSNVWASSDT QNAHVWFYGA GGIESRGVIY APREGTIRLR  420
PDNNDNGGAN GYSFSFGADG RFTCISVNQT SDERVKFDKE PVSNALEKIC SLTGYTFGIQ  480
LTESESVHSA GIIAQDLEKV LPVAVSSGGT GTTPTGEEIN DLKTVDYSAM SALYVEAMKE  540
LANRVKSIES EFAELKARSA I                                           561

SEQ ID NO: 65           moltype = AA  length = 556
FEATURE                 Location/Qualifiers
REGION                  1..556
                        note = Tropical_pNS92 Tail Fiber
source                  1..556
                        mol_type = protein
```

```
                        organism = synthetic construct
SEQUENCE: 65
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDADENIGA WETFATTSAN QSITVTINGT  240
PVTIPGIGKL AQKGTNGALP IDQGGTGATN AADVRTNLGL GDSVTANFGS LEIGAKNASS  300
ASFVDFHFLG TNDYDARILC GGNSNGGMGK GDFTFYAGKY TFIGDSFEFR NPITCQNSIT  360
ASGSISAGGS LRAVTSSNVW ASSDTQNAHV WFYGAGGIES RGVIYAPREG TIRLRPDNND  420
NGGANGYSFS FGADGRFTCI SVNQTSDERV KFDKEPVSNA LEKICSLTGY TFGIQLTESE  480
SVHSAGIIAQ DLEKVLPVAV SSGGTGTTPT GEEINDLKTV DYSAMSALYV EAMKELANRV  540
KSIESEFAEL KARSAI                                                 556

SEQ ID NO: 66           moltype = AA  length = 975
FEATURE                 Location/Qualifiers
REGION                  1..975
                        note = Violet Tail Fiber
source                  1..975
                        mol_type = protein
                        organism = synthetic construct
SEQUENCE: 66
MNDVTVVTSV TYPSPESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPAGVSA ITQEMIDTSE RINRTIGIDI  180
SDSVTSTRSD VAASSLAVKK AYDLAKSKYT AQDASITQKG LVQLSSATNS DSETMAATPK  240
AVKSIKDLAD TKAPIESPSL TGTPSAPTAA QGTNSTQIAN TAFVKAAITA LINGAPGTLD  300
TLKEIAAAIN NDPNFSTTVN NALALKAPLA SPALTGIPTA PTAAQGTNNT QIATTAYVRA  360
AISALVGSSP EALDTLNELA AALGNDPNFA TTMTNALAGK QPLDATLTAL AGLATGANKL  420
PYFTGKDTVA QTDLTSVGRD ILAKTSVLAV IQYLGLRELG TSGEKIPLLS TANTWSARQT  480
FNGGITGALT GNADTATKLK TAININGVRF DGSTNISIPT ITSRGRVTAL TGTTQGAATG  540
LQMYEAYNNG YPTTYGNVLH LKGAASTGEG ELLIGWSGTN GAHAPAFIRS KRDITAAAWS  600
EWAQIYTSKD SVPGVNTKGN QDTSGNAATA TKLQTACTIN GVSFDGSKNI ELTAADLNLE  660
QTVELAAGAL QKNQNGADIP GKDTFTKNIG ACRAYSAWLN IGGDSQVWTT AQFISWLESQ  720
GAFNHPYWMC KGSWAYANNK VITDTGCGNI CLAGAVVEVI GTRGAMTIRV TTPSTSSGGG  780
ITNAQFTYIN HGDAYAPGWR RDYNTKNQQP AFALGQTGSR VANDKAVGWN WNSGVYDADI  840
SGASTLILHF NMNAGSCPAV QFRVNYKNGG IFYRSARDGY GFEANWSEFY TTTRKPSAGD  900
VGAYTQAECN SRFITGIRLG GLSSVQTWNG PGWSDRSGYV VTGSVNGNRD ELIDTTQARP  960
IQYCINGTWY NAGSI                                                  975

SEQ ID NO: 67           moltype = AA  length = 175
FEATURE                 Location/Qualifiers
REGION                  1..175
                        note = Asparagus Chaperone
source                  1..175
                        mol_type = protein
                        organism = synthetic construct
SEQUENCE: 67
MMHLKNIKSE NPKTKEQYQL TKNFDVIWLW SEDGKNWYEE VNNFQDDTIK IVYDENNIIV  60
AITKDASTLN PEGFSVVEIP DITANRRADD SGKWMFKDGA VVKRIYTADE QQQQAESQKA  120
ALLSEAESVI QPLERAVRLN MATDEERARL ESWERYSVLV SRVDTANPEW PQKPE       175

SEQ ID NO: 68           moltype = AA  length = 140
FEATURE                 Location/Qualifiers
REGION                  1..140
                        note = Banana Chaperone
source                  1..140
                        mol_type = protein
                        organism = synthetic construct
SEQUENCE: 68
MRIYFSPSEI GFYHESDKQA YLLAGTWPND LLEISEKWFL YLLEGQQKGK VITVNDYDQP  60
VLVDPPTATK EQLLAEADAQ KEALMNSASA VIEPLKDAVE LGMSTDEEEG LLLAWQQYRV  120
LLMRVDTSHA PDIEWPVLPA                                             140

SEQ ID NO: 69           moltype = AA  length = 203
FEATURE                 Location/Qualifiers
REGION                  1..203
                        note = Bittersweet Chaperone
source                  1..203
                        mol_type = protein
                        organism = synthetic construct
SEQUENCE: 69
MDNAILNSEL IAIQAGNIIV YNYDGGNREY ISASTEYLAV GVGIPANSCL DAPGSHKAGY  60
AILRSEDLSS WEYVPDHRGE TVYSIDTGNP EEITVLGDYP ENTTTIAPLT PYDKWDGEKW  120
VVDTEAQHSA AVEAAETKRQ SLIDTAMDSI SLIQLKLRAG RKLTQAETTQ LNSVLDYIDE  180
LNAMDLTTAP DLNWPEKQLS TAS                                         203

SEQ ID NO: 70           moltype = AA  length = 203
FEATURE                 Location/Qualifiers
REGION                  1..203
```

```
                        note = Cobalt Chaperone
source                  1..203
                        mol_type = protein
                        organism = synthetic construct
SEQUENCE: 70
MDNAILNSEL IAIQAGNIIV YNYDGGNREY ISASTEYLAV GVGIPANSCL DAPGSHKAGY  60
AILRSEDLSS WEYVPDHRGE TVYSIDTGNP EEITVLGDYP ENTTTIAPLT PYDKWDGEKW  120
VVDTEAQHSA AVEAAETKRQ SLIDTAMDSI SLIQLKLRAG RKLTQAETTQ LNSVLDYIDE  180
LNAMDLTTAP DLNWPEKQLS TAS                                         203

SEQ ID NO: 71           moltype = AA  length = 203
FEATURE                 Location/Qualifiers
REGION                  1..203
                        note = Denim Chaperone
source                  1..203
                        mol_type = protein
                        organism = synthetic construct
SEQUENCE: 71
MDNAILNSEL IAIQAGNIIV YNYDGGNREY ISASTEYLAV GVGIPANSCL DAPGSHKAGY  60
AILRSEDLSS WEYVPDHRGE TVYSIDTGNP EEITVLGDYP ENTTTIAPLT PYDKWDGEKW  120
VVDTEAQHSA AVEAAETKRQ SLIDTAMDSI SLIQLKLRAG RKLTQAETTQ LNSVLDYIDE  180
LNAMDLTTAP DLNWPEKQLS TAS                                         203

SEQ ID NO: 72           moltype = AA  length = 175
FEATURE                 Location/Qualifiers
REGION                  1..175
                        note = Eggplant Chaperone
source                  1..175
                        mol_type = protein
                        organism = synthetic construct
SEQUENCE: 72
MQHLKNIRSG NPKTKEQYQL TKNFDVIWLW SEDGKNWYEE VKNFQPDTIK IVYDENNIIV  60
AITKDASTLN PEGFSVVEVP DITANRRADD SGKWMFKDGA VVKRIYTADE QQQQAESQKA  120
ALLSEAESVI QPLERAVRLN MATDEERTRL EAWERYSVLV SRVDTANPEW PQKPE       175

SEQ ID NO: 73           moltype = AA  length = 175
FEATURE                 Location/Qualifiers
REGION                  1..175
                        note = Fern Chaperone
source                  1..175
                        mol_type = protein
                        organism = synthetic construct
SEQUENCE: 73
MQHLKNIKSG NPKTKEQYQL TKNFDVIWLW SEDGKNWYEE VKNFQPDTIK IVYDANNIIV  60
AITKDASTLN PEGYSVVEVP DITANRRADD SGKWMFKDGA VVKRIYTADE QQQQAESQKA  120
ALLSEAENVI QPLERAVRLN MATDEERARL ESWERYSVLV SRVDTANPEW PQKPE       175

SEQ ID NO: 74           moltype = AA  length = 177
FEATURE                 Location/Qualifiers
REGION                  1..177
                        note = Fuchsia Chaperone
source                  1..177
                        mol_type = protein
                        organism = synthetic construct
SEQUENCE: 74
MMHLRNITAG NPKTKEQYQL TKQFNIKWLY TEDGKNWYEE QKNFQYDTLK MAYDHNGVII  60
CIEKDVSAIN PEGASVVELP DITANRRADI SGKWMFKDGV VVKRTYTEEE QRQQAENEKQ  120
SLLQLVRDKT QLWDSQLRLG IISAENKQKL TEWMLFAQKV ESTDTSSLPV TFPEQPE     177

SEQ ID NO: 75           moltype = AA  length = 197
FEATURE                 Location/Qualifiers
REGION                  1..197
                        note = Fuzzy Chaperone
source                  1..197
                        mol_type = protein
                        organism = synthetic construct
SEQUENCE: 75
MQETMTRIEL SGVLGKTFGK VHYRLIKNIN EAGEALSATI PGFERFMISS EERGLTYAVF  60
KGNKNIGHDD LGFPVSGEII RIVPVIIGSK KAGILQTILG AVIVAASVAY GFFTEDWANA  120
AYGIQAGGAM MLGGVVQMLS PQPAGLARKE SADNKASYAF GGVTNTASQG YPVPLLYGKR  180
RIGGAIISAG IYVEDQQ                                                197

SEQ ID NO: 76           moltype = AA  length = 152
FEATURE                 Location/Qualifiers
REGION                  1..152
                        note = Inchworm Chaperone
source                  1..152
                        mol_type = protein
                        organism = synthetic construct
```

```
SEQUENCE: 76
MKGEYYFSPS QVAFYPASLR EVYEYAGCWP VDGEWVSAEL HEQLMNEQAA GRAISSDVNG  60
NPVAIERPPL SRQQRSTHER RWRDSQLLAT DGLVVRHRDQ LETGKETTLL PVQYHELMSY  120
RASLRDWPEE PLFPDSGGRP SVPDWLRRYV TP                                152

SEQ ID NO: 77          moltype = AA  length = 203
FEATURE                Location/Qualifiers
REGION                 1..203
                       note = Indian Chaperone
source                 1..203
                       mol_type = protein
                       organism = synthetic construct
SEQUENCE: 77
MDNAILNSEL IAIQAGNIIV YNYDGGNREY ISASTEYLAV GVGIPANSCL DAPGSHKAGY  60
AILRSEDLSS WEYVPDHRGE TVYSIDTGNP EEITVLGDYP ENTTTIAPLT PYDKWDGEKW  120
VVDTEAQHSA AVEAAETKRQ SLIDTAMDSI SLIQLKLRAG RKLTQAETTQ LNSVLDYIDE  180
LNAMDLTTAP DLNWPEKQLS TAS                                          203

SEQ ID NO: 78          moltype = AA  length = 203
FEATURE                Location/Qualifiers
REGION                 1..203
                       note = Indigo Chaperone
source                 1..203
                       mol_type = protein
                       organism = synthetic construct
SEQUENCE: 78
MDNAILNSEL IAIQAGNIIV YNYDGGNREY ISASTEYLAV GVGIPANSCL DAPGSHKAGY  60
AILRSEDLSS WEYVPDHRGE TVYSIDTGNP EEITVLGDYP ENTTTIAPLT PYDKWDGEKW  120
VVDTEAQHSA AVEAAETKRQ SLIDTAMDSI SLIQLKLRAG RKLTQAETTQ LNSVLDYIDE  180
LNAMDLTTAP DLNWPEKQLS TAS                                          203

SEQ ID NO: 79          moltype = AA  length = 205
FEATURE                Location/Qualifiers
REGION                 1..205
                       note = Jazzberry Chaperone
source                 1..205
                       mol_type = protein
                       organism = synthetic construct
SEQUENCE: 79
MAFRMSEQSR TVKIYNLLAG TNEFIGEGDA YIPPHTGLPA NSTDIAPPEI PAGFVAVFNS  60
ENESWNIVED HRGKTVYDVA SGDALFISEP GPLPENVTWL SPAGEYQKWD GVSWVKDEEA  120
EKLFRIREAE EKKARLIQEA TDNIAILQDA VNLEIATNEE NSQLDSWRKY RVLVSRIDTS  180
TAPDIVWPEL MNQGYVREDE QITSD                                        205

SEQ ID NO: 80          moltype = AA  length = 177
FEATURE                Location/Qualifiers
REGION                 1..177
                       note = Jungle Chaperone
source                 1..177
                       mol_type = protein
                       organism = synthetic construct
SEQUENCE: 80
MMHLKNITAG NPKTKEQYQL TKQFNIKWLY TEDGKNWYEE QKNFQPDTLK MVYDHNGVII  60
CIEKDVSAIN PEGANVVEVP DITANRRADI SGKWMFKDGV VIKRTYTEEE QRQQAENEKQ  120
SLLQLVRDKT QLWDSQLRLG IISDENKQKL TEWMLYAQKV ESTDTSSLPV TFPEQPE     177

SEQ ID NO: 81          moltype = AA  length = 140
FEATURE                Location/Qualifiers
REGION                 1..140
                       note = Mango Chaperone
source                 1..140
                       mol_type = protein
                       organism = synthetic construct
SEQUENCE: 81
MGYVYCHATG AFYNDALVAD YRSAGSWPDN YVTVLDDDYE SLMAGQAVGK MIVSDNNGYP  60
VLTEPPEPTH EEQVNQASSQ KLFLMKTANE IITPLEDAVE LGIATDEEAA TLLLWKRYRV  120
LLNRLDLSKA PDIQWPERPA                                              140

SEQ ID NO: 82          moltype = AA  length = 203
FEATURE                Location/Qualifiers
REGION                 1..203
                       note = Maroon Chaperone
source                 1..203
                       mol_type = protein
                       organism = synthetic construct
SEQUENCE: 82
MDNAILNSEL IAIQAGNIIV YNYDGGNREY ISASTEYLAV GVGIPANSCL DAPGSHKAGY  60
AILRSEDLSS WEYVPDHRGE TVYSIDTGNP EEITVLGDYP ENTTTIAPLT PYDKWDGEKW  120
VVDTEAQHSA AVEAAETKRQ SLIDTAMDSI SLIQLKLRAG RKLTQAETTQ LNSVLDYIDE  180
```

```
LNAMDLTTAP DLNWPEKQLS TAS                                   203

SEQ ID NO: 83           moltype = AA  length = 177
FEATURE                 Location/Qualifiers
REGION                  1..177
                        note = Mulberry Chaperone
source                  1..177
                        mol_type = protein
                        organism = synthetic construct
SEQUENCE: 83
MMHLRNITAG NPKTKEQYQL TKQFNIKWLY TEDGKNWYEE QKNFQYDTLK MAYDHNGVII  60
CIEKDVSAIN PEGASVVELP DITANRRADI SGKWMFKDGV VVKRTYTEEE QRQQAENEKQ  120
SLLQLVRDKT QLWDSQLRLG IISAENKQKL TEWMLFAQKV ESTDTSSLPV TFPEQPE     177

SEQ ID NO: 84           moltype = AA  length = 177
FEATURE                 Location/Qualifiers
REGION                  1..177
                        note = MISC_FEATURE - P1_U' Chaperone
source                  1..177
                        mol_type = protein
                        organism = Bacteriophage P1
SEQUENCE: 84
MMHLRNITAG NPKTKEQYQL TKQFNIKWLY TEDGKNWYEE QKNFQYDTLK MAYDHNGVII  60
CIEKDVSAIN PEGASVVELP DITANRRADI SGKWMFKDGV VVKRTYTEEE QRQQAENEKQ  120
SLLQLVRDKT QLWDSQLRLG IISAENKQKL TEWMLFAQKV ESTDTSSLPV TFPEQPE     177

SEQ ID NO: 85           moltype = AA  length = 175
FEATURE                 Location/Qualifiers
REGION                  1..175
                        note = Pine Chaperone
source                  1..175
                        mol_type = protein
                        organism = synthetic construct
SEQUENCE: 85
MQHLKNIKSG NPKTKEQYQL TKNFDVIWLW SEDGKNWYEE VKNFQPDTIK IVYDENNIIV  60
AITRDASTLN PEGFSVVEVP DITSNRRADD SGKWMFKDGA VVKRIYTADE QQQQAESQKA  120
ALLSEAENVI QPLERAVRLN MATDEERARL ESWERYSVLV SRVDPANPEW PEMPQ       175

SEQ ID NO: 86           moltype = AA  length = 205
FEATURE                 Location/Qualifiers
REGION                  1..205
                        note = Plum Chaperone
source                  1..205
                        mol_type = protein
                        organism = synthetic construct
SEQUENCE: 86
MAFRMSEQSR TVKIYNLLAG TNEFIGEGDA YIPPHTGLPA NSTDIAPPEI PAGFVAVFNS  60
ENESWNIVED HRGKTVYDVA SGDALFISEP GPLPENVTWL SPAGEYQKWD GVSWVKDEEA  120
EKLFRIREAE EKKARLIQEA TDNIAILQDA VNLEIATNEE NSQLDSWRKY RVLVSRIDTS  180
TAPDIVWPEL MNQGYVREDE QITSD                                 205

SEQ ID NO: 87           moltype = AA  length = 170
FEATURE                 Location/Qualifiers
REGION                  1..170
                        note = Queen Chaperone
source                  1..170
                        mol_type = protein
                        organism = synthetic construct
SEQUENCE: 87
MNNFKNFAPY TPGEDKRELV DAGVLFLLDE NGNDWYECQK LFSECTKVIA YDSNNIVVSI  60
TDDASTLWPI GLSVAEVDSL PEDVDINGGW VFRDNSVVKR IYSDTELQQQ AESKKAALLS  120
HAESVIVTLE RAVKLNMATD EERAKLEAWE RYSVLVYRVD TAKPEWPEEP            170

SEQ ID NO: 88           moltype = AA  length = 93
FEATURE                 Location/Qualifiers
REGION                  1..93
                        note = Razzmatazz Chaperone A
source                  1..93
                        mol_type = protein
                        organism = synthetic construct
SEQUENCE: 88
MMHLKNITAG NPKTKEQYQL TKQFNIKWLY TEDGKNWYEE QKNFQPDTLK MVYDHNDVII  60
CIEKDVSAIN PEGASVVEVP DITANRRADI SGK                        93

SEQ ID NO: 89           moltype = AA  length = 83
FEATURE                 Location/Qualifiers
REGION                  1..83
                        note = Razzmatazz Chaperone B
source                  1..83
```

```
                        mol_type = protein
                        organism = synthetic construct
SEQUENCE: 89
MFKDGVVIKR TYTEEEQRQQ AENEKQSLLQ LVRDKTQLWD SQLRLGIISD ENKQKLTEWM  60
LYAQKVESTD TSSLPVTFPE QPE                                          83

SEQ ID NO: 90           moltype = AA  length = 176
FEATURE                 Location/Qualifiers
REGION                  1..176
                        note = Salmon Chaperone
source                  1..176
                        mol_type = protein
                        organism = synthetic construct
SEQUENCE: 90
MMQHLKNIKS GNPKTKEQYQ LTKNFDVIWL WSEDDKNWYE EVKNFQPDTI KIVYDANNII  60
VAITKDASTL NPEGFSVVEV PDITANRRAD DSGKWMFKDG AVVKRIYTAD EQQQQAESQK  120
AALLSEAESV IQPLERAVRL NMATDEERTR LEAWERYSVL VSRVDTANPE WPQKPE      176

SEQ ID NO: 91           moltype = AA  length = 203
FEATURE                 Location/Qualifiers
REGION                  1..203
                        note = Scarlet Chaperone
source                  1..203
                        mol_type = protein
                        organism = synthetic construct
SEQUENCE: 91
MDNAILNSEL IAIQAGNIIV YNYDGGNREY ISASTEYLAV GVGIPANSCL DAPGSHKAGY  60
AILRSEDLSS WEYVPDHRGE TVYSIDTGNP EEITVLGDYP ENTTTIAPLT PYDKWDGEKW  120
VVDTEAQHSA AVEAAETKRQ SLIDTAMDSI SLIQLKLRAG RKLTQAETTQ LNSVLDYIDE  180
LNAMDLTTAP DLNWPEKQLS TAS                                          203

SEQ ID NO: 92           moltype = AA  length = 175
FEATURE                 Location/Qualifiers
REGION                  1..175
                        note = Shamrock Chaperone
source                  1..175
                        mol_type = protein
                        organism = synthetic construct
SEQUENCE: 92
MMHLKNIKAG NAKTLEQYEL TKKHGVIWLY AEDGKNWYEE VKNFQPDTIK IVYDENNIIV  60
AVTKDASTLN PEGFSVVEIP DITANRRADD SGKWMFKDGA VVRRTYTADE QQQQAESQKA  120
ALLSEAESVI QPLERAVRLN MATDEEHARL ESWERYSVLV SRVDTANPEW PQKPE       175

SEQ ID NO: 93           moltype = AA  length = 203
FEATURE                 Location/Qualifiers
REGION                  1..203
                        note = Sunset Chaperone
source                  1..203
                        mol_type = protein
                        organism = synthetic construct
SEQUENCE: 93
MDNAILNSEL IAIQAGNIIV YNYDGGNREY ISASTEYLAV GVGIPANSCL DAPGSHKAGY  60
AILRSEDLSS WEYVPDHRGE TVYSIDTGNP EEITVLGDYP ENTTTIAPLT PYDKWDGEKW  120
VVDTEAQHSA AVEAAETKRQ SLIDTAMDSI SLIQLKLRAG RKLTQAETTQ LNSVLDYIDE  180
LNAMDLTTAP DLNWPEKQLS TAS                                          203

SEQ ID NO: 94           moltype = AA  length = 203
FEATURE                 Location/Qualifiers
REGION                  1..203
                        note = Tangerine Chaperone
source                  1..203
                        mol_type = protein
                        organism = synthetic construct
SEQUENCE: 94
MDNAILNSEL IAIQAGNIIV YNYDGGNREY ISASTEYLAV GVGIPANSCL DAPGSHKAGY  60
AILRSEDLSS WEYVPDHRGE TVYSIDTGNP EEITVLGDYP ENTTTIAPLT PYDKWDGEKW  120
VVDTEAQHSA AVEAAETKRQ SLIDTAMDSI SLIQLKLRAG RKLTQAETTQ LNSVLDYIDE  180
LNAMDLTTAP DLNWPEKQLS TAS                                          203

SEQ ID NO: 95           moltype = AA  length = 175
FEATURE                 Location/Qualifiers
REGION                  1..175
                        note = Thistle Chaperone
source                  1..175
                        mol_type = protein
                        organism = synthetic construct
SEQUENCE: 95
MQHLKNIRSG NPKTKEQYQL TKNFDVIWLW SEDGKNWYEE VKNFQPDTIK IVYDENNIIV  60
AITKDASTLN PEGFSVVEVP DITANRRADD SGKWMFKDGA VVKRIYTADE QQQQAESQKA  120
```

```
ALLSEAESVI QPLERAVRLN MATDEERTRL EAWERYSVLV SRVDTANPEW PQKPE       175

SEQ ID NO: 96          moltype = AA  length = 177
FEATURE                Location/Qualifiers
REGION                 1..177
                       note = Violet Chaperone
source                 1..177
                       mol_type = protein
                       organism = synthetic construct
SEQUENCE: 96
MMHLKNITAG NPKTKEQYQL TKQFNIKWLY TEDGKNWYEE QKNFQPDTLK MVYDHNDVII  60
CIEKDVSAIN PEGASVVEVP DITANRRADI SGKWMFKDGV VIKRTYTEEE QRQQAENEKQ  120
SLLQLVRDKT QLWDSQLRLG IISDENKQKL TEWMLYAQKV ESTDTSSLPV TFPEQPE     177

SEQ ID NO: 97          moltype = DNA  length = 4494
FEATURE                Location/Qualifiers
misc_feature           1..4494
                       note = P1 Bald Chassis Tail Fiber Region
source                 1..4494
                       mol_type = other DNA
                       organism = synthetic construct
SEQUENCE: 97
taatcacccc gtccgcaggg cggggtgaca agttacttat cttacaatga ggcttcacaa  60
cattgattag ggaaaatcat gtctgacgtc tcaacaaacc tctataagag tcagttgttg  120
gactattact atcagcggcg cgctgaatcg tccattaaca aaggctctcg atttttaatc  180
agcaaggccg ttttcggtac cagttcgctg gttactaaga aaggagatgg cacttatgag  240
attggagaac tgccaaaggc tttcgaactg gcagaactga ccagtcaatt ttgcaccatc  300
aacctcgtcc caacctactc aggcgggata attactgtcc gaatggacct tgatcaaagc  360
cagttgcagg aagggaaaaa ctacccattc aacactctgg ttgttctgga taacgagaac  420
aagccaatcg ccattatttg tgtccaggaa gactcgctgt atgtgggcaa aacatatacc  480
gcagttatgg ccataaacac gactacagca taaggatatg cttgcggaat ctgtgggtaa  540
ctttgtatgt gtccgcagcg cccgccgcag tctcacgccc ggagcgtagc gaccgagtga  600
gctagctatt tgtttatttt tctaaataca ttcaaatatg tatccgctca tgagacaata  660
accctgataa atgcttcaat aatattgaaa aaggaagagt atgagggaag cggtgatcgc  720
cgaagtatcg actcaactat cagaggtagt tggcgtcatc gagcgccatc tcgaaccgac  780
gttgctggcc gtacatttgt acggctccgc agtggatggc ggcctgaagc cacacagtga  840
tattgatttg ctggttacgg tgaccgtaag gcttgatgaa acaacgcggc gagctttgat  900
caacgacctt ttggaaactt cggcttcccc tggagagagc gagattctcc gcgctgtaga  960
agtcaccatt gttgtgcacg acgacatcat tccgtggcgt tatccagcta agcgcgaact  1020
gcaatttgga gaatggcagc gcaatgacat tcttgcaggt atcttcgagc cagccacgat  1080
cgacattgat ctggctatct tgctgacaaa agcaagagaa catagcgttg ccttggtagg  1140
tccagcggcg gaggaactct ttgatccggt tcctgaacag gatctatttg aggcgctaaa  1200
tgaaacctta acgctatgga actcgccgcc cgactgggct ggcgatgagc gaaatgtagt  1260
gcttacgttg tcccgcattt ggtacagcgc agtaaccggc aaaatcgcgc cgaaggatgt  1320
cgctgccgac tgggcaatgg agcgcctgcc ggcccagtat cagcccgtca tacttgaagc  1380
tagacaggct tatcttggac aagaagaaga tcgcttggcc tcgcgcgcag atcagttgga  1440
agaatttgtc cactacgtga aaggcgagat caccaaggta gtcggcaaat aatgtctaac  1500
aattcgttca agccgagtat ggcaacagac gaggaacgca cacgactgga agcatgggaa  1560
cgctacagtg ttctggtcag ccgtgtggat acggcaaatc ctgaatggcc acaaaagcct  1620
gaataaaaat taaggcccgc tatcgggcct tgtctcattc aggttgttcg ggaaatgtta  1680
ctggtaggct ggaggtgtct gtggattcga ctttctgcgc aaagagcatc cactcggtta  1740
atttctgctt attctcggcg gaaatgatac ccagccgtag ctgtgagtcc catagctggg  1800
ttttatccct gacgagctgt agcagacttt gcttttcatt ttccgcttgt tgcctctgct  1860
cttcctcggt ataagttcgc tttaccacta cgccatcttt gaacatccat ttaccagaaa  1920
tatcagcccg gcgatttgct gtaatatcag gtaattcaac gacgcttgcg ccttctggat  1980
taattgctga aacatccttt tcaatacaaa taataacgcc gttgtggtca taggccattt  2040
tcaacgtatc atactggaaa ttcttttgtt cctcatacca gtttttttcca tcctctgtat  2100
aaagccattt gatgttaaat tgtttcgtta gctggtattg ctcttttgtt ttagggttgc  2160
cagctgtaat atttcttaag tgcatcataa ttaaatactc cccgcgttat accacgtccc  2220
attaatgcaa tactgaattg gccttgcctg tgttgtatca attaattcat cacggttccc  2280
gttaactgaa cccgtaacga cataacctga cctgtcagac cagccggggc cattccatgt  2340
ctggacagat gacagaccgc ccaggcgaat acctgtaata aaccttgagt tacattctgc  2400
ctgcgtatat gcaccaacat cccccgcaga gggtttgcgg gttgtggtgt aaaactctga  2460
ccagtcagcc tcaaatccat aaccatcacg cgctgaacga taataaatac cgccgttctt  2520
ataattcacg cgtaattgta cagccgggca gctacccgcg ttcatattga aatgaagaat  2580
taatgttgat gcgcctttta ggtctgcatc ataaacaccg ctattccagt tccagccaac  2640
agctttatca tttgcaaccc tgtttcctgt ctgccctaaa gcaaatgcag gttgcaggtt  2700
tttcgtgttg tagtctcgtc gccagccagg agcgtaagca tcaccatgat taatataagt  2760
gaattgagcg ttagtgattc cgccaccgct ggaagtgctt ggtgttgtta cacggatggt  2820
catggcacct ttattaccca taacctcaat aacgcaacct gcaagatgaa tagttccaca  2880
gccagtatcg gttataattt tattattgcc gtacgaccat gaacatttgc acatccagta  2940
tgggtgattg aatgcccctt gagaatccag ccattcaatc aattgtgccg ttgtccagtt  3000
ccctgcacct gtactaatag aactgtgaaa agcgcgacat gcaccaatat tttttgtgaa  3060
ggtatctttt ccaggaatat ccgcgccgtt ctgatttttc tgcaatgacc cagcggctaa  3120
ttctactgtt cgctcaagat ttaaattttc agccgttagc tcaatatttt tagaaccatc  3180
aaacgagaca ccgttgatag tacatgctgt ctgcaacttg gtcgctgtag ccgcattacc  3240
agaggtatcc tgatcccctt tggcattgac gccgggaatt gaatcttttg acgtatagac  3300
ctgcgcccat tcagaccagt tggcagaatc agtatcccgc cgcgaacgga tatgtacggg  3360
cgcatgggca ccgctcgtgc cactccagcc aatgaataac tcaccttcgc cagcagcggt  3420
```

```
ggcaccttta aggtgaagca cattgccata gggggaaggg tagccattgt tgtatgcctc  3480
atacagctga atcccggatg ttccctgtgc attcgcctcc agggccgtta cgcgaccgcg  3540
cgataccaga gtattgatat taatgtcacc agaaccatcg aacctgacgc cattaatgtt  3600
tctggctgtt ttcaatttcg ttgcggtatc ggcgttccct gtcagcgccc cggtgatccc  3660
gccgttgaaa gtctggcgtg cactccatgt gttagccgtg ctcaacaggg ggatcttttc  3720
accgctggta ccgagttctc ttaaaccaag gtttaggatt gaaatgatga cgccggaaac  3780
ttcttataaa gcgtggaaac agccacatca tagatgattg caacctgctt acgggggatg  3840
cccttctcca gcaatcgccg catttgctgc catgtttctt cttggtattt aggccgacgc  3900
ccacctatac gaccttctgc gcgagctgca tcaagtccag cgcgtgtacg ttcaacgata  3960
agctcacgtt ccatttctgc cagcgccccc attacgtgaa agaaaaagcg ccccattggt  4020
gtactggtgt cgatggagtc agtgagactc cggaagttaa tgcctctgtc acgcagctct  4080
tccaccagca caactaagtg acgcatgctg cgcccaagac ggtctaactt ccatacgacc  4140
agggtatcac ctctggaaag catacggagt accttttta acccagggcg ctcagccttt  4200
ttgccgctcg ccttgtcctc aaaaattagc tcacatcctg cgctttcaag agcgtttcgt  4260
tgtaaagcag tgttttgttc atttgttgat acgcgtacat agcctattag catatttct  4320
gctcactatc gttatttata gcaagctgcg gattttaatt aacaaaaacc agtatgtgtg  4380
gaaatcacaa agtacatacc gtttcccaat gatatttaat tcactattaa ggaaatagtt  4440
atgtgtgatt tcacaataat gctcctctcc atccttggcg gggtgcattc gttt        4494

SEQ ID NO: 98          moltype = DNA  length = 1950
FEATURE                Location/Qualifiers
misc_feature           1..1950
                       note = Rio Tail Fiber S gene
source                 1..1950
                       mol_type = other DNA
                       organism = synthetic construct
SEQUENCE: 98
atgaatgacg ttacagttgt tacatcggtt acttacccat catccgagtc gttggctctg  60
gtggccgatg tgcaatacca cgaaccatat ctgtcagccg cgctaaaccg aaaattcagg  120
gggattgttg acccgggatt ttatgccggt ttcttaccta agcctggcgg tgggatgaac  180
ctgttaatta cctcagtgga tggtgataaa accgcaggcg cggcgtcggt ggatattggt  240
gaattttacc aggtaactat tcagcaacgt aaggatattt ctcttgcact tagtgcaggc  300
aagaaatatg caattgtgct gaagggaaga tacctccttg gagaagatac ctaccaggtg  360
aataccgcgt cacatattca tgcggctgaa tttgttgcca gaacctatac cgattcatat  420
cagttaggag atggggagct gcttgtttgt acggtgaata tccctgctag tgtatctgcc  480
attacccagg agatgattga tacatccgag cgtatcaacc gctcgatcgg cattgatatt  540
tcagactctg taaccagtac cagaagtgat gttgctgcaa gttcgctggc agttaaaaaa  600
gcctacgatc tggcgaaaag caagtatacg gcacaggatg caacaacaac agtaaaaggc  660
tttacaaagt taaataatca ggtgggtgac agtgaaaata ccgcattaac tccttacggc  720
gctaaaaaag aattagaaaa ctatcaaccc aaaggcaatt atcaacccgc tggtaattat  780
gtcactactg cgacatttaa tttagaaatc aataaaaaaa tagataaagc aagtctctca  840
cagcaacttg gtaatgatgt aaataaagta cctagtttag atttggtgac taaagagcta  900
gggaataaac aacctaaagg tgattatgca ttaaaaacat gggttgataa tatttattat  960
aaacgagatg acagtccttc atttaatgaa attagtgcta cagctattcg agtgaatagt  1020
gttaacgtcg cgctaaaagg ggattgctat acaaaatcag aatctgataa taaatattct  1080
ccgaaattac cctttgtata ctcttcgggt gaggagtcaa aaatcatatc accaaacaat  1140
aaaatcctta tttttgttaa tgataatgga acaacaggag ggtatgacag ggatactcaa  1200
gcaacagtct ggggggtttga taaacgtgga tttatgacaa gaggcactgt gcattttgac  1260
agaatgtcag gtgtttattc acaatcacag gtagatgcta agttaaaaga gtgcctaaat  1320
ttaaaaacat catcaaaaca atttattgca agtgatatat atgcacccac tttcattaca  1380
ggctcgcagt atggagaacg ttcctattta gaacataaaa gtgatgagct tactattact  1440
cacatatcgc caaaatcagg ggcaacaaat attacttgta gaaataaaag tggtacctta  1500
gcactattgg gtgatctcga agatgttaat aatatccctg ttggttcccc tattccgtgg  1560
tcattagcta cagcaccctc tggttatcta atctgtaatg gtcaaacatt taataaatca  1620
acatacccaa aacttgccgt tgcttatcca tcaggaaaac tacctgattt gcgcggtgag  1680
tttattcgtg gtttggacag cggcgcggt attgatgcgg ggcgttcggt attatcagtt  1740
caaaaaggta atagcttgtt atccagtaat atttttggtg gattgagttc atcggaatca  1800
aacaaatggc ataaagcaat taattatatc ggtattacag gtactgataa tgacggtggt  1860
tatggagttc accagcaaat agaaggcgct aatggaaatg aaactcgccc acgtaatatc  1920
gccttttat atatagtgag agcagcataa                                   1950

SEQ ID NO: 99          moltype = DNA  length = 621
FEATURE                Location/Qualifiers
misc_feature           1..621
                       note = Rio Tail Fiber U gene
source                 1..621
                       mol_type = other DNA
                       organism = synthetic construct
SEQUENCE: 99
atgagcaaat atagtttaga tatccagaaa ggaaaaatcg gtgataatgg tttggcagaa  60
atcgcaggtt gggttaagtg ttatttagct catccaatta cgcatgaata tatgggcgca  120
accatggaaa atgtcatgtt tgatgtttca ttatctgcgg gtgcttattt agatgaacca  180
ccattacccc aaaaagaaaa tcaagccgtt agacgtagag aagatggtag tgcatgggag  240
attgttgacg attgccgagg tttaaccgcc tacaatacgc aaacaaagca acctatcatc  300
attgatttta tggggccatt gcctgaatct ctcacattgt taaaaccgaa tagtgagttt  360
gataaatggg atggtaagaa ctggattgtt gacacagaag cccaaaaagc ggcactcatt  420
acacagatta aacaggagaa atcacgacgc ttagatgaag cagataatat aatcacatat  480
ttgcaagaag ctgttgatgt tgacttagcc acagaagaag aggctacagc actgcaaaaa  540
tggaaaaaat accgagttct gttaaatcgt gttgatattt caacggcgcc agatatcgaa  600
```

```
tggccggaga aaccgcaatg a                                         621

SEQ ID NO: 100          moltype = DNA  length = 1746
FEATURE                 Location/Qualifiers
misc_feature            1..1746
                        note = Limon Tail Fiber S gene
source                  1..1746
                        mol_type = other DNA
                        organism = synthetic construct
SEQUENCE: 100
atgaatgacg ttacagttgt tacatcggtt acttacccat catccgagtc gttggctctg  60
gtggccgatg tgcaatacca cgaaccatat ctgtcagccg cgctaaaccg aaaattcagg  120
gggattgttg acccgggatt ttatgccggt ttcttaccta agcctggcgg tgggatgaac  180
ctgttaatta cctcagtgga tggtgataaa accgcaggcg cggcgtcggt ggatattggt  240
gaattttacc aggtaactat tcagcaacgt aaggatattt ctcttgcact tagtgcaggc  300
aagaaatatg caattgtgct gaagggaaga tacctccttg gagaagatac ctaccaggtg  360
aataccgcgt cacatattca tgcggctgaa tttgttgcca gaacctatac cgattcatat  420
cagttaggag atggggagct gcttgtttgt acggtgaata tccctgctag tgtatctgcc  480
attacccagg agatgattga tacatccgag cgtatcaacc gctcgatcgg cattgatatt  540
tcagactctg taaccagtac cagaagtgat gttgctgcaa gttcgctggc agttaaaaaa  600
gcctacgatc tggcgaaaag caagtatacg gcacaggatg caaccacagc aagaaaaggt  660
atcgtccagt taagcagtgc aacggacagc accagcgaag aactggctgc tacattgaaa  720
gcggttaaaa tcgcgatgga taacgccaac gcgcgtcttg caaaagagcg taacggtgga  780
gacgttccga ataaacctct gtttattcaa aacattggtt tgcaggaaac agttaacaaa  840
gcagccggag cagtgcagcg aagtgaggtc cagacttctc aggatgatat tactgccgga  900
aaattgctgg ttaatggtag cgctattgct gttcgtggca tccgcgcaat caatggagga  960
caggtagacg atgctaataa ccttccggtt aacgcagtat cgtttgtcta tggtgatgcc  1020
aaaaactcac cgagtggaaa tacagggact atcctggatg tttccgggct tggtagtggt  1080
tatagcatcc agctattcgc taactactcg acaggcgaaa tactggcgtt tcgtgcgcgt  1140
aatggtgata acagaacatg gaataaatgg aattatgtgt ttcacacggg aaataaacca  1200
acctctacag atgtgggggc gctaccaata acaggtggtg atttaaaggg gcaactttcc  1260
ttttcgttct cgcaacccag aaatggcgct aaccacttaa tatacaacgg cgatgataac  1320
ggagtactgg cttgcggata tggttattat caggacagat ttgatattca tttttatgac  1380
attaaaggtg cgtgggaatc aaatccatta accataggac gcaatggaaa tacgacagtt  1440
agtggtaatt tgtcaggtcg tgctgtttat gaaggtaaca ctcgcgttta ttcacccaac  1500
aacccgcagc ccgttagctt tgaaggttat gcaacgcaaa gctgggtgtt gcagaacttt  1560
gtccaaaata ttgacctgac agcacctgct gaagttggat ttcgtgatgg gtgggggtat  1620
ccacgaggga cagatggcgc agccatgtac aactttaata tggttggtgg tagcagtaac  1680
gttggtaatt ttatcattcg ttatatgcgg aaacaggtga ataacacctg gtatgtgatt  1740
aattaa                                                          1746

SEQ ID NO: 101          moltype = DNA  length = 534
FEATURE                 Location/Qualifiers
misc_feature            1..534
                        note = Limon Tail Fiber U gene
source                  1..534
                        mol_type = other DNA
                        organism = synthetic construct
SEQUENCE: 101
atgcaacgct ttggcaaatt caccccatat acaccagaca ctactgacag gccaagaatt  60
attgatggtc agaatgttat gtttttgcag gatgataaag gtaatgactg gtatgacgtt  120
attgaattat ttgatgaatc aaaaacgctg aaaattggat atgacgatga tggtcgtgta  180
agaacgttca cgacaaatat tcatgcgctt ttcccggtca atctgagtgt tgtcgagctt  240
ccggccacaa aagctaattt gcgcgtcacg ctgggtgatg actggtttta taaagacggc  300
aaattacagc aaatccgcaa ttacctggct gacgctgaag cggaacgtgg caaccgtatg  360
gcggaggtta caacgcgtat tgactggctg gaggatgcgc aaaaagacgg tgatatttca  420
tcctatgagg aaacagaact ggcaacacta cgcgcttacc gcactgcttt gcgccgtctg  480
gatctgagca cagcgccaga tattaactgg ccggaggtgc ctgatgtggc gtga        534

SEQ ID NO: 102          moltype = DNA  length = 3210
FEATURE                 Location/Qualifiers
misc_feature            1..3210
                        note = Orchid Tail Fiber S gene
source                  1..3210
                        mol_type = other DNA
                        organism = synthetic construct
SEQUENCE: 102
atgaatgacg ttacagttgt tacatcggtt acttacccat catccgagtc gttggctctg  60
gtggccgatg tgcaatacca cgaaccatat ctgtcagccg cgctaaaccg aaaattcagg  120
gggattgttg acccgggatt ttatgccggt ttcttaccta agcctggcgg tgggatgaac  180
ctgttaatta cctcagtgga tggtgataaa accgcaggcg cggcgtcggt ggatattggt  240
gaattttacc aggtaactat tcagcaacgt aaggatattt ctcttgcact tagtgcaggc  300
aagaaatatg caattgtgct gaagggaaga tacctccttg gagaagatac ctaccaggtg  360
aataccgcgt cacatattca tgcggctgaa tttgttgcca gaacctatac cgattcatat  420
cagttaggag atggggagct gcttgtttgt acggtgaata tccctgctag tgtatctgcc  480
attacccagg agatgattga tacatccgag cgtatcaacc gctcgatcgg cattgatatt  540
tcagactctg taaccagtac cagaagtgat gttgctgcaa gttcgctggc agttaaaaaa  600
gcctacgatc tggcgaaaag caagtatacg gcacaggatg caagcacaac gcaaaaggga  660
ttagttcagc tcagtagcgc aactaacagc gacagcgaaa caatggcggc taccccctaaa  720
```

```
gctgttaagt ctataaaaga tctggctgat accaaagcgc caatagaaag cccgagtctg  780
acaggaacgc caaccgcgcc gacggcagcg caaggtacaa acagcacgca gatcgcaaat  840
acagcctttg ttaaggcagc tataactgca cttatcaacg gtgcgcctgg cacactggat  900
acgctgaaag aaatagcggc tgcgatcaat aacgacccga attacagcac aactatcaac  960
aatgccttgg ctctcaaagc gcctttggca agccctgcat taacgggtgt ccctactgcg  1020
cctacggctg cacagggcac aaacaatacg cagatcgcta cgactgctta cgtacgggct  1080
gctatctctg cattggtcgg ctcatcacct gaagctcttg ataccctgta tgagcttgca  1140
gcagcactgg gcaatgaccc gaactttgcg acaacaatga caaatgcgct ggcagggaaa  1200
cagccacttg atgcaacttt aaccgcgctt gctggtcttg cgacaggcgc aaataaattg  1260
ccgtacttta ccggtacaga cactgtttct cagactgact taacgtcagt tggtcgcgat  1320
attctggcca aaacaagcat tcttgctgtt atccaatacc ttggtttaag agaactcggt  1380
accagcggtg aaaagatccc cctgttgagc acggctaaca catggagtgc acgccagact  1440
ttcaacggcg ggatcaccgg ggcgctgaca gggaacgccg ataccgcaac gaaattgaaa  1500
acagccgcac gctcgattgg cggtgtggca tttgatggct cggccaatat caatcttcca  1560
ggtgtaaata caacaggtaa ccagaacacc acggggaatg ctgctaccgc gacgaaactt  1620
gcgacggcaa gaaacatcaa cggtgttaaa tttgatggtt ctgtggacat ttcgatacca  1680
acaattacgt ccagagggcg tgttactgcg ctcaccggta caacacaagg tgctgctact  1740
ggattgcaaa tgtatgaggc gtacaacaac ggctatcctt ctgcttacgg gaatgtgctt  1800
catcttaagg gcgcaacggc agttggtgaa ggtgagttgt tcataggttg gagcggtaca  1860
agtggcgctc atgcacctgt acatgtacgt tcgcgacgag atactgatac agccagttgg  1920
tcagagtggg cgcaggtcta cacatcgaag gattccatcc ctggtgtaaa taccacgggc  1980
aaccagaaca caaccggaaa cgcggcgtct gcaacgaaat tacaaacggc aagaactatt  2040
ggtggtgttt catttaatgg caccgcaaac atcgacctgc cgggcgtgaa taaaacaggt  2100
aatcagaaca caaccggtaa tgcagcgaca gcgaccaagt tacaaaccgc tcgaactata  2160
aatggggtct cgtttgatgg ttctaaaaat attgagctaa cggcggaaga tttaaatcta  2220
caggaattta ttaataaagc aaataatgcc gttcagcgtt caggcgatac tttgtccggt  2280
gggcttactt ttaaaaatga ctcaatcctt gcctggattc gaaatactga ctgggcgaag  2340
attggattta aaaatgatgc tgatggtgac actgattcat acatgtggtt tgaaacaggc  2400
gacaacggca atgaatattt caaatggaga agcaaacaaa gcaccacaac aaaagacctg  2460
atgaatctta aatgggatgc tttgtatgtt cttgtcaatg ccattgtaaa tggcgaagtc  2520
atatcaaaat cagcaaacgg cctacgtatt gcttatggta attacggatt ctttattcgt  2580
aatgatggtt cagatacata cttcatgttg accaactccg gtgacaacat ggggacttat  2640
aacggattaa ggccattatg gattaataac gctactggcg ctgtttcgat ggggcgtggc  2700
cttaatgttt caggggagac actttcagac cgttttgcta ttaacagcag tacaggcatg  2760
tggattaata tgcgtgacca gaacgttatt atgggacgta atgcggtatc cactgatggt  2820
gctcaggcct tgctccgtca ggaccatgcc gaccgcaaat ttatgattgg cggtctggga  2880
aataagcaat ttggcatcta catgattaat aactcaagga cagccaatgg caccgatggt  2940
caggcgtaca tggacaataa cggtaactgg ctttgcggtg cgcaaattat tcccggaaat  3000
tatggcaatt ttgactcacg ctatgtgaaa gatgttcgcc tgggtacgcg tgttgttcaa  3060
ttgatggcgc gtggtggtcg ttatgaaaaa gccggacacg caattaccgg attaagaatc  3120
attggtgaag tagatggcga tgatgaagcc atcttcagac caatacaaaa atacatcaat  3180
ggcacatggt ataacgtagc acaggtgtaa                                3210
```

```
SEQ ID NO: 103          moltype = DNA  length = 528
FEATURE                 Location/Qualifiers
misc_feature            1..528
                        note = Orchid Tail Fiber U gene
source                  1..528
                        mol_type = other DNA
                        organism = synthetic construct
SEQUENCE: 103
atgcagcatt taaaaaatat taagtctgga aatcctaaaa cgaaagaaca atatcagcta  60
acaaagaatt ttgatgttat ctggttatgg tccgaagacg gtaaaaactg gtatgaggaa  120
gtaaataact ttcaggacga caccataaag attgtatacg acgaaaataa tattattgtt  180
gccataacca aagatgcctc aacgcttaat cccgaaggct ttagtgtcgt tgagattcca  240
gatataacag ccaatcgtcg tgccgatgat tcagggaagt ggatgtttaa ggatggatct  300
gtagttaaac ggatttatac ggcagacgaa cagcaacaac aagccgaatc acaaaaggcc  360
gcattgcttt ccgaagctga atcagtcatc cagccgctgg aacgcgctgt caggttgaat  420
atggcaacag acgaggaacg cacacgactg gaagcatggg aacgctacag tgttctggtc  480
agccgtgtgg atacggcaaa tcctgaatgg ccacaaaagc ctgaataa              528
```

```
SEQ ID NO: 104          moltype = DNA  length = 2016
FEATURE                 Location/Qualifiers
misc_feature            1..2016
                        note = Gold Tail Fiber S gene
source                  1..2016
                        mol_type = other DNA
                        organism = synthetic construct
SEQUENCE: 104
atgaatgacg ttacagttgt tacatcggtt acttacccat catccgagtc gttggctctg  60
gtggccgatg tgcaatacca cgaaccatat ctgtcagccg cgctaaaccg aaaattcagg  120
gggattgttg acccgggatt ttatgccggt ttcttaccta agcctggcgg tgggatgaac  180
ctgttaatta cctcagtgga tggtgataaa accgcaggcg cggcgtcggt ggatattggt  240
gaattttacc aggtaactat tcagcaacgt aaggatattt ctcttgcact tagtgcaggc  300
aagaaatatg caattgtgct gaagggaaga tacctccttg gagaagatac ctaccaggtg  360
aataccgcgt cacatattca tgcggctgaa tttgttgcca gaacctatac cgattcatat  420
cagttaggag atggggagct gcttgtttgt acggtgaata tccctgctag tgtatctgcc  480
attacccagg agatgattga tacatccgag cgtatcaacc gctcgatcgg cattgatatt  540
tcagactctg taaccagtac cagaagtgat gttgctgcaa gttcgctggc agttaaaaaa  600
```

```
gcctacgatc tggcgaaaag caagtatacg gcacaggatg caaccttgct ggcaaagggt  660
ttcactcaat tgagcaacga cagcaatagc ggtagcgaaa cgctggccgc taccccgaaa  720
gccgtcaaag cggttaacga tgcctcgctg aaaatcgcgg cgaacctgaa agacctgcca  780
aacaagtccg tcgcgcgcgg caacctggag ctgggtactg ccgccacacg caacgtcggc  840
gcgcaaaaaa ccaacctgat ggaggtgggc gcgttcggtt tgggggggggg cccgatacat  900
cgcgaagacg ctctgagcaa ccgtggcgaa atctatcggg ttacgggtgc atcgaaaaat  960
gcgccgggcg gcggtgttta tggcgtcttg aacctgccgt gtgacggcgg cccttccagc  1020
ggctatctgg cgatccagcc taatggatca tcttacatcg gcacgtccac gacccctgac  1080
aaaccgctga actggtaccg aatttacact accggcttta aaccgacggc cacagacgtc  1140
gacgcctaca gcaaggcgga agccgacggg aagttcgtca aacagagcgg cgataccatt  1200
accggcgctt taacggtcaa tggagcgatt gagagtaaat ccggcctcac tacaccctct  1260
ttagccgtaa atggcagcgt aaccatcgcc ggagcgttga ccacaaaagc cggtgtcgag  1320
ctgttcggta ccacccccta tctggatttt cattacggca atagcaacgg tgacttcgat  1380
gtcagactca tcaatgacaa caaaggcacc ttagcctttc acggcaatga atattacgtc  1440
aatggcaagc tgagcgcgac gggtgatgcc tggataggcg gaaaggccaa tatcaacggt  1500
atggccgctt tttatagttc tgattttatt actaaacaag gaaatcttac tcatcccgac  1560
ggcaatcgcc aaacaaacgg tatgcgtcta caggggcaag gtaatctgct cgtcgatctt  1620
taccactatg agaaggtcgg gagccaccat gagttcggta tccatgttgc caacggcggg  1680
gccgatggct ggttcagctt ccgtaataac ggtgaactcc gcgcgaacgg caccttattt  1740
gctgcaggtg ccgcttatca aacagacggc aatattaacg gcggcatttg gggaggctat  1800
ttaagcaact atctcaatca caactttgtg cgggatgttc gcctgggtaa tgtggaaagt  1860
atcgctacct ggcgaggccc cggctattcg gatagcgcgg gttatgtcct gaccggcgca  1920
gcaaacaaca acgtggatga atacatcgac gtaattttcc gtcgtccgct gcaaaaacac  1980
attggtggca attgggttac cgtctggagc gtataa                          2016
```

```
SEQ ID NO: 105         moltype = DNA  length = 558
FEATURE                Location/Qualifiers
misc_feature           1..558
                       note = Gold Tail Fiber U gene
source                 1..558
                       mol_type = other DNA
                       organism = synthetic construct
SEQUENCE: 105
atgatgaata acatgaaaaa ctttaccctc gccgcgccgg aaacggtaga acagaaacag  60
ctggccgcct cgcacggtgt tttgttttta aaatccgatg ccggggaaga ctggtatgaa  120
tgtcaaaaaa gcttccgtcc tgagacggta aaactgatgt atgacaagga cgggatcatt  180
cgttcaatca ccgcgaaacc gaatgccgaa ggccattatg acgtttccgg atttttccca  240
gaaaatatga gtgtggcgga ggtcgaaaac ttgccggaag gcgctgatat caacggccgc  300
tggatttttg atggagaaaa catcatacca agatcgtatt caactcagga gctacggcaa  360
caggccgcca ataaaaaaca agagttgatt aagcaaagtt cgctgcagat agaaacgctt  420
aacgacgcta ctgacctggg aatggcaagc gaagaggaac tgcggctgct gacccgctgg  480
aaaacctacc gcgtattgct taatcgggtc gatcccgaag cggccccgga tatcgactgg  540
ccgcaaccac cgcaataa                                                558
```

```
SEQ ID NO: 106         moltype = DNA  length = 2760
FEATURE                Location/Qualifiers
misc_feature           1..2760
                       note = Bluetiful Tail Fiber S gene
source                 1..2760
                       mol_type = other DNA
                       organism = synthetic construct
SEQUENCE: 106
atgaatgacg ttacagttgt tacatcggtt acttacccat catccgagtc gttggctctg  60
gtggccgatg tgcaatacca cgaaccatat ctgtcagccg cgctaaaccg aaaattcagg  120
gggattgttg acccgggatt ttatgccggt ttcttaccta agcctggcgg tgggatgaac  180
ctgttaatta cctcagtgga tggtgataaa accgcaggcg cggcgtcggt ggatattggt  240
gaattttacc aggtaactat tcagcaacgt aaggatattt ctcttgcact tagtgcaggc  300
aagaaatatg caattgtgct gaagggaaga tacctccttg gagaagatac ctaccaggtg  360
aataccgcgt cacatattca tgcggctgaa tttgttgcca gaacctatac cgattcatat  420
cagttaggag atggggagct gcttgtttgt acggtgaata tccctgctag tgtatctgcc  480
attacccagg agatgattga tacatccgag cgtatcaacc gctcgatcgg cattgatatt  540
tcagactctg taaccagtac cagaagtgat gttgctgcaa gttcgctggc agttaaaaaa  600
gcctacgatc tggcgaaaag caagtatacg gcacaggatg caagcaccac ggcgaaaggg  660
ctggtgcagc tgagtagcgc gacgaccagc acagacgaaa cgaaagccag cacgcctaag  720
gcgcttaaaa ctgtcagtga tgccagcatg aaaaaggccg ccaatctgtc cgacgtggcc  780
gacaaggccg ccgcgcgtgg caatttagca ctgggtacgg ccgcgacgaa aaacgtcggg  840
gtggatggcg ggcagttgat ggaggtcggc gcctttggat tgggaagcgg ctcacgtcat  900
cgagaggatg cttattgcaa tcagggggaa atctatcggg ttaatggctc atcaaagaat  960
gcaccgggcg gcgatgttta tggcgtgctg agtttacctt gtgacggcgg cccgtcgggt  1020
gcgtatcttg cggtacaaaa cagcggtaac gcatttttttg gccgttcaaa tatcgcggaa  1080
aacggtgtga cttggtttca ggcttacacg acgaagttta aaccgactgc ggcagacgtc  1140
ggggcatgga gcaaagcaga agccgatggc cgttttctga tgctttccgg cggcacagta  1200
aaaaaactgg cgattaagcc cggcaacgcg gaaacagagg gtagcacact caatattgag  1260
ggaaatcagc atacgccctt agtgatgagc cgtctctctg ctcaaggaaa tctctctatc  1320
ggattccaag tcgccggaaa ggcgttaatg cgccttggtt ttggggctga tgacgagttg  1380
cattggggga cagaagctaa tcaggcgtcg aatccgcgca tttatacgac ggctaagccg  1440
cctacagcac aagaaaccgg ggcgttgacg gatgcgcagg ccgtaaagaa atacgcgctg  1500
cgctctatca aagtcaacgg taagccgttg agcggcgatg tcaatctgtt ggcaggggat  1560
gtcaacgcat ggaacaaaac cgaagcggat ggccgctatg taaaacagag cggcgacacg  1620
```

```
atgaaagggg cattaactct gccgcgtatc gtattcccga acgaaaatac cgccaatgct  1680
gacgatgact taaatcgcga aaatggcttt accgttgagt cattggttgc cactaccaat  1740
aagggctatc ccgtgccggg cggcatgggg gtgttgttta ccgggaaagt gaacgagttc  1800
cgcaatgtgc aatttgccgt aggctccggc gatatggcgt tttatttgcg ctcgatgcga  1860
aaagacaact cggcttcgct ccgctgggcg cgagtttata cgacggacta caaaccgacg  1920
gcggctgacg ttggcgcgct gacggatgcg caagccgcgc agaaatacgc gctgcgctct  1980
atcaaggtga acggtaagcc gctgtccgct gatgtgaatt tgttggccgg tgacgttaac  2040
gcgtggaata agacagaagc ggatggccgc tatttggcta aaaccggcgg caatattacg  2100
ggcggggtat cgtcaagctc ctgggtatct gctgcggcgt tgacatcgga ttatcacggc  2160
accggcgata acacgaataa agccccggaa ggcgccggag cgtacagcaa tcagcttgcc  2220
acgcgcgcgc ctttttacca gactgatttt cagtgggaag caaacagcgg cgcgatttat  2280
gtgccactgg tgaaaggtaa atcgacgcgt aagggcaagg gctggccgac cgcagttagc  2340
tacggctatt tgatgccggg cgagaatatg catgctcatc ccgttattca tgcgcttggt  2400
gatggagtgg aaagtatttg gcagtttaat acccaaactg gcggcattat tagtgggaaa  2460
atgggcgagt tcgcgagtca ggcatgggtt aacaatgggt tgaatggtcg ggttgactgg  2520
ccctccttta atcagcatgt gggcgccaga gcgacaattg actgggttaa tcagaacttt  2580
attcaaaatg tcagatacag cgcggaaatg catgtcggcg cgaccgggat ttatacctat  2640
cacgataata ccgtactaac cggtttcaat aacaaagacg gcgattactc tgctgaggaa  2700
ctgttttgga gctacatcca aatttataaa aatggtcagt ggatcacagt aggacgataa  2760

SEQ ID NO: 107         moltype = DNA  length = 546
FEATURE                Location/Qualifiers
misc_feature           1..546
                       note = Bluetiful Tail Fiber U gene
source                 1..546
                       mol_type = other DNA
                       organism = synthetic construct
SEQUENCE: 107
gtgaagaata ttaaaaactt tcagctcggc gagccaaaaa caccggagca attaaaatta  60
cgcaatcagc ataatgccat gttccttttc tctgacgatg gtaaggagtg gtatcactgc  120
cagaaagatt ttgcggccga tacgataaaa gttgcctacg atgaaaaagg tattatccgc  180
agcattgccg ccaacaacga tatttctacg ttgtggcctg tcgggctaag cgtcgcggaa  240
gtggcaaaca caaccgccaa tcgccgggcc gatatttcag gcggttgggt atttgatggg  300
aaagccattg ttaaacgcag ttattcgcct gacgaatatc aggaacaagc gaaaaaggaa  360
caggttgccc gcattgcggc ggtggcgcgg catatcgcgc cattacagga tgctgttgat  420
ttggacatgg cgaccgagga agaaaaagcg ctgttggcgg actggaaaaa ataccgtgtg  480
atgctgaatc gtctggatat gtcgtcggcc ccggatattg actggccagt ggcgcccagt  540
gcctaa                                                            546

SEQ ID NO: 108         moltype = AA  length = 649
FEATURE                Location/Qualifiers
REGION                 1..649
                       note = Rio Tail Fiber (S)
source                 1..649
                       mol_type = protein
                       organism = synthetic construct
SEQUENCE: 108
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDATTTVKG FTKLNNQVGD SENTALTPYG  240
AKKELENYQP KGNYQPAGNY VTTATFNLEI NKKIDKASLS QQLGNDVNKV PSLDLVTKEL  300
GNKQPKGDYA LKTWVDNIYY KRDDSPSFNE ISATAIRVNS VNVALKGDCY TKSESDNKYS  360
PKLPFVYSSG EESKIISPNN KILIFVNDNG TTGGYDRDTQ ATVWGFDKRG FMTRGTVHFD  420
RMSGVYSQSQ VDAKLKECLN LKTSSKQFIA SDIYAPTFIT GSQYGERSYL EHKSDELTIT  480
HISPKSGATN ITCRNKSGTL ALLGDLEDVN NIPVGSPIPW SLATAPSGYL ICNGQTFNKS  540
TYPKLAVAYP SGKLPDLRGE FIRGLDSGRG IDAGRSVLSV QKGNSLLSSN IFGGLSSSES  600
NKWHKAINYI GITGTDNDGG YGVHQQIEGA NGNETRPRNI AFLYIVRAA             649

SEQ ID NO: 109         moltype = AA  length = 581
FEATURE                Location/Qualifiers
REGION                 1..581
                       note = Limon Tail Fiber (S)
source                 1..581
                       mol_type = protein
                       organism = synthetic construct
SEQUENCE: 109
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDATTARKG IVQLSSATDS TSEELAATLK  240
AVKIAMDNAN ARLAKERNGG DVPNKPLFIQ NIGLQETVNK AAGAVQRSEV QTSQDDITAG  300
KLLVNGSAIA VRGIRAINGG QVDDANNLPV NAVSFVYGDA KNSPSGNTGT ILDVSGLGSG  360
YSIQLFANYS TGEILAFRAR NGDNRTWNKW NYVFHTGNKP TSTDVGALPI TGGDLKGQLS  420
FSFSQPRNGA NHLIYNGDDN GVLACGYGYY QDRFDIHFYD IKGAWESNPL TIGRNGNTTV  480
SGNLSGRAVY EGNTRVYSPN NPQPVSFEGY ATQSWVLQNF VQNIDLTAPA EVGFRDGWGY  540
PRGTDGAAMY NFNMVGGSSN VGNFIIRYMR KQVNNTWYVI N                      581

SEQ ID NO: 110         moltype = AA  length = 1069
```

```
FEATURE                Location/Qualifiers
REGION                 1..1069
                       note = Orchid Tail Fiber (S)
source                 1..1069
                       mol_type = protein
                       organism = synthetic construct
SEQUENCE: 110
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTQKG LVQLSSATNS DSETMAATPK  240
AVKSIKDLAD TKAPIESPSL TGTPTAPTAA QGTNSTQIAN TAFVKAAITA LINGAPGTLD  300
TLKEIAAAIN NDPNYSTTIN NALALKAPLA SPALTGVPTA PTAAQGTNNT QIATTAYVRA  360
AISALVGSSP EALDTLYELA AALGNDPNFA TTMTNALAGK QPLDATLTAL AGLATGANKL  420
PYFTGTDTVS QTDLTSVGRD ILAKTSILAV IQYLGLRELG TSGEKIPLLS TANTWSARQT  480
FNGGITGALT GNADTATKLK TAARSIGGVA FDGSANINLP GVNTTGNQNT TGNAATATKL  540
ATARNINGVK FDGSVDISIP TITSRGRVTA LTGTTQGAAT GLQMYEAYNN GYPSAYGNVL  600
HLKGATAVGE GELFIGWSGT SGAHAPVHVR SRRDTDTASW SEWAQVYTSK DSIPGVNTTG  660
NQNTTGNAAS ATKLQTARTI GGVSFNGTAN IDLPGVNKTG NQNTTGNAAT ATKLQTARTI  720
NGVSFDGSKN IELTAEDLNL QEFINKANNA VQRSGDTLSG GLTFKNDSIL AWIRNTDWAK  780
IGFKNDADGD TDSYMWFETG DNGNEYFKWR SKQSTTTKDL MNLKWDALYV LVNAIVNGEV  840
ISKSANGLRI AYGNYGFFIR NDGSDTYFML TNSGDNMGTY NGLRPLWINN ATGAVSMGRG  900
LNVSGETLSD RFAINSSTGM WINMRDQNVI MGRNAVSTDG AQALLRQDHA DRKFMIGGLG  960
NKQFGIYMIN NSRTANGTDG QAYMDNNGNW LCGAQIIPGN YGNFDSRYVK DVRLGTRVVQ  1020
LMARGGRYEK AGHAITGLRI IGEVDGDDEA IFRPIQKYIN GTWYNVAQV            1069

SEQ ID NO: 111         moltype = AA  length = 671
FEATURE                Location/Qualifiers
REGION                 1..671
                       note = Gold Tail Fiber (S)
source                 1..671
                       mol_type = protein
                       organism = synthetic construct
SEQUENCE: 111
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDATLLAKG FTQLSNDSNS GSETLAATPK  240
AVKAVNDASL KIAANLKDLP NKSVARGNLE LGTAATRNVG AQKTNLMEVG AFGLGGGPIH  300
REDALSNRGE IYRVTGASKN APGGGVYGVL NLPCDGGPSS GYLAIQPNGS SYIGTSTTPD  360
KPLNWYRIYT TGFKPTATDV DAYSKAEADG KFVKQSGDTI TGALTVNGAI ESKSGLTTPS  420
LAVNGSVTIA GALTTKAGVE LFGTTPYLDF HYGNSNGDFD VRLINDNKGT LAFHGNEYYV  480
NGKLSATGDA WIGGKANING MAAFYSSDFI TKQGNLTHPD GNRQTNGMRL QGQGNLLVDL  540
YHYEKVGSHH EFGIHVANGG ADGWFSFRNN GELRANGTLF AAGAAYQTDG NINGGIWGGY  600
LSNYLNHNFV RDVRLGNVES IATWRGPGYS DSAGYVLTGA ANNNVDEYID VIFRRPLQKH  660
IGGNWVTVWS V                                                      671

SEQ ID NO: 112         moltype = AA  length = 919
FEATURE                Location/Qualifiers
REGION                 1..919
                       note = Bluetiful Tail Fiber (S)
source                 1..919
                       mol_type = protein
                       organism = synthetic construct
SEQUENCE: 112
MNDVTVVTSV TYPSSESLAL VADVQYHEPY LSAALNRKFR GIVDPGFYAG FLPKPGGGMN  60
LLITSVDGDK TAGAASVDIG EFYQVTIQQR KDISLALSAG KKYAIVLKGR YLLGEDTYQV  120
NTASHIHAAE FVARTYTDSY QLGDGELLVC TVNIPASVSA ITQEMIDTSE RINRSIGIDI  180
SDSVTSTRSD VAASSLAVKK AYDLAKSKYT AQDASTTAKG LVQLSSATTS TDETKASTPK  240
ALKTVSDASM KKAANLSDVA DKAAARGNLA LGTAATKNVG VDGGQLMEVG AFGLGSGSRH  300
REDAYCNQGE IYRVNGSSKN APGGDVYGVL SLPCDGGPSG AYLAVQNSGN AFFGRSNIAE  360
NGVTWFQAYT TKFKPTAADV GAWSKAEADG RFLMLSGGTV KKLAIKPGNA ETEGSTLNIE  420
GNQHTPLVMS RLSAQGNLSI GFQVAGKALM RLGFGADDEL HWGTEANQAS NPRIYTTAKP  480
PTAQETGALT DAQAVKKYAL RSIKVNGKPL SGDVNLLAGD VNAWNKTEAD GRYVKQSGDT  540
MKGALTLPRI VFPNENTANA DDDLNRENGF TVESLVATTN KGYPVPGGMG VLFTGKVNEF  600
RNVQFAVGSG DMAFYLRSMR KDNSASLRWA RVYTTDYKPT AADVGALTDA QAAQKYALRS  660
IKVNGKPLSA DVNLLAGDVN AWNKTEADGR YLAKTGGNIT GGVSSSSWVS AAALTSDYHG  720
TGDNTNKAPE GAGAYSNQLA TRAPFYQTDF QWEANSGAIY VPLVKGKSTR KGKGWPTAVS  780
YGYLMPGENM HAHPVIHALG DGVESIWQFN TQTGGIISGK MGEFASQAWV NNGLNGRVDW  840
PSFNQHVGAR ATIDWVNQNF IQNVRYSAEM HVGATGIYTY HDNTVLTGFN NKDGDYSAEE  900
LFWSYIQIYK NGQWITVGR                                              919

SEQ ID NO: 113         moltype = AA  length = 206
FEATURE                Location/Qualifiers
REGION                 1..206
                       note = Rio Chaperone (U)
source                 1..206
                       mol_type = protein
                       organism = synthetic construct
```

-continued

```
SEQUENCE: 113
MSKYSLDIQK GKIGDNGLAE IAGWVKCYLA HPITHEYMGA TMENVMFDVS LSAGAYLDEP  60
PLPQKENQAV RRREDGSAWE IVDDCRGLTA YNTQTKQPII IDFMGPLPES LTLLKPNSEF  120
DKWDGKNWIV DTEAQKAALI TQIKQEKSRR LDEADNIITY LQEAVDVDLA TEEEATALQK  180
WKKYRVLLNR VDISTAPDIE WPEKPQ                                      206

SEQ ID NO: 114         moltype = AA  length = 177
FEATURE                Location/Qualifiers
REGION                 1..177
                       note = Limon Chaperone (U)
source                 1..177
                       mol_type = protein
                       organism = synthetic construct
SEQUENCE: 114
MQRFGKFTPY TPDTTDRPRI IDGQNVMFLQ DDKGNDWYDV IELFDESKTL KIGYDDDGRV  60
RTFTTNIHAL FPVNLSVVEL PATKANLRVT LGDDWFYKDG KLQQIRNYLA DAEAERGNRM  120
AEVTTRIDWL EDAQKDGDIS SYEETELATL RAYRTALRRL DLSTAPDINW PEVPDVA     177

SEQ ID NO: 115         moltype = AA  length = 175
FEATURE                Location/Qualifiers
REGION                 1..175
                       note = Orchid Chaperone (U)
source                 1..175
                       mol_type = protein
                       organism = synthetic construct
SEQUENCE: 115
MQHLKNIKSG NPKTKEQYQL TKNFDVIWLW SEDGKNWYEE VNNFQDDTIK IVYDENNIIV  60
AITKDASTLN PEGFSVVEIP DITANRRADD SGKWMFKDGS VVKRIYTADE QQQQAESQKA  120
ALLSEAESVI QPLERAVRLN MATDEERTRL EAWERYSVLV SRVDTANPEW PQKPE       175

SEQ ID NO: 116         moltype = AA  length = 185
FEATURE                Location/Qualifiers
REGION                 1..185
                       note = Gold Chaperone (U)
source                 1..185
                       mol_type = protein
                       organism = synthetic construct
SEQUENCE: 116
MMNNMKNFTL AAPETVEQKQ LAASHGVLFL KSDAGEDWYE CQKSFRPETV KLMYDKDGII  60
RSITAKPNAE GHYDVSGFFP ENMSVAEVEN LPEGADINGR WIFDGENIIP RSYSTQELRQ  120
QAANKKQELI KQSSLQIETL NDATDLGMAS EEELRLLTRW KTYRVLLNRV DPEAAPDIDW  180
PQPPQ                                                             185

SEQ ID NO: 117         moltype = AA  length = 181
FEATURE                Location/Qualifiers
REGION                 1..181
                       note = Bluetiful Chaperone (U)
source                 1..181
                       mol_type = protein
                       organism = synthetic construct
SEQUENCE: 117
VKNIKNFQLG EPKTPEQLKL RNQHNAMFLF SDDGKEWYHC QKDFAADTIK VAYDEKGIIR  60
SIAANNDIST LWPVGLSVAE VANTTANRRA DISGGWVFDG KAIVKRSYSP DEYQEQAKKE  120
QVARIAAVAR HIAPLQDAVD LDMATEEEKA LLADWKKYRV MLNRLDMSSA PDIDWPVAPS  180
A                                                                 181
```